(12) United States Patent
Bur et al.

(10) Patent No.: US 8,536,209 B2
(45) Date of Patent: Sep. 17, 2013

(54) AMINOTRIAZOLE DERIVATIVES AS ALX AGONISTS

(75) Inventors: Daniel Bur, Therwil (CH); Olivier Corminboeuf, Allschwil (CH); Sylvaine Cren, Zürich (CH); Corinna Grisostomi, Allschwil (CH); Xavier Leroy, Steinsoultz (FR); Sylvia Richard-Bildstein, Dietwiller (FR)

(73) Assignee: Actelion Pharmaceuticals Ltd., Allschwil (CH)

( * ) Notice: Subject to any disclaimer, the term of this patent is extended or adjusted under 35 U.S.C. 154(b) by 237 days.

(21) Appl. No.: 12/809,545

(22) PCT Filed: Dec. 17, 2008

(86) PCT No.: PCT/IB2008/055375
§ 371 (c)(1),
(2), (4) Date: Jun. 18, 2010

(87) PCT Pub. No.: WO2009/077990
PCT Pub. Date: Jun. 25, 2009

(65) Prior Publication Data
US 2010/0331378 A1    Dec. 30, 2010

(30) Foreign Application Priority Data

Dec. 18, 2007    (WO) .................. PCT/IB2007/055199
Oct. 23, 2008    (WO) .................. PCT/IB2008/054369

(51) Int. Cl.
| A61K 31/427 | (2006.01) |
| A61K 31/422 | (2006.01) |
| A61K 31/4192 | (2006.01) |
| C07D 263/02 | (2006.01) |
| C07D 249/04 | (2006.01) |
| C07D 277/04 | (2006.01) |
| A61P 37/02 | (2006.01) |

(52) U.S. Cl.
USPC ........................................................ 514/365

(58) Field of Classification Search
None
See application file for complete search history.

(56) References Cited

FOREIGN PATENT DOCUMENTS

| JP | 62-234018 | 10/1987 |
| WO | WO 03/035006 | 5/2003 |
| WO | WO 03/082314 | 10/2003 |
| WO | WO 2005/047899 | 5/2005 |
| WO | WO 2007/055941 | * 5/2007 |
| WO | WO 2007/125405 | * 11/2007 |
| WO | WO 2009/025793 | 2/2009 |
| WO | WO 2009/077954 | 6/2009 |
| WO | WO 2010/134014 | 11/2010 |
| WO | WO 2010/143116 | 12/2010 |
| WO | WO 2010/143158 | 12/2010 |

OTHER PUBLICATIONS

Das, U.N. Journal of Inflammation Research, 2010:3, pp. 143-170.*
NINDS (Creutzfeld-Jakob Disease Information Page, www.ninds.nih.gov/disorders/cjd/cjd.htm; accesseed from the internet Aug. 11, 2012.*
Yazawa et al. in FSAEB J., 2001 15, 2454-2462.*
Romano et al. in The Scientific World Journal (2007) 7, 1393-1412.*
Mallamo et al. (1992) Journal of Medicinal Chemistry 35(10): 1663-1670.
Obushak et al. (2004) Russian Journal of Organic Chemistry 40(3): 383-389.
Wermuth, (1996) The Practice of Medicinal Chemistry, Third Edition: 203-237.
Chiang et al., Pharmacological Reviews, vol. 58, No. 3, pp. 463-487 (2006).
Schwab et al., Current Opinion in Pharmacology, vol. 6, pp. 414-420, (2006).
Le et al., Protein and Peptide Letters., vol. 14, pp. 846-853 (2007).
Yazawa et al., The FASEB Journal, vol. 15, pp. 2454-2462 (2001).
Ying et al., The Journal of Immunology, vol. 172, pp. 7078-7085 (2004).
Gould, International Journal Pharmaceutics, vol. 33, pp. 201-217 (1986).
Index of The Science and Practice of Pharmacy, 21st Edition, Part 5, Pharmaceutical (published by Lippincott Williams & Wilkins) (2005).
Greene et al., Preface and Index of "Protective Groups in Organic Synthesis," Third Edition, A Wiley-Interscience Publication, ISBN 0-471-22057-4 (1999).
Eagles et al., Organic Preparations and Procedures, vol. 2 No. 2, pp. 117-119 (1970).
Neuman, Journal of Heterocyclic Chemistry, vol. 8, pp. 51-56 (1971).
Burli et al, Bioorganic & Medicinal Chemistry Letters, Pergamon, Elsevier Science, GB, vol. 16, No. 14, pp. 3713-3718 (2006).
Yamaguchi, U.S. Appl. No. 10/380,753, filed Mar. 19, 2003.

* cited by examiner

*Primary Examiner* — Dennis Heyer
(74) *Attorney, Agent, or Firm* — Hunton & Williams LLP

(57) ABSTRACT

The invention relates to aminotriazole derivatives of formula (I),

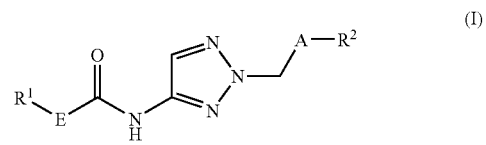

wherein A, E, $R^1$ and $R^2$ are as defined in the description, their preparation and their use as pharmaceutically active compounds.

22 Claims, No Drawings

AMINOTRIAZOLE DERIVATIVES AS ALX AGONISTS

CROSS REFERENCE TO RELATED APPLICATIONS

This application is a national phase filing of International Patent Application No. PCT/IB2008/055375 filed Dec. 17, 2008, which claims priority to PCT/IB2007/055199, filed Dec. 18, 2007, and to PCT/IB2008/054369, filed Oct. 24, 2008. The disclosures of each of these applications are hereby incorporated by reference in their entirety.

The present invention relates to novel aminotriazole derivatives of formula (I) and their use as pharmaceuticals. The invention also concerns related aspects including processes for the preparation of the compounds, pharmaceutical compositions containing one or more compounds of formula (I), and especially their use as ALX receptor agonists.

BACKGROUND

ALXR (alias Lipoxin A4 Receptor, FPRL1; disclosed in WO2003/082314 as nucleotide sequence SEQ ID NO:1) is a member of the G-protein coupled receptor family. ALXR was found to mediate calcium mobilisation in response to high concentration of the formyl-methionine-leucyl-phenylalanine peptide. Furthermore, a lipid metabolite, lipoxin A4 (LXA4), and its analogues, were found to bind ALXR with high affinity and increase arachidonic acid production and G-protein activation in ALXR transfected cells (Chiang et al., Pharmacol. Rev., 2006, 58, 463-487). The effects of LXA4 have been evaluated in a variety of animal models of diseases; and LXA4 was demonstrated to have potent anti-inflammatory and pro-resolution activities. The disease models where LXA4, or derivatives, or stable analogs, demonstrated in vivo activities are for example dermal inflammation, dorsal air pouch, ischemia/reperfusion injury, peritonitis, colitis, mesangioproliferative nephritis, pleuritis, asthma, cystic fibrosis, sepsis, corneal injury, angiogenesis, periodontitis, carrageenan-induced hyperalgesia, and graft-vs-host disease (GvHD) (Serhan and Chiang, Br. J. Pharmacol., 2007, 1-16). ALXR was also identified as a functional receptor of a various number of peptides, including a fragment of the prion protein, a peptide derived from gp120 of the Human Immunodeficiency Virus (HIV)-1$_{LM}$ strain, and amyloid-beta 1-42 (Ab42) (for review, Le et al., Protein Pept Lett., 2007,14, 846-853), and has been suggested to participate in the pathogenesis of Alzheimer's Disease (AD) in several crucial ways (Yazawa et al., FASEB J., 2001, 15, 2454-2462). Activation of ALXR on macrophages and microglial cells initiates a G protein-mediated signalling cascade that increases directional cell migration, phagocytosis, and mediator release. These events may account for the recruitment of mononuclear cells to the vicinity of senile plaques in the diseased areas of AD brain where Ab42 is overproduced and accumulated. Although accumulation of leukocytes at the sites of tissue injury may be considered an innate host response aimed at the clearance of noxious agents, activated mononuclear phagocytes also release a variety of substances such as superoxide anions that may be toxic to neurons. Thus, ALXR may mediate pro-inflammatory responses elicited by Ab42 in AD brain and exacerbate disease progression. It was also reported that humanin (HN), a peptide with neuroprotective capabilities, shares the human ALXR with Ab42 on mononuclear phagocytes and neuronal cell lines and it has been suggested that the neuroprotective activity of HN may be attributed to its competitive occupation of ALXR (Ying et al., J. Immunol., 2004, 172, 7078-7085). The biological properties of ALXR agonists include, but are not limited to, monocyte/macrophage/microglia migration/activation, neutrophil migration/activation, regulation of lymphocyte activation, proliferation and differentiation regulation of inflammation, regulation of cytokine production and/or release, regulation of proinflammatory mediator production and/or release, regulation of immune reaction.

SUMMARY OF THE INVENTION

The present invention provides aminotriazole derivatives, which are non-peptide agonists of human ALX receptor. The compounds are useful for the prevention or treatment of diseases, which respond to the modulation of the ALX receptor such as inflammatory diseases, obstructive airway diseases, allergic conditions, HIV-mediated retroviral infections, cardiovascular disorders, neuroinflammation, neurological disorders, pain, prion-mediated diseases and amyloid-mediated disorders (especially Alzheimer's disease); in addition they are useful for the prevention or treatment of autoimmune diseases and for the modulation of immune responses (especially those elicited by vaccination).

DETAILED DESCRIPTION OF THE INVENTION

Various embodiments of the invention are presented hereafter:

1) The present invention relates to aminotriazole derivatives of the formula (I),

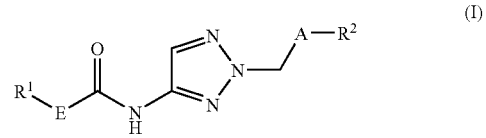

wherein

A represents a phenyl- or a heterocyclyl-group, wherein the two substituents are in a 1,3-arrangement; or A represents propan-1,3-diyl;

E represents *—($C_1$-$C_4$)alkyl-O—, —CH=CH— or

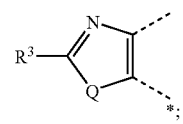

wherein the asterisks indicate the bond which is linked to $R^1$;

Q represents O or S;

$R^3$ represents hydrogen, ($C_1$-$C_4$)alkyl, cyclopropyl, ($C_1$-$C_4$)alkoxy-($C_1$-$C_2$)alkyl, benzyl or $CH_2CH_2C(O)OtBu$;

$R^1$ represents a pyridyl- or an aryl-group, which group is unsubstituted, mono-, di- or tri-substituted, wherein the substituents are independently selected from the group consisting of halogen, ($C_1$-$C_4$)alkyl, ($C_1$-$C_4$)alkoxy, ($C_1$-$C_4$)fluoroalkyl, ($C_1$-$C_4$)fluoroalkoxy, di-[($C_1$-$C_3$)alkyl]-amino and ($C_1$-$C_4$)alkoxy-($C_1$-$C_2$)alkyl; and $R^2$ represents —CO—($C_1$-$C_3$)alkyl, —$CF_2$—($C_1$-$C_3$)alkyl, or —$SO_2$—($C_1$-$C_3$)alkyl.

The compounds of formula (I) according to embodiment 1) may contain one or more stereogenic or asymmetric centers, such as one or more asymmetric carbon atoms. Substituents at a double bond may be present in the (Z)- or (E)-configuration unless indicated otherwise. The compounds of formula (I) may thus be present as mixtures of stereoisomers or preferably as pure stereoisomers. Mixtures of stereoisomers may be separated in a manner known to a person skilled in the art.

In case E represents —CH=CH— the double bond may be present in (Z)- or (E)-configuration, preferably it is present in (E)-configuration.

The following paragraphs provide definitions of the various chemical moieties for the compounds according to the invention and are intended to apply uniformly throughout the specification and claims unless an otherwise expressly set out definition provides a broader or narrower definition.

The term "alkyl", used alone or in combination, refers to a straight or branched chain alkyl group containing one to four carbon atoms. The term "$(C_x–C_y)$alkyl" (x and y each being an integer), refers to an alkyl group as defined before containing x to y carbon atoms. For example a $(C_1-C_4)$alkyl group contains from one to four carbon atoms. Representative examples of alkyl groups include methyl, ethyl, n-propyl, iso-propyl, n-butyl, iso-butyl, sec-butyl and tent-butyl. Preferred are $(C_1-C_3)$alkyl groups such as methyl, ethyl, n-propyl and iso-propyl. More preferred are $(C_1-C_3)$alkyl groups such as methyl and ethyl. Most preferred is methyl.

An example of a $(C_1-C_3)$alkyl group as used in $R^2$ representing —CO—$(C_1-C_3)$alkyl, —CF$_2$—$(C_1-C_3)$alkyl or —SO$_2$—$(C_1-C_3)$alkyl is methyl.

In a bridging $(C_1-C_4)$alkyl group as used in E representing *—$(C_1-C_4)$alkyl-O—, the oxygen atom and the rest $R^1$ are preferably attached to the same carbon atom of the bridging $(C_1-C_4)$alkyl group. An example of such bridging $(C_1-C_4)$alkyl groups is a methylene group.

The term "alkoxy", used alone or in combination, refers to an alkyl-O— group wherein the alkyl group is as defined before. The term "$(C_x—C_y)$alkoxy" (x and y each being an integer) refers to an alkoxy group as defined before containing x to y carbon atoms. For example a $(C_1-C_4)$alkoxy group contains from one to four carbon atoms. Representative examples of alkoxy groups include methoxy, ethoxy, n-propoxy, iso-propoxy, n-butoxy, iso-butoxy, sec-butoxy and tert-butoxy. Preferred are ethoxy and methoxy. Most preferred is methoxy.

The term "fluoroalkyl" refers to an alkyl group as defined before containing one to four (preferably one to three) carbon atoms in which one or more (and possibly all) hydrogen atoms have been replaced with fluorine. The term "$(C_x—C_y)$fluoroalkyl" (x and y each being an integer) refers to a fluoroalkyl group as defined before containing x to y carbon atoms. For example a $(C_1-C_3)$fluoroalkyl group contains from one to three carbon atoms in which one to seven hydrogen atoms have been replaced with fluorine. Representative examples of fluoroalkyl groups include trifluoromethyl and 2,2,2-trifluoroethyl. Preferred is $(C_1)$fluoroalkyl such as trifluoromethyl and difluoromethyl. Most preferred is trifluoromethyl.

The term "fluoroalkoxy" refers to an alkoxy group as defined before containing one to four (preferably one to three) carbon atoms in which one or more (and possibly all) hydrogen atoms have been replaced with fluorine. The term "$(C_x—C_y)$fluoroalkoxy" (x and y each being an integer) refers to a fluoroalkoxy group as defined before containing x to y carbon atoms. For example a $(C_1-C_3)$fluoroalkoxy group contains from one to three carbon atoms in which one to seven hydrogen atoms have been replaced with fluorine. Representative examples of fluoroalkoxy groups include trifluoromethoxy, difluoromethoxy and 2,2,2-trifluoroethoxy. Preferred are $(C_1)$fluoroalkoxy groups such as trifluoromethoxy and difluoromethoxy. Most preferred is trifluoromethoxy.

The term "hydroxy-$(C_1-C_2)$alkyl" refers to an alkyl group as defined before containing one or two carbon atoms in which one hydrogen atom has been replaced with hydroxy. Examples of hydroxy-$(C_1-C_2)$alkyl groups are hydroxy-methyl and hydroxy-ethyl. Preferred are hydroxy-methyl and 2-hydroxy-ethyl.

The term "$(C_1-C_4)$alkoxy-$(C_1-C_2)$alkyl" refers to an alkyl group as defined before containing one or two carbon atoms in which one hydrogen atom has been replaced with $(C_1-C_4)$ alkoxy as defined before. Representative examples of $(C_1-C_4)$ alkoxy-$(C_1-C_2)$alkyl groups include methoxy-methyl, methoxy-ethyl (notably 2-methoxy-ethyl), ethoxy-methyl, ethoxy-ethyl (notably 2-ethoxy-ethyl), isopropoxy-methyl and isopropoxy-ethyl (notably 2-isopropoxy-ethyl); and preferably methoxy-methyl, methoxy-ethyl (notably 2-methoxy-ethyl), ethoxy-methyl and ethoxy-ethyl (notably 2-ethoxy-ethyl).

Preferred examples of $(C_1-C_4)$alkoxy-$(C_1-C_2)$alkyl groups as used in $R^1$ are methoxy-methyl, methoxy-ethyl (notably 2-methoxy-ethyl), ethoxy-methyl, ethoxy-ethyl (notably 2-ethoxy-ethyl), isopropoxy-methyl and isopropoxy-ethyl (notably 2-isopropoxy-ethyl). Most preferred are methoxy-methyl and methoxy-ethyl (notably 2-methoxy-ethyl).

Preferred examples of $(C_1-C_4)$alkoxy-$(C_1-C_2)$alkyl groups as used in $R^3$ are methoxy-methyl and methoxy-ethyl (notably 2-methoxy-ethyl). Most preferred is methoxy-methyl.

The term "di-[$(C_1-C_3)$alkyl]-amino" refers to an amino group which is substituted by two $(C_1-C_3)$alkyl groups as defined above, wherein the two $(C_1-C_3)$alkyl groups may be the same or different. Representative examples of di-[$(C_1-C_3)$ alkyl]-amino groups include, but are not limited to dimethylamino, methyl-ethyl-amino and diethylamino. Preferred is dimethylamino.

The term halogen means fluoro, chloro, bromo or iodo, preferably fluoro, chloro or bromo and most preferably fluoro or chloro.

The term "aryl", alone or in any combination, means phenyl (preferred) or naphthyl. The aryl group is unsubstituted, mono-, di-, or tri-substituted (preferably unsubstituted, mono- or di-substituted and most preferably unsubstituted, or mono-substituted), wherein the substituents are independently selected from the group consisting of halogen, $(C_1-C_4)$ alkyl, $(C_1-C_4)$alkoxy, $(C_1-C_4)$fluoroalkyl, $(C_1-C_4)$fluoroalkoxy, di-[$(C_1-C_3)$alkyl]-amino and $(C_1-C_4)$alkoxy-$(C_1-C_2)$ alkyl and preferably from halogen, $(C_1-C_4)$alkyl, $(C_1-C_4)$ alkoxy, $(C_1-C_4)$fluoroalkyl and $(C_1-C_4)$fluoroalkoxy. Examples are phenyl, 2-chlorophenyl, 3-chlorophenyl, 4-chlorophenyl, 2-chloro-4-fluorophenyl, 3-fluorophenyl, 4-fluorophenyl, 2-methylphenyl, 3-methylphenyl, 4-methylphenyl, 3,5-dimethylphenyl, 3-methoxyphenyl, 4-methoxyphenyl, 3-methoxy-4-methylphenyl, 3-methoxymethyl-phenyl, 3-methoxyethyl-phenyl, 3-dimethylamino-phenyl, 2-trifluoromethyl-phenyl, 3-trifluoromethylphenyl, 4-trifluoromethylphenyl, and 3-trifluoromethoxyphenyl. Further examples are 3-isopropoxymethyl-phenyl and 3-(2-isopropoxy-ethyl)-phenyl. Preferred examples are phenyl, 3-methoxyphenyl and 4-trifluoromethylphenyl.

The term "heterocyclyl", alone or in combination, means a 5- or 6-membered monocyclic aromatic ring containing 1, 2 or 3 heteroatoms independently selected from oxygen, nitrogen and sulfur. Examples of such heterocyclyl groups are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl, and pyrazinyl. Preferred examples are furanyl (especially furan-2,5-diyl), thienyl (especially thiophen-2,4-diyl and thiophen-2,5-diyl), thiazolyl (especially thiazol-2,4-diyl), and pyridyl (especially pyridin-2,4-diyl and pyridin-2,6-diyl). A further preferred example is oxazolyl (especially oxazol-2,4-diyl and oxazol-2,5-diyl). More preferred examples are furan-2,5-diyl, oxazol-2,4-diyl, oxazol-2,5-diyl, thiophen-2,5-diyl and thiazol-2,4-diyl. Most preferred examples are furan-2,5-diyl and thiophen-2,5-diyl and especially furan-2,5-diyl.

The term "1,3-arrangement" as used in the specification of "A" means that the two atoms of the phenyl or heterocyclyl group which are attached to the triazole-methyl moiety and to the residue $R^2$ respectively are separated from each other by one atom; for example, if "A" represents phenyl the arrangement of the substituents is as shown in the figure below

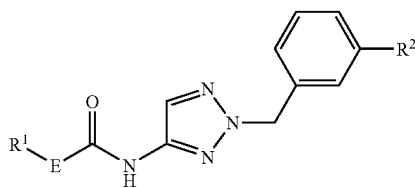

In this patent application, a dotted line shows the point of attachment of the radical drawn. For example, the radical drawn below

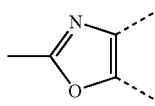

is the 2-methyl-oxazole-4,5-diyl group.

2) A further embodiment of the invention relates to aminotriazole derivatives according to embodiment 1), wherein A represents a phenyl- or a heterocyclyl-group, wherein the two substituents are in a 1,3-arrangement; or A represents propan-1,3-diyl;

E represents *—$CH_2$—O—, —CH=CH— or

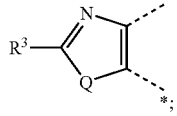

wherein the asterisks indicate the bond which is linked to $R^1$;
Q represents O or S;
$R^3$ represents hydrogen, $(C_1-C_4)$alkyl, cyclopropyl or $(C_1-C_4)$alkoxy-$(C_1-C_2)$alkyl;
$R^1$ represents an aryl-group, which group is unsubstituted, mono-, di- or tri-substituted, wherein the substituents are independently selected from the group consisting of halogen, $(C_1-C_4)$alkyl, $(C_1-C_4)$alkoxy, $(C_1-C_4)$fluoroalkyl, $(C_1-C_4)$fluoroalkoxy, di-[$(C_1-C_3)$alkyl]-amino and $(C_1-C_4)$alkoxy-$(C_1-C_2)$alkyl; and
$R^2$ represents —CO—$(C_1-C_3)$alkyl, —$CF_2$—$(C_1-C_3)$alkyl, or —$SO_2$—$(C_1-C_3)$alkyl.

3) A further embodiment of the invention relates to aminotriazole derivatives according to embodiment 1), wherein A represents a phenyl- or a heterocyclyl-group, wherein the two substituents are in a 1,3-arrangement; or A represents propan-1,3-diyl;

E represents *—$(C_1-C_4)$alkyl-O—, —CH=CH— or

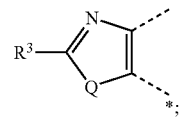

wherein the asterisks indicate the bond which is linked to $R^1$;
Q represents O or S;
$R^3$ represents hydrogen, $(C_1-C_4)$alkyl, or cyclopropyl;
$R^1$ represents an aryl-group, which group is unsubstituted, mono-, di- or tri-substituted, wherein the substituents are independently selected from the group consisting of halogen, $(C_1-C_4)$alkyl, $(C_1-C_4)$alkoxy, $(C_1-C_4)$fluoroalkyl, $(C_1-C_4)$fluoroalkoxy, di-[$(C_1-C_3)$alkyl]-amino and $(C_1-C_4)$alkoxy-$(C_1-C_2)$alkyl; and
$R^2$ represents —CO—$(C_1-C_3)$alkyl, —$CF_2$—$(C_1-C_3)$alkyl, or —$SO_2$—$(C_1-C_3)$alkyl.

4) A further embodiment of the invention relates to aminotriazole derivatives according to any one of embodiments 1) or 2), wherein A represents phenyl-1,3-diyl, furan-2,5-diyl, oxazol-2,4-diyl, oxazol-2,5-diyl, thiophen-2,4-diyl, thiophen-2,5-diyl, thiazol-2,4-diyl, thiazol-2,5-diyl, pyridin-2,4-diyl, pyridin-2,6-diyl or propan-1,3-diyl;

E represents *—$CH_2$—O—, —CH=CH— or

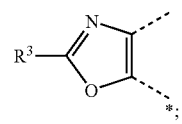

wherein the asterisks indicate the bond which is linked to $R^1$;
$R^3$ represents hydrogen, $(C_1-C_4)$alkyl, cyclopropyl or $(C_1-C_4)$alkoxy-$(C_1-C_2)$alkyl;
$R^1$ represents an aryl-group, which group is unsubstituted, mono-, di- or tri-substituted, wherein the substituents are independently selected from the group consisting of halogen, $(C_1-C_4)$alkyl, $(C_1-C_4)$alkoxy, $(C_1-C_4)$fluoroalkyl, $(C_1-C_4)$fluoroalkoxy, di-[$(C_1-C_3)$alkyl]-amino and $(C_1-C_4)$alkoxy-$(C_1-C_2)$alkyl; and
$R^2$ represents —CO—$(C_1-C_3)$alkyl, —$CF_2$—$(C_1-C_3)$alkyl, or —$SO_2$—$(C_1-C_3)$alkyl.

5) A further embodiment of the invention relates to aminotriazole derivatives according to any one of embodiments 1) to 4), wherein at least one, preferably all of the following characteristics are present:

A represents phenyl-1,3-diyl, furan-2,5-diyl, thiophen-2,4-diyl, thiophen-2,5-diyl, thiazol-2,4-diyl, pyridin-2,4-diyl, pyridin-2,6-diyl or propan-1,3-diyl;

E represents *—$CH_2$—O—, —CH=CH— or

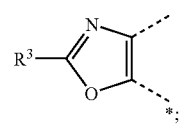

wherein the asterisks indicate the bond which is linked to $R^1$;
$R^3$ represents hydrogen, $(C_1-C_4)$alkyl, or cyclopropyl;

$R^1$ represents an aryl-group, which group is unsubstituted, mono-, di- or tri-substituted, wherein the substituents are independently selected from the group consisting of halogen, $(C_1-C_4)$alkyl, $(C_1-C_4)$alkoxy, $(C_1-C_4)$fluoroalkyl, $(C_1-C_4)$fluoroalkoxy, di-[$(C_1-C_3)$alkyl]-amino and $(C_1-C_4)$alkoxy-$(C_1-C_2)$alkyl; and $R^2$ represents —CO—$(C_1-C_3)$alkyl, —CF$_2$—$(C_1-C_3)$alkyl, or —SO$_2$—$(C_1-C_3)$alkyl.

6) A further embodiment of the invention relates to aminotriazole derivatives according to any one of embodiments 1) to 4), wherein A represents furan-2,5-diyl, oxazol-2,4-diyl, oxazol-2,5-diyl, thiophen-2,5-diyl or thiazol-2,4-diyl;

E represents *—CH$_2$—O—, —CH=CH— or

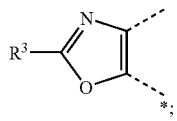

wherein the asterisks indicate the bond which is linked to $R^1$;

$R^3$ represents hydrogen, methyl, ethyl or cyclopropyl;

$R^1$ represents a phenyl-group, which group is unsubstituted, mono- or di-substituted, wherein the substituents are independently selected from the group consisting of halogen, methyl, methoxy, trifluoromethyl, trifluoromethoxy, and dimethylamino; and $R^2$ represents —CO—CH$_3$.

7) A further embodiment of the invention relates to aminotriazole derivatives according to any one of embodiments 1) to 6), wherein at least one, preferably all of the following characteristics are present:

A represents furan-2,5-diyl or thiophen-2,5-diyl (especially furan-2,5-diyl);

E represents

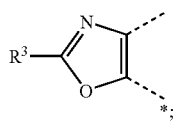

wherein the asterisk indicates the bond which is linked to $R^1$;

$R^3$ represents hydrogen or methyl;

$R^1$ represents a phenyl-group, which group is unsubstituted, mono- or di-substituted, wherein the substituents are independently selected from the group consisting of halogen, methyl, methoxy, trifluoromethyl, trifluoromethoxy, and dimethylamino; and $R^2$ represents —CO—CH$_3$.

8) A further embodiment of the invention relates to compounds of formula (I) that are also compounds of formula ($I_p$)

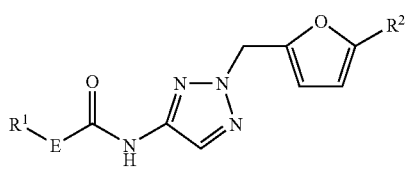

Formula ($I_p$)

wherein

E represents *—$(C_1-C_4)$alkyl-O—, —CH=CH— or

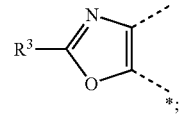

wherein the asterisks indicate the bond which is linked to $R^1$;

$R^3$ represents hydrogen or $(C_1-C_4)$alkyl;

$R^1$ represents aryl, which is unsubstituted, mono-, di- or tri-substituted, wherein the substituents are independently selected from the group consisting of halogen, $(C_1-C_4)$alkyl, $(C_1-C_4)$alkoxy, $(C_1-C_4)$fluoroalkyl and $(C_1-C_4)$fluoroalkoxy; and $R^2$ represents —CO—$(C_1-C_3)$alkyl.

9) A further embodiment of the invention relates to aminotriazole derivatives according to any one of embodiments 1) to 3), wherein A represents heterocyclyl, wherein the two substituents are in a 1,3-arrangement.

10) A further embodiment of the invention relates to aminotriazole derivatives according to any one of embodiments 1) to 4), wherein A represents phenyl-1,3-diyl, furan-2,5-diyl, oxazol-2,4-diyl, oxazol-2,5-diyl (especially with $R^2$ being attached in 2-position), thiophen-2,4-diyl, thiophen-2,5-diyl, thiazol-2,4-diyl (especially with $R^2$ being attached in 4-position), thiazol-2,5-diyl, pyridin-2,4-diyl, pyridin-2,6-diyl or propan-1,3-diyl.

11) A further embodiment of the invention relates to aminotriazole derivatives according to any one of embodiments 1) to 5) or 10), wherein A represents phenyl-1,3-diyl, furan-2,5-diyl, thiophen-2,4-diyl (with $R^2$ being attached in 2-position), thiophen-2,5-diyl, thiazol-2,4-diyl (with $R^2$ being attached in 4-position), pyridin-2,4-diyl, pyridin-2,6-diyl or propan-1,3-diyl.

12) A further embodiment of the invention relates to aminotriazole derivatives according to any one of embodiments 1) to 4), 6), 9) or 10), wherein A represents furan-2,5-diyl, oxazol-2,4-diyl with $R^2$ being attached in 2-position, oxazol-2,4-diyl with $R^2$ being attached in 4-position, oxazol-2,5-diyl with $R^2$ being attached in 2-position, thiophen-2,5-diyl or thiazol-2,4-diyl with $R^2$ being attached in 4-position.

13) A further embodiment of the invention relates to aminotriazole derivatives according to any one of embodiments 1) to 7) or 9) to 12), wherein A represents furan-2,5-diyl or thiophen-2,5-diyl.

14) A further embodiment of the invention relates to aminotriazole derivatives according to any one of embodiments 1) to 6) or 9) to 12), wherein A represents thiazol-2,4-diyl (with $R^2$ being attached in 4-position).

15) A further embodiment of the invention relates to aminotriazole derivatives according to any one of embodiments 1) to 7) or 9) to 13), wherein A represents thiophen-2,5-diyl.

16) A further embodiment of the invention relates to aminotriazole derivatives according to any one of embodiments 1) to 7) or 9) to 13), wherein A represents furan-2,5-diyl.

17) A further embodiment of the invention relates to aminotriazole derivatives according to any one of embodiments 1) to 4), 6), 9), 10) or 12), wherein A represents oxazol-2,4-diyl with $R^2$ being attached in 2-position or oxazol-2,4-diyl with $R^2$ being attached in 4-position.

18) A further embodiment of the invention relates to aminotriazole derivatives according to any one of embodiments 1) to 4), 6), 9), 10) or 12), wherein
A represents oxazol-2,4-diyl with $R^2$ being attached in 2-position.

19) A further embodiment of the invention relates to aminotriazole derivatives according to any one of embodiments 1) to 4), 6), 9), 10) or 12), wherein
A represents oxazol-2,4-diyl with $R^2$ being attached in 4-position.

20) A further embodiment of the invention relates to aminotriazole derivatives according to any one of embodiments 1) to 4), 6), 9) or 10), wherein
A represents oxazol-2,5-diyl with $R^2$ being attached in 2-position or oxazol-2,5-diyl with $R^2$ being attached in 5-position.

21) A further embodiment of the invention relates to aminotriazole derivatives according to any one of embodiments 1) to 4), 6), 9), 10) or 12), wherein
A represents oxazol-2,5-diyl with $R^2$ being attached in 2-position.

22) A further embodiment of the invention relates to aminotriazole derivatives according to any one of embodiments 1) to 5), 10) or 11), wherein
A represents phenyl-1,3-diyl.

23) A further embodiment of the invention relates to aminotriazole derivatives according to any one of embodiments 1) to 5), 10) or 11), wherein
A represents propan-1,3-diyl.

24) A further embodiment of the invention relates to aminotriazole derivatives according to any one of embodiments 1) to 6) or 8) to 23), wherein
E represents *—($C_1$-$C_4$)alkyl-O— (preferably *—$CH_2$—O—) or —CH=CH—,
wherein the asterisk indicates the bond which is linked to $R^1$.

25) A further embodiment of the invention relates to aminotriazole derivatives according to any one of embodiments 1) to 6) or 8) to 24), wherein
E represents *—($C_1$-$C_4$)alkyl-O— (preferably *—$CH_2$—O—),
wherein the asterisk indicates the bond which is linked to $R^1$.

26) A further embodiment of the invention relates to aminotriazole derivatives according to any one of embodiments 1) to 6) or 8) to 24), wherein
E represents —CH=CH—.

27) A further embodiment of the invention relates to aminotriazole derivatives according to any one of embodiments 1) to 23), wherein E represents

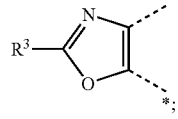

wherein the asterisk indicates the bond which is linked to $R^1$.

28) A further embodiment of the invention relates to aminotriazole derivatives according to any one of embodiments 1), 2), 4), 9) to 23) or 27), wherein $R^3$ represents hydrogen, ($C_1$-$C_4$)alkyl, cyclopropyl, methoxy-methyl or 2-methoxy-ethyl.

29) A further embodiment of the invention relates to aminotriazole derivatives according to any one of embodiments 1) to 23) or 27), wherein
$R^3$ represents hydrogen or methyl.

30) A further embodiment of the invention relates to aminotriazole derivatives according to any one of embodiments 1) to 3) or 9) to 23), wherein Q represents O.

31) A further embodiment of the invention relates to aminotriazole derivatives according to any one of embodiments 1) to 5) or 9) to 30), wherein
$R^1$ represents phenyl, which is unsubstituted, mono- or di-substituted, wherein the substituents are independently selected from the group consisting of halogen, ($C_1$-$C_4$)alkyl (especially methyl), ($C_1$-$C_4$)alkoxy (especially methoxy), trifluoromethyl, trifluoromethoxy, and dimethylamino.

32) A further embodiment of the invention relates to aminotriazole derivatives according to any one of embodiments 1) to 31), wherein $R^1$ represents phenyl, which is unsubstituted or mono-substituted wherein the substituent is selected from the group consisting of halogen, ($C_1$-$C_4$)alkoxy (especially methoxy) and trifluoromethyl.

33) A further embodiment of the invention relates to aminotriazole derivatives according to any one of embodiments 1) or 9) to 30), wherein
$R^1$ represents pyridyl, which is unsubstituted, mono-, di- or tri-substituted, wherein the substituents are independently selected from the group consisting of halogen, ($C_1$-$C_4$)alkyl, ($C_1$-$C_4$)alkoxy, ($C_1$-$C_4$)fluoroalkyl, ($C_1$-$C_4$)fluoroalkoxy, di-[($C_1$-$C_3$)alkyl]-amino and ($C_1$-$C_4$)alkoxy-($C_1$-$C_2$)alkyl.

34) A further embodiment of the invention relates to aminotriazole derivatives according to any one of embodiments 1) or 9) to 30), wherein
$R^1$ represents pyridyl, which is mono-substituted with ($C_1$-$C_4$)fluoroalkyl (especially trifluoromethyl).

35) A further embodiment of the invention relates to aminotriazole derivatives according to any one of embodiments 1) to 5) or 9) to 34), wherein $R^2$ represents —CO—($C_1$-$C_3$)alkyl (especially —CO—$CH_3$) or —$CF_2$—($C_1$-$C_3$)alkyl (especially —$CF_2$—$CH_3$).

36) A further embodiment of the invention relates to aminotriazole derivatives according to any one of embodiments 1) to 5) or 9) to 35), wherein $R^2$ represents —$CF_2$—($C_1$-$C_3$)alkyl (especially —$CF_2$—$CH_3$).

37) A further embodiment of the invention relates to aminotriazole derivatives according to any one of embodiments 1) to 35), wherein $R^2$ represents —CO—($C_1$-$C_3$)alkyl (especially —CO—$CH_3$).

38) Preferred compounds of formula (I) as defined in embodiment 1) are selected from the group consisting of:
5-Phenyl-oxazole-4-carboxylic acid [2-(5-acetyl-furan-2-ylmethyl)-2H-[1,2,3]triazol-4-yl]-amide;
N-[2-(5-Acetyl-furan-2-ylmethyl)-2H-[1,2,3]triazol-4-yl]-3-(4-trifluoromethyl-phenyl)-acrylamide (preferably (E)-N-[2-(5-Acetyl-furan-2-ylmethyl)-2H-[1,2,3]triazol-4-yl]-3-(4-trifluoromethyl-phenyl)-acrylamide);
5-(3-Methoxy-phenyl)-2-methyl-oxazole-4-carboxylic acid [2-(5-acetyl-furan-2-ylmethyl)-2H-[1,2,3]triazol-4-yl]-amide;
[2-(5-Acetyl-furan-2-ylmethyl)-2H-[1,2,3]triazol-4-yl]-carbamic acid 2-chloro-benzyl ester;
wherein the double bond of acrylamide derivatives cited in the above list may be in (E)- or (Z)-configuration (preferably in (E)-configuration).

39) Further preferred compounds of formula (I) as defined in embodiment 1) are selected from the group consisting of:

5-Phenyl-oxazole-4-carboxylic acid [2-(5-oxo-hexyl)-2H-[1,2,3]triazol-4-yl]-amide;
N-[2-(5-Acetyl-furan-2-ylmethyl)-2H-[1,2,3]triazol-4-yl]-3-(4-chloro-phenyl)-acrylamide (preferably (E)-N-[2-(5-Acetyl-furan-2-ylmethyl)-2H-[1,2,3]triazol-4-yl]-3-(4-chloro-phenyl)-acrylamide);
N-[2-(5-Acetyl-furan-2-ylmethyl)-2H-[1,2,3]triazol-4-yl]-3-(2-trifluoromethyl-phenyl)-acrylamide (preferably (E)-N-[2-(5-Acetyl-furan-2-ylmethyl)-2H-[1,2,3]triazol-4-yl]-3-(2-trifluoromethyl-phenyl)-acrylamide);
N-[2-(5-Acetyl-furan-2-ylmethyl)-2H-[1,2,3]triazol-4-yl]-3-(3-trifluoromethoxy-phenyl)-acrylamide (preferably (E)-N-[2-(5-Acetyl-furan-2-ylmethyl)-2H-[1,2,3]triazol-4-yl]-3-(3-trifluoromethoxy-phenyl)-acrylamide);
N-[2-(5-Acetyl-furan-2-ylmethyl)-2H-[1,2,3]triazol-4-yl]-3-o-tolyl-acrylamide (preferably (E)-N-[2-(5-Acetyl-furan-2-ylmethyl)-2H-[1,2,3]triazol-4-yl]-3-o-tolyl-acrylamide);
N-[2-(5-Acetyl-furan-2-ylmethyl)-2H-[1,2,3]triazol-4-yl]-3-(2-chloro-4-fluoro-phenyl)-acrylamide (preferably (E)-N-[2-(5-Acetyl-furan-2-ylmethyl)-2H-[1,2,3]triazol-4-yl]-3-(2-chloro-4-fluoro-phenyl)-acrylamide);
N-[2-(5-Acetyl-furan-2-ylmethyl)-2H-[1,2,3]triazol-4-yl]-3-m-tolyl-acrylamide (preferably (E)-N-[2-(5-Acetyl-furan-2-ylmethyl)-2H-[1,2,3]triazol-4-yl]-3-m-tolyl-acrylamide);
N-[2-(5-Acetyl-furan-2-ylmethyl)-2H-[1,2,3]triazol-4-yl]-3-p-tolyl-acrylamide (preferably (E)-N-[2-(5-Acetyl-furan-2-ylmethyl)-2H-[1,2,3]triazol-4-yl]-3-p-tolyl-acrylamide);
N-[2-(5-Acetyl-furan-2-ylmethyl)-2H-[1,2,3]triazol-4-yl]-3-(4-methoxy-phenyl)-acrylamide (preferably (E)-N-[2-(5-Acetyl-furan-2-ylmethyl)-2H-[1,2,3]triazol-4-yl]-3-(4-methoxy-phenyl)-acrylamide);
5-(3,5-Dimethyl-phenyl)-2-methyl-oxazole-4-carboxylic acid [2-(5-acetyl-furan-2-ylmethyl)-2H-[1,2,3]triazol-4-yl]-amide;
5-(3-Trifluoromethyl-phenyl)-oxazole-4-carboxylic acid [2-(5-acetyl-furan-2-ylmethyl)-2H-[1,2,3]triazol-4-yl]-amide;
5-(3-Fluoro-phenyl)-2-methyl-oxazole-4-carboxylic acid [2-(5-acetyl-furan-2-ylmethyl)-2H-[1,2,3]triazol-4-yl]-amide;
5-(4-Chloro-phenyl)-oxazole-4-carboxylic acid [2-(5-acetyl-furan-2-ylmethyl)-2H-[1,2,3]triazol-4-yl]-amide;
2-Methyl-5-m-tolyl-oxazole-4-carboxylic acid [2-(5-acetyl-furan-2-ylmethyl)-2H-[1,2,3]triazol-4-yl]-amide;
5-(3-Trifluoromethoxy-phenyl)-oxazole-4-carboxylic acid [2-(5-acetyl-furan-2-ylmethyl)-2H-[1,2,3]triazol-4-yl]-amide;
5-(3-Chloro-phenyl)-2-methyl-oxazole-4-carboxylic acid [2-(5-acetyl-furan-2-ylmethyl)-2H-[1,2,3]triazol-4-yl]-amide;
5-(3-Methoxy-4-methyl-phenyl)-oxazole-4-carboxylic acid [2-(5-acetyl-furan-2-ylmethyl)-2H-[1,2,3]triazol-4-yl]-amide;
5-(4-Fluoro-phenyl)-oxazole-4-carboxylic acid [2-(5-acetyl-furan-2-ylmethyl)-2H-[1,2,3]triazol-4-yl]-amide;
5-m-Tolyl-oxazole-4-carboxylic acid [2-(5-acetyl-furan-2-ylmethyl)-2H-[1,2,3]triazol-4-yl]-amide;
5-(3-Methoxy-phenyl)-oxazole-4-carboxylic acid [2-(5-acetyl-furan-2-ylmethyl)-2H-[1,2,3]triazol-4-yl]-amide;
2-Methyl-5-phenyl-oxazole-4-carboxylic acid [2-(5-acetyl-furan-2-ylmethyl)-2H-[1,2,3]triazol-4-yl]-amide;
2-Methyl-5-(3-trifluoromethyl-phenyl)-oxazole-4-carboxylic acid [2-(5-acetyl-furan-2-ylmethyl)-2H-[1,2,3]triazol-4-yl]-amide;
2-Methyl-5-(3-trifluoromethoxy-phenyl)-oxazole-4-carboxylic acid [2-(5-acetyl-furan-2-ylmethyl)-2H-[1,2,3]triazol-4-yl]-amide;
2-Methyl-5-o-tolyl-oxazole-4-carboxylic acid [2-(5-acetyl-furan-2-ylmethyl)-2H-[1,2,3]triazol-4-yl]-amide;
2-Ethyl-5-phenyl-oxazole-4-carboxylic acid [2-(5-acetyl-furan-2-ylmethyl)-2H-[1,2,3]triazol-4-yl]-amide;
2-Cyclopropyl-5-phenyl-oxazole-4-carboxylic acid [2-(5-acetyl-furan-2-ylmethyl)-2H-[1,2,3]triazol-4-yl]-amide;
5-(3-Fluoro-phenyl)-oxazole-4-carboxylic acid [2-(5-acetyl-furan-2-ylmethyl)-2H-[1,2,3]triazol-4-yl]-amide;
5-(3-Chloro-phenyl)-oxazole-4-carboxylic acid [2-(5-acetyl-furan-2-ylmethyl)-2H-[1,2,3]triazol-4-yl]-amide;
5-Phenyl-oxazole-4-carboxylic acid [2-(5-acetyl-thiophen-2-ylmethyl)-2H-[1,2,3]triazol-4-yl]-amide;
5-Phenyl-oxazole-4-carboxylic acid [2-(3-acetyl-benzyl)-2H-[1,2,3]triazol-4-yl]-amide;
[2-(3-Acetyl-benzyl)-2H-[1,2,3]triazol-4-yl]-carbamic acid 2-chloro-benzyl ester;
5-Phenyl-oxazole-4-carboxylic acid [2-(5,5-difluoro-hexyl)-2H-[1,2,3]triazol-4-yl]-amide;
5-Phenyl-oxazole-4-carboxylic acid [2-(5-methanesulfonyl-furan-2-ylmethyl)-2H-[1,2,3]triazol-4-yl]-amide;
5-(3-Dimethylamino-phenyl)-oxazole-4-carboxylic acid [2-(5-acetyl-furan-2-ylmethyl)-2H-[1,2,3]triazol-4-yl]-amide;
5-Phenyl-oxazole-4-carboxylic acid [2-(4-acetyl-thiazol-2-ylmethyl)-2H-[1,2,3]triazol-4-yl]-amide;
[2-(4-Acetyl-thiazol-2-ylmethyl)-2H-[1,2,3]triazol-4-yl]-carbamic acid 2-chloro-benzyl ester;
[2-(4-Acetyl-pyridin-2-ylmethyl)-2H-[1,2,3]triazol-4-yl]-carbamic acid 2-chloro-benzyl ester;
5-[3-(2-Methoxy-ethyl)-phenyl]-oxazole-4-carboxylic acid [2-(5-acetyl-furan-2-ylmethyl)-2H-[1,2,3]triazol-4-yl]-amide;
5-Phenyl-oxazole-4-carboxylic acid [2-(6-acetyl-pyridin-2-ylmethyl)-2H-[1,2,3]triazol-4-yl]-amide;
5-(3-Methoxymethyl-phenyl)-oxazole-4-carboxylic acid [2-(5-acetyl-furan-2-ylmethyl)-2H-[1,2,3]triazol-4-yl]-amide;
5-Phenyl-oxazole-4-carboxylic acid [2-(2-acetyl-thiazol-4-ylmethyl)-2H-[1,2,3]triazol-4-yl]-amide;
5-Phenyl-oxazole-4-carboxylic acid [2-(4-acetyl-pyridin-2-ylmethyl)-2H-[1,2,3]triazol-4-yl]-amide;
5-Phenyl-oxazole-4-carboxylic acid [2-(2-acetyl-pyridin-4-ylmethyl)-2H-[1,2,3]triazol-4-yl]-amide;
[2-(2-Acetyl-pyridin-4-ylmethyl)-2H-[1,2,3]triazol-4-yl]-carbamic acid 2-chloro-benzyl ester;
5-Phenyl-oxazole-4-carboxylic acid [2-(5-acetyl-thiophen-3-ylmethyl)-2H-[1,2,3]triazol-4-yl]-amide; and
2-Methyl-5-m-tolyl-thiazole-4-carboxylic acid [2-(5-acetyl-furan-2-ylmethyl)-2H-[1,2,3]triazol-4-yl]-amide:
wherein the double bond of acrylamide derivatives cited in the above list may be in (E)- or (Z)-configuration (preferably in (E)-configuration).

40) Further preferred compounds of formula (I) as defined in embodiment 1) are selected from the group consisting of:
5-Phenyl-oxazole-4-carboxylic acid [2-(3-acetyl-isoxazol-5-ylmethyl)-2H-[1,2,3]triazol-4-yl]-amide;
5-(3-Isopropoxymethyl-phenyl)-oxazole-4-carboxylic acid [2-(5-acetyl-furan-2-ylmethyl)-2H-[1,2,3]triazol-4-yl]-amide;
5-[3-(2-Isopropoxy-ethyl)-phenyl]-oxazole-4-carboxylic acid [2-(5-acetyl-furan-2-ylmethyl)-2H-[1,2,3]triazol-4-yl]-amide;
2-Methyl-5-m-tolyl-oxazole-4-carboxylic acid [2-(5-acetyl-thiophen-2-ylmethyl)-2H-[1,2,3]triazol-4-yl]-amide;

5-(3-Chloro-phenyl)-2-methyl-oxazole-4-carboxylic acid [2-(5-acetyl-thiophen-2-ylmethyl)-2H-[1,2,3]triazol-4-yl]-amide;

5-m-Tolyl-oxazole-4-carboxylic acid [2-(5-acetyl-thiophen-2-ylmethyl)-2H-[1,2,3]triazol-4-yl]-amide;

2-Methyl-5-phenyl-oxazole-4-carboxylic acid [2-(5-acetyl-thiophen-2-ylmethyl)-2H-[1,2,3]triazol-4-yl]-amide;

2-Methyl-5-(3-trifluoromethyl-phenyl)-oxazole-4-carboxylic acid [2-(5-acetyl-thiophen-2-ylmethyl)-2H-[1,2,3]triazol-4-yl]-amide;

5-(3-Fluoro-phenyl)-oxazole-4-carboxylic acid [2-(5-acetyl-thiophen-2-ylmethyl)-2H-[1,2,3]triazol-4-yl]-amide;

5-(3-Dimethylamino-phenyl)-oxazole-4-carboxylic acid [2-(5-acetyl-thiophen-2-ylmethyl)-2H-[1,2,3]triazol-4-yl]-amide;

5-(3-Chloro-phenyl)-oxazole-4-carboxylic acid [2-(5-acetyl-thiophen-2-ylmethyl)-2H-[1,2,3]triazol-4-yl]-amide;

2-Methyl-5-(3-trifluoromethoxy-phenyl)-oxazole-4-carboxylic acid [2-(5-acetyl-thiophen-2-ylmethyl)-2H-[1,2,3]triazol-4-yl]-amide;

5-(4-Fluoro-phenyl)-oxazole-4-carboxylic acid [2-(5-acetyl-thiophen-2-ylmethyl)-2H-[1,2,3]triazol-4-yl]-amide;

5-(3-Trifluoromethoxy-phenyl)-oxazole-4-carboxylic acid [2-(5-acetyl-thiophen-2-ylmethyl)-2H-[1,2,3]triazol-4-yl]-amide;

5-(3-Methoxy-phenyl)-oxazole-4-carboxylic acid [2-(5-acetyl-thiophen-2-ylmethyl)-2H-[1,2,3]triazol-4-yl]-amide;

5-(3-Fluoro-phenyl)-thiazole-4-carboxylic acid [2-(5-acetyl-furan-2-ylmethyl)-2H-[1,2,3]triazol-4-yl]-amide;

5-Phenyl-oxazole-4-carboxylic acid [2-(2-acetyl-thiazol-5-ylmethyl)-2H-[1,2,3]triazol-4-yl]-amide;

[2-(2-Acetyl-thiazol-5-ylmethyl)-2H-[1,2,3]triazol-4-yl]-carbamic acid 2-chloro-benzyl ester;

N-[2-(2-Acetyl-thiazol-5-ylmethyl)-2H-[1,2,3]triazol-4-yl]-3-(4-trifluoromethyl-phenyl)-acrylamide;

5-Phenyl-oxazole-4-carboxylic acid [2-(2-acetyl-oxazol-5-ylmethyl)-2H-[1,2,3]triazol-4-yl]-amide;

[2-(5-Acetyl-thiazol-2-ylmethyl)-2H-[1,2,3]triazol-4-yl]-carbamic acid 2-chloro-benzyl ester;

5-Phenyl-oxazole-4-carboxylic acid [2-(4-acetyl-thiophen-2-ylmethyl)-2H-[1,2,3]triazol-4-yl]-amide;

5-Phenyl-oxazole-4-carboxylic acid [2-(5-acetyl-thiazol-2-ylmethyl)-2H-[1,2,3]triazol-4-yl]-amide;

N-[2-(5-Acetyl-thiazol-2-ylmethyl)-2H-[1,2,3]triazol-4-yl]-3-(4-trifluoromethyl-phenyl)-acrylamide;

2-Methyl-5-m-tolyl-oxazole-4-carboxylic acid [2-(4-acetyl-thiazol-2-ylmethyl)-2H-[1,2,3]triazol-4-yl]-amide;

5-(3-Chloro-phenyl)-2-methyl-oxazole-4-carboxylic acid [2-(4-acetyl-thiazol-2-ylmethyl)-2H-[1,2,3]triazol-4-yl]-amide;

2-Methyl-5-phenyl-oxazole-4-carboxylic acid [2-(4-acetyl-thiazol-2-ylmethyl)-2H-[1,2,3]triazol-4-yl]-amide;

2-Methyl-5-(3-trifluoromethyl-phenyl)-oxazole-4-carboxylic acid [2-(4-acetyl-thiazol-2-ylmethyl)-2H-[1,2,3]triazol-4-yl]-amide;

5-(3-Fluoro-phenyl)-oxazole-4-carboxylic acid [2-(4-acetyl-thiazol-2-ylmethyl)-2H-[1,2,3]triazol-4-yl]-amide;

5-(3-Dimethylamino-phenyl)-oxazole-4-carboxylic acid [2-(4-acetyl-thiazol-2-ylmethyl)-2H-[1,2,3]triazol-4-yl]-amide;

5-(3-Chloro-phenyl)-oxazole-4-carboxylic acid [2-(4-acetyl-thiazol-2-ylmethyl)-2H-[1,2,3]triazol-4-yl]-amide;

2-Methyl-5-(3-trifluoromethoxy-phenyl)-oxazole-4-carboxylic acid [2-(4-acetyl-thiazol-2-ylmethyl)-2H-[1,2,3]triazol-4-yl]-amide;

5-(4-Fluoro-phenyl)-oxazole-4-carboxylic acid [2-(4-acetyl-thiazol-2-ylmethyl)-2H-[1,2,3]triazol-4-yl]-amide;

5-(3-Trifluoromethoxy-phenyl)-oxazole-4-carboxylic acid [2-(4-acetyl-thiazol-2-ylmethyl)-2H-[1,2,3]triazol-4-yl]-amide;

5-(3-Methoxy-phenyl)-oxazole-4-carboxylic acid [2-(4-acetyl-thiazol-2-ylmethyl)-2H-[1,2,3]triazol-4-yl]-amide;

N-[2-(4-Acetyl-thiazol-2-ylmethyl)-2H-[1,2,3]triazol-4-yl]-3-(4-trifluoromethyl-phenyl)-acrylamide;

N-[2-(4-Acetyl-thiazol-2-ylmethyl)-2H-[1,2,3]triazol-4-yl]-3-(3-trifluoromethoxy-phenyl)-acrylamide;

5-(3-Methoxy-phenyl)-2-methyl-oxazole-4-carboxylic acid [2-(4-acetyl-thiazol-2-ylmethyl)-2H-[1,2,3]triazol-4-yl]-amide;

5-(3-Fluoro-phenyl)-2-methyl-oxazole-4-carboxylic acid [2-(4-acetyl-thiazol-2-ylmethyl)-2H-[1,2,3]triazol-4-yl]-amide;

2-Methyl-5-m-tolyl-thiazole-4-carboxylic acid [2-(4-acetyl-thiazol-2-ylmethyl)-2H-[1,2,3]triazol-4-yl]-amide;

5-Phenyl-oxazole-4-carboxylic acid [2-(4-acetyl-oxazol-2-ylmethyl)-2H-[1,2,3]triazol-4-yl]-amide;

2-Methoxymethyl-5-phenyl-oxazole-4-carboxylic acid [2-(5-acetyl-furan-2-ylmethyl)-2H-[1,2,3]triazol-4-yl]-amide;

2-(2-Methoxy-ethyl)-5-phenyl-oxazole-4-carboxylic acid [2-(5-acetyl-furan-2-ylmethyl)-2H-[1,2,3]triazol-4-yl]-amide;

2-Butyl-5-phenyl-oxazole-4-carboxylic acid [2-(5-acetyl-furan-2-ylmethyl)-2H-[1,2,3]triazol-4-yl]-amide;

2-Isopropyl-5-phenyl-oxazole-4-carboxylic acid [2-(5-acetyl-furan-2-ylmethyl)-2H-[1,2,3]triazol-4-yl]-amide;

N-[2-(4-Acetyl-thiazol-2-ylmethyl)-2H-[1,2,3]triazol-4-yl]-3-(2-trifluoromethyl-phenyl)-acrylamide;

2-Benzyl-5-phenyl-oxazole-4-carboxylic acid [2-(5-acetyl-furan-2-ylmethyl)-2H-[1,2,3]triazol-4-yl]-amide;

3-{4-[2-(5-Acetyl-furan-2-ylmethyl)-2H-[1,2,3]triazol-4-ylcarbamoyl]-5-phenyl-oxazol-2-yl}-propionic acid tert-butyl ester;

5-(3-Fluoro-phenyl)-2-methyl-oxazole-4-carboxylic acid [2-(2-acetyl-oxazol-5-ylmethyl)-2H-[1,2,3]triazol-4-yl]-amide;

2-Methyl-5-m-tolyl-oxazole-4-carboxylic acid [2-(2-acetyl-oxazol-5-ylmethyl)-2H-[1,2,3]triazol-4-yl]-amide;

5-(3-Chloro-phenyl)-2-methyl-oxazole-4-carboxylic acid [2-(2-acetyl-oxazol-5-ylmethyl)-2H-[1,2,3]triazol-4-yl]-amide;

5-m-Tolyl-oxazole-4-carboxylic acid [2-(2-acetyl-oxazol-5-ylmethyl)-2H-[1,2,3]triazol-4-yl]-amide;

2-Methyl-5-(3-trifluoromethoxy-phenyl)-oxazole-4-carboxylic acid [2-(2-acetyl-oxazol-5-ylmethyl)-2H-[1,2,3]triazol-4-yl]-amide;

[2-(2-Acetyl-oxazol-4-ylmethyl)-2H-[1,2,3]triazol-4-yl]-carbamic acid 2-chloro-benzyl ester; and 5-(6-Trifluoromethyl-pyridin-2-yl)-oxazole-4-carboxylic acid [2-(5-acetyl-furan-2-ylmethyl)-2H-[1,2,3]triazol-4-yl]-amide;

wherein the double bond of acrylamide derivatives cited in the above list may be in (E)- or (Z)-configuration (preferably in (E)-configuration).

Any reference hereinbefore or hereinafter to a compound of formula (I) is to be understood as referring also to the salts, especially the pharmaceutically acceptable salts, of such compound of formula (I), as appropriate and expedient.

The term "pharmaceutically acceptable salts" refers to non-toxic, inorganic or organic acid and/or base addition salts, Lit. e.g. "Salt selection for basic drugs", *Int. J. Pharm.* (1986), 33, 201-217.

Where the plural form is used for compounds, salts, pharmaceutical compositions, diseases and the like, this is intended to mean also a single compound, salt, or the like.

The compounds of formula (I) according to any one of embodiments 1) to 40), or pharmaceutically acceptable salts thereof, are suitable for use as medicaments. In particular, compounds of formula (I) modulate the ALX receptor, i.e. they act as ALX receptor agonists, and are useful for the prevention or treatment of diseases which respond to the activation of the ALX receptor such as inflammatory diseases, obstructive airway diseases, allergic conditions, HIV-mediated retroviral infections, cardiovascular disorders, neuroinflammation, neurological disorders, pain, prion-mediated diseases and amyloid-mediated disorders (especially Alzheimer's disease); in addition they are useful for the modulation of immune responses (especially those elicited by vaccination). Especially, compounds of formula (I) are useful for the prevention or treatment of diseases such as inflammatory diseases, obstructive airway diseases, allergic conditions, cardiovascular disorders, neuroinflammation, neurological disorders, pain, prion-mediated diseases and amyloid-mediated disorders (especially Alzheimer's disease).

In particular, the compounds of formula (I) according to any one of embodiments 1) to 40), or pharmaceutically acceptable salts thereof, are suitable for the prevention or treatment of diseases selected from inflammatory diseases, obstructive airway diseases and allergic conditions.

Inflammatory diseases, obstructive airway diseases and allergic conditions include, but are not limited to, one, several or all of the following groups of diseases and disorders:

1) Acute lung injury (ALI); adult/acute respiratory distress syndrome (ARDS); chronic obstructive pulmonary, airway or lung disease (COPD, COAD or COLD), including chronic bronchitis or dyspnea associated therewith; emphysema; as well as exacerbation of airway hyper reactivity consequent to other drug therapy, in particular other inhaled drug therapy. Especially, inflammatory diseases, obstructive airway diseases and allergic conditions include COPD, COAD and COLD.
2) Further inflammatory diseases, obstructive airway diseases and allergic conditions include bronchitis of whatever type or genesis.
3) Further inflammatory diseases, obstructive airway diseases and allergic conditions include bronchiectasis, and pneumoconiosis of whatever type or genesis.
4) Further inflammatory diseases, obstructive airway diseases and allergic conditions include asthma of whatever type or genesis, including intrinsic (non-allergic) asthma and extrinsic (allergic) asthma, mild asthma, moderate asthma, severe asthma, bronchitic asthma, exercise-induced asthma, occupational asthma and induced asthma following bacterial infection.
5) In a further embodiment the compounds of formula (I) according to any one of embodiments 1) to 40), or pharmaceutically acceptable salts thereof, are particularly suitable for the prevention or treatment of inflammatory diseases. Inflammatory diseases include one, several or all of the following groups of diseases and disorders:
   5a) In particular, inflammatory diseases refer to neutrophil related disorders, especially neutrophil related disorders of the airway including hyper-neutrophilia as it affects the airway and/or lungs. Further neutrophil related disorders also include periodontitis, glomerulonephritis, and cystic fibrosis.
   5b) Further inflammatory diseases include skin diseases such as psoriasis, contact dermatitis, atopic dermatitis, dermatitis herpetiformis, scleroderma, hypersensitivity angiitis, urticaria, lupus erythematosus, and epidermolysis.
   5c) Further inflammatory diseases also relate to diseases or conditions having an inflammatory component. Diseases or conditions having an inflammatory component include, but are not limited to, diseases and conditions affecting the eye such as conjunctivitis, keratoconjunctivitis sicca, and vernal conjunctivitis; diseases affecting the nose including allergic rhinitis; and inflammatory diseases in which autoimmune reactions are implicated or which have an autoimmune component or aetiology, such as systemic lupus erythematosus, polychondritis, scleroderma, Wegener granulamatosis, dermatomyositis, chronic active hepatitis, myasthenia gravis, Stevens-Johnson syndrome, idiopathic sprue, autoimmune inflammatory bowel disease (e.g. ulcerative colitis and Crohn's disease), endocrine opthalmopathy, chronic hypersensitivity pneumonitis, primary billiary cirrhosis, keratoconjunctivitis sicca and vernal keratoconjunctivitis, interstitial lung fibrosis, psoriatic arthritis and glomerulonephritis.
   5d) Further inflammatory diseases in which autoimmune reactions are implicated or which have an autoimmune component or aetiology include rheumatoid arthritis, hishimoto's thyroid and diabetes type I or II.

Further, the compounds of formula (I) according to any one of embodiments 1) to 40), or pharmaceutically acceptable salts thereof, are suitable for the prevention or treatment of HIV-mediated retroviral infections.

HIV-mediated retroviral infections include, but are not limited to, one, several or all of the groups of diseases and disorders caused by HIV-1 and HIV-2 strains such as GUN-4-v, GUN-7 wt, AG204, AG206, AG208, HCM305, HCM308, HCM342, mSTD104, and HCM309.

Further, the compounds of formula (I) according to any one of embodiments 1) to 40), or pharmaceutically acceptable salts thereof, are suitable for the prevention or treatment of cardiovascular disorders.

Cardiovascular disorders refer to one or more disease states of the cardiovascular tree (including the heart) and to diseases of dependent organs. Disease states of the cardiovascular tree and diseases of dependent organs include, but are not limited to, disorders of the heart muscle (cardiomyopathy or myocarditis) such as idiopathic cardiomyopathy, metabolic cardiomyopathy which includes diabetic cardiomyopathy, alcoholic cardiomyopathy, drug-induced cardiomyopathy, ischemic cardiomyopathy, and hypertensive cardiomyopathy; atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries; toxic, drug-induced, and metabolic (including hypertensive and/or diabetic) disorders of small blood vessels (microvascular disease) such as the retinal arterioles, the glomerular arterioles, the vasa nervorum, cardiac arterioles, and associated capillary beds of the eye, the kidney, the heart, and the central and peripheral nervous systems; and, plaque rupture of atheromatous lesions of major blood vessels such as the aorta, the coronary arteries, the carotid arteries, the cerebrovascular arteries, the renal arteries, the iliac arteries, the femoral arteries and the popliteal arteries.

Further, the compounds of formula (I) according to any one of embodiments 1) to 40), or pharmaceutically acceptable salts thereof, are suitable for the prevention or treatment of neuroinflammation. Neuroinflammation refers to cell signalling molecule production, activation of glia or glial activation pathways and responses, proinflammatory cytokines or chemokines, activation of astrocytes or astrocyte activation pathways and responses, activation of microglia or microglial activation pathways and responses, oxidative stress-related responses such as nitric oxide synthase production and nitric oxide accumulation, acute phase proteins, loss of synaptophysin and Post Synaptic Density-95 Protein (PSD-95), components of the complement cascade, loss or reduction of synaptic function, protein kinase activity (e.g., death associated protein kinase activity), behavioral deficits, cell damage (e.g., neuronal cell damage), cell death (e.g., neuronal cell death), and/or amyloid β deposition of amyloid plaques.

Further, the compounds of formula (I) according to any one of embodiments 1) to 40), or pharmaceutically acceptable salts thereof, are suitable for the prevention or treatment of neurological disorders.

In particular, neurological disorders include, but are not limited to, epilepsy, stroke, cerebral ischemia, cerebral palsy, relapsing multiple sclerosis, progressive multiple sclerosis, Alpers' disease, amyotrophic lateral sclerosis (ALS), senile dementia, dementia with Lewy bodies, Rhett syndrome, spinal cord trauma, traumatic brain injury, trigeminal neuralgia, glossopharyngeal neuralgia, Bell's palsy, myasthenia gravis, muscular dystrophy, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies, mild cognitive decline, cognitive decline, Alzheimer's disease, Parkinson's disease, and Huntington's chorea.

Further, the compounds of formula (I) according to any one of embodiments 1) to 40), or pharmaceutically acceptable salts thereof, are suitable for the prevention or treatment of pain. Pain includes, but is not limited to, neuropathic pain exemplified by conditions such as diabetic neuropathy, postherpetic neuralgia, trigeminal neuralgia, painful diabetic polyneuropathy, post-stroke pain, post-amputation pain, myelopathic or radiculopathic pain, atypical facial pain and causalgia-like syndromes.

Further, the compounds of formula (I) according to any one of embodiments 1) to 40), or pharmaceutically acceptable salts thereof, are suitable for the prevention or treatment of prion-mediated diseases. Prion-mediated diseases, also known as transmissible spongiform encephalopathies (TSEs), include, but are not limited to, kuru, Gerstmann-Sträussler-Scheinker syndrome (GSS), Fatal Familial Insomnia (FFI) and Creutzfeldt-Jakob Disease (CJD).

Further, the compounds of formula (I) according to any one of embodiments 1) to 40), or pharmaceutically acceptable salts thereof, are suitable for the treatment of amyloid-mediated disorders. Amyloid-mediated disorders are defined as diseases and disorders, that are caused by or associated with amyloid or amyloid-like proteins. Diseases and disorders caused by or associated with amyloid or amyloid-like proteins include, but are not limited to, Alzheimer's Disease (AD), including diseases or conditions characterized by a loss of cognitive memory capacity such as, for example, mild cognitive impairment (MCI); dementia with Lewy bodies; Down's syndrome; cerebral hemorrhage with amyloidosis. In another embodiment, diseases and disorders caused by or associated with amyloid or amyloid-like proteins include progressive supranuclear palsy, multiple sclerosis, Creutzfeld Jakob disease, Parkinson's disease, HIV-related dementia, Amyotrophic Lateral Sclerosis (ALS), inclusion-body myositis (IBM), Adult Onset Diabetes, and senile cardiac amyloidosis.

Further, the compounds of formula (I) according to any one of embodiments 1) to 40), or pharmaceutically acceptable salts thereof, are suitable for the modulation of immune responses. The modulation of immune responses includes, but is not limited to, methods based on the administration to a subject a composition of at least one antigen and at least one compound of formula (I) according to any one of embodiments 1) to 40), or pharmaceutically acceptable salts thereof. In some cases, the antigen-containing composition is administrated first, followed by administration of a composition of at least one compounds of formula (I) according to any one of embodiments 1) to 40), or pharmaceutically acceptable salts thereof. In other cases, the antigen-containing composition is administrated last. The different compositions may be administrated simultaneously, closely in sequence, or separated in time. Those methods and compositions are provided for therapeutic and prophylactic immunisation (i.e., the deliberate provocation, enhancement, intensification or modulation of an adaptative and/or innate immune response). Particular advantages may include one or more of the following:

1) An accelerated immune response following administration of at least one compound of formula (I) according to any one of embodiments 1) to 40), or pharmaceutically acceptable salts thereof, and the antigen, as compared to sole administration of the antigen;
2) A greater sensitivity to small amounts of antigen (e.g., toxin or pathogen) or antigens that do not habitually induce strong immune responses; and
3) More effective anti-tumor therapies.

Further, the compounds of formula (I) according to any one of embodiments 1) to 40), or pharmaceutically acceptable salts thereof, are suitable for the prevention or treatment of cystic fibrosis, pulmonary fibrosis, pulmonary hypertension, wound healing, diabetic nephropathy, reduction of inflammation in transplanted tissue, inflammatory diseases caused by pathogenic organisms.

Especially, compounds of formula (I) according to any one of embodiments 1) to 40), or pharmaceutically acceptable salts thereof, are suitable for the prevention or treatment of diseases selected from one, several or all of the following groups of diseases and disorders:

1) Inflammatory diseases, obstructive airway diseases and allergic conditions such as acute lung injury (ALI); adult/acute respiratory distress syndrome (ARDS); and asthma of whatever type or genesis, including intrinsic (non-allergic) asthma and extrinsic (allergic) asthma, mild asthma, moderate asthma, severe asthma, bronchitic asthma, exercise-induced asthma, occupational asthma and induced asthma following bacterial infection;
2) Inflammatory diseases such as neutrophil related disorders, especially neutrophil related disorders of the airway including hyper-neutrophilia as it affects the airway and/or lungs; periodontitis; glomerulonephritis; cystic fibrosis; and skin diseases such as psoriasis, contact dermatitis, atopic dermatitis, dermatitis herpetiformis, scleroderma, hypersensitivity angiitis, urticaria, lupus erythematosus, and epidermolysis;
3) Diseases having an inflammatory component such as diseases and conditions affecting the eye such as conjunctivitis, keratoconjunctivitis sicca, and vernal conjunctivitis; inflammatory disease in which autoimmune reactions are implicated or which have an autoimmune component or aetiology; and autoimmune inflammatory bowel disease (e.g. ulcerative colitis and Crohn's disease);
4) HIV-mediated retroviral infections such as diseases and disorders caused by HIV-1 and HIV-2 strains such as GUN- 4-v, GUN-7 wt, AG204, AG206, AG208, HCM305, HCM308, HCM342, mSTD104, and HCM309;
5) Neuroinflammation which refers to cell signalling molecule production, activation of glia or glial activation pathways and responses, proinflammatory cytokines or chemokines, activation of astrocytes or astrocyte activation pathways and responses, activation of microglia or microglial activation pathways and responses, oxidative stress-related responses such as amyloid β deposition of amyloid plaques;
6) Neurological disorders such as stroke, cerebral ischemia, Alzheimer's disease, and Parkinson's disease;
7) Prion-mediated diseases, also known as transmissible spongiform encephalopathies (TSEs), such as kuru, Gerstmann-Sträussler-Scheinker syndrome (GSS), Fatal Familial Insomnia (FFI) and Creutzfeldt-Jakob Disease (CJD);
8) Amyloid-mediated disorders;
9) Cystic fibrosis, wound healing and inflammatory diseases caused by pathogenic organisms.

The invention also relates to the use of a compound of formula (I) according to any one of embodiments 1) to 40) for the preparation of pharmaceutical compositions for the treatment and/or prophylaxis of the above-mentioned diseases.

The present invention also relates to pharmaceutically acceptable salts and to pharmaceutical compositions and formulations of compounds of formula (I) according to any one of embodiments 1) to 40).

A pharmaceutical composition according to the present invention contains at least one compound of formula (I) according to any one of embodiments 1) to 40) (or a pharmaceutically acceptable salt thereof) as the active agent and optionally carriers and/or diluents and/or adjuvants.

The compounds of formula (I) according to any one of embodiments 1) to 40) and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) according to any one of embodiments 1) to 40), or a pharmaceutically acceptable salt thereof.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C. Besides, the term "room temperature" (rt) as used herein refers to a temperature of about 25° C.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

If not indicated otherwise, the generic groups A, E, Q, $R^1$, $R^2$ and $R^3$ are as defined for formula (I). Other abbreviations used are defined in the experimental section. Generic group Ru as used in structures 4b, 4c and 7 below represents hydrogen or $(C_1-C_3)$alkyl. Generic groups $R^x$ as used in structure 4 and 6 below represent $(C_1-C_2)$alkyl or both $R^x$ together form an ethane-1,2-diyl bridge. Generic group $R^y$ as used in structure 4 and 6 below represents $(C_1-C_3)$alkyl.

Generic group $R^z$ as used in scheme 4 below represents $(C_1-C_4)$alkyl. The generic carboxyl protecting group R as used e.g. in structure 3 or 5, in the schemes below and in the general procedures of the experimental part represents $(C_1-C_4)$alkyl, preferably methyl or ethyl. The generic group $Si^{PG}$ as used in structure 4c and 7 below represents an appropriate silyl protecting group such as TMS, TIPS, TBDMS or TBDPS, preferably TBDMS.

Reactions of alcohols with methanesulfonyl chloride may result in the formation of the respective chloride or the respective mesylate derivative depending on the reaction conditions used; it is well known in the art that already small changes in such reaction conditions may have an influence on the outcome of said reactions; it should be understood that normally both reagents, the chloride and the mesylate, might be useful as electrophiles in reactions discussed below.

In some instances the generic groups A, E, Q, $R^1$, $R^2$ and $R^3$ might be incompatible with the assembly illustrated in the schemes below and will therefore require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups are as necessary in place.

A. Synthesis of Final Products

Sections A.a) to A.d) hereafter describe general methods for preparing compounds of formula (I).

A.a) The compounds of formula (I) can be prepared from amines of structure 1 by reaction with the appropriate chloroformate $R^1$-E-COCl (E represents *—$(C_1-C_4)$alkyl-O—) at a temperature about rt or the appropriate carboxylic acid chloride of formula $R^1$-E-COCl (E represents an oxazole or a thiazole radical as defined in formula (I) or —CH═CH—) at a temperature about rt in a suitable solvent such as $CH_2Cl_2$ in presence of a base such as $Et_3N$ or DIPEA. If not commercially available, the appropriate chloroformate can be prepared at a temperature about rt from the corresponding alcohol by reaction with phosgene in a suitable solvent such as $CH_2Cl_2$ in presence of a base such as $Et_3N$. If not commercially available, the appropriate carboxylic acid chloride can be prepared at a temperature about rt from the corresponding carboxylic acid by reaction with a reagent such as oxalyl chloride in presence of DMF in a suitable solvent such as toluene. Alternatively, amines of structure 1 can be coupled with the corresponding carboxylic acid of formula $R^1$-E-COOH using standard amide coupling conditions such as EDC/HOBt/DMAP, TBTU, HBTU or PyBOP in presence of a base such as DIPEA or $Et_3N$ at a temperature about rt in a suitable solvent such as $CH_2Cl_2$. In case E represents *—$(C_1-C_4)$alkyl-O—, amines of structure 1 can be coupled with the corresponding alcohol of formula $R^1$-E-H by activation of the compounds of structure 1 e.g. with 4-nitrophenyl chloroformate in a suitable solvent such as AcCN in presence of a base such as Et₃N or DIPEA or, alternatively, by in-situ formation of the chloroformate from R¹-E-H (E represents *—(C₁-C₄)alkyl-O—) with, for example, phosgene in a suitable solvent such as CH₂Cl₂ in presence of a base such as Et₃N or DIPEA.

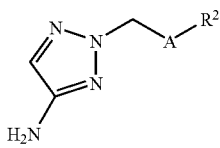

Structure 1

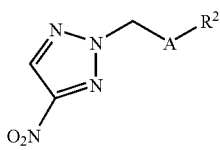

Structure 2

Compounds of structure 1 can be obtained from compounds of structure 2 by reduction of the nitro group either by hydrogenation in the presence of a metal catalyst such as Pd/C, Pt/C or PtO₂ at a temperature about rt in a suitable solvent such as MeOH or EtOH, or by reduction with a metal such as iron in a solvent mixture such as H₂O/EtOH in the presence of ammonium chloride at a temperature ranging from rt to 95° C.

A.b) Alternatively, the compounds of formula (I) wherein R² represents —CO—(C₁-C₃)alkyl may be prepared by a sequence comprising:

Reduction of an ester of structure 3 to the corresponding alcohol under standard reducing conditions using a reagent such as NaBH₄ in a solvent such as MeOH at a temperature about rt or, alternatively, a reagent such as DiBAL in a solvent such as THF at a temperature ranging from about −78° C. to rt;

Oxidation of the alcohol to the corresponding aldehyde under standard oxidative conditions using reagents such as MnO₂, pyridinium chlorochromate or NMO/TPAP in a solvent such as AcCN or CH₂Cl₂ at a temperature about rt;

Addition of an alkyl Grignard reagent at a temperature below rt (preferably about −78° C.) in a solvent such as THF, or, alternatively, addition of a trialkylaluminum reagent at a temperature about 0° C. in a solvent such as CH₂Cl₂ providing the corresponding secondary alcohol; and Oxidation of the alcohol under standard oxidative conditions using reagents such as TPAP/NMO or MnO₂ in a solvent such as CH₂Cl₂ or AcCN at a temperature about rt to provide the compound of formula (I).

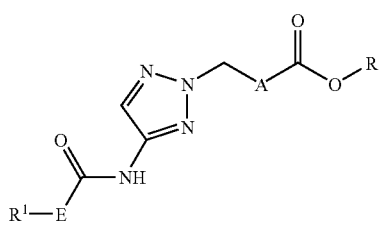

Structure 3

A.c) Alternatively, the compounds of formula (I) can be prepared by deprotecting a ketal of structure 4 using standard conditions like:

using an acid such as diluted aqueous HCl in a solvent such as THF at a temperature about rt; or
using SCX silica gel in a solvent such as MeOH; or
using a silica gel bound acid such as tosic acid in a solvent such as MeOH; or
using an acid such as formic acid in a solvent such as water at a temperature ranging from about 0° C. to about 50° C.

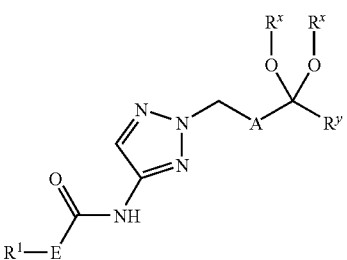

Structure 4

A.d) Alternatively, the compounds of formula (I) wherein R² represents —CO—(C₁-C₃)alkyl may be prepared either by:

Oxidation of an alcohol of structure 4b (R^u represents (C₁-C₃)alkyl)) under standard oxidative conditions using reagents such as TPAP/NMO or MnO₂ in a solvent such as CH₂Cl₂ or AcCN at a temperature about rt;

or by:

The oxidation-addition-oxidation sequence described in the last three steps under A.b) starting from an alcohol of structure 4b (R^u represents hydrogen).

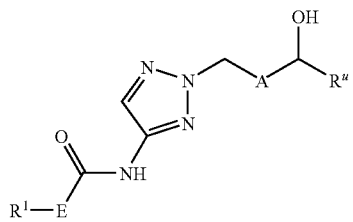

Structure 4b

B. Synthesis of Intermediates:

Compounds of structure 2 wherein R² represents —CO—(C₁-C₃)alkyl can be prepared from compounds of structure 5 following the procedure as described in section A.b) or from compounds of structure 6 following the procedure as described in section A.c) above. Compounds of structure 2 wherein R² represents —CF₂—(C₁-C₃)alkyl may be prepared from compounds of structure 2 wherein R² represents —CO—(C₁-C₃)alkyl with a fluorinating agent such as (diethylamino)sulphur trifluoride or (bis(2-methoxyethyl)amino)sulphur trifluoride in a solvent such as toluene at a temperature about 60° C.

Compounds of structure 2 wherein A represents oxazole-2,4-diyl may be prepared by reacting methanesulfonic acid 4-acetyl-oxazol-2-ylmethyl ester with 4-nitro-2H-[1,2,3]triazole in the presence of a base such as K₂CO₃ or Cs₂CO₃ in a solvent such as acetone or AcCN at a temperature about rt or 80° C. (with or without addition of tetrabutylammonium bromide). Alternatively, the reaction may be performed in the presence of a base such as DIPEA in a solvent such as DMF, acetone or a mixture of both at a temperature about rt or 50° C.

Compounds of structure 2 wherein A represents isoxazole-2,4-diyl may be prepared by reacting 1-(5-chloromethyl-isoxazol-3-yl)-ethanone with 4-nitro-2H-[1,2,3]triazole in the presence of a base such as K₂CO₃ or Cs₂CO₃ in a solvent such as acetone or AcCN at a temperature about rt or 80° C. (with or without addition of tetrabutylammonium bromide). Alternatively, the reaction may be performed in the presence of a base such as DIPEA in a solvent such as DMF, acetone or a mixture of both at a temperature about rt or 50° C.

In a more general way:

Compounds of structure 2 may be prepared by reacting Ms-O—CH₂-A-C(O)—(C₁-C₃)alkyl or Cl—CH₂-A-C(O)—(C₁-C₃)alkyl (especially 1-(5-chloromethyl-isoxazol-3-yl)-ethanone or methanesulfonic acid 4-acetyl-oxazol-2-ylmethyl ester) with 4-nitro-2H-[1,2,3]triazole in the presence of a base such as K₂CO₃ or Cs₂CO₃ in a solvent such as acetone or AcCN at a temperature about rt or 80° C. (with or without addition of tetrabutylammonium bromide). Alternatively, the reaction may be performed in the presence of a base such as DIPEA in a solvent such as DMF, acetone or a mixture of both at a temperature about rt or 50° C.

Compounds of structure 2 wherein R² represents —SO₂—(C₁-C₃)alkyl may be prepared by reacting 4-nitro-2H-[1,2,3]triazole (T. E. Eagles et al. *Organic preparations and procedures* 2 (2), 117-119, 1970, P. N. Neuman *J. Heterocycl. Chem.* 8, 51-56, 1971) in the presence of a base such as K₂CO₃ or Cs₂CO₃ (with or without addition of tetrabutylammonium bromide) in a solvent such as acetone or AcCN at a temperature about rt or 80° C. with Cl—CH₂-A-SO₂—(C₁-C₃)alkyl (especially 2-chloromethyl-5-methanesulfonyl-furan). Alternatively, the reaction may be performed in the presence of a base such as DIPEA in a solvent such as DMF, acetone or a mixture of both at a temperature about rt or 50° C.

Compounds of structures 3 and 4 can be prepared in analogy to the procedures described in section A.a) from compounds of structure 5 and 6 respectively.

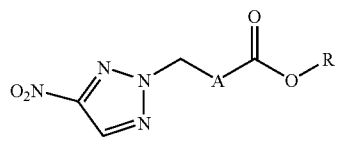

Structure 5

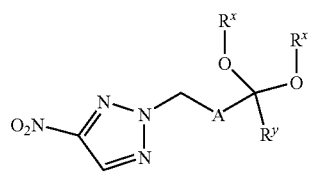

Structure 6

Compounds of structure 4b can be prepared starting from the respective compounds of structure 3 by the first step (Rᵘ represents hydrogen) or the first three steps (Rᵘ represents (C₁-C₃)alkyl) of the sequence described under A.b).

Alternatively, compounds of structure 4b can be prepared starting from the respective compounds of structure 4c by silyl deprotection using TBAF in a solvent like THF.

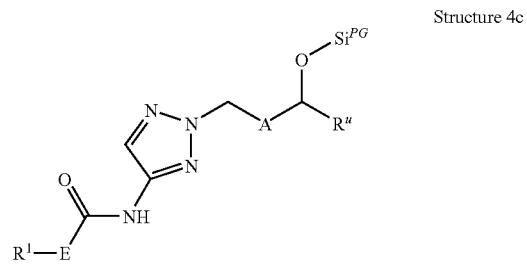

Structure 4c

Compounds of structure 4c may be prepared in analogy to the procedures described in section A.a) from compounds of structure 7

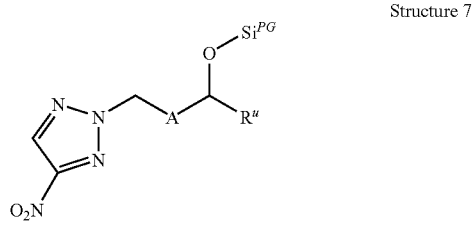

Structure 7

Compounds of structure 5 may be prepared by reacting 4-nitro-2H-[1,2,3]triazole (T. E. Eagles et al. *Organic preparations and procedures* 2 (2), 117-119, 1970, P. N. Neuman *J. Heterocycl. Chem.* 8, 51-56, 1971) with, for instance, a commercially available 5-chloromethyl-furan-2-carboxylic acid ester (A represents furan-2,5-diyl), or a commercially available 5-bromo-pentanoic acid ester (A represents propan-1,3-diyl) or a 4-chloromethyl-thiazole-2-carboxylic acid ester (A represents thiazol-2,4-diyl). The reaction may be performed in the presence of a base such as K₂CO₃ or Cs₂CO₃ in a solvent such as acetone or AcCN at a temperature about rt or 80° C. with addition of tetrabutylammonium bromide, where appropriate. Alternatively, the reaction may be performed in the presence of a base such as DIPEA in a solvent such as DMF, acetone or a mixture of both at a temperature about rt or 50° C.

Compounds of structure 6 may be prepared in analogy to those of structure 5 using, in case A represents furan-2,5-diyl, an appropriate protected furane derivative such as 2-(5-chloromethyl-furan-2-yl)-2-methyl-[1,3]dioxolane or, in case A represents propan-1,3-diyl, an appropriate protected 4-bromo-butyl ketone derivative such as 2-(4-bromo-butyl)-2-methyl-[1,3]dioxolane or, in case A represents thiophen-2,5-diyl, an appropriate protected thiophene derivative such as 2-(5-chloromethyl-thiophen-2-yl)-2-methyl-[1,3]dioxolane or, in case A represents phenyl-1,3-diyl, an appropriate protected phenyl derivative such as methanesulfonic acid 3-(2-methyl-[1,3]dioxolan-2-yl)-benzyl ester or, in case A represents pyridine-2,6-diyl, an appropriate protected pyridine derivative such as methanesulfonic acid 6-(2-methyl-[1,3]dioxolan-2-yl)-pyridin-2-ylmethyl ester or, in case A represents pyridine-2,4-diyl, an appropriate protected pyridine derivative such as methanesulfonic acid 4-(2-methyl-[1,3]dioxolan-2-yl)-pyridin-2-ylmethyl ester or methanesulfonic acid 2-(2-methyl-[1,3]dioxolan-2-yl)-pyridin-4-ylmethyl ester or, in case A represents thiazol-2,4-diyl, an appropriate protected thiazole derivative such as methanesulfonic acid 4-(2-methyl-[1,3]dioxolan-2-yl)-thiazol-2-ylmethyl ester or 4-chloromethyl-2-(2-methyl-[1,3]dioxolan-2-yl)-thiazole or, in case A represents thiophen-2,4-diyl, an appropriate protected thiophene derivative such as 2-(4-chloromethyl-thiophen-2-yl)-2-methyl-[1,3]dioxolane or 2-(5-chloromethyl-thiophen-3-yl)-2-methyl-[1,3]dioxolane or, in case A represents thiazol-2,5-diyl, an appropriate protected thiazole derivative such as methanesulfonic acid 5-(2-methyl-[1,3]dioxolan-2-yl)-thiazol-2-ylmethyl ester or 5-chloromethyl-2-(2-methyl-[1,3]dioxolan-2-yl)-thiazole or, in case A represents oxazole-2,5-diyl, an appropriate protected oxazole derivative such as 2-chloromethyl-5-(2-methyl-[1,3]dioxolan-2-yl)-oxazole, or another appropriate reagent of formula Ms-O—$CH_2$-A-C($OR^x$)$_2$—($C_1$-$C_3$)alkyl or Cl—$CH_2$-A-C($OR^x$)$_2$—($C_1$-$C_3$)alkyl.

Compounds of structure 6 can also be obtained from compounds of structure 2 wherein $R^2$ represents —CO—($C_1$-$C_3$) alkyl using a reagent such as ethylene glycol in the presence of a reagent such as TsOH in a solvent such as toluene at a temperature about 110° C.; or from compounds of structure 2 wherein $R^2$ represents —CO—($C_1$-$C_3$)alkyl using reagents such as $LiBF_4$ and trimethylorthoformate in a solvent such as ethylene glycol at a temperature about 95° C.

Alternatively, compounds of structure 6 may be synthesized from compounds of structure 5 in analogy to the sequence described in section A.b), followed by protection of the keto function using a reagent such as ethylene glycol in the presence of a reagent such as TsOH in a solvent such as toluene at a temperature about 110° C. Alternatively, the ketal formation can be performed using reagents such as $LiBF_4$ and trimethylorthoformate in a solvent such as ethylene glycol at a temperature about 95° C.

Compounds of structure 7 may be prepared from commercially available 4-nitro-2H-[1,2,3]triazole (T. E. Eagles et al. *Organic preparations and procedures* 2 (2), 117-119, 1970, P. N. Neuman *J. Heterocycl. Chem.* 8, 51-56, 1971) in analogy to those of structure 5 using, in case A represents oxazole-2, 5-diyl, an oxazole derivative such as 2-[1-(tert-butyl-dimethyl-silanyloxy)-ethyl]-5-chloromethyl-oxazole or, in case A represents oxazole-2,4-diyl, an appropriate protected oxazole derivative such as methanesulfonic acid 2-(tert-butyl-dimethyl-silanyloxymethyl)-oxazol-4-ylmethyl ester.

2-(5-Chloromethyl-furan-2-yl)-2-methyl-[1,3]dioxolane may be prepared using the following sequence: a) protection of commercially available 1-furan-2-yl-ethanone in the presence of trimethylorthoformate and a catalyst such as $LiBF_4$ in a solvent such as ethylene glycol at a temperature about 95° C.; b) lithiation with an organolithium reagent such as n-butyl lithium in a solvent such as THF at a temperature about −78° C. and subsequent addition of DMF; c) reduction with a reducing agent such as $NaBH_4$ in a solvent such as MeOH at a temperature about 0° C.; and d) chlorination of the alcohol using for example methanesulfonyl chloride in the presence of a base such as $Et_3N$ and DMAP in a solvent such as $CH_2Cl_2$ at a temperature about 0° C.

1-(5-Chloromethyl-isoxazol-3-yl)-ethanone may be prepared using the following sequence: a) protection of 5-hydroxymethyl-isoxazole-3-carboxylic acid ethyl ester using for example tert-butyldimethylsilyl chloride in the presence of a base such as imidazole in a solvent such as THF; b) reduction with a reducing agent such as DiBAL in a solvent such as THF at a temperature below rt; c) oxidation of the alcohol under standard oxidative conditions using reagents such as $MnO_2$ in a solvent such as AcCN at a temperature about rt; d) addition of trimethylaluminum at a temperature about 0° C. in a solvent such as $CH_2Cl_2$; e) oxidation of the alcohol under standard oxidative conditions using reagents such as $MnO_2$ in a solvent such as AcCN at a temperature about rt; f) deprotection of the silyl protecting group in the presence of trimethylorthoformate and a catalyst such as $LiBF_4$ in a solvent such as ethylene glycol at a temperature about 95° C.; g) chlorination of the alcohol using for example methanesulfonyl chloride in the presence of a base such as $Et_3N$ and DMAP in a solvent such as $CH_2Cl_2$ at a temperature about 0° C.

2-(5-Chloromethyl-thiophen-2-yl)-2-methyl-[1,3]dioxolane may be prepared using the following sequence: a) lithiation of commercially available 2-methyl-2-thiophen-2-yl-[1,3]dioxolane with an organolithium reagent such as n-butyl lithium in the presence of N,N,N',N'-tetramethyl-ethylenediamine in a solvent such as THF at a temperature about −78° C. and subsequent addition of DMF; b) reduction with a reducing agent such as $NaBH_4$ in a solvent such as MeOH at a temperature about 0° C.; c) chlorination of the alcohol using for example methanesulfonyl chloride in the presence of a base such as $Et_3N$ and DMAP in a solvent such as $CH_2Cl_2$ at a temperature about 0° C.

Methanesulfonic acid 6-(2-methyl-[1,3]dioxolan-2-yl)-pyridin-2-ylmethyl ester may be prepared by the following sequence: a) reaction of commercially available 2,6-dibromopyridine with an organolithium reagent such as n-butyl lithium in a solvent such as ether at a temperature about −78° C. and subsequent acetylation with N,N-dimethylacetamide at a temperature ranging from −78° C. to rt; b) ketal formation in the presence of trimethylorthoformate and a catalyst such as $LiBF_4$ in a solvent such as ethylene glycol at a temperature about 95° C.; c) lithiation with an organolithium reagent such as n-butyl lithium in a solvent such as ether at a temperature about −78° C. and subsequent formylation with DMF; d) reduction with a reducing agent such as $NaBH_4$ in a solvent such as MeOH at a temperature about rt; e) mesylation using a reagent such as methanesulfonyl chloride in a solvent such as $CH_2Cl_2$ in the presence of a base such as $Et_3N$ and DMAP at a temperature about 0° C. Methanesulfonic acid 2-(2-methyl-[1,3]dioxolan-2-yl)-pyridin-4-ylmethyl ester may be prepared by the following sequence: a) reaction of commercially available 2,4-dibromopyridine with an organolithium reagent such as n-butyl lithium in a solvent such as ether at a temperature about −78° C. and subsequent acetylation with N,N-dimethyl-formamide at a temperature ranging from −78° C. to rt; b) reduction with a reducing agent such as $NaBH_4$ in a solvent such as MeOH at a temperature about rt; c) protection of the alcohol using tert-butyldimethylsilyl chloride in the presence of a base such as imidazole in a solvent such as dichloromethane; d) reaction of the protected alcohol with an organolithium reagent such as n-butyl lithium in a solvent such as ether at a temperature about −78° C. and subsequent acetylation with N,N-dimethylacetamide at a temperature ranging from −78° C. to rt; e) ketal formation in the presence of trimethylorthoformate and a catalyst such as $LiBF_4$ in a solvent such as ethylene glycol at a temperature about 95° C.; f) deprotection of the silyl protecting group under standard conditions such as TBAF in a solvent such as THF at a temperature about rt or 0° C.; g) mesylation using a reagent such as methanesulfonyl chloride in a solvent such as $CH_2Cl_2$ in the presence of a base such as $Et_3N$ and DMAP at a temperature about 0° C.

2-(4-Bromo-butyl)-2-methyl-[1,3]dioxolane may be prepared by reacting commercially available 1-methylcyclopentanol with bromine in the presence of a base such as $K_2CO_3$ in a solvent such as chloroform at a temperature about 0° C. followed by protection with ethylene glycol in the presence of a catalyst such as TsOH.

Methanesulfonic acid 3-(2-methyl-[1,3]dioxolan-2-yl)-benzyl ester may be prepared as described for methanesulfonic acid 6-(2-methyl-[1,3]dioxolan-2-yl)-pyridin-2-yl-methyl ester but starting with commercially available 1,3-dibromobenzene.

Methanesulfonic acid 4-(2-methyl-[1,3]dioxolan-2-yl)-pyridin-2-ylmethyl ester may be prepared as described for methanesulfonic acid 6-(2-methyl-[1,3]dioxolan-2-yl)-pyridin-2-ylmethyl ester but starting with commercially available 2,4-dibromopyridine.

Methanesulfonic acid 2-acetyl-pyridin-4-ylmethyl ester may be prepared by the following sequence: a) reaction of commercially available 2,4-dibromopyridine with an organolithium reagent such as n-butyl lithium in a solvent such as ether at a temperature about −78° C. and subsequent formylation with N,N-dimethylformamide; b) reduction with a reducing agent such as NaBH$_4$ in a solvent such as MeOH at a temperature about rt; c) protection in the presence of silyl protecting agent such as tert-butyldimethylsilyl chloride in a solvent such as CH$_2$Cl$_2$ in the presence of a base such as imidazole; d) lithiation with an organolithium reagent such as n-butyl lithium in a solvent such as ether at a temperature about −78° C. and subsequent acetylation with N,N-dimethylacetamide; e) deprotection of the silyl ether derivative using a fluorinated agent such as TBAF in a solvent such as THF at a temperature about rt; and f) mesylation using a reagent such as methanesulfonyl chloride in a solvent such as CH$_2$Cl$_2$ in the presence of a base such as Et$_3$N and DMAP at a temperature about 0° C.

Methanesulfonic acid 4-(2-methyl-[1,3]dioxolan-2-yl)-thiazol-2-ylmethyl ester may be prepared as described for methanesulfonic acid 2-(2-methyl-[1,3]dioxolan-2-yl)-pyridin-4-ylmethyl ester but starting with commercially available 2,4-dibromo-thiazole.

2-(4-Chloromethyl-thiophen-2-yl)-2-methyl-[1,3]dioxolane may be prepared as described for 2-(5-chloromethyl-furan-2-yl)-2-methyl-[1,3]dioxolane but starting with commercially available 1-(4-bromo-2-thienyl)-ethan-1-one.

4-Chloromethyl-thiazole-2-carboxylic acid ethyl ester may be prepared by the following sequence: a) reaction of commercially available oxalamic acid ethyl ester with Lawesson's reagent in a solvent such as toluene at a temperature about 80° C.; and b) cyclization with 1,3-dichloroacetone in a solvent such as toluene at a temperature about 110° C.

4-Chloromethyl-2-(2-methyl-[1,3]dioxolan-2-yl)-thiazole may be prepared from 4-chloro-methyl-thiazole-2-carboxylic acid ethyl ester by the sequence described under A.b) followed by ketal formation in the presence of trimethylorthoformate and a catalyst such as LiBF$_4$ in a solvent such as ethylene glycol at a temperature about 90° C.

2-Chloromethyl-5-methanesulfonyl-furan may be prepared by the following sequence: a) reaction of commercially available 5-nitro-furan-2-carboxylic acid ethyl ester with sodium methanethiolate in a solvent such as DMSO at a temperature about 100° C.; b) oxidation with an oxidative agent such as, m-CPBA in a solvent such as CH$_2$Cl$_2$ at a temperature about rt; c) reduction with a reducing agent such as DiBAL in a solvent such as THF at a temperature below rt; and d) chlorination using a reagent such as methanesulfonyl chloride in a solvent such as dichloromethane in the presence of a base such as Et$_3$N and DMAP at a temperature about 0° C.

Methanesulfonic acid 5-(2-methyl-[1,3]dioxolan-2-yl)-thiazol-2-ylmethyl ester may be prepared by the following sequence: a) reaction of commercially available 2-bromo-thiazole-5-carbaldehyde with trimethylaluminum in a solvent such as dichloromethane at a temperature about 0° C.; b) oxidation with an oxidative agent such as MnO$_2$ in a solvent such as acetonitrile at a temperature about rt; c) ketal formation in the presence of trimethylorthoformate and a catalyst such as LiBF$_4$ in a solvent such as ethylene glycol at a temperature about 95° C.; d) lithiation with an organolithium reagent such as n-butyl lithium in a solvent such as ether at a temperature about −78° C. and subsequent formylation with N,N-dimethylformamide; e) reduction with a reducing agent such as NaBH$_4$ in a solvent such as MeOH at a temperature about rt; f) mesylation using a reagent such as methanesulfonyl chloride in a solvent such as CH$_2$Cl$_2$ in the presence of a base such as Et$_3$N and DMAP at a temperature about 0° C.

5-Chloromethyl-2-(2-methyl-[1,3]dioxolan-2-yl)-thiazole may be prepared by the following sequence: a) reduction of commercially available 2-bromo-thiazole-5-carbaldehyde with a reducing agent such as NaBH$_4$ in a solvent such as MeOH at a temperature about rt; b) protection of the alcohol using tert-butyldimethylsilyl chloride in a solvent such as CH$_2$Cl$_2$ in the presence of a base such as imidazole; c) lithiation with an organolithium reagent such as n-butyl lithium in a solvent such as ether at a temperature about −78° C. and subsequent acetylation with N,N-dimethylacetamide; d) ketal formation in the presence of trimethylorthoformate and a catalyst such as LiBF$_4$ in a solvent such as ethylene glycol at a temperature about 95° C.; e) deprotection of the silyl ether derivative using a fluorinated agent such as TBAF in a solvent such as THF at a temperature about rt; and f) chlorination using a reagent such as methanesulfonyl chloride in a solvent such as CH$_2$Cl$_2$ in the presence of a base such as Et$_3$N and DMAP at a temperature about 0° C.

2-(5-Chloromethyl-thiophen-3-yl)-2-methyl-[1,3]dioxolane may be prepared as described for 5-chloromethyl-2-(2-methyl-[1,3]dioxolan-2-yl)-thiazole but starting with commercially available 4-bromo-thiophene-2-carbaldehyde.

Methanesulfonic acid 4-acetyl-oxazol-2-ylmethyl ester may be prepared by the following sequence: a) oxazole formation reacting commercially available 3-phenyl-acrylamide with 3-bromo-2-oxo-propionic acid ethyl ester in the presence of a base such as NaHCO$_3$ in a solvent such as THF at a temperature around 60° C.; b) oxidative cleavage using for example silica gel supported NaIO$_4$ and a metal complex such as RuCl$_3$ hydrate in a solvent such as dichloromethane at a temperature about rt; c) reduction with a reducing agent such as NaBH$_4$ in a solvent such as EtOH at a temperature about 0° C.; d) protection of the alcohol using tert-butyldimethylsilyl chloride in a solvent such as CH$_2$Cl$_2$ in the presence of a base such as imidazole; e) reduction to the aldehyde with a reducing agent such as DiBAL in a solvent such as CH$_2$Cl$_2$ at a temperature about −78° C.; f) reaction with trimethylaluminum in a solvent such as dichloromethane at a temperature about 0° C.; g) oxidation with an oxidative agent such as MnO$_2$ in a solvent such as acetonitrile at a temperature about rt; h) deprotection of the silyl ether derivative using a fluorinated agent such as TBAF in a solvent such as THF at a temperature about rt; and i) mesylation using a reagent such as methanesulfonyl chloride in a solvent such as CH$_2$Cl$_2$ in the presence of a base such as Et$_3$N and DMAP at a temperature about 0° C.

Methanesulfonic acid 2-(tert-butyl-dimethyl-silanyloxymethyl)-oxazol-4-ylmethyl ester may be prepared by the following sequence: a) oxazole formation reacting commercially available 3-phenyl-acrylamide with 3-bromo-2-oxopropionic acid ethyl ester in the presence of a base such as NaHCO₃ in a solvent such as THF at a temperature around 60° C.; b) oxidative cleavage using for example silica gel supported NaIO₄ and a metal complex such as RuCl₃ hydrate in a solvent such as CH₂Cl₂ at a temperature about rt; c) reduction with a reducing agent such as NaBH₄ in a solvent such as EtOH at a temperature about 0° C.; d) protection of the alcohol using tert-butyldimethylsilyl chloride in a solvent such as CH₂Cl₂ in the presence of a base such as imidazole; e) reduction to the alcohol with a reducing agent such as DiBAL in a solvent such as THF at a temperature about 0° C.; f) mesylation using a reagent such as methanesulfonyl chloride in a solvent such as CH₂Cl₂ in the presence of a base such as Et₃N and DMAP at a temperature about 0° C.

2-[1-(tert-Butyl-dimethyl-silanyloxy)-ethyl]-5-chloromethyl-oxazole may be prepared using the following sequence: a) reaction of commercially available oxazole with an organomagnesium reagent such as isopropylmagnesium chloride in a solvent such as THF at a temperature about −15° C. and subsequent acetylation with N-methoxy-N-methylacetamide at a temperature ranging from −15° C. to rt; b) reduction with a reducing agent such as NaBH₄ in a solvent such as MeOH at a temperature about rt; c) protection of the alcohol using tert-butyldimethylsilyl chloride in the presence of a base such as imidazole in a solvent such as THF; d) reaction of the protected alcohol with an organolithium reagent such as t-butyl lithium in a solvent such as THF at a temperature ranging from −78° C. to −40° C. and subsequent formylation with N,N-dimethyl-formamide at a temperature ranging from −78° C. to rt; e) reduction with a reducing agent such as NaBH₄ in a solvent such as MeOH at a temperature about rt; g) chlorination using a reagent such as methanesulfonyl chloride in a solvent such as CH₂Cl₂ in the presence of a base such as Et₃N and DMAP at a temperature about 0° C.

2-Chloromethyl-5-(2-methyl-[1,3]dioxolan-2-yl)-oxazole may be prepared using the following sequence: a) lithiation of commercially available oxazole with an organolithium reagent such as n-butyl lithium in a solvent such as THF at a temperature about −78° C. and subsequent addition of DMF; b) reduction with a reducing agent such as NaBH₄ in a solvent such as MeOH at a temperature about 0° C.; c) protection of the alcohol using tert-butyldimethylsilyl chloride in the presence of a base such as imidazole in a solvent such as THF; d) lithiation with an organolithium reagent such as t-butyl lithium in a solvent such as THF at a temperature ranging from −78° C. to −40° C. and subsequent formylation with DMF at a temperature ranging from −78° C. to rt; e) reaction with trimethylaluminum in a solvent such as dichloromethane at a temperature about 0° C.; f) oxidation with an oxidative agent such as MnO₂ in a solvent such as acetonitrile at a temperature about rt; g) ketal formation and deprotection of the silyl protection group in the presence of trimethylorthoformate and a catalyst such as LiBF₄ in a solvent such as ethylene glycol at a temperature about 95° C.; h) chlorination of the alcohol using for example Ms-Cl in the presence of a base such as Et₃N and DMAP in a solvent such as CH₂Cl₂ at a temperature about 0° C.

Chloroformates or acid chlorides of formula R¹-E-COCl or carboxylic acids of formula R¹-E-COOH are commercially available or synthesized according to well known methods e.g. from commercially available benzoic acids, benzaldehydes, benzyl alcohols or their heterocyclic analogues.

Acids of formula R¹-E-COOH, which are also compounds of structure 8 are well known in the art or are prepared according to the methods described below.

Structure 8

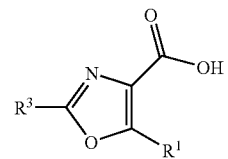

Compounds of structure 8 wherein R³ represents Me may be prepared as described in Scheme 1 by reacting 3-oxo-propionic acid ester derivatives with an aqueous solution of sodium nitrite in presence of an acid such as glacial acetic acid. Subsequent transformation of the oxime with acetic anhydride in presence of an acid such as glacial acetic acid and catalytic amounts of metal chlorides such as mercury chloride or zinc chloride and zinc powder followed by cyclization under dehydrating conditions such as thionyl chloride in chloroform followed by saponification of the ester function using methods known in the art such as treatment with a base such as NaOH in a solvent or a solvent mixture such as ethanol/water or THF afforded the desired acid derivative. The respective 3-oxo-propionic acid ester derivatives are commercially available or well known in the art.

Scheme 1: Oxazole synthesis (1).

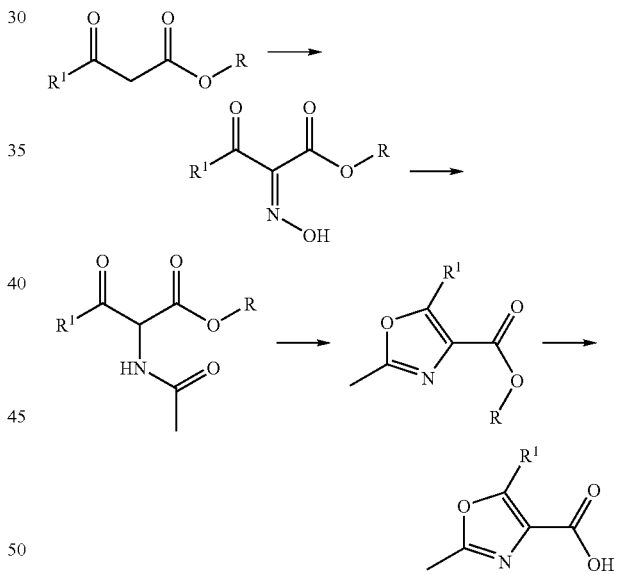

Alternatively, compounds of structure 8 may be prepared as described in Scheme 2 by reacting 3-oxo-propionic acid ester derivatives with a solution of 4-acetamido-benzenesulfonyl azide and a base such as Et₃N. Subsequent treatment with a carboxamide derivative and a catalyst such as tetrakis(acetato)dirhodium(II) dihydrate followed by cyclization using triphenylphosphine and iodine in the presence of a base such as Et₃N afforded the respective ester derivative. Saponification of the ester function using methods known in the art such as treatment with a base such as NaOH in a solvent or a solvent mixture such as ethanol/water or THF afforded the desired acid derivative. The respective 3-oxo-propionic acid ester derivatives are commercially available or well known in the art.

Scheme 2: Oxazole synthesis (2).

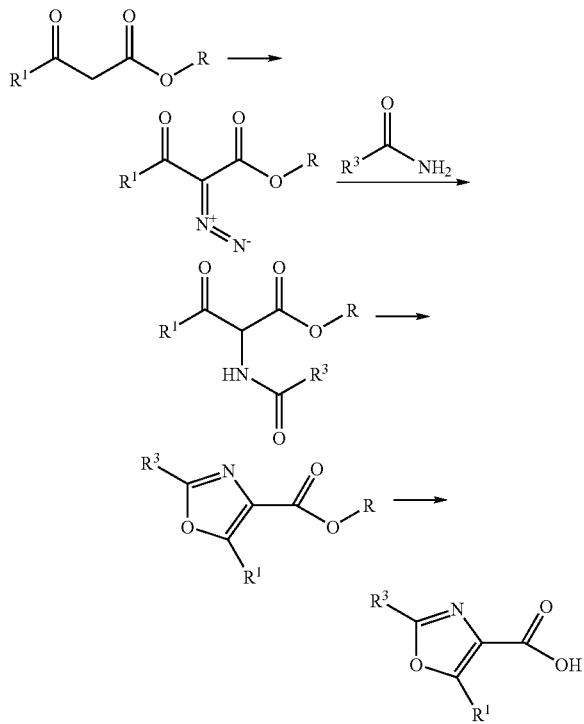

Alternatively, compounds of structure 8 wherein $R^3$ represents hydrogen may be prepared as described in Scheme 2b by reacting a solution of an acid derivative of formula $R^1COOH$ with methyl isocyanoacetate in the presence of a base such as potassium carbonate sesquihydrate or DIPEA and DPPA in a solvent such as DMF. Saponification of the ester function using methods known in the art such as treatment with a base such as NaOH in a solvent or a solvent mixture such as ethanol/water or THF afforded the respective acid derivative. The respective acids $R^1COOH$ are commercially available or well known in the art.

Scheme 2b: Oxazole synthesis (3).

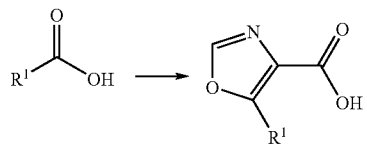

Alternatively, compounds of structure 8 may be prepared as described in Scheme 3 by esterification of a 3-phenylserine derivative using a reagent such as thionylchloride in a solvent such as MeOH at a temperature about 0° C. followed by coupling with a carboxylic acid derivative $R^3$—COOH using standard conditions such as HOBt, DCC, N-methylmorpholine in a solvent such as $CH_2Cl_2$ at a temperature about 0° C. Oxidation of the alcohol with an oxidative reagent such as Dess-Martin periodinane in a solvent such as $CH_2Cl_2$ followed by cyclization using triphenylphosphine and iodine in the presence of a base such as $Et_3N$ afforded the respective oxazole derivative. The desired acid derivatives may be obtained by saponification of the ester function using methods known in the art such as treatment with a base such as aq. LiOH in a solvent such as dioxane.

Scheme 3: Oxazole synthesis (4).

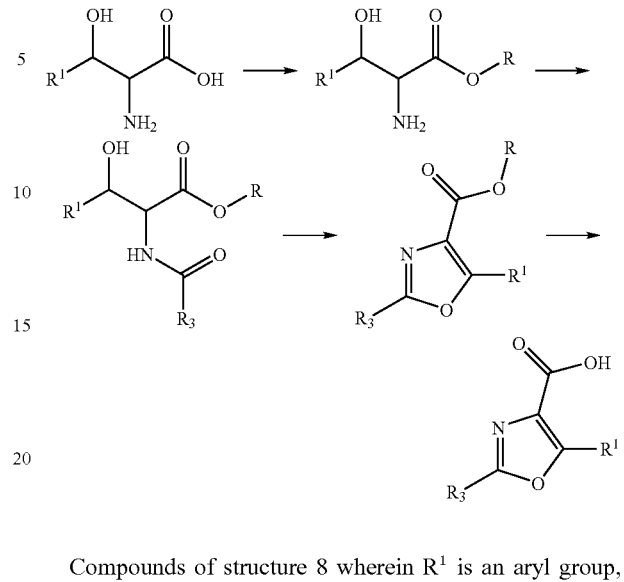

Compounds of structure 8 wherein $R^1$ is an aryl group, which group is substituted with $(C_1-C_4)$alkoxy-$(C_1-C_2)$alkyl can be obtained, for instance, according to Scheme 4 by a sequence comprising:

Saponification of the hydroxy-$(C_1-C_2)$alkyl-substituted 5-phenyl-oxazole derivative (prepared according to Scheme 5 or 6) using methods known in the art such as treatment with a base such as aq. LiOH in a solvent such as THF;

Alkylation of the corresponding alcohol with an alkyl halogenide such as alkyl iodide in presence of a base such as NaH in a solvent such as DMF;

Saponification of the resulting ester using a method known in the art such as treatment with a base such as NaOH in a solvent or a solvent mixture such as ethanol/water or THF.

Scheme 4: Synthesis of $(C_1-C_4)$alkoxy-$(C_1-C_2)$alkyl substituted 5-phenyl-oxazole derivatives ($R^z$ represents $(C_1-C_4)$alkyl and $n$ represents 1 or 2).

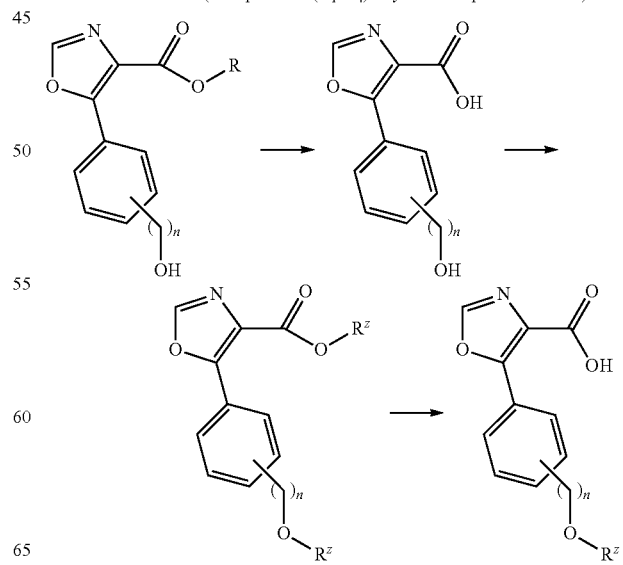

Hydroxy-($C_1$-$C_2$)alkyl-substituted 5-phenyl-oxazole derivatives can be obtained, for instance, according to Scheme 5 by a sequence comprising:

Oxazole formation by reacting a phenyl-dicarboxylic acid mono-ester derivative with methyl isocyanoacetate in analogy to the method described in Scheme 2b;

Selective saponification of the phenyl-bound ester group using any of the methods known in the art (e.g. by acid catalyzed cleavage of a tent-butyl ester with, for instance, TFA);

Reduction of the resulting acid to the respective primary alcohol with a reducing agent like borane;

Scheme 5: Synthesis of hydroxy-($C_1$-$C_2$)alkyl substituted 5-phenyl-oxazole derivatives.

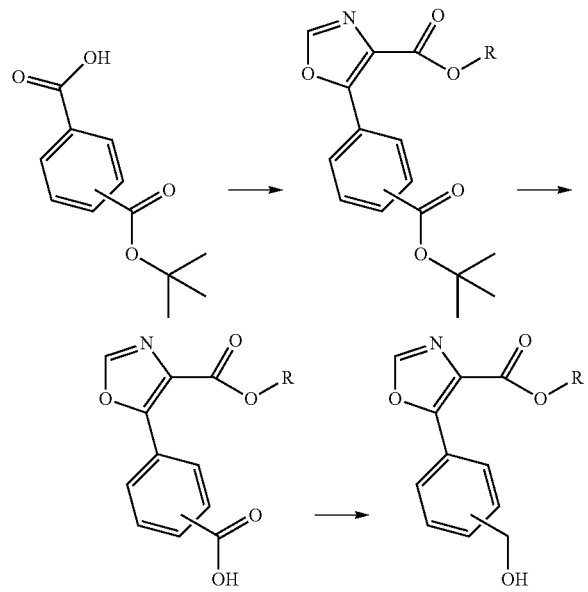

Alternatively, hydroxy-($C_1$-$C_2$)alkyl-substituted 5-phenyl-oxazole derivatives can be obtained, for instance, according to Scheme 6 by a sequence comprising:

Oxazole formation by reacting a hydroxy-($C_1$-$C_2$)alkyl-substituted benzoic acid derivative with methyl isocyanoacetate in analogy to the method described in Scheme 2b;

Scheme 6: Synthesis of hydroxy-($C_1$-$C_2$)alkyl substituted 5-phenyl-oxazole derivatives (2).

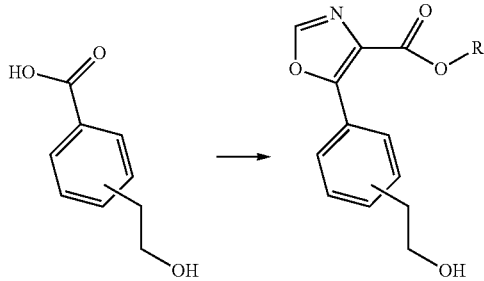

Structure 9

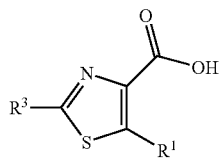

Compounds of structure 9 may be prepared by first reacting methyl dichloroacetate with commercially available benzaldehyde derivatives $R^1$—CHO in the presence of a base such as KOt-Bu in a solvent such as THF. The desired compounds of structure 9 wherein $R^3$ represents ($C_1$-$C_4$)alkyl or cyclopropyl are obtained as described in Scheme 7 by subsequent transformation (cyclization) with the respective thioamides in a solvent such as MeCN followed by saponification of the ester function using methods known in the art such as treatment with a base such as NaOH in a solvent such as MeOH. The respective benzaldehydes $R^1$—CHO are commercially available or well known in the art. The thioamides are commercially available or, alternatively, can be synthesized from commercially available carboxamides with Lawesson's reagent.

Scheme 7: Thiazole synthesis (1), wherein $R^3$ represents ($C_1$-$C_4$)alkyl or cyclopropyl.

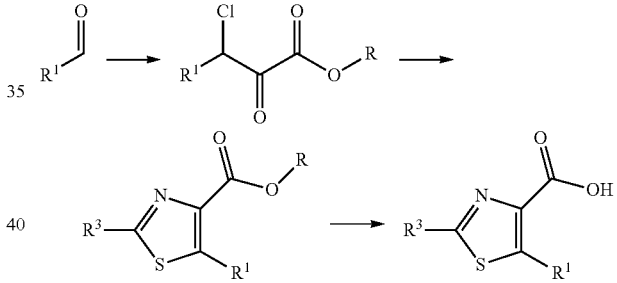

Alternatively, the desired compounds of structure 9 wherein $R^3$ represents hydrogen are obtained as described in Scheme 8 by reacting methyl dichloroacetate with commercially available benzaldehyde derivatives $R^1$—CHO in the presence of a base such as KOt-Bu in a solvent such as THF. A subsequent transformation with commercially available thiourea followed by treatment with a base such as sodium bicarbonate afforded the amino-thiazole derivative. Sandmeyer transformation using a Cu(II) derivative such as $CuBr_2$ followed by hydrogenation in the presence of a metal catalyst such as Pd/C, Pt/C or $PtO_2$ afforded the desired ester. Saponification of the ester function can be performed using methods known in the art such as treatment with a base such as NaOH in a solvent such as MeOH.

Scheme 8: Thiazole synthesis (2).

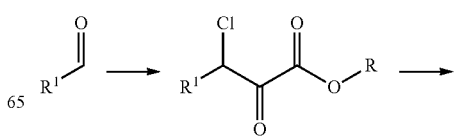

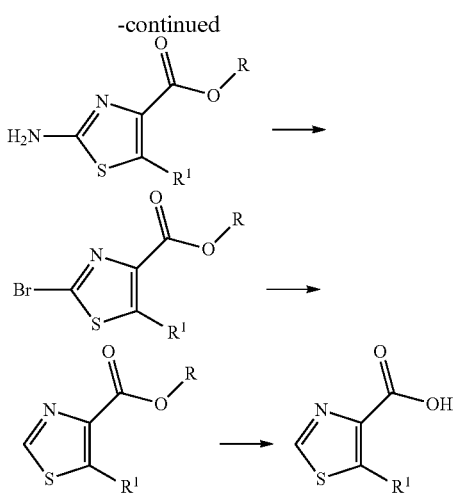

Whenever the compounds of formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as $Et_3N$ or diethylamine) and eluent B (hexane), at a flow rate of 0.8 to 150 mL/min.

EXPERIMENTAL PART

| Abbreviations (as used herein and in the description above) | |
|---|---|
| Ac | acetyl |
| AcCl | acetyl chloride |
| AcCN | acetonitrile |
| AcOH | acetic acid |
| aq. | aqueous |
| atm | atmosphere |
| Boc | tert-butoxycarbonyl |
| BSA | bovine serum albumin |
| Bu | butyl |
| BuLi | n-butyllithium |
| ca. | about |
| cat. | catalytic |
| DCC | N,N'-dicyclohexylcarbodiimide |
| DIPEA | diisopropylethylamine |
| DiBAL | di-iso-butylaluminum hydride |
| DMAP | 4-N,N-dimethylaminopyridine |
| DMF | dimethylformamide |
| DMSO | dimethylsulfoxide |
| DPPA | diphenyl phosphoryl azide |
| EA | ethyl acetate |
| EIA | enzyme immunoassay |
| EDC | N-(3-dimethylaminopropyl)-N'-ethyl-carbodiimide hydrochloride |
| ELSD | evaporative light-scattering detection |
| eq. | equivalent(s) |
| ES+ | electro-spray, positive ionization |
| Et | ethyl |
| ether | diethylether |
| $Et_3N$ | triethylamine |
| EtOH | ethanol |
| FC | flash column chromatography on silica gel |
| h | hour(s) |
| HBTU | O-(benzotriazol-1-yl)-N,N,N',N'-tetramethyluronium hexafluorophosphate |
| hept | heptane |
| HOBt | hydroxybenzotriazole |
| HPLC | high performance liquid chromatography |
| LC-MS | liquid chromatography - mass spectrometry |
| m-CPBA | meta-chloroperbenzoic acid |
| Me | methyl |
| MeOH | methanol |
| min | minute(s) |
| MPLC | medium pressure liquid chromatography |
| MS | mass spectrometry |
| Ms | methanesulfonyl |
| NMO | N-methyl-morpholine-N-oxide |
| NMR | nuclear magnetic resonance |
| OAc | acetate |
| org. | organic |
| p | para |
| p-TsOH | para-toluene sulfonic acid |
| PG | protecting group |
| PyBOP | benzotriazol-1-yl-oxy-tris-pyrrolidino-phosphonium-hexafluoro-phosphate |
| Rochelle's salt | potassium sodium tartrate |
| rf | retention factor |
| rt | room temperature |
| sat. | saturated |
| SCX | strong cation exchanger |
| sol. | solution |
| TBA | tetra-n-butylammonium |
| TBAF | tetra-n-butylammonium fluoride |
| TBDMS | tert-butyl-dimethyl-silyl |
| TBDPS | tert-butyl-diphenyl-silyl |
| TBTU | O-(benzotriazol-1-yl)-N,N,N',N'-tetramethyluronium tetrafluoroborate |
| tBu | tert-butyl, tertiary butyl |
| TFA | trifluoroacetic acid |
| THF | tetrahydrofuran |
| TIPS | tri-isopropyl-silyl |
| TLC | thin layer chromatography |
| TMS | trimethyl-silyl |
| TPAP | tetrapropylammonium perruthenate |
| $t_R$ | retention time |
| TsOH | p-toluene sulfonic acid monohydrate |
| UV | ultra violet |
| Vis | visible |

I Chemistry

General. All temperatures are stated in degrees Celsius (° C.). Unless otherwise indicated, the reactions take place at rt.

As SCX material SiliaBond® SCX from Silicycle was used.

Analytical thin layer chromatography (TLC) was performed with 0.2 mm plates: Merck, Silica gel 60 $F_{254}$. Preparative thin layer chromatography (TLC) was performed with 0.2 or 0.5 mm plates: Merck, Silica gel 60 $F_{254}$. Detection was done with UV or with a solution of $KMnO_4$ (3 g), $K_2CO_3$ (20 g), NaOH 5% (3 mL) and $H_2O$ (300 mL) with subsequent heating.

Flash column chromatography (FC) and filtration were performed using silica gel 60 Merck (0.063-0.200 mm) or Macherey-Nagel silica gel (0.063-0.200 mm); elution with EA, hept, $CH_2Cl_2$, $CHCl_3$, MeOH or mixtures thereof.

MPLC was performed using isolute SPE Flash SI II columns from international sorbent technology, elution with EA, hept, $CH_2Cl_2$, MeOH or mixtures thereof.

LC-MS-conditions 01 (if not indicated otherwise): Analytical: Thermo Finnigan MSQ Surveyor MS with Agilent 1100 Binary Pump and DAD. Column: Zorbax SB-AQ 5 μm, 4.6×50 mm ID from Agilent Technologies. Eluents: A: $H_2O$+ 0.04% TFA; B: AcCN; Gradient: 5% B→95% B over 1 min. Flow: 4.50 mL/min. Detection: UV/Vis+MS, $t_R$ is given in min.

LC-MS-conditions $O_2$ (if not indicated otherwise): Analytical: Thermo Finnigan MSQ Plus MS with Agilent 1100

Binary Pump and DAD. Column: Zorbax SB-AQ 5 μm, 4.6×50 mm ID from Agilent Technologies. Eluents: A: $H_2O$+0.04% TFA; B: AcCN; Gradient: 5% B→95% B over 1 min. Flow: 4.50 mL/min. Detection: UV/Vis and/or ELSD+MS, $t_R$ is given in min.

LC-MS-conditions 05 (if not indicated otherwise): Analytical: Dionex GHP 3200 Binary Pump, MS: Thermo MSQ Plus, DAD: Dionex PDA 3000, ELSD: Sedere Sedex 85. Column: Xbridge C18 5 μM, 4.6×50 mm ID from Waters, thermostated in the Dionex TCC-3200 compartment.

Eluents: A: $H_2O$+0.04% TFA; B: AcCN. Method: Gradient: 5% B→95% B over 1.0 min. Flow: 4.5 mL/min. Detection: UV/Vis and/or ELSD, and MS, $t_R$ is given in min.

LC-MS-conditions 05b (if not indicated otherwise): Analytical: Dionex GHP 3200 Binary Pump, MS: Thermo MSQ Plus, DAD: Dionex PDA 3000, ELSD: Sedere Sedex 85. Column: Zorbax Extend C18 1.8 μM, 4.6×20 mm from Agilent Technologies, thermostated in the Dionex TCC-3200 compartment. Eluents: A: $H_2O$+0.04% TFA; B: AcCN. Method: Gradient: 5% B→95% B over 1.0 min. Flow: 4.5 mL/min. Detection: UV/Vis and/or ELSD, and MS, $t_R$ is given in min.

HPLC preparative: X-Bridge C18 5 μm, 50×19 mm ID from Waters. Eluents: A: $H_2O$+0.5% $NH_4OH$; B: AcCN; Gradient: 10% B→90% B over 5 min. Flow: 40.0 mL/min. Detection: UV/Vis and/or ELSD.

HPLC chiral, analytical: a) Regis Whelk column, 4.6×250 mm, 10 μm. Eluent A: EtOH+0.05% $Et_3N$. Eluent B: hexane. Flow: 1 mL/min. b) ChiralPak AD, 4.6×250 mm, 5 μm. Eluent A: EtOH+0.05% $Et_3N$. Eluent B: hexane. Flow: 1 mL/min. c) ChiralCel OD, 4.6×250 mm, 10 μm. Eluent A: EtOH+0.1% $Et_3N$. Eluent B: hexane. Flow: 0.8 mL/min.

HPLC chiral, preparative: a) Regis Whelk 01 column, 50×250 mm. Flow: 100 mL/min. b) ChiralPak AD, 20×250 mm. Flow: 10 mL/min. c) ChiralCel OD, 20 μm, 50 mm×250 mm. Flow: 100 mL/min.

NMR: Bruker Avance 400 (400 MHz); Varian Mercury 300 (300 MHz); chemical shifts are given in ppm relative to the solvent used; multiplicities: s=singlet, d=doublet, t=triplet, q=quadruplet, p=pentuplet, hex=hextet, hept=heptet, m=multiplet, br=broad, coupling constants are given in Hz.

The following examples illustrate the invention but do not at all limit the scope thereof.

General Procedures

General Procedure A: Amide Coupling:

In a glass vial, under inert atmosphere ($N_2$), to an acid (1.5 eq.) weighed in a glass vial, was added a solution of the aminotriazole (1.0 eq.) in $CH_2Cl_2$ (0.1M). A solution of HOBt (2.0 eq.), DMAP (0.25 eq.), and DIPEA (2.0 eq.) in $CH_2Cl_2$ (10 mL per mmol of HOBt), was added, followed by EDC (1.5 eq.). The resulting mixture was stirred at rt overnight. The reaction mixture was poured on a syringe containing diatomaceous earth (Isolute® HM-N from Separtis) treated with 1M HCl (1.0 mL per g of Isolute®). The product was eluted with $CH_2Cl_2$ (3×1 mL) and the solvent was removed under reduced pressure. Purification of the residue by FC or HPLC gave the desired compound.

General Procedure B: Dioxolane Deprotection (1):

In a glass vial, under inert atmosphere ($N_2$), a 0.07M solution of the dioxolane (1.0 eq.) in THF was treated with 1N HCl (2.7 eq.) and the reaction mixture was stirred at rt until completion. Water was added and the product was extracted twice with EA. The org. layer was dried over $MgSO_4$ filtered, and the solvent was removed under reduced pressure. Purification of the residue by FC or HPLC gave the desired compound.

General Procedure C: Dioxolane Deprotection (2):

To a glass vial containing a 0.05M solution of the dioxolane in MeOH was added SCX silica gel (70 mg per 0.05 mmol of dioxolan) and the reaction mixture was stirred at rt for 18 h. The mixture was filtered and the solvent was removed under reduced pressure. Purification of the residue by FC or HPLC gave the desired compound.

General Procedure D: Carbamate Formation (1):

Step 1:

In a glass vial, under inert atmosphere ($N_2$), a 0.065M solution of the alcohol (1.3 eq.) in $CH_2Cl_2$ was treated with phosgene (1.3 eq., 20% solution in toluene). The resulting mixture was stirred at rt overnight. The reaction mixture was then poured on a syringe containing diatomaceous earth (Isolute® HM-N from Separtis) treated with 1M NaOH (1.25 mL per g of Isolute®). The product was eluted with $CH_2Cl_2$ (3×1 mL) and the solvents were removed under reduced pressure.

Step 2:

The chloroformate was treated with a solution of the appropriate aminotriazole derivative (1.0 eq.) and DIPEA (2.0 eq.) in $CH_2Cl_2$ (20 mL per mmol of aminotriazole derivative) and the resulting mixture was stirred at rt overnight. The reaction mixture was poured on a syringe containing diatomaceous earth (Isolute® HM-N from Separtis) treated with 1M HCl (1.0 mL per g of Isolute®). The product was eluted with $CH_2Cl_2$ (3×1 mL) and the solvent was removed under reduced pressure. Purification of the residue by HPLC gave the desired compound.

General Procedure E: Ester Hydrolysis:

A 0.5M solution of the respective carboxylic acid ester (1.0 eq.) in a 3:1 mixture of THF and the corresponding alkyl alcohol, e.g. MeOH or EtOH, was treated with 1M aq. NaOH (2.0 eq.). After stirring for 3 h, a white suspension was formed and the org. volatiles were removed under reduced pressure. The remaining mixture was diluted with water (half the amount of the 3:1 mixture of THF and MeOH), cooled with an ice-bath and acidified (pH=3-4) by addition of 1M aq. HCl. The suspension was filtered and the residue was washed with cold water to afford the desired carboxylic acid derivative after drying.

General Procedure F: Synthesis of 2-acetylamino-3-oxo-propionic acid ester derivatives

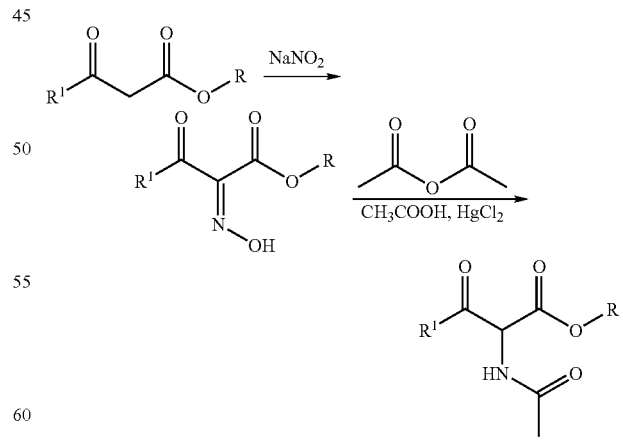

In a flame dried round-bottomed flask equipped with a magnetic stir bar and under inert atmosphere ($N_2$), a 2.5M solution of the respective 3-oxo-propionic acid ester derivative (1.0 eq.) in glacial acetic acid was cooled to 10° C. and at this temperature was added a 8.2M solution of $NaNO_2$ (1.16 eq.) in water. After the addition was complete (15 min), the solution was allowed to warm to rt and stirred for 2 h. The solution was then poured into water (5.3 times the volume of glacial acetic acid) and after a few minutes crystals begun to appear. This suspension was cooled with an ice-bath and crystals were collected by filtration. The cake was washed several times with cold water and the water was removed by azeotrope distillation with toluene under reduced pressure to give the respective 2-hydroxyimino-3-oxo-propionic acid ester derivative, which was dissolved in a 1:1.3 mixture of acetic anhydride and glacial acetic acid (0.66 mL for 1.0 mmol of the respective 3-oxo-propionic acid ester derivative). To this solution was added sodium acetate (0.06 eq.) and $HgCl_2$ (0.002 eq.). The mixture was refluxed for 1 h, then cooled to rt and filtered. The solid was rinsed with ether, the organic filtrate was recovered, washed 3 times with water and once with 1M aq. $K_2CO_3$. The organic layer was dried over $MgSO_4$, filtered and the solvent was removed under reduced pressure. The crude product was purified by FC to afford the desired 2-acetylamino-3-oxo-propionic acid ester derivative.

General Procedure G: Cyclization (1):

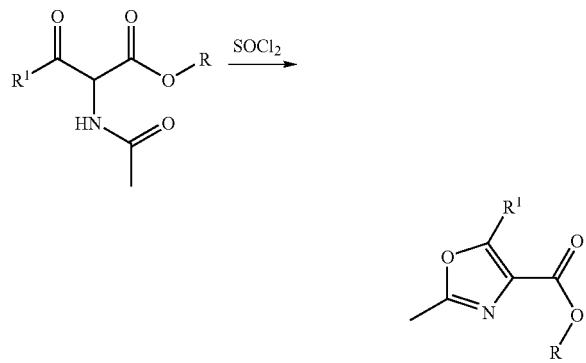

In a flame dried round-bottomed flask equipped with a magnetic stir bar and under inert atmosphere ($N_2$), a 1.6M solution of the respective 2-acetylamino-3-oxo-propionic acid ester derivative (1.0 eq.) in chloroform was cooled to about 0° C. in an ice/NaCl bath. $SOCl_2$ (1.4 eq.) was added to the stirred solution and the temperature was maintained at about 0° C. for 30 minutes. Then the solution was stirred at reflux for one hour. Another 0.25 eq. of $SOCl_2$ was added and the reaction mixture was refluxed for an additional hour. The excess $SOCl_2$ was quenched with 1M aq. $K_2CO_3$. The aq. layer was extracted twice with ether. The combined organic phases were washed once with water and dried over $MgSO_4$, filtered and the solvent was removed under reduced pressure to afford the desired oxazole derivative.

General Procedure H: Cyclization (2):

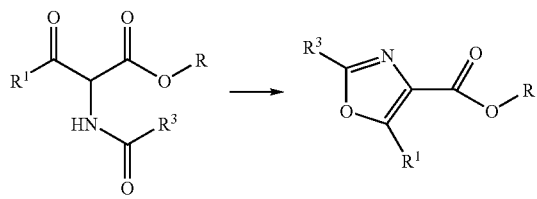

In a flame dried round-bottomed flask equipped with a magnetic stir bar and under an inert atmosphere ($N_2$), $Et_3N$ (4.1 eq.) followed by a 0.1M solution of the respective 2-(car- bonyl-amino)-3-oxo-propionic acid ester derivative (1.0 eq.) in $CH_2Cl_2$ were added to a 0.2M solution of triphenylphosphine (2.0 eq.), and iodine (2.0 eq.) in $CH_2Cl_2$. The reaction mixture was stirred for 1.5 h at rt. The solvent was removed under reduced pressure and the residue purified by FC to afford the desired oxazole derivative.

General Procedure I: N-Insertion:

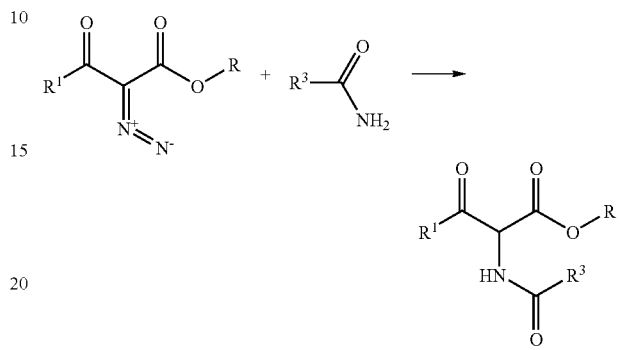

In a flame dried round-bottomed flask equipped with a magnetic stir bar and under an inert atmosphere ($N_2$), a 0.5M solution of the diazo derivative (1.0 eq.) in 1,2-dichloroethane was added over 1.5 h to a refluxing solution of the carboxamide derivative (1.0 eq.) and rhodium(II) acetate (tetrakis (acetato)dirhodium(II) dihydrate, 0.05 eq.) in 1,2-dichloroethane (3 mL per mmol of carboxamide derivative). The reaction mixture was then stirred for 1.5 h at reflux. The solvent was removed under reduced pressure and the residue purified by FC to afford the desired 2-(carbonyl-amino)-3-oxo-propionic acid ester derivative.

General Procedure J: Diazotation:

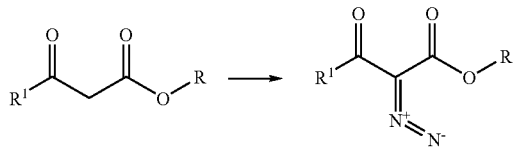

In a flame dried round-bottomed flask equipped with a magnetic stir bar and under an inert atmosphere ($N_2$), a 0.17M solution of the 3-oxo-propionic acid ester derivative (1.0 eq.) in AcCN was treated at 0° C. with 4-acetamidobenzenesulfonyl azide (1.0 eq.) followed by $Et_3N$ (3.0 eq.). The reaction mixture was stirred for 1 h at rt. The solvent was removed under reduced pressure, the residue triturated in ether-light petroleum and filtered. The solvent was removed under reduced pressure and the residue was purified by FC to afford the desired diazo derivative.

General Procedure K: Claisen Condensation:

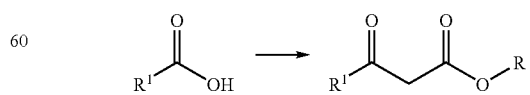

A) In a flame dried round-bottomed flask equipped with a magnetic stir bar and under an inert atmosphere ($N_2$), a 1.3M solution of the acid derivative (1.0 eq.) in 1,2-dichloroethane was treated at rt with a few drops of DMF followed by oxalyl chloride (1.3 eq.). The reaction mixture was stirred for 3 h at rt followed by 20 min at 80° C. The solvent was removed under reduced pressure.

B) In a flame dried round-bottomed flask equipped with a magnetic stir bar and under an inert atmosphere (N$_2$), a 0.83M solution of potassium malonic acid monoethyl ester (2 eq.) in acetonitrile was treated at 10° C. with magnesium chloride (2.5 eq.) and the suspension was stirred at 10° C. for 30 min and at rt for 3 h. The reaction mixture was cooled to 0° C. and treated dropwise over 15 min with the solution of the acid chloride prepared under A, followed by Et$_3$N (2 eq.). The resulting suspension was stirred at rt for 20 h. The solvent was removed under reduced pressure and the residue was striped with toluene. The residue was taken in toluene (1.5 mL per mmol of potassium malonic acid monoethyl ester) and treated at 10° C. with the same amount of 4M HCl as of toluene. The organic layer was washed twice with 4M HCl, water, dried over MgSO$_4$, filtered, and the solvent was removed under reduced pressure. The residue was purified by FC to afford the desired derivative.

General Procedure L: Dioxolane Deprotection (3):

To a glass vial containing a 0.05M solution of the dioxolane in MeOH was added silica gel bound tosic acid (70 mg per 0.05 mmol of dioxolane, R60530B silica gel bound tosic acid from Silicycle) and the reaction mixture was stirred at rt for 18 h. The mixture was filtered. Purification of the residue by FC or HPLC gave the desired compound.

General Procedure M: Cyclization (3):

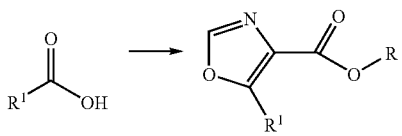

In a flame dried round-bottomed flask equipped with a magnetic stir bar and under an inert atmosphere (N$_2$), a 0.5M solution of the acid (1.0 eq.) in DMF was treated at rt with potassium carbonate sesquihydrate or, alternatively DIPEA (from 1.2 eq. to 1.5 eq.) followed by a 2.0M solution of methyl isocyanoacetate (from 1.5 eq. to 3.2 eq.) in DMF and the mixture was stirred at rt for 5 min. The reaction mixture was cooled to 0° C. and treated with a 0.67M solution of DPPA (1.1 eq.) in DMF. The resulting suspension was stirred at 0° C. for 2 h and at rt for 15 h. It was then poured in a 1:1 mixture of EA and toluene and the organic layer was washed with water, 10% citric acid, water and sat. aq. NaHCO$_3$. The organic layer was dried over MgSO$_4$, filtered, and the solvent was removed under reduced pressure. The residue was purified by FC to afford the desired derivative.

General Procedure N: Dioxolane Deprotection (4):

In a glass vial, under inert atmosphere (N$_2$), a 0.1M solution of the dioxolane (1.0 eq.) in water was treated with formic acid (same volume as water) and the reaction mixture was stirred at a temperature ranging between 0° C. and 50° C. (preferably rt). pH was adjusted to 8-9 using 1N NaOH and the product was extracted twice with EA. The org. layer was dried over MgSO$_4$, filtered, and the solvent was removed under reduced pressure. Purification of the residue by FC or HPLC gave the desired compound.

General Procedure O: Carbamate Formation (2):

In a glass vial, under inert atmosphere (N$_2$), to a solution of the appropriate aminotriazole derivative (1.0 eq.) in AcCN (or CH$_2$Cl$_2$) (0.05M solution), was added 4-nitrophenyl chloroformate (1.1 eq.) and DIPEA (1.0 eq.). The mixture was stirred for 30 min, and then it was transferred to glass vials containing the appropriate alcohol (1.4 eq.), under inert atmosphere. After adding DIPEA (1.0 eq.), the mixture was stirred at 60° C. for 12 h. The reaction mixture was poured on a syringe containing diatomaceous earth (Isolute® HM-N from Separtis) treated with 1M NaOH (1.25 mL per g of Isolute®). The product was eluted with CH$_2$Cl$_2$ (3×1 mL). The solvent was removed under reduced pressure. Purification of the residue by FC or HPLC gave the desired compound.

General Procedure P: Grignard Addition

In a flame dried round-bottomed flask equipped with a magnetic stir bar and under inert atmosphere (N$_2$), a 0.1M solution of the aldehyde (1.0 eq.) in THF was treated at −78° C. with the appropriate cyclopropyl- or alkyl-magnesium bromide (4.0 eq.). The reaction mixture was stirred at −78° C. for 90 min and at rt for 45 min before being quenched by pouring in sat. aq. NH$_4$Cl, extracted with EA and the combined org. extracts were dried over MgSO$_4$, filtered, and the solvents were removed under reduced pressure. Purification of the residue by FC gave the desired compound.

General Procedure Q: Alcohol Oxidation

In a flame dried round-bottomed flask equipped with a magnetic stir bar and under inert atmosphere (N$_2$), a 0.1M solution of the alcohol (1.0 eq.) in CH$_2$Cl$_2$ was treated at rt with NMO (3.0 eq.) and the reaction mixture was stirred for 5 min. TPAP (0.1 eq.) was then added and the reaction mixture was stirred for 2 h at rt and then the solvent was removed under reduced pressure. Purification of the residue by FC gave the desired compound.

General Procedure R: Condensation:

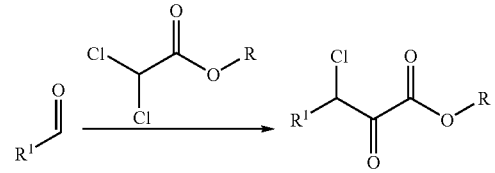

In a flame dried round-bottomed flask equipped with a magnetic stir bar and under inert atmosphere (N$_2$), a solution of the aldehyde derivative (1 eq.) in dichloro-acetic acid methyl ester (1.0 eq.) was added over 1 h to a 1.45M suspension of KOt-Bu (1.0 eq.) in THF at −78° C. The reaction mixture was stirred at −78° C. for 5 h and at rt overnight. The solvent was removed under reduced pressure and the residue was dissolved in EA and washed with water. The organic layer was dried over MgSO$_4$ and concentrated under reduced pressure to afford the corresponding 3-chloro-2-oxo-propionic acid methyl ester derivative.

General Procedure S: Cyclization (4)

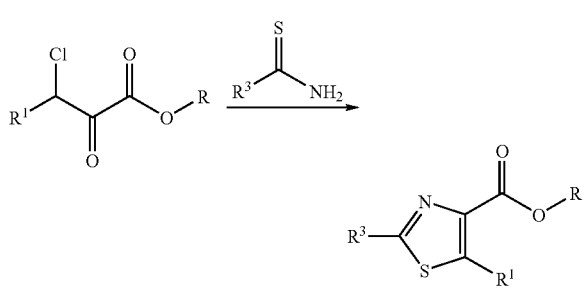

R$^3$ represents (C$_1$-C$_4$)alkyl or cyclopropyl.

In a flame dried round-bottomed flask equipped with a magnetic stir bar and under inert atmosphere (N$_2$), a 0.5M solution of the respective thioamide (1.0 eq.) in MeCN was added to a 2.2M solution of the respective 3-chloro-2-oxo-propionic acid ester derivative (1.0 eq.) in MeCN along with molecular sieves 4A (91 mg per mmol of thioamide). After stirring at rt for 5 h, the mixture was cooled with an ice-bath and the obtained precipitate was filtered off. The residue was washed with cold MeCN, dried, dissolved in MeOH (1.12 times the amount of MeCN as used for the thioamide) and stirred at 50° C. for 6 h. The solvents were removed under reduced pressure to give the corresponding thiazole-4-carboxylic acid ester derivative.

General Procedure T: Cyclization (5)

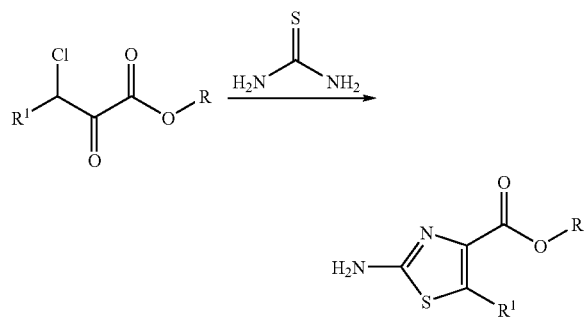

In a flame dried round-bottomed flask equipped with a magnetic stir bar and under an inert atmosphere (N$_2$), a 0.57M solution of the 3-chloro-2-oxo-propionic acid ester derivative (1.0 eq.) in acetone was added to a 0.72M solution of thiourea (1.0 eq.) in acetone. The reaction mixture was stirred overnight at 57° C. The cooled reaction mixture was filtered and the solvent was removed under reduced pressure. The residue was dissolved in water to obtain a 0.2M solution, which was treated with sat. aq. NaHCO$_3$ until pH 7 was reached. The mixture was then extracted with ether, organic layers were combined, dried over MgSO$_4$ and the solvent was removed under reduced pressure to afford the desired 2-amino-thiazole derivative.

General Procedure U: Sandmeyer Reaction:

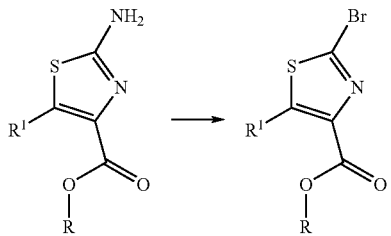

In a flame dried round-bottomed flask equipped with a magnetic stir bar and under an inert atmosphere (N$_2$) atmosphere, a 0.18M solution of CuBr$_2$ (0.97 eq.) in AcCN was carefully treated with isoamylnitrite (1.45 eq.) at 5° C. The reaction mixture was stirred for 30 min and the 2-amino-thiazole-4-carboxylic acid ester derivative (0.86 eq.) was then added portionwise. The resulting mixture was stirred at rt for 15 min, then at 40° C. for 30 min and at 65° C. for 1 h. The solvent was removed under reduced pressure and the residue was purified by FC to afford the desired bromo derivative.

General Procedure V: Dehalogenation

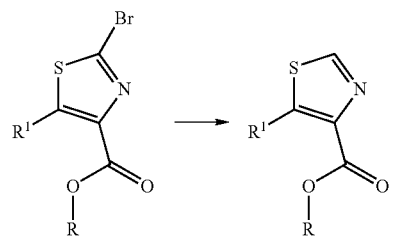

In a flame dried round-bottomed flask equipped with a magnetic stir bar and under an H$_2$ atmosphere, a 0.16M solution of the bromide (1.0 eq.), in EtOH was reduced with Pd/C (10% Pd, 200 mg for 1 mmol of the bromide). The reaction mixture was filtered over Celite and the solvent was removed under reduced pressure to afford the desired reduced derivative.

General Procedure W: Esterification

In a flame dried round-bottomed flask equipped with a magnetic stir bar and under inert atmosphere (N$_2$), a 1M solution of the acid (1.0 eq) in MeOH was treated at 0° C. with thionylchloride (1.1 eq). The resulting mixture was then stirred at rt overnight. The volatiles were removed under reduced pressure and the residue was triturated in EA and filtered to give the desired compound. Purification of the residue by FC or HPLC gave the desired compound.

General Procedure X: Amide Coupling:

In a flame dried round-bottomed flask equipped with a magnetic stir bar and under inert atmosphere (N$_2$), a 0.2M solution of the acid (1.0 eq) in CH$_2$Cl$_2$ was treated at 0° C. with HOBt (1.1 eq), DCC (1.1 eq) N-methylmorpholine (1.5 eq) and the amine (1 eq). The resulting mixture was stirred at rt for 2 h, poured in 5% KHSO$_4$, stirred for 15 min, filtered and washed with CH$_2$Cl$_2$. The aqueous phase was extracted with CH$_2$Cl$_2$ and the combined organic phases were washed with sat. aq. NaHCO$_3$, brine, dried over MgSO$_4$, filtered, and the solvent removed under reduced pressure. Purification of the residue gave the title compound.

General Procedure Y: Cyclization

In a flame dried round-bottomed flask equipped with a magnetic stir bar and under inert atmosphere (N$_2$), a 0.13M solution of the amide (1 eq) in CH$_2$Cl$_2$ was treated at 0° C. with Dess-Martin periodinane (1.0 eq). The resulting mixture was stirred at rt for 1 h and filtered through a short plug of basic alumina (activity I) and sand into a flask containing a freshly prepared solution of triphenylphosphine (2.02 eq), I$_2$ (2.0 eq) and Et$_3$N (4.0 eq) in CH$_2$Cl$_2$ (same amount as in the oxidation step). The filter cake was washed with CH$_2$Cl$_2$. After 15 min, the reaction mixture was transferred to a separatory funnel, treated with sat. aq. Na$_2$S$_2$O$_3$ and extracted with CH$_2$Cl$_2$. The organic layer was washed with sat. aq. NaHCO$_3$, filtered, and the solvent was removed under reduced pressure. Purification of the residue gave the desired compound.

General Procedure Z: Ester hydrolysis

A 0.2M solution of the respective carboxylic acid ester (1.0 eq.) in a 1:1 mixture of THF and the corresponding alkyl alcohol, e.g. MeOH or EtOH, was treated with 1M aq. NaOH (5.0 eq.) and the reaction mixture was stirred at rt until completion. The reaction mixture was acidified (pH=3-4) by addition of 1M aq. HCl and the mixture was extracted with EtOAc. The combined org. extracts were dried over MgSO$_4$, filtered, and the solvents were removed under reduced pressure to afford the desired carboxylic acid derivative after drying.

General Procedure Z1: Amide Coupling

In a glass vial, under inert atmosphere ($N_2$), a 0.04M solution of the lithium carboxylate (1.0 eq.) in DMF was treated with HATU (1.0 eq) and the reaction mixture was stirred at rt for 10 min. A 0.07M solution of the amine (1.0 eq) in DMF was then added followed by DIPEA (2.84 eq) and the resulting mixture was stirred at rt until completion. Water was added and the aq. layer was extracted twice with EtOAc. The combined org. extracts were dried over $Na_2SO_4$, filtered, and the solvents were removed under reduced pressure. Purification of the residue by FC or HPLC gave the desired compound.

Synthesis of Intermediates 5-(4-Nitro-[1,2,3]triazol-2-ylmethyl)-furan-2-carboxylic acid methyl ester In a flame dried round-bottomed flask equipped with a magnetic stir bar and under inert atmosphere ($N_2$), a solution of 4-nitro-2H-[1,2,3]triazole (1.50 g, 13.15 mmol) in acetone (26.3 mL) was treated with 5-chloromethyl-furan-2-carboxylic acid methyl ester (2.66 g, 14.47 mmol) followed by $K_2CO_3$ (9.18 g, 65.75 mmol) and TBA bromide (848 mg, 2.63 mmol). The reaction mixture was stirred at rt overnight. The solvent was removed under reduced pressure, water (50 mL) was added and the product was extracted with EA (3×30 mL) and the combined org. extracts were dried over $MgSO_4$, filtered, and the solvents were removed under reduced pressure. Purification of the residue by FC (50:50 hept-EA) gave the title compound as a yellow oil: TLC:rf (50:50 hept-EA)=0.22. LC-MS-conditions 02: $t_R$=0.90 min.

[5-(4-Nitro-[1,2,3]triazol-2-ylmethyl)-furan-2-yl]-methanol

In a flame dried round-bottomed flask equipped with a magnetic stir bar and under inert atmosphere ($N_2$), a solution of 5-(4-nitro-[1,2,3]triazol-2-ylmethyl)-furan-2-carboxylic acid methyl ester (325 mg, 1.28 mmol) in THF (13.0 mL) was treated dropwise, at −10° C. with DiBAL (4.36 mL of a 1M solution in toluene, 4.36 mmol). The reaction mixture was stirred at −10° C. for 1 h followed by 1 h at rt. Sat. aq. Rochelle's salt (40 mL) was added and the reaction mixture was stirred for 1 h at rt. The aq. layer was extracted with EA (2×30 mL). The combined org. extracts were dried over $MgSO_4$, filtered, and the solvents were removed under reduced pressure. Purification of the residue by FC (50:50 hept-EA) gave the title compound: TLC:rf (50:50 hept-EA)=0.28. LC-MS-conditions 02: $t_R$=0.77 min.

5-(4-Nitro-[1,2,3]triazol-2-ylmethyl)-furan-2-carbaldehyde

In a flame dried round-bottomed flask equipped with a magnetic stir bar and under inert atmosphere ($N_2$), a solution of [5-(4-nitro-[1,2,3]triazol-2-ylmethyl)-furan-2-yl]-methanol (248 mg, 1.11 mmol) in AcCN (11.0 mL) was treated at rt with $MnO_2$ (644 mg, 6.67 mmol). The reaction mixture was stirred at rt overnight before being filtered through Celite and the solvent was removed under reduced pressure. Purification of the residue by FC (40:60 hept-EA) gave the title compound: TLC:rf (40:60 hept-EA)=0.26. LC-MS-conditions 02: $t_R$=0.84 min.

1-[5-(4-Nitro-[1,2,3]triazol-2-ylmethyl)-furan-2-yl]-ethanol

In a flame dried round-bottomed flask equipped with a magnetic stir bar and under inert atmosphere ($N_2$), a solution of 5-(4-nitro-[1,2,3]triazol-2-ylmethyl)-furan-2-carbaldehyde (180 mg, 0.81 mmol) in $CH_2Cl_2$ (8.0 mL) was treated at −10° C. with trimethylaluminum (0.32 mL of a 2M solution in heptane, 0.64 mmol). The reaction mixture was stirred at 0° C. for 2 h then poured on sat. aq. $NH_4Cl$ (5 mL), diluted with $CH_2Cl_2$ (10.0 mL) followed by 1N HCl (10 mL). The mixture was extracted with $CH_2Cl_2$ (2×20 mL). The combined org. extracts were dried over $MgSO_4$, filtered, and the solvents were removed under reduced pressure. Purification of the residue by FC (50:50 hept-EA) gave the title compound as a yellow oil: TLC:rf (50:50 hept-EA)=0.31. LC-MS-conditions 02: $t_R$=0.82 min.

1-[5-(4-Nitro-[1,2,3]triazol-2-ylmethyl)-furan-2-yl]-ethanone

In a flame dried round-bottomed flask equipped with a magnetic stir bar and under inert atmosphere ($N_2$), a solution of 1-[5-(4-nitro-[1,2,3]triazol-2-ylmethyl)-furan-2-yl]-ethanol (98 mg, 0.41 mmol) in AcCN (4.0 mL) was treated at rt with $MnO_2$ (238 mg, 2.47 mmol) and the reaction mixture was stirred for 2 days at rt before being filtered though Celite. The solvent was removed under reduced pressure to give the title compound as a white solid. LC-MS-conditions 02: $t_R$=0.86 min.

2-[5-(2-Methyl-[1,3]dioxolan-2-yl)-furan-2-ylmethyl]-4-nitro-2H-[1,2,3]triazole

In a flame dried round-bottomed flask equipped with a magnetic stir bar and a Dean-Stark under inert atmosphere ($N_2$), a solution of 1-[5-(4-nitro-[1,2,3]triazol-2-ylmethyl)-furan-2-yl]-ethanone (180 mg, 0.76 mmol) in ethylene glycol (0.85 mL, 15.24 mmol) was treated with trimethylorthoformate (0.17 mL, 1.52 mmol) and lithium tetrafluoroborate (14 mg, 0.15 mmol). The resulting mixture was heated to 95° C. overnight. The reaction mixture was allowed to cool to rt. $NaHCO_3$ (10 mL) and EA (10 mL) were added and the aq. phase was extracted with EA (2×10 mL). The combined org. extracts were washed with brine (10 mL), dried over $MgSO_4$, filtered, and the solvents were removed under reduced pressure. Purification of the residue by FC (60:30 hept-EA) gave the title compound as a colorless oil: TLC:rf (60:30 hept-EA)=0.31. LC-MS-conditions 02: $t_R$=0.94 min; $[M+H]^+$=281.01.

2-[5-(2-Methyl-[1,3]dioxolan-2-yl)-furan-2-ylmethyl]-2H-[1,2,3]triazol-4-ylamine In a flame dried round-bottomed flask equipped with a magnetic stir bar and under inert atmosphere ($N_2$), a mixture of 2-[5-(2-methyl-[1,3]dioxolan-2-yl)-furan-2-ylmethyl]-4-nitro-2H-[1,2,3]triazole (218 mg, 0.78 mmol), iron powder (132 mg, 2.33 mmol) and $NH_4Cl$ (210 mg, 3.89 mmol) in a mixture of EtOH (4.0 mL) and water (2.0 mL) was stirred at 75° C. for 0.5 h. The reaction mixture was filtered while hot and concentrated under reduced pressure. $CH_2Cl_2$ (20 mL) was added followed by 1M NaOH (20 mL). The aq. layer was extracted with $CH_2Cl_2$ (2×20 mL). The combined org. extracts were dried over $MgSO_4$, filtered, and the solvents were removed under reduced pressure to give the title compound as a yellow oil. LC-MS-conditions 02: $t_R$=0.71 min; $[M+H]^+$=251.16.

2-Furan-2-yl-2-methyl-[1,3]dioxolane

In a flame dried round-bottomed flask equipped with a magnetic stir bar and under inert atmosphere ($N_2$), a solution of 1-furan-2-yl-ethanone (50.00 g, 454.0 mmol) in ethylene glycol (500.0 mL) was treated with trimethylorthoformate (100.0 mL, 908.0 mmol) followed by LiBF$_4$ (7.00 g, 75 mmol). The reaction mixture was heated at 95° C. overnight. Sat. aq. NaHCO$_3$ (500 mL) was added and the mixture was extracted with EA (500 mL). The org. extracts were washed with brine (2×250 mL), dried over MgSO$_4$, filtered, and the solvent was removed under reduced pressure. Purification of the residue by distillation (11 mbar, 71-73° C.) gave the title compound as a colorless oil.

[5-(2-Methyl-[1,3]dioxolan-2-yl)-furan-2-yl]-methanol

In a flame dried round-bottomed flask equipped with a magnetic stir bar and under inert atmosphere (N$_2$), to a solution of n-BuLi (14.6 mL of a 1.6M solution in hexane, 23.35 mmol) in THF (21 mL) at −78° C. was added dropwise a solution of 2-furan-2-yl-2-methyl-[1,3]dioxolane (3.00 g, 19.46 mmol) in THF (6.0 mL). The reaction mixture was then stirred for 1 h at −78° C. before DMF (4.52 mL, 58.38 mmol) was added dropwise. The reaction mixture was stirred for 1 h at −78° C. Sat. aq. NH$_4$Cl (50 mL) was added and the mixture was extracted with EA (2×50 mL). The combined org. extracts were dried over MgSO$_4$, filtered, and the solvent was removed under reduced pressure to give 5.91 g of crude 5-(2-methyl-[1,3]dioxolan-2-yl)-furan-2-carbaldehyde as an orange oil. LC-MS-conditions 02: $t_R$=0.75 min; [M+H]$^+$= 183.23. The crude material was dissolved, under inert atmosphere (N$_2$) in MeOH (59.0 mL) and treated at 0° C., portionwise, over 20 min, with NaBH$_4$ (1.53 g, 38.92 mmol in five equal portions). The reaction mixture was stirred for 45 min at rt. The reaction mixture was poured on water (80 mL) and the aq. layer was extracted with EA (2×60 mL). The combined org. extracts were dried over MgSO$_4$, filtered, and the solvents were removed under reduced pressure. Purification of the residue by FC (50:50 hept-EA) gave the title compound: TLC:rf (50:50 hept-EA)=0.27. LC-MS-conditions 02: $t_R$=0.65 min; [M+H]$^+$=185.28.

2-[5-(2-Methyl-[1,3]dioxolan-2-yl)-furan-2-ylmethyl]-4-nitro-2H-[1,2,3]triazole

In a flame dried round-bottomed flask equipped with a magnetic stir bar and under inert atmosphere (N$_2$), a solution of [5-(2-methyl-[1,3]dioxolan-2-yl)-furan-2-yl]-methanol (3.20 g, 17.37 mmol) in dry CH$_2$Cl$_2$ (32.0 mL) was treated at 0° C. with Et$_3$N (3.14 mL, 22.59 mmol) followed by DMAP (212 mg, 1.74 mmol) and Ms-Cl (1.62 mL, 20.85 mmol). After stirring at rt for 2 h, the reaction mixture was quenched with water (30 mL), extracted with CH$_2$Cl$_2$ (30 mL) and the combined org. extracts were dried over MgSO$_4$, filtered, and the solvents were removed under reduced pressure to give 4.49 g of crude 2-(5-chloromethyl-furan-2-yl)-2-methyl-[1,3]dioxolane as an brown oil. The crude material in acetone (43 mL) was treated, under inert atmosphere (N$_2$) with 4-nitro-2H-[1,2,3]triazole (1.97 g, 17.27 mmol), K$_2$CO$_3$ (7.16 g, 51.82 mmol) followed by TBA bromide (1.11 g, 3.45 mmol). The reaction mixture was stirred for 2 days at rt. Water (30 mL), followed by EA (40 mL) was added. The aq. layer was extracted with EA (40 mL) and the combined org. extracts were dried over MgSO$_4$, filtered, and the solvents were removed under reduced pressure. Purification of the residue by FC (60:40 hept-EA) gave the title compound as an orange oil: TLC:rf (60:40 hept-EA)=0.28. LC-MS-conditions 02: $t_R$=0.95 min; [M+H]$^+$=281.01.

2-(5-Chloromethyl-furan-2-yl)-2-methyl-[1,3]dioxolane

In a flame dried round-bottomed flask equipped with a magnetic stir bar and under inert atmosphere (N$_2$), a solution of [5-(2-methyl-[1,3]dioxolan-2-yl)-furan-2-yl]-methanol (3.50 g, 19.00 mmol) in dry CH$_2$Cl$_2$ (35.0 mL) was treated at 0° C. with Et$_3$N (3.44 mL, 22.80 mmol) followed by DMAP (232 mg, 1.90 mmol) and Ms-Cl (1.77 mL, 22.80 mmol). After stirring at rt for 2 h, the reaction mixture was quenched with water (40 mL), extracted with CH$_2$Cl$_2$ (40 mL) and the combined org. extracts were dried over MgSO$_4$, filtered, and the solvents were removed under reduced. Purification of the residue by FC (8:2:0.1 hept-EA-Et$_3$N) gave the title compound as a yellow oil: TLC:rf (4:1 hept-EA)=0.35.

2-[5-(2-Methyl-[1,3]dioxolan-2-yl)-furan-2-ylmethyl]-4-nitro-2H-[1,2,3]triazole

In a flame dried round-bottomed flask equipped with a magnetic stir bar and under inert atmosphere (N$_2$), a solution of 4-nitro-2H-[1,2,3]triazole (875 mg, 7.67 mmol) in DMF (7.0 mL) was treated at rt with DIPEA (2.63 mL, 15.34 mmol). After 30 min, a solution of 2-(5-chloromethyl-furan-2-yl)-2-methyl-[1,3]dioxolane (1.87 g, 9.21 mmol) in DMF (7.0 mL) was added and the reaction mixture was stirred for 16 h at 50° C. Water (100 mL), followed by EA (100 mL) were added. The aq. layer was extracted with EA (100 mL) and the combined org. extracts were dried over MgSO$_4$, filtered, and the solvents were removed under reduced pressure. Purification of the residue by FC (2:1 hept-EA) gave the title compound as an orange oil: TLC:rf (2:1 hept-EA)=0.26. LC-MS-conditions 02: $t_R$=0.95 min; [M+H]$^+$=281.01.

6-Bromo-hexan-2-one

In a flame dried round-bottomed flask equipped with a magnetic stir bar and under inert atmosphere (N$_2$), a solution of commercially available 1-methylcyclopentanol (4.00 g, 39.94 mmol) in CHCl$_3$ (130 mL) at 0° C. was treated with K$_2$CO$_3$ (33.11 g, 239.62 mmol) and the reaction mixture was stirred for 15 min. Bromine (10.23 mL, 199.68 mmol) was then added and the reaction mixture was stirred at 0° C. for 2.5 h. The reaction mixture was slowly poured to an ice-chilled sat. aq. Na$_2$S$_2$O$_3$ solution (100 mL). The org. layer was washed with water (2×100 mL), dried over MgSO$_4$, filtered, and the solvent was removed under reduced pressure. Purification of the residue by FC (gradient hept→75:25 hept-EA) gave the title compound as a yellow oil: TLC:rf (75:25 hept-EA)=0.36. $^1$H NMR (400 MHz, CDCl$_3$) δ1.66-1.80 (m, 2H), 1.82-1.93 (m, 2H), 2.15 (s, 3H), 2.48 (t, J=7.3 Hz, 2H), 3.41 (t, J=6.5 Hz, 2H).

2-(4-Bromo-butyl)-2-methyl-[1,3]dioxolane

In a flame dried round-bottomed flask equipped with a magnetic stir bar and a Dean-Stark under inert atmosphere (N$_2$), a solution of 6-bromo-hexan-2-one (3.34 g, 18.65 mmol) in toluene (71.3 mL) was treated with ethylene glycol (10.4 mL, 186.92 mmol) and TsOH (35 mg, 0.19 mmol). The reaction mixture was heated to reflux for 3 h, allowed to cool to rt and sat. aq. NaHCO$_3$ (100 mL) and ether (100 mL) were added and the aq. phase was washed with water (2×100 mL), dried over MgSO$_4$, filtered, and the solvents were removed under reduced pressure to give the title compound. $^1$H NMR (400 MHz, CDCl$_3$) δ1.34 (s, 3H), 1.50-1.65 (m, 2H), 1.65-1.75 (m, 2H), 1.84-1.98 (m, 2H), 3.43 (t, J=6.8 Hz, 2H), 3.90-4.04 (m, 4H).

2-[4-(2-Methyl-[1,3]dioxolan-2-yl)-butyl]-4-nitro-2H-[1,2,3]triazole

In a flame dried round-bottomed flask equipped with a magnetic stir bar and under inert atmosphere (N$_2$), a solution of 4-nitro-2H-[1,2,3]triazole (100 mg, 0.88 mmol) and Cs$_2$CO$_3$ (315 mg, 0.96 mmol) in AcCN (1.0 mL) was treated with a solution of 2-(4-bromo-butyl)-2-methyl-[1,3]dioxolane (215 mg, 0.96 mmol) in AcCN (1.0 mL). The reaction mixture was stirred at 80° C. for 16 h. Water (20 mL), followed by EA (30 mL) were added. The aq. layer was extracted with EA (30 mL) and the combined org. extracts were dried over MgSO$_4$, filtered, and the solvents were removed under reduced pressure. Purification of the residue by FC (2:1 hept-EA) gave the title compound: TLC:rf (2:1 hept-EA)=0.33. LC-MS-conditions 02: $t_R$=0.92 min.

2-[4-(2-Methyl-[1,3]dioxolan-2-yl)-butyl]-2H-[1,2,3] triazol-4-ylamine

In a flame dried round-bottomed flask equipped with a magnetic stir bar and under inert atmosphere (N$_2$), a mixture of 2-[4-(2-methyl-[1,3]dioxolan-2-yl)-butyl]-4-nitro-2H-[1,2,3]triazole (250 mg, 0.98 mmol), iron powder (165 mg, 2.93 mmol) and NH$_4$Cl (264 mg, 4.88 mmol) in a mixture of EtOH (3.0 mL) and water (1.5 mL) was stirred at 85° C. for 30 min. The reaction mixture was filtered while hot and concentrated under reduced pressure. CH$_2$Cl$_2$ (20 mL) was added followed by water (20 mL). The aq. layer was extracted with CH$_2$Cl$_2$ (2×20 mL) and the combined org. extracts were dried over MgSO$_4$, filtered, and the solvents were removed under reduced pressure to give the title compound as a pale yellow oil. LC-MS-conditions 02: $t_R$=0.66 min; [M+H]$^+$=227.47.

[5-(2-Methyl-[1,3]dioxolan-2-yl)-thiophen-2-yl]-methanol

In a flame dried round-bottomed flask equipped with a magnetic stir bar and under inert atmosphere (N$_2$), to a solution of commercially available 2-methyl-2-thiophen-2-yl-[1,3]dioxolane (5.00 g, 28.49 mmol) in THF (145.0 mL) at −78° C. was added dropwise N,N,N',N'-tetramethyl-ethylendiamine (4.41 mL, 29.06 mmol) followed by n-BuLi (18.14 mL of a 1.6M solution in hexane, 29.06 mmol), maintaining the temperature at −78° C. The reaction mixture was then stirred for 2 h at −78° C. before DMF (6.74 mL, 87.22 mmol) was added dropwise. The cooling bath was removed and the reaction mixture was stirred for 16 h. The reaction mixture was poured on sat. aq. NaH$_4$Cl (200 mL) and extracted with EA (2×200 mL). The combined org. extracts were dried over MgSO$_4$, filtered, and the solvent was removed under reduced pressure to give crude 5-(2-methyl-[1,3]dioxolan-2-yl)-thiophene-2-carbaldehyde as an yellow oil. LC-MS-conditions 02: $t_R$=0.87 min; [M+AcCN]$^+$=240.32. The crude material was dissolved, under inert atmosphere (N$_2$) in MeOH (51.2 mL) and treated at 0° C., portionwise, over 20 min, with NaBH$_4$ (1.35 g, 34.19 mmol in five equal portions). The reaction mixture was stirred for 45 min at rt. The reaction mixture was poured on water (90 mL) and the aq. layer was extracted with EA (2×225 mL). The combined org. extracts were dried over MgSO$_4$, filtered, and the solvents were removed under reduced pressure. Purification of the residue by FC (50:50 hept-EA) gave the title compound: TLC:rf (50:50 hept-EA)=0.40. LC-MS-conditions 02: $t_R$=0.73 min; [M+H]$^+$=201.46.

2-[5-(2-Methyl-[1,3]dioxolan-2-yl)-thiophen-2-ylmethyl]-4-nitro-2H-[1,2,3]triazole In a flame dried round-bottomed flask equipped with a magnetic stir bar and under inert atmosphere (N$_2$), a solution of [5-(2-methyl-[1,3]dioxolan-2-yl)-thiophen-2-yl]-methanol (2.5 g, 12.48 mmol) in dry CH$_2$Cl$_2$ (25.0 mL) was treated at 0° C. with Et$_3$N (2.26 mL, 16.23 mmol) followed by DMAP (152 mg, 1.25 mmol) and Ms-Cl (1.16 mL, 14.98 mmol). The reaction mixture was stirred at rt for 2 h before being quenched with water (30 mL), extracted with CH$_2$Cl$_2$ (50 mL) and the combined org. extracts were dried over MgSO$_4$, filtered, and the solvents were removed under reduced pressure to give 2.16 g of crude 2-(5-chloromethyl-thiophen-2-yl)-2-methyl-[1,3]dioxolane as a yellow oil. A solution of the crude material 2.11 g) in DMF (15 mL) was treated at rt with a solution of (4-nitro-2H-[1,2,3]triazole (226 mg, 2.00 mmol) in DMF (15.0 mL) pretreated for 30 min with DIPEA (2.76 mL, 16.13 mmol). The resulting mixture was stirred overnight at 50° C. Water (100 mL), followed by EA (100 mL) were added. The org. extract was washed with water (100 mL), dried over MgSO$_4$, filtered, and the solvents were removed under reduced pressure. Purification of the residue by FC (2:1 hept-EA) gave the title compound as a white solid: TLC:rf (2:1 hept-EA)=0.17. LC-MS-conditions 02: $t_R$=0.98 min; [M+H]$^+$=297.08.

2-[5-(2-Methyl-[1,3]dioxolan-2-yl)-thiophen-2-ylmethyl]-2H-[1,2,3]triazol-4-ylamine In a flame dried round-bottomed flask equipped with a magnetic stir bar and under inert atmosphere (N$_2$), a mixture of 2-[5-(2-methyl-[1,3]dioxolan-2-yl)-thiophen-2-ylmethyl]-4-nitro-2H-[1,2,3]triazole (1.09 g, 3.68 mmol), iron powder (623 mg, 11.05 mmol) and NH$_4$Cl (995 mg, 18.41 mmol) in a mixture of EtOH (10.0 mL) and water (5.0 mL) was stirred at 85° C. for 20 min. The reaction mixture was filtered while hot and concentrated under reduced pressure. CH$_2$Cl$_2$ (30 mL) was added followed by 1M NaOH (20 mL). The aq. layer was extracted with CH$_2$Cl$_2$ (2×20 mL) and the combined org. extracts were dried over MgSO$_4$, filtered, and the solvents were removed under reduced pressure to give the title compound as a yellow oil. LC-MS-conditions 02: $t_R$=0.78 min; [M+H]$^+$=267.30.

1-(3-Bromo-phenyl)-ethanone

In a flame dried round-bottomed flask equipped with a magnetic stir bar and under inert atmosphere (N$_2$), a suspension of 1,3-dibromobenzene (2.45 g, 10.07 mmol) in THF (25.0 mL) was treated at −78° C. with n-BuLi (4.0 mL of a 2.5M solution in hexane, 10.00 mmol). The reaction mixture was stirred for 30 min before N,N-dimethylacetaminde (1.50 mL, 16.13 mmol) was added and the solution was then allowed to warm to rt over 1 h. Sat. aq. NH$_4$Cl was then added and the aq. layer was extracted with Et$_2$O (3×50 mL) and the combined org. extracts were dried over Na$_2$SO$_4$, filtered, and the solvents were removed under reduced pressure. Purification of the residue by FC (20:1 hept-EA) gave the title compound as a white solid: TLC:rf (10:1 hept-EA)=0.28. LC-MS-conditions 02: $t_R$=0.95 min.

2-(3-Bromo-phenyl)-2-methyl-[1,3]dioxolane

In a flame dried round-bottomed flask equipped with a magnetic stir bar and under inert atmosphere (N$_2$), a solution of 1-(3-bromo-phenyl)-ethanone (1360 mg, 6.83 mmol) in ethylene glycol (8.00 mL, 143.46 mmol) was treated with trimethylorthoformate (1.50 mL, 13.68 mmol) followed by LiBF$_4$ (131 mg, 1.37 mmol). The reaction mixture was heated at 95° C. for 15 h. Sat. aq. Na$_2$CO$_3$ was added and the mixture was extracted twice with ether and the combined organic extracts were dried over Na$_2$SO$_4$, filtered, and the solvent was removed under reduced pressure. Purification of the residue by FC (20:1 hept-EA) gave the title compound as a pale yellow oil: TLC:rf (10:1 hept-EA)=0.34. LC-MS-conditions 02: $t_R$=1.01 min.

3-(2-Methyl-[1,3]dioxolan-2-yl)-benzaldehyde

In a flame dried round-bottomed flask equipped with a magnetic stir bar and under inert atmosphere (N$_2$), to a solution of 2-(3-bromo-phenyl)-2-methyl-[1,3]dioxolane (944 mg, 3.88 mmol) in THF (20.0 mL) at −78° C. was added dropwise n-BuLi (1.60 mL of a 2.5M solution in hexane, 4.00 mmol). The reaction mixture was then stirred for 30 min at −78° C. before DMF (0.40 mL, 5.17 mmol) was added dropwise. The reaction mixture was allowed to warm to rt over 1 h. Sat. aq. NH$_4$Cl was added and the mixture was extracted three times with Et$_2$O. The combined org. extracts were dried over NaSO$_4$, filtered, and the solvent was removed under reduced pressure to give the crude title compound as a pale yellow oil. LC-MS-conditions 02: $t_R$=0.87 min.

[3-(2-Methyl-[1,3]dioxolan-2-yl)-phenyl]-methanol

In a flame dried round-bottomed flask equipped with a magnetic stir bar and under inert atmosphere (N$_2$), to a ice-cold solution of 3-(2-methyl-[1,3]dioxolan-2-yl)-benzaldehyde (896 mg, 4.66 mmol) in MeOH (10.0 mL) was added NaBH$_4$ (228 mg, 5.79 mmol in four equal portion). The reaction mixture was then stirred for 1 h at rt. Water was added and the mixture was extracted twice with EA. The combined org. extracts were washed with brine, dried over Na$_2$SO$_4$, filtered, and the solvent was removed under reduced pressure to give the title compound as a colorless oil: TLC:rf (50:50 hept-EA)=0.28. LC-MS-conditions 02: $t_R$=0.74 min; [M+H]$^+$=195.71.

Methanesulfonic acid 3-(2-methyl-[1,3]dioxolan-2-yl)-benzyl ester

In a flame dried round-bottomed flask equipped with a magnetic stir bar and under inert atmosphere (N$_2$), a solution of [3-(2-methyl-[1,3]dioxolan-2-yl)-phenyl]-methanol (786 mg, 4.05 mmol) in dry CH$_2$Cl$_2$ (10.0 mL) was treated at 0° C. with Et$_3$N (0.75 mL, 5.33 mmol) followed by DMAP (49 mg, 0.41 mmol) and Ms-Cl (0.40 mL, 5.15 mmol). After stirring at 0° C. for 1 h, the reaction mixture was quenched with water (10 mL), extracted with CH$_2$Cl$_2$ (10 mL) and the combined org. extracts were dried over Na$_2$SO$_4$, filtered, and the solvents were removed under reduced pressure. Purification of the residue by FC (80:20 to 20:10 hept-EA) gave the title compound as a white solide. LC-MS-conditions 02: $t_R$=0.91 min.

2-[3-(2-Methyl-[1,3]dioxolan-2-yl)-benzyl]-4-nitro-2H-[1,2,3]triazole

In a flame dried round-bottomed flask equipped with a magnetic stir bar and under inert atmosphere (N$_2$), a solution of 4-nitro-2H-[1,2,3]triazole (50 mg, 0.43 mmol) in DMF (1.0 mL) was treated with DIPEA (0.15 mL, 0.87 mmol). After 30 min, a solution of methanesulfonic acid 3-(2-methyl-[1,3]dioxolan-2-yl)-benzyl ester (106 mg, 0.52 mmol) in DMF (1.0 mL) was added and the reaction mixture was stirred for 3 days at 50° C. Water (10 mL), followed by EA (10 mL) were added. The aq. layer was extracted with EA (10 mL) and the combined org. extracts were dried over Na$_2$SO$_4$, filtered, and the solvents were removed under reduced pressure. Purification of the residue by FC (2:1 hept-EA) gave the title compound as a colorless oil: TLC:rf (1:2 hept-EA)=0.42. LC-MS-conditions 02: $t_R$=0.99 min.

2-[3-(2-Methyl-[1,3]dioxolan-2-yl)-benzyl]-2H-[1,2,3]triazol-4-ylamine

In a flame dried round-bottomed flask equipped with a magnetic stir bar and under inert atmosphere (N$_2$), a mixture of 2-[3-(2-methyl-[1,3]dioxolan-2-yl)-benzyl]-4-nitro-2H-[1,2,3]triazole (33 mg, 0.11 mmol), iron powder (19 mg, 0.34 mmol) and NH$_4$Cl (31 mg, 0.57 mmol) in a mixture of EtOH (2.0 mL) and water (1.0 mL) was stirred at 75° C. for 1 h. The reaction mixture was filtered while hot and concentrated under reduced pressure. CH$_2$Cl$_2$ (10 mL) was added followed by 1N NaOH (10 mL). The aq. layer was extracted with CH$_2$Cl$_2$ (2×10 mL) and the combined org. extracts were dried over Na$_2$SO$_4$, filtered, and the solvents were removed under reduced pressure to give the title compound as a yellow oil. LC-MS-conditions 02: $t_R$=0.78 min; [M+H]$^+$=261.13.

6-(4-Nitro-[1,2,3]triazol-2-yl)-hexan-2-one

In a flame dried round-bottomed flask equipped with a magnetic stir bar and under inert atmosphere (N$_2$), a suspension of 4-nitro-2H-[1,2,3]triazole (114 mg, 1.00 mmol) in DMF (1.0 mL) was treated with DIPEA (0.34 mL, 2.00 mmol). After 30 min, a solution of 6-bromo-hexan-2-one (179 mg, 1.00 mmol) in DMF (1.0 mL) was added and the reaction mixture was stirred for 24 h at 50° C. Water (10 mL), followed by EA (10 mL) were added. The aq. layer was extracted with EA (10 mL) and the combined org. extracts were dried over Na$_2$SO$_4$, filtered, and the solvents were removed under reduced pressure. Purification of the residue by FC (2:1 hept-EA) gave the title compound as a yellow oil: TLC:rf (2:1 hept-EA)=0.26. LC-MS-conditions 02: $t_R$=0.86 min.

2-(5,5-Difluoro-hexyl)-4-nitro-2H-[1,2,3]triazole

In a flame dried round-bottomed flask equipped with a magnetic stir bar and under inert atmosphere (N$_2$), a solution of 6-(4-nitro-[1,2,3]triazol-2-yl)-hexan-2-one (118 mg, 0.56 mmol) was dissolved at rt in (diethylamino)sulphur trifluoride (0.15 mL, 1.11 mmol) and the reaction mixture was stirred overnight at 50° C. The reaction mixture was poured on ice (20 mL) and the mixture was extracted with CH$_2$Cl$_2$ (2×20 mL), washed with water (30 mL), brine (30 mL), dried over MgSO$_4$, filtered, and the solvents were removed under reduced pressure. Purification of the residue by FC (4:1 hept-EA) gave the title compound as a yellow oil: TLC:rf (4:1 hept-EA)=0.32. LC-MS-conditions 02: $t_R$=1.01 min.

2-(5,5-Difluoro-hexyl)-2H-[1,2,3]triazol-4-ylamine

In a flame dried round-bottomed flask equipped with a magnetic stir bar and under inert atmosphere (N$_2$), a mixture of 2-(5,5-difluoro-hexyl)-4-nitro-2H-[1,2,3]triazole (71 mg, 0.30 mmol), iron powder (51 mg, 0.91 mmol) and NH$_4$Cl (82 mg, 1.52 mmol) in a mixture of EtOH (1.0 mL) and water (0.5 mL) was stirred at 85° C. for 20 min. The reaction mixture was filtered while hot and concentrated under reduced pressure. CH$_2$Cl$_2$ (10 mL) was added followed by water (10 mL). The aq. layer was extracted with CH$_2$Cl$_2$ (2×10 mL) and the combined org. extracts were dried over MgSO$_4$, filtered, and the solvents were removed under reduced pressure to give the title compound as a yellow oil. LC-MS-conditions 02: $t_R$=0.79 min; [M+H]$^+$=205.54.

5-Methylsulfanyl-furan-2-carboxylic acid ethyl ester

In a flame dried round-bottomed flask equipped with a magnetic stir bar and under inert atmosphere (N$_2$), a solution of commercially available 5-nitro-furan-2-carboxylic acid ethyl ester (5.00 g, 27.01 mmol) in DMSO (34.5 mL) was treated at rt with sodium methanethiolate (2.05 g 27.82 mmol). The mixture was then stirred overnight at 100° C., treated at rt with sat. aq. NH$_4$Cl (250 mL) and the aqueous layer was extracted with EA (3×100 mL). The combined org. extracts were washed with sat. aq. NaHCO$_3$ (100 mL) and brine (100 mL), dried over MgSO$_4$, filtered, and the solvents were removed under reduced pressure. Purification of the residue by FC (70:30 hept-EA) gave the title compound: TLC:rf (70:30 hept-EA)=0.52. LC-MS-conditions 02: $t_R$=0.96 min; [M+AcCN+N+H]$^+$=228.23.

5-Methanesulfonyl-furan-2-carboxylic acid ethyl ester

In a flame dried round-bottomed flask equipped with a magnetic stir bar and under inert atmosphere (N$_2$), a solution of 5-methylsulfanyl-furan-2-carboxylic acid ethyl ester (1.74 g, 9.34 mmol) in CH$_2$Cl$_2$ (16.0 mL) was carefully treated at rt with m-CPBA (3.28 g, 13.32 mmol). The mixture was then stirred for 2 h at rt, treated at rt with sat. aq. Na$_2$CO$_3$ and the organic layer was washed with water and brine, dried over MgSO$_4$, filtered, and the solvents were removed under reduced pressure to give the title compound as a yellow solid. LC-MS-conditions 02: $t_R$=0.83 min.

(5-Methanesulfonyl-furan-2-yl)-methanol

In a flame dried round-bottomed flask equipped with a magnetic stir bar and under inert atmosphere (N$_2$), a solution of 5-methanesulfonyl-furan-2-carboxylic acid ethyl ester (1.26 g) in THF (57.0 mL) was treated at −78° C. with DiBAL-H (19.50 mL of a 1M solution in THF, 19.50 mmol) and the reaction mixture was stirred at this temperature for 2 h. The reaction mixture was poured on Rochelle's salt (100 mL) and stirred at rt for 12 h. The aq. layer was extracted with EA (2×100 mL). The combined org. extracts were dried over MgSO$_4$, filtered, and the solvents were removed under reduced pressure. Purification of the residue by FC (30:70 hept-EA) gave the title compound as a yellow oil: TLC:rf (30:70 hept-EA)=0.28. LC-MS-conditions 02: $t_R$=0.50 min.

2-(5-Methanesulfonyl-furan-2-ylmethyl)-4-nitro-2H-[1,2,3]triazole

In a flame dried round-bottomed flask equipped with a magnetic stir bar and under inert atmosphere (N$_2$), a solution of (5-methanesulfonyl-furan-2-yl)-methanol (692 mg, 3.93 mmol) in dry CH$_2$Cl$_2$ (7.0 mL) was treated at 0° C. with Et$_3$N (0.71 mL, 5.11 mmol) followed by DMAP (50 mg, 0.39 mmol) and Ms-Cl (0.37 mL, 4.71 mmol). After stirring at rt for 2 h, the reaction mixture was quenched with water (10 mL), extracted with CH$_2$Cl$_2$ (20 mL) and the combined org. extracts were dried over MgSO$_4$, filtered, and the solvents were removed under reduced pressure to give 868 mg of crude 2-chloromethyl-5-methanesulfonyl-furan as a yellow oil. 183 mg of this crude material in DMF (0.7 mL) was added to a solution of 4-nitro-2H-[1,2,3]triazole (90 mg, 0.79 mmol) in DMF (0.7 mL) pre-treated for 1 h with DIPEA (0.27 mL, 1.59 mmol) and the reaction mixture was stirred for 48 h at rt. Water (10 mL), followed by EA (10 mL) were added. The aq. layer was extracted with EA (10 mL) and the combined org. extracts were dried over Na$_2$SO$_4$, filtered, and the solvents were removed under reduced pressure. Purification of the residue by FC (4:6 hept-EA) gave the title compound as a yellow oil: TLC:rf (4:6 hept-EA)=0.36. LC-MS-conditions 02: $t_R$=0.85 min.

2-(5-Methanesulfonyl-furan-2-ylmethyl)-2H-[1,2,3]triazol-4-ylamine

In a flame dried round-bottomed flask equipped with a magnetic stir bar and under inert atmosphere (N$_2$), a mixture of 2-(5-methanesulfonyl-furan-2-ylmethyl)-4-nitro-2H-[1,2,3]triazole (62 mg, 0.23 mmol), iron powder (39 mg, 0.68 mmol) and NH$_4$Cl (62 mg, 1.14 mmol) in a mixture of EtOH (1.0 mL) and water (0.5 mL) was stirred at 85° C. for 30 min. The reaction mixture was filtered while hot and concentrated under reduced pressure. CH$_2$Cl$_2$ (10 mL) was added followed by water (10 mL). The aq. layer was extracted with CH$_2$Cl$_2$ (2×10 mL) and the combined org. extracts were dried over MgSO$_4$, filtered, and the solvents were removed under reduced pressure to give the title compound as a yellow oil. LC-MS-conditions 02: $t_R$=0.63 min; [M+H]$^+$=243.27.

4-Bromo-thiazole-2-carbaldehyde

In a flame dried round-bottomed flask equipped with a magnetic stir bar and under inert atmosphere (N$_2$), a solution of commercially available 2,4-dibromo-thiazole (3.50 g, 14.41 mmol) in dry Et$_2$O (120 mL) was treated with n-BuLi (5.9 mL of a 2.5M solution in hexanes, 14.72 mmol) at −78° C. The reaction mixture was stirred at this temperature for 30 min. N,N-Dimethylformamide (1.35 mL, 14.47 mmol) was then added and the mixture allowed to warm to rt over a period of 1 h. The reaction was quenched by the addition of sat. aq. NH$_4$Cl (50 mL). The layers were separated and the aq. layer extracted with Et$_2$O (3×50 mL). The combined org. extracts dried over Na$_2$SO$_4$, filtered, and the solvents were removed under reduced pressure. Purification of the residue by FC (10:1->3:1 hept-EA) gave the title compound as a pale yellow solid. TLC:rf (1:1 hept-EA)=0.21. LC-MS-conditions 02: $t_R$=0.81 min.

(4-Bromo-thiazol-2-yl)-methanol

In a flame dried round-bottomed flask equipped with a magnetic stir bar and under inert atmosphere (N$_2$), 4-bromo-thiazole-2-carbaldehyde (1.68 g, 8.75 mmol) was dissolved in MeOH (10 mL). NaBH$_4$ (428 mg, 10.86 mmol) was added portionwise at 0° C. and the reaction mixture stirred at rt for 1 h. Water (10 mL) was added and the mixture extracted with EA (3×20 mL). The combined org. extracts were dried over Na$_2$SO$_4$, filtered, and the solvents were removed under reduced pressure. Purification of the residue by FC (6:1->2:1 hept-EA) gave the title compound as a pale yellow solid. TLC:rf (1:1 hept-EA)=0.31. LC-MS-conditions 02: $t_R$=0.62 min [M+H]$^+$=194.31.

4-Bromo-2-(tert-butyl-dimethyl-silanyloxymethyl)-thiazole

In a flame dried round-bottomed flask equipped with a magnetic stir bar and under inert atmosphere ($N_2$), (4-bromo-thiazol-2-yl)-methanol (1.37 g, 7.06 mmol) was dissolved in dry $CH_2Cl_2$ (21 mL). tert-Butyldimethylsilyl chloride (1.17 g, 7.77 mmol) was added at 0° C. followed by imidazole (985 mg, 14.47 mmol). The reaction mixture was stirred at rt for 2 h. 10% Aq. $K_2CO_3$ (10 mL) was added, the layers separated and the aq. layer extracted with $CH_2Cl_2$ (2×20 mL). The combined org. extracts were dried over $MgSO_4$, filtered, and the solvent removed under reduced pressure to give the title compound as a colorless oil. TLC:rf (1:1 hept-EA)=0.80.

1-[2-(tert-Butyl-dimethyl-silanyloxymethyl)-thiazol-4-yl]-ethanone

In a flame dried round-bottomed flask equipped with a magnetic stir bar and under inert atmosphere ($N_2$), to a solution of 4-bromo-2-(tert-butyl-dimethyl-silanyloxymethyl)-thiazole (1.94 g, 6.29 mmol) in dry $Et_2O$ (50 mL) was added n-BuLi (2.76 mL of a 2.5M solution in hexanes, 6.92 mmol) at −78° C. The reaction mixture was then stirred for 30 min at −78° C. before N,N-dimethylacetamide (1.17 mL, 12.58 mmol) was added dropwise. The reaction mixture was allowed to warm up to rt over a period of 1 h and stirred at this temperature for 20 min. Sat. aq. $NH_4Cl$ (20 mL) was added, the layers separated and the aq. layer extracted with $Et_2O$ (3×30 mL). The combined org. extracts were dried over $Na_2SO_4$, filtered, and the solvent was removed under reduced pressure. Purification of the residue by FC (20:1->5:1 hept-EA) gave the title compound as a yellow solid. TLC:rf (1:1 hept-EA)=0.51. LC-MS-conditions 02: $t_R$=1.11 min; $[M+H]^+$=272.39.

2-(tert-Butyl-dimethyl-silanyloxymethyl)-4-(2-methyl-[1,3]dioxolan-2-yl)-thiazole In a flame dried round-bottomed flask equipped with a magnetic stir bar and under inert atmosphere ($N_2$), a solution of 1-[2-(tert-butyl-dimethyl-silanyloxymethyl)-thiazol-4-yl]-ethanone (1.77 g, 6.52 mmol) in ethylene glycol (7 mL) was treated with trimethylorthoformate (1.46 mL, 13.29 mmol) followed by $LiBF_4$ (125 mg, 1.30 mmol). The reaction mixture was heated at 95° C. for 4 h. Sat. aq. $Na_2CO_3$ (5 mL) was added and the mixture was extracted with $Et_2O$ (2×20 mL). The org. extracts were dried over $Na_2SO_4$, filtered, and the solvent was removed under reduced pressure. Purification of the residue by FC (20:1->3:1 hept-EA) gave the title compound as a brown oil. TLC:rf (1:1 hept-EA)=0.56. LC-MS-conditions 02: $t_R$=1.11 min; $[M+H]^+$=316.36.

[4-(2-Methyl-[1,3]dioxolan-2-yl)-thiazol-2-yl]-methanol

In a flame dried round-bottomed flask equipped with a magnetic stir bar and under inert atmosphere ($N_2$), a solution of 2-(tert-butyl-dimethyl-silanyloxymethyl)-4-(2-methyl-[1,3]dioxolan-2-yl)-thiazole (1.30 g, 4.12 mmol) in dry THF (10 mL) was treated at 0° C. with TBAF (6.2 mL of a 1M solution in THF, 6.20 mmol). The reaction mixture was stirred at 0° C. for 5 min and at rt for 1 h 30. The mixture was then diluted with EA (10 mL), washed with brine (3×10 mL), dried over $MgSO_4$, filtered and concentrated under reduced pressure. Purification of the residue by FC (5:1->1:3 hept-EA) gave the title compound as a yellow oil. TLC:rf (1:2 hept-EA)=0.20. LC-MS-conditions 02: $t_R$=0.59 min; $[M+H]^+$=202.48.

2-[4-(2-Methyl-[1,3]dioxolan-2-yl)-thiazol-2-ylmethyl]-4-nitro-2H-[1,2,3]triazole In a flame dried round-bottomed flask equipped with a magnetic stir bar and under inert atmosphere ($N_2$), a solution of [4-(2-methyl-[1,3]dioxolan-2-yl)-thiazol-2-yl]-methanol (745 mg, 3.70 mmol) in dry $CH_2Cl_2$ (5 mL) was treated at 0° C. with $Et_3N$ (0.67 mL, 4.79 mmol) followed by DMAP (46 mg, 0.37 mmol) and Ms-Cl (0.37 mL, 4.67 mmol). After stirring at 0° C. for 1 h 30, the reaction was quenched with water (5 mL). The org. layer was dried over $MgSO_4$, filtered, and the solvents were removed under reduced pressure to give 1.03 g (quant.) of crude methanesulfonic acid 4-(2-methyl-[1,3]dioxolan-2-yl)-thiazol-2-ylmethyl ester as a yellow oil. Part of this crude material (323 mg) in DMF (2.0 mL) was added to a solution of 4-nitro-2H-[1,2,3]triazole (120 mg, 1.05 mmol) in DMF (2.0 mL) pre-treated for 30 min with DIPEA (0.36 mL, 2.10 mmol) and the reaction mixture was stirred for 24 h at 50° C. Water (10 mL), followed by EA (10 mL) were added. The aq. layer was extracted with EA (10 mL) and the combined org. extracts were dried over $Na_2SO_4$, filtered, and the solvents were removed under reduced pressure. Purification of the residue by FC (1:2 hept-EA) gave the title compound as a yellow oil: TLC:rf (1:2 hept-EA)=0.33. LC-MS-conditions 02: $t_R$=0.88 min, $[M+H]^+$=298.16.

2-[4-(2-Methyl-[1,3]dioxolan-2-yl)-thiazol-2-ylmethyl]-2H-[1,2,3]triazol-4-ylamine In a flame dried round-bottomed flask equipped with a magnetic stir bar and under inert atmosphere ($N_2$), a mixture of 2-[4-(2-methyl-[1,3]dioxolan-2-yl)-thiazol-2-ylmethyl]-4-nitro-2H-[1,2,3]triazole (145 mg, 0.49 mmol), iron powder (83 mg, 1.46 mmol) and $NH_4Cl$ (132 mg, 2.44 mmol) in a mixture of EtOH (2.0 mL) and water (1.0 mL) was stirred at 75° C. for 1 h. The reaction mixture was filtered while hot and the filter cake rinsed with EtOH. The filtrate was concentrated under reduced pressure and the residue partitioned between $CH_2Cl_2$ (10 mL) and aq. 1M NaOH (10 mL). The aq. layer was extracted with $CH_2Cl_2$ (2×10 mL). The combined org. extracts were dried over $MgSO_4$, filtered, and the solvent removed under reduced pressure to give the title compound as a yellow oil (120 mg, 92%). LC-MS-conditions 02: $t_R$=0.68 min, $[M+H]^+$=268.05.

1-(2-Bromo-pyridin-4-yl)-ethanone

In a flame dried round-bottomed flask equipped with a magnetic stir bar and under inert atmosphere ($N_2$), a suspension of commercially available 2,4-dibromo-pyridine (3.30 g, 13.9 mmol) in dry $Et_2O$ (75 mL) was treated with n-BuLi (5.85 mL of a 2.5M solution in hexanes, 14.6 mmol) at −78° C. The reaction mixture was stirred at this temperature for 30 min. N,N-Dimethyl-acetamide (2.6 mL, 27.9 mmol) was then added and the mixture allowed to warm to rt over a period of 1 h and stirred at this temperature for 30 min. The reaction was quenched by the addition of sat. aq. $NH_4Cl$ (50 mL). The layers were separated and the aq. layer extracted with $Et_2O$ (2×50 mL). The combined org. extracts were dried over $Na_2SO_4$, filtered, and the solvent was removed under reduced pressure. Purification of the residue by FC (20:1 to 5:1 hept-EA) gave the title compound as a white solid. TLC:rf (1:1 hept-EA)=0.41. LC-MS-conditions 02: $t_R$=0.81 min; $[M+H]^+$=200.61.

2-Bromo-4-(2-methyl-[1,3]dioxolan-2-yl)-pyridine

In a flame dried round-bottomed flask equipped with a magnetic stir bar and under inert atmosphere ($N_2$), a mixture of 1-(2-bromo-pyridin-4-yl)-ethanone (1650 mg, 8.25 mmol) in ethylene glycol (8.8 mL) was treated with trimethylorthoformate (1.85 mL, 16.88 mmol) followed by $LiBF_4$ (158 mg, 1.65 mmol). The reaction mixture was heated at 95° C. overnight. Sat. aq. $Na_2CO_3$ (20 mL) was added and the mixture was extracted with $Et_2O$ (2×30 mL). The org. extracts were dried over $Na_2SO_4$, filtered, and the solvent was removed under reduced pressure. Purification of the residue by FC (6:1 to 2:1 hept-EA) gave the title compound as a yellow oil. TLC:rf (1:1 hept-EA)=0.57. LC-MS-conditions 02: $t_R$=0.88 min; $[M+H]^+$=244.19.

4-(2-Methyl-[1,3]dioxolan-2-yl)-pyridine-2-carbaldehyde

In a flame dried round-bottomed flask equipped with a magnetic stir bar and under inert atmosphere ($N_2$), to a solution of 2-bromo-4-(2-methyl-[1,3]dioxolan-2-yl)-pyridine (1950 mg, 7.99 mmol) in dry $Et_2O$ (40 mL) was added n-BuLi (3.60 mL of a 2.5M solution in hexanes, 8.79 mmol) at −78° C. The reaction mixture was then stirred for 30 min at −78° C. before DMF (0.75 mL, 9.69 mmol) was added dropwise. The reaction mixture was allowed to warm up to rt and stirred at this temperature for 10 min. Sat. aq. $NH_4Cl$ (30 mL) was added, the layers separated and the aq. layer extracted with $Et_2O$ (3×30 mL). The combined org. extracts were dried over $Na_2SO_4$, filtered, and the solvent was removed under reduced pressure. Purification of the residue by FC (10:1 to 2:1 hept-EA) gave the title compound as a pale yellow oil. TLC:rf (1:1 hept-EA)=0.40.

[4-(2-Methyl-[1,3]dioxolan-2-yl)-pyridin-2-yl]-methanol

In a flame dried round-bottomed flask equipped with a magnetic stir bar and under inert atmosphere ($N_2$), 4-(2-methyl-[1,3]dioxolan-2-yl)-pyridine-2-carbaldehyde (1100 mg, 5.69 mmol) was dissolved in MeOH (15 mL). $NaBH_4$ (278 mg, 7.05 mmol) was added portionwise at 0° C. and the reaction mixture was stirred at rt for 1 h. Water was added and the mixture extracted with EA (3×30 mL). The combined org. extracts were dried over $Na_2SO_4$, filtered, and the solvents were removed under reduced pressure to give the title compound as a yellow oil. LC-MS-conditions 02: $t_R$=0.41 min; $[M+H]^+$=196.51.

Methanesulfonic acid 4-(2-methyl-[1,3]dioxolan-2-yl)-pyridin-2-ylmethyl ester In a flame dried round-bottomed flask equipped with a magnetic stir bar and under inert atmosphere ($N_2$), a solution of [4-(2-methyl-[1,3]dioxolan-2-yl)-pyridin-2-yl]-methanol (950 mg, 4.87 mmol) in dry $CH_2Cl_2$ (5 mL) was treated at 0° C. with $Et_3N$ (0.88 mL, 6.29 mmol) followed by DMAP (60 mg, 0.49 mmol) and Ms-Cl (0.49 mL, 6.15 mmol). After stirring at rt for 2 h, the reaction was quenched with water (5 mL). The org. layer was dried over $MgSO_4$, filtered, and the solvent was removed under reduced pressure. Purification of the residue by FC (5:1 to 2:1 hept-EA) gave the title compound as a yellow oil. LC-MS-conditions 02: $t_R$=0.76 min, $[M+H]^+$=274.30.

4-(2-Methyl-[1,3]dioxolan-2-yl)-2-(4-nitro-[1,2,3]triazol-2-ylmethyl)-pyridine In a flame dried round-bottomed flask equipped with a magnetic stir bar and under inert atmosphere ($N_2$), a solution of methanesulfonic acid 4-(2-methyl-[1,3]dioxolan-2-yl)-pyridin-2-ylmethyl ester (315 mg, 1.15 mmol) in DMF (2.0 mL) was added to a solution of 4-nitro-2H-[1,2,3]triazole (120 mg, 1.05 mmol) in DMF (2.0 mL) pre-treated for 30 min with DIPEA (0.36 mL, 2.10 mmol) and the reaction mixture was stirred for 48 h at 50° C. Water (10 mL), followed by EA (10 mL) were added. The aq. layer was extracted with EA (10 mL) and the combined org. extracts were dried over $NaSO_4$, filtered, and the solvents were removed under reduced pressure. Purification of the residue by FC (5:1 to 1:4 hept-EA) gave the title compound as a pale yellow solid: TLC:rf (1:2 hept-EA)=0.24. LC-MS-conditions 02: $t_R$=0.89 min, $[M+H]^+$=292.27.

2-[4-(2-Methyl-[1,3]dioxolan-2-yl)-pyridin-2-ylmethyl]-2H-[1,2,3]triazol-4-ylamine In a flame dried round-bottomed flask equipped with a magnetic stir bar and under inert atmosphere ($N_2$), a mixture of 4-(2-methyl-[1,3]dioxolan-2-yl)-2-(4-nitro-[1,2,3]triazol-2-ylmethyl)-pyridine (210 mg, 0.71 mmol), iron powder (120 mg, 2.12 mmol) and $NH_4Cl$ (191 mg, 3.53 mmol) in a mixture of EtOH (2.0 mL) and water (1.0 mL) was stirred at 75° C. for 1 h. The reaction mixture was filtered while hot and the filter cake rinsed with EtOH. The filtrate was concentrated under reduced pressure and the residue partitioned between $CH_2Cl_2$ (10 mL) and aq. 1M NaOH (10 mL). The aq. layer was extracted with $CH_2Cl_2$ (2×10 mL). The combined org. extracts were dried over $MgSO_4$, filtered, and the solvent removed under reduced pressure. Purification of the residue by FC (99:1 to 19:1 $CH_2Cl_2$-MeOH) gave the title compound as a brown oil: TLC:rf (19:1 $CH_2Cl_2$-MeOH)=0.33. LC-MS: $t_R$=0.64 min, $[M+H]^+$=262.29.

1-(6-Bromo-pyridin-2-yl)-ethanone

In a flame dried round-bottomed flask equipped with a magnetic stir bar and under inert atmosphere ($N_2$), a suspension of 2,6-dibromopyridine (2.44 g, 10.00 mmol) in ether (25.0 mL) was treated at −78° C. with n-BuLi (4.0 mL of a 2.5M solution in hexane, 10.00 mmol). The reaction mixture was stirred for 30 min before N,N-dimethylacetaminde (1.50 mL, 16.13 mmol) was added and the solution was then allowed to warm to rt over 1 h. Sat. aq. $NH_4Cl$ was then added and the aq. layer was extracted with $Et_2O$ (2×50 mL). The combined org. extracts were dried over $Na_2SO_4$, filtered, and the solvents were removed under reduced pressure. Purification of the residue by FC (20:1 hept-EA) gave the title compound as a white solid: TLC:rf (20:1 hept-EA)=0.25. LC-MS-conditions 02: $t_R$=0.98 min.

2-Bromo-6-(2-methyl-[1,3]dioxolan-2-yl)-pyridine

In a flame dried round-bottomed flask equipped with a magnetic stir bar and under inert atmosphere ($N_2$), a solution of 1-(6-bromo-pyridin-2-yl)-ethanone (1880 mg, 9.40 mmol) in ethylene glycol (10.00 mL, 179.32 mmol) was treated with trimethylorthoformate (2.10 mL, 19.16 mmol) followed by $LiBF_4$ (180 mg, 1.88 mmol). The reaction mixture was heated at 95° C. for 5 h. Sat. aq. $Na_2CO_3$ was added and the mixture was extracted twice with ether and the combined organic extracts were dried over $Na_2SO_4$, filtered, and the solvent was removed under reduced pressure. Purification of the residue by FC (20:1 hept-EA) gave the title compound as a pale yellow oil: TLC:rf (50:50 hept-EA)=0.57.

6-(2-Methyl-[1,3]dioxolan-2-yl)-pyridine-2-carbaldehyde

In a flame dried round-bottomed flask equipped with a magnetic stir bar and under inert atmosphere ($N_2$), to a solution of 2-bromo-6-(2-methyl-[1,3]dioxolan-2-yl)-pyridine (2.21 g, 9.05 mmol) in $Et_2O$ (60.0 mL) at −78° C. was added dropwise n-BuLi (3.70 mL of a 2.5M solution in hexane, 9.25 mmol). The reaction mixture was then stirred at −78° C. for 30 min before DMF (0.85 mL, 11.00 mmol) was added dropwise. The reaction mixture was allowed to warm to rt over 1 h. 5% aq. $NaHCO_3$ was added and the mixture was extracted three times with $Et_2O$. The combined org. extracts were dried over $Na_2SO_4$, filtered, and the solvent was removed under reduced pressure. Purification of the residue by FC (4:1 hept-EA to pure EA) gave the title compound as a pale yellow solid.

[6-(2-Methyl-[1,3]dioxolan-2-yl)-pyridin-2-yl]-methanol

In a flame dried round-bottomed flask equipped with a magnetic stir bar and under inert atmosphere ($N_2$), to a ice-cold solution of 6-(2-methyl-[1,3]dioxolan-2-yl)-pyridine-2-carbaldehyde (713 mg, 3.69 mmol) in MeOH (10.0 mL) was added $NaBH_4$ (180 mg, 4.57 mmol in four equal portions). The reaction mixture was then stirred for 1 h at rt. Water was added and the mixture was extracted with EA followed twice with EA-MeOH 9:1. The combined org. extracts were dried over $Na_2SO_4$, filtered, and the solvent was removed under reduced pressure to give the title compound as a pale yellow solid. LC-MS-conditions 02: $t_R$=0.46 min; $[M+H]^+$=196.49.

Methanesulfonic acid 6-(2-methyl-[1,3]dioxolan-2-yl)-pyridin-2-ylmethyl ester In a flame dried round-bottomed flask equipped with a magnetic stir bar and under inert atmosphere ($N_2$), a solution of [6-(2-methyl-[1,3]dioxolan-2-yl)-pyridin-2-yl]-methanol (729 mg, 3.74 mmol) in dry $CH_2Cl_2$ (10.0 mL) was treated at 0° C. with $Et_3N$ (0.67 mL, 4.83 mmol) followed by DMAP (46 mg, 0.37 mmol) and Ms-Cl (0.37 mL, 4.72 mmol). After stirring at 0° C. for 1 h, the reaction mixture was quenched with water (10 mL), extracted with $CH_2Cl_2$ (10 mL) and the combined org. extracts were dried over $Na_2SO_4$, filtered, and the solvents were removed under reduced pressure. Purification of the residue by FC (70:30 to 50:50 hept-EA) gave the title compound as a pale yellow oil. LC-MS-conditions 02: $t_R$=0.79 min; $[M+H]^+$=274.39.

2-(2-Methyl-[1,3]dioxolan-2-yl)-6-(4-nitro-[1,2,3]triazol-2-ylmethyl)-pyridine In a flame dried round-bottomed flask equipped with a magnetic stir bar and under inert atmosphere ($N_2$), a solution of methanesulfonic acid 6-(2-methyl-[1,3]dioxolan-2-yl)-pyridin-2-ylmethyl ester (164 mg, 0.6 mmol) in DMF (2.0 mL) was added to a solution of 4-nitro-2H-[1,2,3]triazole (57 mg, 0.5 mmol) in DMF (1.0 mL) pre-treated for 30 min with DIPEA (0.20 mL, 1.17 mmol) and the reaction mixture was stirred for 48 h at 50° C. Water (10 mL), followed by EA (10 mL) were added. The aq. layer was extracted with EA (10 mL) and the combined org. extracts were dried over $Na_2SO_4$, filtered, and the solvents were removed under reduced pressure. Purification of the residue by FC (4:1 to 1:1 hept-EA) gave the title compound as a pale yellow oil: TLC:rf (1:1 hept-EA)=0.50. LC-MS-conditions 02: $t_R$=0.90 min, $[M+H]^+$=292.35.

2-[6-(2-Methyl-[1,3]dioxolan-2-yl)-pyridin-2-ylmethyl]-2H-[1,2,3]triazol-4-ylamine In a flame dried round-bottomed flask equipped with a magnetic stir bar and under inert atmosphere ($N_2$), a mixture of 2-(2-methyl-[1,3]dioxolan-2-yl)-6-(4-nitro-[1,2,3]triazol-2-ylmethyl)-pyridine (66 mg, 0.23 mmol), iron powder (38 mg, 0.68 mmol) and $NH_4Cl$ (61 mg, 1.13 mmol) in a mixture of EtOH (2.0 mL) and water (1.0 mL) was stirred at 75° C. for 1 h. The reaction mixture was filtered while hot and concentrated under reduced pressure. $CH_2Cl_2$ (20 mL) was added followed by 1N NaOH (20 mL). The aq. layer was extracted with $CH_2Cl_2$ (2×20 mL) and the combined org. extracts were dried over $MgSO_4$, filtered, and the solvents were removed under reduced pressure to give the title compound as a pale green oil: TLC: rf (EA)=0.50. LC-MS-conditions $O_2$: $t_R$=0.67 min; $[M+H]^+$=262.40.

3-(2-Hydroxy-ethyl)-benzoic acid

In a flame dried round-bottomed flask equipped with a magnetic stir bar and under inert atmosphere ($N_2$), to a solution of 3-bromophenethyl alcohol (2.34 g, 11.29 mmol) and N,N,N',N'-tetramethylethylendiamine (3.24 mL, 22.58 mmol) in $Et_2O$ (29.0 mL) at −78° C. was added dropwise n-BuLi (14.0 mL of a 1.6M solution in hexane, 22.59 mmol), maintaining the temperature at −78° C. The reaction mixture was then stirred at −20° C. for 2 h. Dry carbon dioxide gas was then bubbled for 10 min through the reaction mixture at −78° C. The cooling bath was removed and the reaction mixture was stirred for 1 h. The reaction mixture was extracted with water (50 mL). The aqueous layer was acidified to pH=1 with 2N HCl and extracted with EA (2×75 mL). The combined org. extracts were dried over $MgSO_4$, filtered, and the solvents were removed under reduced pressure to give the title compound as a beige solid: LC-MS-conditions 02: $t_R$=0.67 min.

5-[3-(2-Methoxy-ethyl)-phenyl]-oxazole-4-carboxylic acid methyl ester

In a flame dried round-bottomed flask equipped with a magnetic stir bar and under inert atmosphere ($N_2$), a solution of 5-[3-(2-hydroxy-ethyl)-phenyl]-oxazole-4-carboxylic acid (100 mg, 0.43 mmol) in DMF (1.0 mL) was treated at 0° C. with NaH (56 mg, 1.29 mmol) and the resulting mixture was stirred for 45 min at 0° C. Methyl iodide (0.14 mL, 2.14 mmol) was then added and the reaction mixture was stirred at rt for 45 min. The reaction mixture was quenched with sat. aq. $NH_4Cl$ (20 mL), extracted with EA (2×20 mL) and the combined org. extracts were washed with water (2×20 mL) dried over $MgSO_4$, filtered, and the solvents were removed under reduced pressure to give the title compound. LC-MS-conditions 02: $t_R$=0.92 min; $[M+H]^+$=262.38.

5-(3-tert-Butoxycarbonyl-phenyl)-oxazole-4-carboxylic acid methyl ester

In a flame dried round-bottomed flask equipped with a magnetic stir bar and under inert atmosphere ($N_2$), a suspension of isophthalic acid mono-tent-butyl ester (4.00 g, 18.00 mmol) and potassium carbonate sesquihydrate (6.03 g, 43.20 mmol) in DMF (36.0 mL) was treated with a solution of methyl isocyanoacetate (3.45 mL, 36.00 mmol) in DMF (6.0 mL). After 5 min, the reaction mixture was cooled to 0° C. and a solution of DPPA (4.01 mL, 18.00 mmol) in DMF (6 mL) was added dropwise. The resulting mixture was stirred at 0° C. for 2 h and then overnight at rt. A 1:1 mixture of toluene: EA (400 mL) was added and the organic layer was washed with water (150 mL), 10% aq. citric acid solution (150 mL) and sat. aq. NaHCO$_3$ (150 mL). The organic layer was dried over MgSO$_4$, filtered, and the solvent removed under reduced pressure. Purification of the residue by FC (60:40 hept-EA) gave the title compound as a white solid. TLC:rf (60:40 hept-EA)=0.27. LC-MS-conditions 02: $t_R$=1.04 min, [M+H]$^+$=304.32.

5-(3-Carboxy-phenyl)-oxazole-4-carboxylic acid methyl ester

In a flame dried round-bottomed flask equipped with a magnetic stir bar and under inert atmosphere (N$_2$), a solution of 5-(3-tert-butoxycarbonyl-phenyl)-oxazole-4-carboxylic acid methyl ester (1.00 g, 3.30 mmol) in TFA (13.3 mL) was stirred at rt for 45 min. The TFA was removed under reduced pressure and the residue was triturate in Et$_2$O, filtered and washed with Et$_2$O to give the title compound as a white powder. LC-MS-conditions 02: $t_R$=0.79 min, [M+H]$^+$=248.20.

5-(3-Hydroxymethyl-phenyl)-oxazole-4-carboxylic acid methyl ester

In a flame dried round-bottomed flask equipped with a magnetic stir bar and under inert atmosphere (N$_2$), a suspension of 5-(3-carboxy-phenyl)-oxazole-4-carboxylic acid methyl ester (500 mg, 2.02 mmol) in THF (14.0 mL) at 0° C. was treated dropwise with BH$_3$ (10.1 mL of a 1M solution in THF, 10.11 mmol). The resulting mixture was stirred at 0° C. for 4 h. MeOH (14 mL) was then added dropwise. After 30 min, the solvent was removed under reduced pressure. EA (20 mL) was added and the organic phase was washed with 1N NaOH (10 mL), water (10 mL) and brine (10 mL). The organic layer was dried over MgSO$_4$, filtered, and the solvent removed under reduced pressure. Purification of the residue by FC (93:7 CH$_2$Cl$_2$-MeOH) gave the title compound as a white solid. TLC:rf (93:7 CH$_2$Cl$_2$-MeOH)=0.32. LC-MS-conditions 02: $t_R$=0.76 min, [M+H]$^+$=234.39.

5-(3-Hydroxymethyl-phenyl)-oxazole-4-carboxylic acid

In a flame dried round-bottomed flask equipped with a magnetic stir bar and under inert atmosphere (N$_2$), a solution of 5-(3-hydroxymethyl-phenyl)-oxazole-4-carboxylic acid methyl ester (265 mg, 1.13 mmol) in THF (11.0 mL) was treated with a 1N NaOH (5.5 mL). The resulting mixture was stirred for 1.5 h then acidified with 1N HCl, extracted twice with EA (2×25 mL) and the combined organic phases were washed with brine (10 mL). The organic layer was dried over MgSO$_4$, filtered, and the solvent removed under reduced pressure to give the title compound as a white solid. LC-MS-conditions 02: $t_R$=0.67 min, [M+AcCN+N+H]$^+$=261.29.

5-(3-Methoxymethyl-phenyl)-oxazole-4-carboxylic acid methyl ester

In a flame dried round-bottomed flask equipped with a magnetic stir bar and under inert atmosphere (N$_2$), a solution of 5-(3-hydroxymethyl-phenyl)-oxazole-4-carboxylic acid (100 mg, 0.43 mmol) at 0° C. in DMF (1.0 mL) was treated with NaH (56 mg, 1.29 mmol) and the resulting mixture was stirred at 0° C. for 45 min. MeI (0.14 mL, 2.14 mmol) was added and the reaction mixture was stirred at rt for 1.5 h. Sat. aq. NH$_4$Cl (20 mL) was added and the aqueous layer extracted twice with EA (2×20 mL). The combined organic layers were washed with water (2×10 mL), dried over MgSO$_4$, filtered, and the solvent removed under reduced pressure to give the title compound as a yellow oil. LC-MS-conditions 02: $t_R$=0.89 min, [M+H]$^+$=248.36.

5-(3-Methoxymethyl-phenyl)-oxazole-4-carboxylic acid

In a flame dried round-bottomed flask equipped with a magnetic stir bar and under inert atmosphere (N$_2$), a solution of 5-(3-methoxymethyl-phenyl)-oxazole-4-carboxylic acid methyl ester (280 mg, 1.13 mmol) in THF (11.0 mL) was treated with a 1N NaOH (5.5 mL). The resulting mixture was stirred for 1.5 h then acidified with 1N HCl, extracted twice with EA (2×20 mL) and the combined organic phases were washed with brine (20 mL). The organic layer was dried over MgSO$_4$, filtered, and the solvent removed under reduced pressure to give the title compound as a white solid. LC-MS-conditions 02: $t_R$=0.77 min, [M+AcCN+H]$^+$=275.35.

Amino-thioxo-acetic acid ethyl ester

In a flame dried round-bottomed flask equipped with a magnetic stir bar and under inert atmosphere (N$_2$), a solution of commercially available oxalamic acid ethyl ester (43.429 g, 370.86 mmol) and Lawesson's reagent (150.00 g, 370.86 mmol) in toluene (550.0 mL) was stirred at 80° C. for 2 h. The resulting mixture was cooled to rt and CH$_2$Cl$_2$ (300 mL) was added.

The mixture was filtered and the solvents were removed under reduced pressure. Purification of the residue by FC(CH$_2$Cl$_2$) gave the title compound as an orange solid.

4-Chloromethyl-thiazole-2-carboxylic acid ethyl ester

In a flame dried round-bottomed flask equipped with a magnetic stir bar and under inert atmosphere (N$_2$), a mixture of amino-thioxo-acetic acid ethyl ester (2.50 g, 18.77 mmol) and 1,3-dichloro-propan-2-one (2.88 g, 21.59 mmol) in toluene (20.0 mL) was stirred for 2 h at reflux. EtOAc (20 mL) was added at rt and the mixture was washed with sat. aq. NaHCO$_3$ (10 mL) followed by brine (20 mL). The organic layer was dried over MgSO$_4$, filtered, and the solvent removed under reduced pressure. Purification of the residue by FC (4:1 hept-EA) gave the title compound as a light yellow oil. TLC:rf (4:1 hept-EA)=0.26. LC-MS-conditions 02: $t_R$=0.89 min, [M+H]$^+$=206.40.

(4-Chloromethyl-thiazol-2-yl)-methanol

In a flame dried round-bottomed flask equipped with a magnetic stir bar and under inert atmosphere (N$_2$), a solution of 4-chloromethyl-thiazole-2-carboxylic acid ethyl ester (2.47 g, 12.03 mmol) in THF (120.0 mL) was treated at −78° C. with DiBAL (36.09 mL of a 1M sol in THF, 36.09 mmol) and the reaction mixture was stirred for 1 h at −78° C. and the allowed to warm to rt over 1 h. The reaction mixture was poured over a sat. aq. Rochelle's salt sol. and stirred for 1 h at rt. The aq. layer was extracted with EtOAc (2×150 mL) and the combined org. layer was washed with brine (200 mL). The organic layer was dried over MgSO$_4$, filtered, and the solvent removed under reduced pressure. Purification of the residue by FC (1:1 hept-EA) gave the title compound as a light yellow oil. TLC:rf (1:1 hept-EA)=0.30. LC-MS-conditions 02: $t_R$=0.59 min, [M+H]$^+$=164.07.

4-Chloromethyl-thiazole-2-carbaldehyde

In a flame dried round-bottomed flask equipped with a magnetic stir bar and under inert atmosphere (N$_2$), a solution of (4-chloromethyl-thiazol-2-yl)-methanol (1.60 g, 9.80 mmol) in AcCN (98.0 mL) was treated at rt with MnO$_2$ (4.73 g, 49.01 mmol). The reaction mixture was stirred at rt overnight before being filtered through Celite and the solvent was removed under reduced pressure. Purification of the residue by FC (4:1 hept-EA) gave the title compound as a colorless oil. TLC:rf (4:1 hept-EA)=0.37. LC-MS-conditions 02: $t_R$=0.77 min.

1-(4-Chloromethyl-thiazol-2-yl)ethanol

In a flame dried round-bottomed flask equipped with a magnetic stir bar and under inert atmosphere (N$_2$), a solution of 4-chloromethyl-thiazole-2-carbaldehyde (1.05 g, 6.49 mmol) in CH$_2$Cl$_2$ (65.0 mL) was treated at 0° C. with trimethylaluminum (32.45 mL of a 1M solution in heptane, 32.45 mmol). The reaction mixture was then stirred at 0° C. for 45 min. CH$_2$Cl$_2$ (100.0 mL) followed by sat. aq. NH$_4$Cl (80 mL) was then added. The mixture was then treated with 1N HCl (100 mL) and the aq. layer was extracted with CH$_2$Cl$_2$ (100 mL). The combined org. extracts were dried over MgSO$_4$, filtered, and the solvents were removed under reduced pressure to give the title compound as a yellow oil. LC-MS-conditions 02: $t_R$=0.66 min, [M+H]$^+$=178.50.

1-(4-Chloromethyl-thiazol-2-yl)ethanone

In a flame dried round-bottomed flask equipped with a magnetic stir bar and under inert atmosphere (N$_2$), a solution of 1-(4-chloromethyl-thiazol-2-yl)-ethanol (1.09 g, 6.15 mmol) in AcCN (61.0 mL) was treated at rt with MnO$_2$ (2.97 g, 30.76 mmol) and the reaction mixture was stirred for 16 h at rt before being filtered through Celite. The solvent was removed under reduced pressure to give the title compound as a yellow oil. LC-MS-conditions 02: $t_R$=0.84 min, [M+H]$^+$=176.41.

4-Chloromethyl-2-(2-methyl-[1,3]dioxolan-2-yl)-thiazole

In a flame dried round-bottomed flask equipped with a magnetic stir bar and a Dean-Stark apparatus under inert atmosphere (N$_2$), a solution of 1-(4-chloromethyl-thiazol-2-yl)-ethanone (992 mg, 5.65 mmol) in ethylene glycol (6.30 mL, 112.96 mmol) was treated with trimethylorthoformate (1.24 mL, 11.30 mmol) followed by LiBF$_4$ (106 mg, 1.13 mmol). The reaction mixture was heated at 95° C. for 2 h. Sat. aq. NaHCO$_3$ (50 mL) was added and the mixture was extracted with EA (50 mL). The org. extracts were washed with brine (2×50 mL), dried over MgSO$_4$, filtered, and the solvent was removed under reduced pressure. Purification of the residue by FC (4:1 hept-EA) gave the title compound as a yellow oil: TLC:rf (4:1 hept-EA)=0.30. LC-MS-conditions 02: $t_R$=0.84 min, [M+H]$^+$=220.36.

2-[2-(2-Methyl-[1,3]dioxolan-2-yl)-thiazol-4-ylmethyl]-4-nitro-2H-[1,2,3]triazole In a flame dried round-bottomed flask equipped with a magnetic stir bar and under inert atmosphere (N$_2$), a solution of 4-chloromethyl-2-(2-methyl-[1,3]dioxolan-2-yl)-thiazole (231 mg, 1.05 mmol) in DMF (1.5 mL) was added to a solution of 4-nitro-2H-[1,2,3]triazole (100 mg, 0.88 mmol) in DMF (1.5 mL) pre-treated for 30 min with DIPEA (0.30 mL, 1.75 mmol) and the reaction mixture was stirred for 48 h at 50° C. Water (10 mL), followed by EA (10 mL) were added. The aq. layer was extracted with EA (10 mL) and the combined org. extracts were dried over NaSO$_4$, filtered, and the solvents were removed under reduced pressure. Purification of the residue by FC (6:4 hept-EA) gave the title compound as a pale yellow oil: TLC:rf (6:4 hept-EA)=0.33. LC-MS-conditions 02: $t_R$=0.90 min, [M+H]$^+$=298.23.

2-[2-(2-Methyl-[1,3]dioxolan-2-yl)-thiazol-4-ylmethyl]-2H-[1,2,3]triazol-4-ylamine In a flame dried round-bottomed flask equipped with a magnetic stir bar and under inert atmosphere (N$_2$), a mixture of 2-[2-(2-methyl-[1,3]dioxolan-2-yl)-thiazol-4-ylmethyl]-4-nitro-2H-[1,2,3]triazole (86 mg, 0.29 mmol), iron powder (49 mg, 0.87 mmol) and NH$_4$Cl (78 mg, 1.45 mmol) in a mixture of EtOH (1.0 mL) and water (0.5 mL) was stirred at 75° C. for 60 min. The reaction mixture was filtered while hot and concentrated under reduced pressure. CH$_2$Cl$_2$ (10 mL) was added followed by 1N NaOH (10 mL). The aq. layer was extracted with CH$_2$Cl$_2$ (2×10 mL) and the combined org. extracts were dried over MgSO$_4$, filtered, and the solvents were removed under reduced pressure to give the title compound as an oil. LC-MS-conditions 02: $t_R$=0.68 min; [M+H]$^+$=268.25.

2-Bromo-pyridine-4-carbaldehyde

In a flame dried round-bottomed flask equipped with a magnetic stir bar and under inert atmosphere (N$_2$), a suspension of 2,4-dibromo-pyridine (1.90 g, 8.02 mmol) in dry Et$_2$O (40 mL) was treated with n-BuLi (3.36 mL of a 2.5M solution in hexanes, 8.42 mmol) at −78° C. The reaction mixture was stirred at this temperature for 30 min. N,N-Dimethyl-formamide (0.78 mL, 10.03 mmol) was then added and the mixture allowed to warm to rt over a period of 1 h and stirred at this temperature for 20 min. The reaction was quenched by the addition of sat. aq. NH$_4$Cl (30 mL). The layers were separated and the aq. layer extracted with Et$_2$O (3×50 mL). The combined org. extracts were dried over Na$_2$SO$_4$, filtered, and the solvent removed under reduced pressure. Purification of the residue by FC (10:1 to 2:1 hept-EA) gave the title compound as a white solid. TLC:rf (1:1 hept-EA)=0.44.

(2-Bromo-pyridin-4-yl)-methanol

In a flame dried round-bottomed flask equipped with a magnetic stir bar and under inert atmosphere (N$_2$), 2-bromo-pyridine-4-carbaldehyde (904 mg, 4.86 mmol) was dissolved in MeOH (10 mL). NaBH$_4$ (236 mg, 5.99 mmol) was added portionwise at 0° C. and the reaction mixture stirred at rt for 1 h. Water (10 mL) was added and the mixture extracted with EA (3×20 mL). The combined org. extracts were dried over Na$_2$SO$_4$, filtered, and the solvents were removed under reduced pressure to give the title compound as a white solid. TLC:rf (1:1 hept-EA)=0.22. LC-MS-conditions 02: $t_R$=0.63 min; [M+H]$^+$=188.33.

2-Bromo-4-(tert-butyl-dimethyl-silanyloxymethyl)-pyridine

In a flame dried round-bottomed flask equipped with a magnetic stir bar and under inert atmosphere ($N_2$), (2-bromo-pyridin-4-yl)-methanol (780 mg, 4.15 mmol) was dissolved in dry $CH_2Cl_2$ (21 mL). tert-Butyldimethylsilyl chloride (688 mg, 4.56 mmol) was added at 0° C. followed by imidazole (579 mg, 8.50 mmol). The reaction mixture was stirred at rt for 2 h. 10% Aq. $K_2CO_3$ (10 mL) was added, the layers separated and the aq. layer extracted with $CH_2Cl_2$ (2×20 mL). The combined org. extracts were dried over $MgSO_4$, filtered, and the solvent removed under reduced pressure to give the title compound as a colorless oil. TLC:rf (1:1 hept-EA)=0.80. LC-MS-conditions 02: $t_R$=1.17 min; [M+H]$^+$=302.29.

1-[4-(tert-Butyl-dimethyl-silanyloxymethyl)-pyridin-2-yl]-ethanone

In a flame dried round-bottomed flask equipped with a magnetic stir bar and under inert atmosphere ($N_2$), to a solution of 2-bromo-4-(tert-butyl-dimethyl-silanyloxymethyl)-pyridine (1.04 g, 3.44 mmol) in dry $Et_2O$ (50 mL) was added n-BuLi (1.60 mL of a 2.5M solution in hexanes, 3.96 mmol) at −78° C. The reaction mixture was then stirred for 1 h at −78° C. before N,N-dimethylacetamide (0.64 mL, 6.88 mmol) was added dropwise. The reaction mixture was allowed to warm up to rt and stirred at this temperature for 10 min. Sat. aq. $NH_4Cl$ (20 mL) was added, the layers separated and the aq. layer extracted with $Et_2O$ (3×30 mL). The combined org. extracts were dried over $Na_2SO_4$, filtered, and the solvent was removed under reduced pressure. Purification of the residue by FC (20:1 to 5:1 hept-EA) gave the title compound as a pale yellow oil. TLC:rf (1:2 hept-EA)=0.64. LC-MS-conditions 02: $t_R$=1.12 min; [M+H]$^+$=265.84.

4-(tert-Butyl-dimethyl-silanyloxymethyl)-2-(2-methyl-[1,3]dioxolan-2-yl)-pyridine In a flame dried round-bottomed flask equipped with a magnetic stir bar and a Dean-Stark apparatus under inert atmosphere ($N_2$), a solution of 1-[4-(tert-butyl-dimethyl-silanyloxymethyl)-pyridin-2-yl]-ethanone (1.78 g, 6.71 mmol) in ethylene glycol (7.14 mL, 127.95 mmol) was treated with trimethylorthoformate (1.50 mL, 13.67 mmol) followed by $LiBF_4$ (128 mg, 1.34 mmol). The reaction mixture was heated at 95° C. overnight. Sat. aq. $NaHCO_3$ (50 mL) was added and the mixture was extracted with EA (50 mL). The org. extracts were washed with brine (2×50 mL), dried over $MgSO_4$, filtered, and the solvent was removed under reduced pressure. Purification of the residue by FC (20:1 to 1:1 hept-EA) gave the title compound as a yellow oil. TLC:rf (1:1 hept-EA)=0.50. LC-MS-conditions 02: $t_R$=0.91 min, [M+H]$^+$=310.40.

[2-(2-Methyl-[1,3]dioxolan-2-yl)-pyridin-4-yl]-methanol

In a flame dried round-bottomed flask equipped with a magnetic stir bar and under inert atmosphere ($N_2$), a solution of 4-(tert-butyl-dimethyl-silanyloxymethyl)-2-(2-methyl-[1,3]dioxolan-2-yl)-pyridine (840 mg, 2.71 mmol) in dry THF (15 mL) was treated at 0° C. with TBAF (4.70 mL of a 1M solution in THF, 4.70 mmol). The reaction mixture was stirred at 0° C. for 5 min and at rt for 1.5 h. The mixture was then diluted with EA (10 mL), washed with brine (3×10 mL), dried over $MgSO_4$, filtered and concentrated under reduced pressure. Purification of the residue by FC (5:1 to 1:3 hept-EA) gave the title compound as a yellow oil. TLC:rf (1:2 hept-EA)=0.10. LC-MS-conditions 02: $t_R$=0.33 min; [M+H]$^+$=196.54.

Methanesulfonic acid 2-(2-methyl-[1,3]dioxolan-2-yl)-pyridin-4-ylmethyl ester In a flame dried round-bottomed flask equipped with a magnetic stir bar and under inert atmosphere ($N_2$), a solution of [2-(2-methyl-[1,3]dioxolan-2-yl)-pyridin-4-yl]-methanol (530 mg, 2.72 mmol) in dry $CH_2Cl_2$ (5 mL) was treated at 0° C. with $Et_3N$ (0.50 mL, 3.56 mmol) followed by DMAP (34 mg, 0.27 mmol) and Ms-Cl (0.27 mL, 3.46 mmol). After stirring at rt for 2 h, the reaction was quenched with water (5 mL). The org. layer was dried over $MgSO_4$, filtered, and the solvent was removed under reduced pressure. Purification of the residue by FC (5:1 to 2:1 hept-EA) gave the title compound as a light brown oil. TLC:rf (1:2 hept-EA)=0.36.

2-(2-Methyl-[1,3]dioxolan-2-yl)-4-(4-nitro-[1,2,3]triazol-2-ylmethyl)-pyridine In a flame dried round-bottomed flask equipped with a magnetic stir bar and under inert atmosphere ($N_2$), a solution of methanesulfonic acid 2-(2-methyl-[1,3]dioxolan-2-yl)-pyridin-4-ylmethyl ester (303 mg, 1.11 mmol) in DMF (2.0 mL) was added to a solution of 4-nitro-2H-[1,2,3]triazole (115 mg, 1.01 mmol) in DMF (2.0 mL) pre-treated for 30 min with DIPEA (0.35 mL, 2.02 mmol) and the reaction mixture was stirred for 48 h at 50° C. Water (10 mL), followed by EA (10 mL) were added. The aq. layer was extracted with EA (10 mL) and the combined org. extracts were dried over $Na_2SO_4$, filtered, and the solvents were removed under reduced pressure. Purification of the residue by FC (5:1 to 2:1 hept-EA) gave the title compound as a pale yellow oil: TLC:rf (1:2 hept-EA)=0.20. LC-MS-conditions 02: $t_R$=0.77 min, [M+H]$^+$=292.24.

2-[2-(2-Methyl-[1,3]dioxolan-2-yl)-pyridin-4-ylmethyl]-2H-[1,2,3]triazol-4-ylamine In a flame dried round-bottomed flask equipped with a magnetic stir bar and under inert atmosphere ($N_2$), a mixture of 2-(2-methyl-[1,3]dioxolan-2-yl)-4-(4-nitro-[1,2,3]triazol-2-ylmethyl)-pyridine (145 mg, 0.50 mmol), iron powder (84 mg, 1.49 mmol) and $NH_4Cl$ (134 mg, 2.49 mmol) in a mixture of EtOH (2.0 mL) and water (1.0 mL) was stirred at 75° C. for 60 min. The reaction mixture was filtered while hot and concentrated under reduced pressure. $CH_2Cl_2$ (10 mL) was added followed by 1N NaOH (10 mL). The aq. layer was extracted with $CH_2Cl_2$ (2×10 mL) and the combined org. extracts were dried over $MgSO_4$, filtered, and the solvents were removed under reduced pressure to give the title compound as a light yellow oil. LC-MS-conditions 02: $t_R$=0.54 min; [M+H]$^+$=261.78.

2-(4-Bromo-thiophen-2-yl)-2-methyl-[1,3]dioxolane

In a flame dried round-bottomed flask equipped with a magnetic stir bar and under inert atmosphere ($N_2$), a solution of commercially available 1-(4-bromo-2-thienyl)ethan-1-one (2.00 g, 9.75 mmol) in ethylene glycol (10.7 mL) was treated with trimethylorthoformate (2.14 mL, 19.51 mmol) followed by $LiBF_4$ (150 mg, 1.60 mmol). The reaction mixture was heated at 95° C. overnight. Sat. aq. $NaHCO_3$ (20 mL) was added and the mixture was extracted with EA (20 mL). The org. extracts were washed with brine (2×20 mL), dried over MgSO$_4$, filtered, and the solvent was removed under reduced pressure. Purification of the residue by FC (20:80 EA-Hept) gave the title compound as a white solid. TLC:rf (20:80 EA-Hept)=0.50. LC-MS-conditions 02: t$_R$=0.99 min.

[5-(2-Methyl-[1,3]dioxolan-2-yl)-thiophen-3-yl]-methanol

In a flame dried round-bottomed flask equipped with a magnetic stir bar and under inert atmosphere (N$_2$), to a solution of 2-(4-bromo-thiophen-2-yl)-2-methyl-[1,3]dioxolane (1.00 g, 4.01 mmol) in Et$_2$O (36.0 mL) at −78° C. was added dropwise n-BuLi (2.5 mL of a 1.6M solution in hexane, 4.00 mmol) over 15 min. The reaction mixture was then stirred at −78° C. for 15 min before DMF (3.1 mL, 40.14 mmol) was added dropwise. The cooling bath was removed and the reaction mixture was stirred for 10 min. Sat. aq. NaH$_4$Cl (40 mL) was added and the aqueous layer was extracted with EA (2×100 mL). The combined org. extracts were dried over MgSO$_4$, filtered, and the solvent was removed under reduced pressure to give crude 5-(2-methyl-[1,3]dioxolan-2-yl)-thiophene-3-carbaldehyde as an yellow oil. LC-MS-conditions 02: t$_R$=0.84 min. The crude material was dissolved, under inert atmosphere (N$_2$) in MeOH (9.98 mL) and treated at 0° C., portionwise with NaBH$_4$ (284 mg, 7.21 mmol). The reaction mixture was stirred at rt for 2 h. The reaction mixture was poured in water (16 mL) and the aq. layer was extracted with EA (2×100 mL). The combined org. extracts were dried over MgSO$_4$, filtered, and the solvents were removed under reduced pressure. Purification of the residue by FC (50:50 hept-EA) gave the title compound as a yellow oil. TLC:rf (50:50 EA-Hept)=0.21. LC-MS-conditions 02: t$_R$=0.71 min; [M+H]$^+$=201.49.

2-(4-Chloromethyl-thiophen-2-yl)-2-methyl-[1,3]dioxolane

In a flame dried round-bottomed flask equipped with a magnetic stir bar and under inert atmosphere (N$_2$), a solution of [5-(2-methyl-[1,3]dioxolan-2-yl)-thiophen-3-yl]-methanol (460 mg, 2.30 mmol) in dry CH$_2$Cl$_2$ (4.6 mL) was treated at 0° C. with Et$_3$N (0.42 mL, 2.99 mmol) followed by DMAP (28 mg, 0.23 mmol) and Ms-Cl (0.21 mL, 2.76 mmol). After stirring at rt for 2 h, the reaction mixture was quenched with water (10 mL), extracted with CH$_2$Cl$_2$ (20 mL) and the combined org. extracts were dried over NaSO$_4$, filtered, and the solvents were removed under reduced pressure. Purification of the residue by FC (4:1 hept-EA) gave the title compound as a pale yellow oil. TLC:rf (1:4 EA-Hept)=0.35.

2-[5-(2-Methyl-[1,3]dioxolan-2-yl)-thiophen-3-ylmethyl]-4-nitro-2H-[1,2,3]triazole In a flame dried round-bottomed flask equipped with a magnetic stir bar and under inert atmosphere (N$_2$), a solution of 2-(4-chloromethyl-thiophen-2-yl)-2-methyl-[1,3]dioxolane (230 mg, 1.05 mmol) in DMF (1.5 mL) was added to a solution of 4-nitro-2H-[1,2,3]triazole (100 mg, 0.88 mmol) in DMF (1.5 mL) pre-treated for 30 min with DIPEA (0.30 mL, 1.75 mmol) and the reaction mixture was stirred for 16 h at 50° C. Water (10 mL), followed by EA (10 mL) were added. The aq. layer was extracted with EA (10 mL) and the combined org. extracts were dried over NaSO$_4$, filtered, and the solvents were removed under reduced pressure. Purification of the residue by FC (2:1 hept-EA) gave the title compound as a pale yellow oil: TLC:rf (2:1 hept-EA)=0.47. LC-MS-conditions 02: t$_R$=0.98 min.

2-[5-(2-Methyl-[1,3]dioxolan-2-yl)-thiophen-3-ylmethyl]-2H-[1,2,3]triazol-4-ylamine In a flame dried round-bottomed flask equipped with a magnetic stir bar and under inert atmosphere (N$_2$), a mixture of 2-[5-(2-methyl-[1,3]dioxolan-2-yl)-thiophen-3-ylmethyl]-4-nitro-2H-[1,2,3]triazole (50 mg, 0.17 mmol), iron powder (29 mg, 0.51 mmol) and NH$_4$Cl (46 mg, 0.84 mmol) in a mixture of EtOH (1.0 mL) and water (0.5 mL) was stirred at 85° C. for 15 min. The reaction mixture was filtered while hot and concentrated under reduced pressure. CH$_2$Cl$_2$ (10 mL) was added followed by 1N NaOH (10 mL). The aq. layer was extracted with CH$_2$Cl$_2$ (2×10 mL) and the combined org. extracts were dried over MgSO$_4$, filtered, and the solvents were removed under reduced pressure to give the title compound as a light yellow oil. LC-MS-conditions 02: t$_R$=0.78 min; [M+H]$^+$=267.28.

5-(tert-Butyl-dimethyl-silanyloxymethyl)-isoxazole-3-carboxylic acid ethyl ester In a flame dried round-bottomed flask equipped with a magnetic stir bar and under inert atmosphere (N$_2$), commercially available 5-hydroxymethyl-isoxazole-3-carboxylic acid ethyl ester (5.00 g, 26.29 mmol) was dissolved in dry THF (200 mL). tert-Butyldimethylsilyl chloride (4.04 g, 26.82 mmol) was added at rt followed by imidazole (1.97 g, 28.92 mmol). The reaction mixture was stirred at rt overnight. Sat. aq. NH$_4$Cl (150 mL) was added followed by EA (100 mL) and the layers were separated. The aq. layer extracted with EA (2×100 mL). The combined org. extracts were dried over MgSO$_4$, filtered, and the solvent removed under reduced pressure. Purification of the residue by FC (9:1 hept-EA) gave the title compound as a light yellow oil TLC:rf (9:1 hept-EA)=0.37. LC-MS-conditions 02: t$_R$=1.14 min; [M+AcCN+H]$^+$=327.51.

[5-(tert-Butyl-dimethyl-silanyloxymethyl)-isoxazol-3-yl]-methanol

In a flame dried round-bottomed flask equipped with a magnetic stir bar and under inert atmosphere (N$_2$), a solution of 5-(tert-butyl-dimethyl-silanyloxymethyl)-isoxazole-3-carboxylic acid ethyl ester (5.77 g, 20.22 mmol) in THF (200 mL) was treated at −78° C. with DiBAL-H (40.00 mL of a 1M solution in THF, 40.43 mmol). The reaction mixture was stirred at this temperature for 1 h before to be allowed to warm to rt. The reaction mixture was poured onto Rochelle's salt (200 mL) and stirred at rt for 1 h. The aq. layer was extracted with EA (2×200 mL). The combined org. extracts were dried over MgSO$_4$, filtered, and the solvents were removed under reduced pressure. Purification of the residue by FC (70:30 hept-EA) gave the title compound as a yellow oil: TLC:rf (70:30 hept-EA)=0.28. LC-MS-conditions 02: t$_R$=0.99 min; [M+H]$^+$=244.35.

5-(tert-Butyl-dimethyl-silanyloxymethyl)-isoxazole-3-carbaldehyde

In a flame dried round-bottomed flask equipped with a magnetic stir bar and under inert atmosphere (N$_2$), a solution of [5-(tert-butyl-dimethyl-silanyloxymethyl)-isoxazol-3-yl]-methanol (2.94 g, 12.08 mmol) in AcCN (120.0 mL) was treated at rt with MnO$_2$ (8.17 g, 84.56 mmol) and the reaction mixture was stirred for 24 h at rt before being filtered through Celite. The solvent was removed under reduced pressure to give the title compound as a yellow oil: TLC:rf (9:1 hept-EA)=0.32. LC-MS-conditions 02: $t_R$=0.92 min.

1-[5-(tert-Butyl-dimethyl-silanyloxymethyl)-isoxazol-3-yl]-ethanol

In a flame dried round-bottomed flask equipped with a magnetic stir bar and under inert atmosphere (N$_2$), a solution of 5-(tert-butyl-dimethyl-silanyloxymethyl)-isoxazole-3-carbaldehyde (1.74 g, 7.22 mmol) in CH$_2$Cl$_2$ (72.0 mL) was treated at 0° C. with trimethylaluminum (22.0 mL of a 1M solution in heptane, 22.0 mmol). The reaction mixture was then stirred at 0° C. for 50 min. CH$_2$Cl$_2$ (80.0 mL) followed by sat. aq. NH$_4$Cl (80 mL) were then added. The mixture was then treated with 1N HCl (50 mL) and the aq. layer was extracted with CH$_2$Cl$_2$ (100 mL). The combined org. extracts were dried over MgSO$_4$, filtered, and the solvents were removed under reduced pressure to give the title compound as a colorless oil: TLC:rf (7:3 hept-EA)=0.32. LC-MS-conditions 02: $t_R$=1.01 min, [M+H]$^+$=258.41.

1-[5-(tert-Butyl-dimethyl-silanyloxymethyl)-isoxazol-3-yl]-ethanone

In a flame dried round-bottomed flask equipped with a magnetic stir bar and under inert atmosphere (N$_2$), a solution of 1-[5-(tert-butyl-dimethyl-silanyloxymethyl)-isoxazol-3-yl]-ethanol (1.79 g, 6.95 mmol) in AcCN (70.0 mL) was treated at rt with MnO$_2$ (3.36 g, 34.77 mmol) and the reaction mixture was stirred for 72 h at rt before being filtered through Celite. The solvent was removed under reduced pressure to give the title compound as a yellow oil. LC-MS-conditions 2: $t_R$=1.13 min.

1-(5-Hydroxymethyl-isoxazol-3-yl)-ethanone

In a flame dried round-bottomed flask equipped with a magnetic stir bar and under inert atmosphere (N$_2$), a solution of 1-[5-(tert-butyl-dimethyl-silanyloxymethyl)-isoxazol-3-yl]-ethanone (1.99 g, 7.79 mmol) in ethylene glycol (8.69 mL) was treated with trimethylorthoformate (1.71 mL, 15.58 mmol) followed by LiBF$_4$ (146 mg, 1.56 mmol). The reaction mixture was heated at 95° C. overnight. Sat. aq. NaHCO$_3$ (50 mL) was added and the mixture was extracted with EA (2×50 mL). The combined org. extracts were washed with brine (2×50 mL), dried over MgSO$_4$, filtered, and the solvent was removed under reduced pressure. Purification of the residue by FC (40:60 EA-Hept) gave the title compound as a yellow oil. TLC:rf (40:60 EA-Hept)=0.25. LC-MS-conditions 02: $t_R$=0.54 min.

1-[5-(4-Nitro-[1,2,3]triazol-2-ylmethyl)-isoxazol-3-yl]-ethanone

In a flame dried round-bottomed flask equipped with a magnetic stir bar and under inert atmosphere (N$_2$), a solution of 1-(5-hydroxymethyl-isoxazol-3-yl)-ethanone (262 mg, 1.86 mmol) in dry CH$_2$Cl$_2$ (2.6 mL) was treated at 0° C. with Et$_3$N (0.34 mL, 2.41 mmol) followed by DMAP (23 mg, 0.19 mmol) and Ms-Cl (0.17 mL, 2.23 mmol). After stirring at rt for 2 h, the reaction mixture was quenched with water (10 mL), extracted with CH$_2$Cl$_2$ (2×10 mL) and the combined org. extracts were dried over NaSO$_4$, filtered, and the solvents were removed under reduced pressure to give crude 1-(5-chloromethyl-isoxazol-3-yl)-ethanone as a pale yellow oil. In a flame dried round-bottomed flask equipped with a magnetic stir bar and under inert atmosphere (N$_2$), a solution of this crude 1-(5-chloromethyl-isoxazol-3-yl)-ethanone in DMF (3.0 mL) was added to a solution of 4-nitro-2H-[1,2,3]triazole (210 mg, 1.84 mmol) in DMF (3.0 mL) pre-treated for 30 min with DIPEA (0.63 mL, 3.68 mmol) and the reaction mixture was stirred for 16 h at 50° C. Water (10 mL), followed by EA (10 mL) were added. The aq. layer was extracted with EA (10 mL) and the combined org. extracts were dried over NaSO$_4$, filtered, and the solvents were removed under reduced pressure. Purification of the residue by FC (2:1 hept-EA) gave the title compound as a pale yellow oil: TLC:rf (2:1 hept-EA)=0.26. LC-MS-conditions 02: $t_R$=0.90 min.

2-[3-(2-Methyl-[1,3]dioxolan-2-yl)-isoxazol-5-ylmethyl]-4-nitro-2H-[1,2,3]triazole In a flame dried round-bottomed flask equipped with a magnetic stir bar and under inert atmosphere (N$_2$), a solution of 1-[5-(4-nitro-[1,2,3]triazol-2-ylmethyl)-isoxazol-3-yl]-ethanone (122 mg, 0.51 mmol) in ethylene glycol (0.57 mL) was treated with trimethylorthoformate (0.11 mL, 1.03 mmol) followed by LiBF$_4$ (10 mg, 0.10 mmol). The reaction mixture was heated at 95° C. overnight. Sat. aq. NaHCO$_3$ (10 mL) was added and the mixture was extracted with EA (2×10 mL). The combined org. extracts were washed with brine (2×10 mL), dried over MgSO$_4$, filtered, and the solvent was removed under reduced pressure. Purification of the residue by FC (40:60 EA-Hept) gave the title compound as a yellow oil. TLC:rf (40:60 EA-Hept)=0.26. LC-MS-conditions 02: $t_R$=0.89 min.

2-[3-(2-Methyl-[1,3]dioxolan-2-yl)-isoxazol-5-ylmethyl]-2H-[1,2,3]triazol-4-ylamine In a flame dried round-bottomed flask equipped with a magnetic stir bar and under inert atmosphere (N$_2$), a mixture of 2-[3-(2-methyl-[1,3]dioxolan-2-yl)-isoxazol-5-ylmethyl]-4-nitro-2H-[1,2,3]triazole (95 mg, 0.34 mmol), iron powder (57 mg, 1.01 mmol) and NH$_4$Cl (91 mg, 1.69 mmol) in a mixture of EtOH (2.0 mL) and water (1.0 mL) was stirred at 85° C. for 15 min. The reaction mixture was filtered while hot and concentrated under reduced pressure. CH$_2$Cl$_2$ (10 mL) was added followed by 1N NaOH (10 mL). The aq. layer was extracted with CH$_2$Cl$_2$ (2×10 mL) and the combined org. extracts were dried over MgSO$_4$, filtered, and the solvents were removed under reduced pressure to give the title compound as a light yellow oil. LC-MS-conditions 02: $t_R$=0.66 min; [M+H]$^+$=252.34.

5-(3-Isopropoxymethyl-phenyl)-oxazole-4-carboxylic acid isopropyl ester

In a flame dried round-bottomed flask equipped with a magnetic stir bar and under inert atmosphere (N$_2$), a solution of 5-(3-hydroxymethyl-phenyl)-oxazole-4-carboxylic acid (200 mg, 0.912 mmol) at 0° C. in DMF (2.5 mL) was treated with NaH (239 mg, 5.48 mmol) and the resulting mixture was stirred at 0° C. for 45 min. 2-Iodopropane (0.93 mL, 9.12 mmol) was added and the reaction mixture was stirred at rt until completion. Sat. aq. NH$_4$Cl (20 mL) was added and the aqueous layer extracted twice with EA (2×20 mL). The combined organic layers were washed with water (2×10 mL), dried over MgSO$_4$, filtered, and the solvent removed under reduced pressure. Purification of the residue by FC (1:1 Hept- EA) gave the title compound as a yellow oil. TLC:rf (1:1 Hept-EA)=0.45. LC-MS-conditions 02: $t_R$=1.05 min, $[M+H]^+$=304.28.

5-(3-Isopropoxymethyl-phenyl)-oxazole-4-carboxylic acid

In a flame dried round-bottomed flask equipped with a magnetic stir bar and under inert atmosphere ($N_2$), a solution of 5-(3-isopropoxymethyl-phenyl)-oxazole-4-carboxylic acid isopropyl ester (78 mg, 0.26 mmol) in THF (2.5 mL) was treated with a 1N NaOH (1.3 mL). The resulting mixture was stirred for 1.5 h then acidified with 1N HCl, extracted twice with EA (2×20 mL) and the combined organic phases were washed with brine (20 mL). The organic layer was dried over $MgSO_4$, filtered, and the solvent removed under reduced pressure to give the title compound as a yellow oil. LC-MS-conditions 02: $t_R$=0.87 min, $[M+AcCN+H]^+$=303.18.

5-[3-(2-Isopropoxy-ethyl)-phenyl]-oxazole-4-carboxylic acid isopropyl ester

In a flame dried round-bottomed flask equipped with a magnetic stir bar and under inert atmosphere ($N_2$), a solution of 5-[3-(2-hydroxy-ethyl)-phenyl]-oxazole-4-carboxylic acid (200 mg, 0.86 mmol) in DMF (2.0 mL) was treated at 0° C. with NaH (112 mg, 2.57 mmol) and the resulting mixture was stirred for 45 min at 0° C. 2-Iodopropane (0.44 mL, 4.28 mmol) was then added and the reaction mixture was stirred at rt until completion. The reaction mixture was quenched with sat. aq. $NH_4Cl$ (20 mL), extracted with EA (2×20 mL) and the combined org. extracts were washed with water (2×20 mL) dried over $MgSO_4$, filtered, and the solvents were removed under reduced pressure. Purification of the residue by FC (1:1 hept-EA) gave the title compound as a white solid. TLC:rf (1:1 hept-EA)=0.49. LC-MS-conditions 02: $t_R$=1.06 min; $[M+H]^+$=318.36.

(2-Bromo-thiazol-5-yl)methanol

In a flame dried round-bottomed flask equipped with a magnetic stir bar and under inert atmosphere ($N_2$), commercially available 2-bromo-thiazole-5-carbaldehyde (2.100 g, 10.94 mmol) was dissolved in MeOH (50 mL). $NaBH_4$ (535 mg, 13.58 mmol) was added portionwise at 0° C. and the reaction mixture stirred at rt for 1 h. Water (50 mL) was added and the mixture extracted with EA (3×50 mL). The combined org. extracts were dried over $Na_2SO_4$, filtered, and the solvents were removed under reduced pressure to give the title compound as a yellow solid. TLC:rf (1:1 hept-EA)=0.31. LC-MS-conditions 01: $t_R$=0.56 min; $[M+AcCN+H]^+$=234.84.

2-Bromo-5-(tert-butyl-dimethyl-silanyloxymethyl)-thiazole

In a flame dried round-bottomed flask equipped with a magnetic stir bar and under inert atmosphere ($N_2$), (2-bromo-thiazol-5-yl)-methanol (2.17 g, 11.18 mmol) was dissolved in dry $CH_2Cl_2$ (30 mL). tert-Butyldimethylsilyl chloride (1.85 g, 12.30 mmol) was added at 0° C. followed by imidazole (1.56 g, 22.92 mmol). The reaction mixture was stirred at rt for 16 h. 10% Aq. $K_2CO_3$ (10 mL) was added, the layers separated and the aq. layer extracted with $CH_2Cl_2$ (2×20 mL). The combined org. extracts were dried over $MgSO_4$, filtered, and the solvent removed under reduced pressure. Purification of the residue by FC (hept to 10:1 hept-EA) gave the title compound as a yellow oil. TLC:rf (2:1 hept-EA)=0.80. LC-MS-conditions 02: $t_R$=1.13 min; $[M+H]^+$=307.90.

1-[5-(tert-Butyl-dimethyl-silanyloxymethyl)-thiazol-2-yl]-ethanone

In a flame dried round-bottomed flask equipped with a magnetic stir bar and under inert atmosphere ($N_2$), a solution of 2-bromo-5-(tert-butyl-dimethyl-silanyloxymethyl)-thiazole (3.00 g, 9.73 mmol) in dry $Et_2O$ (20 mL) was added to a n-BuLi (4.30 mL of a 2.5M solution in hexanes, 10.70 mmol) solution in $Et_2O$ (50 mL) at −78° C. The reaction mixture was then stirred for 40 min at −78° C. before N,N-dimethylacetamide (1.81 mL, 19.46 mmol) was added dropwise. The reaction mixture was allowed to warm up to −50° C. and stirred at this temperature for 20 min. Sat. aq. $NH_4Cl$ (20 mL) was added, the layers separated and the aq. layer extracted with $Et_2O$ (3×20 mL). The combined org. extracts were dried over $Na_2SO_4$, filtered, and the solvent was removed under reduced pressure to give the title compound as a yellow oil. TLC:rf (1:2 hept-EA)=0.80. LC-MS-conditions 01: $t_R$=1.09 min, $[M+1-1]^+$=271.98.

[2-(2-Methyl-[1,3]dioxolan-2-yl)-thiazol-5-yl]-methanol

In a flame dried round-bottomed flask equipped with a magnetic stir bar and a condenser under inert atmosphere ($N_2$), a solution of 1-[5-(tert-butyl-dimethyl-silanyloxymethyl)-thiazol-2-yl]-ethanone (2.70 g, 9.95 mmol) in ethylene glycol (10.68 mL, 191.48 mmol) was treated with trimethylorthoformate (2.22 mL, 20.27 mmol) followed by $LiBF_4$ (190 mg, 1.99 mmol). The reaction mixture was heated at 95° C. for 4 days. Sat. aq. $Na_2CO_3$ (50 mL) was added and the mixture was extracted with $Et_2O$ (2×50 mL), dried over $MgSO_4$, filtered, and the solvent was removed under reduced pressure to give 3.50 g of a brown oil as a mixture of 5-(tert-butyl-dimethyl-silanyloxymethyl)-2-(2-methyl-[1,3]dioxolan-2-yl)-thiazole (TLC:rf (1:1 hept-EA)=0.41, LC-MS-conditions 02: $t_R$=1.11 min, $[M+H]^+$=316.38) along with [2-(2-methyl-[1,3]dioxolan-2-yl)-thiazol-5-yl]-methanol (TLC:rf (1:1 hept-EA)=0.13, LC-MS-conditions 02: $t_R$=0.61 min, $[M+H]^+$=202.47). A solution of this mixture in dry THF (15 mL) was treated at 0° C. with TBAF (3.0 mL of a 1M solution in THF, 3.00 mmol). The reaction mixture was stirred at 0° C. for 5 min and at rt for 3 h. The mixture was then diluted with EA (10 mL), washed with brine (3×10 mL), dried over $MgSO_4$, filtered and concentrated under reduced pressure. Purification of the residue by FC (5:1->1:3 hept-EA) gave the title compound as a yellow oil. TLC:rf (1:2 hept-EA)=0.20. LC-MS-conditions 01: $t_R$=0.56 min; $[M+H]^+$=201.92.

5-Chloromethyl-2-(2-methyl-[1,3]dioxolan-2-yl)-thiazole

In a flame dried round-bottomed flask equipped with a magnetic stir bar and under inert atmosphere ($N_2$), a solution of [2-(2-methyl-[1,3]dioxolan-2-yl)-thiazol-5-yl]-methanol (560 mg, 2.78 mmol) in dry $CH_2Cl_2$ (5.0 mL) was treated at 0° C. with $Et_3N$ (0.50 mL, 3.60 mmol) followed by DMAP (34 mg, 0.28 mmol) and Ms-Cl (0.28 mL, 3.51 mmol). After stirring at 0° C. for 1 h, the reaction mixture was quenched with water (10 mL), extracted with $CH_2Cl_2$ (10 mL) and the combined org. extracts were dried over $Na_2SO_4$, filtered, and the solvents were removed under reduced pressure. Purification of the residue by FC (5:1 to 2:1 hept-EA) gave the title compound as a pale yellow oil. TLC:rf (1:2 hept-EA)=0.50. LC-MS-conditions 01: $t_R$=0.81 min; [M+H]$^+$=219.89.

2-[2-(2-Methyl-[1,3]dioxolan-2-yl)-thiazol-5-ylmethyl]-4-nitro-2H-[1,2,3]triazole In a flame dried round-bottomed flask equipped with a magnetic stir bar and under inert atmosphere (N$_2$), a solution of 5-chloromethyl-2-(2-methyl-[1,3]dioxolan-2-yl)-thiazole (339 mg, 1.54 mmol) in DMF (2.0 mL) was added to a solution of 4-nitro-2H-[1,2,3]triazole (160 mg, 1.40 mmol) in DMF (2.0 mL) pre-treated for 30 min with DIPEA (0.48 mL, 2.81 mmol) and the reaction mixture was stirred for 72 h at 50° C. Water (10 mL), followed by EA (10 mL) were added. The aq. layer was extracted with EA (10 mL) and the combined org. extracts were dried over NaSO$_4$, filtered, and the solvents were removed under reduced pressure. Purification of the residue by FC (5:1 to 2:1 hept-EA) gave the title compound as a pale yellow oil: TLC:rf (1:2 hept-EA)=0.39. LC-MS-conditions 02: $t_R$=0.89 min; [M+H]$^+$=298.13.

2-[2-(2-Methyl-[1,3]dioxolan-2-yl)-thiazol-5-ylmethyl]-2H-[1,2,3]triazol-4-ylamine In a flame dried round-bottomed flask equipped with a magnetic stir bar and under inert atmosphere (N$_2$), a mixture of 2-[2-(2-methyl-[1,3]dioxolan-2-yl)-thiazol-5-ylmethyl]-4-nitro-2H-[1,2,3]triazole (201 mg, 0.68 mmol), iron powder (114 mg, 2.03 mmol) and NH$_4$Cl (183 mg, 3.38 mmol) in a mixture of EtOH (3.0 mL) and water (1.5 mL) was stirred at 75° C. for 60 min. The reaction mixture was filtered while hot and concentrated under reduced pressure. CH$_2$Cl$_2$ (10 mL) was added followed by 1N NaOH (10 mL). The aq. layer was extracted with CH$_2$Cl$_2$ (2×10 mL) and the combined org. extracts were dried over MgSO$_4$, filtered, and the solvents were removed under reduced pressure to give the title compound as a yellow oil: TLC:rf (19:1 CH$_2$Cl$_2$-MeOH)=0.2. LC-MS-conditions 02: $t_R$=0.68 min; [M+H]$^+$=268.25.

1-Oxazol-2-yl-ethanone

In a flame dried round-bottomed flask equipped with a magnetic stir bar and under inert atmosphere (N$_2$), a solution of commercially available oxazole (3.25 mL, 48.49 mmol) in dry THF (34 mL) at −15° C. was treated over 30 min with isopropylmagnesium chloride (24.2 mL of a 2.0M solution in THF, 48.49 mmol) while keeping the temperature below −10° C. The reaction mixture was then stirred for 40 min at −15° C. before N-methoxy-N-methylacetamide (4.12 mL, 38.79 mmol) in THF (10 mL) was added dropwise. The reaction mixture was allowed to warm up to rt and stirred overnight at rt. 20% NH$_4$Cl (150 mL) was added, the layers separated and the aq. layer extracted with Et$_2$O (3×100 mL). The combined org. extracts were dried over MgSO$_4$, filtered, and the solvent was removed under reduced pressure. Purification of the residue by FC (4:6 Et$_2$O-hexane) gave the title compound as an orange oil. TLC:rf (4:6 Et$_2$O-hexane)=0.27. LC-MS-conditions 02: $t_R$=0.47 min.

1-Oxazol-2-yl-ethanol

In a flame dried round-bottomed flask equipped with a magnetic stir bar and under inert atmosphere (N$_2$), 1-oxazol-2-yl-ethanone (446 mg, 4.01 mmol) was dissolved in MeOH (8.0 mL). NaBH$_4$ (206 mg, 5.22 mmol) was added portionwise at 0° C. and the reaction mixture stirred at rt for 30 min. Water (16 mL) was added and the mixture extracted with EA (3×20 mL). The combined org. extracts were dried over MgSO$_4$, filtered, and the solvents were removed under reduced pressure to give the title compound as a colorless oil. LC-MS-conditions 02: $t_R$=0.33 min.

2-[1-(tert-Butyl-dimethyl-silanyloxy)-ethyl]-oxazole

In a flame dried round-bottomed flask equipped with a magnetic stir bar and under inert atmosphere (N$_2$), 1-oxazol-2-yl-ethanol (348 mg, 3.08 mmol) was dissolved in dry THF (15 mL). tert-Butyldimethylsilyl chloride (580 mg, 3.85 mmol) was added at rt followed by imidazole (262 mg, 3.85 mmol). The reaction mixture was stirred at rt for 16 h. Sat. aq. NH$_4$Cl (20 mL) was added, the layers separated and the aq. layer extracted with EA (2×20 mL). The combined org. extracts were dried over MgSO$_4$, filtered, and the solvent removed under reduced pressure. Purification of the residue by FC (1:4 Et$_2$O-hexane) gave the title compound as a colorless oil. TLC:rf (1:4 Et$_2$O-hexane)=0.39. LC-MS-conditions 02: $t_R$=1.08 min, [M+H]$^+$=228.48

2-[1-(tert-Butyl-dimethyl-silanyloxy)-ethyl]-oxazole-5-carbaldehyde

In a flame dried round-bottomed flask equipped with a magnetic stir bar and under inert atmosphere (N$_2$), a solution of 2-[1-(tert-butyl-dimethyl-silanyloxy)-ethyl]-oxazole (733 mg, 3.22 mmol) in dry THF (16 mL) at −78° C. was treated with t-butyllithium (2.62 mL of a 1.6M solution in pentane, 4.19 mmol) while keeping the temperature below −70° C. The reaction mixture was then stirred for 1 h at −40° C. DMF (0.50 mL, 6.45 mmol) was added dropwise at −78° C. The reaction mixture was allowed to warm up to rt and stirred for 2 h at rt. Water (30 mL) was added followed by sat. aq. NH$_4$Cl (20 mL) and EA (20 mL), the layers separated and the aq. layer extracted with EA (2×30 mL). The combined org. extracts were dried over MgSO$_4$, filtered, and the solvent was removed under reduced pressure. Purification of the residue by FC (1:4 EA-Hept) gave the title compound as a colorless oil. TLC:rf (1:4 EA-Hept)=0.33. LC-MS-conditions 02: $t_R$=1.08 min, [M+H]$^+$=256.38.

{2-[1-(tert-Butyl-dimethyl-silanyloxy)-ethyl]-oxazol-5-yl}-methanol

In a flame dried round-bottomed flask equipped with a magnetic stir bar and under inert atmosphere (N$_2$), 2-[1-(tert-butyl-dimethyl-silanyloxy)-ethyl]-oxazole-5-carbaldehyde (457 mg, 1.79 mmol) was dissolved in MeOH (8.0 mL). NaBH$_4$ (92 mg, 2.33 mmol) was added portionwise at 0° C. and the reaction mixture stirred at rt for 20 min. Water (16 mL) was added and the mixture extracted with EA (3×20 mL). The combined org. extracts were dried over MgSO$_4$, filtered, and the solvents were removed under reduced pressure to give the title compound as a colorless oil. LC-MS-conditions 02: $t_R$=0.97 min, [M+H]$^+$=258.32.

2-[1-(tert-Butyl-dimethyl-silanyloxy)-ethyl]-5-chloromethyl-oxazole

In a flame dried round-bottomed flask equipped with a magnetic stir bar and under inert atmosphere (N$_2$), a solution of {2-[1-(tert-butyl-dimethyl-silanyloxy)-ethyl]-oxazol-5-yl}-methanol (455 mg, 1.77 mmol) in dry CH$_2$Cl$_2$ (4.5 mL) was treated at 0° C. with Et$_3$N (0.32 mL, 2.30 mmol) followed by DMAP (22 mg, 0.18 mmol) and Ms-Cl (0.17 mL, 2.12 mmol). After stirring at rt for 2 h, the reaction mixture was quenched with water (10 mL), extracted with CH$_2$Cl$_2$ (10 mL) and the combined org. extracts were dried over Na$_2$SO$_4$, filtered, and the solvents were removed under reduced pressure to give in a 2:1 ratio the title compound (LC-MS-conditions 02: t$_R$=1.13 min, [M+H]$^+$=276.06) along with methanesulfonic acid 2-[1-(tert-butyl-dimethyl-silanyloxy)-ethyl]-oxazol-5-ylmethyl ester (LC-MS-conditions 02: t$_R$=1.07 min, [M+H]$^+$=336.45) as a pale yellow oil.

2-{2-[1-(tert-Butyl-dimethyl-silanyloxy)-ethyl]-oxazol-5-ylmethyl}-4-nitro-2H-[1,2,3]triazole In a flame dried round-bottomed flask equipped with a magnetic stir bar and under inert atmosphere (N$_2$), a solution of 2-[1-(tert-butyl-dimethyl-silanyloxy)-ethyl]-5-chloromethyl-oxazole (247 mg, 0.89 mmol) in DMF (1.0 mL) was added to a solution of 4-nitro-2H-[1,2,3]triazole (850 mg of a 10% solution in acetone, 0.75 mmol) in DMF (1.0 mL) pretreated for 30 min with DIPEA (0.26 mL, 1.49 mmol) and the reaction mixture was stirred for 48 h at 50° C. Water (10 mL), followed by EA (20 mL) were added. The aq. layer was extracted with EA (10 mL) and the combined org. extracts were dried over NaSO$_4$, filtered, and the solvents were removed under reduced pressure. Purification of the residue by FC (2:1 hept-EA) gave the title compound as a yellow oil. TLC:rf (2:1 hept-EA)=0.36. LC-MS-conditions 02: t$_R$=1.11 min; [M+H]$^+$=354.34.

2-{2-[1-(tert-Butyl-dimethyl-silanyloxy)-ethyl]-oxazol-5-ylmethyl}-2H-[1,2,3]triazol-4-ylamine In a flame dried round-bottomed flask equipped with a magnetic stir bar and under inert atmosphere (N$_2$), a solution of 2-{2-[1-(tert-butyl-dimethyl-silanyloxy)-ethyl]-oxazol-5-ylmethyl}-4-nitro-2H-[1,2,3]triazole (100 mg, 0.28 mmol), iron powder (48 mg, 0.85 mmol) and NH$_4$Cl (76 mg, 1.42 mmol) in a mixture of EtOH (2.0 mL) and water (1.0 mL) was stirred at 85° C. for 20 min. The reaction mixture was filtered while hot and concentrated under reduced pressure. CH$_2$Cl$_2$ (10 mL) was added followed by water (10 mL). The aq. layer was extracted with CH$_2$Cl$_2$ (2×10 mL) and the combined org. extracts were dried over MgSO$_4$, filtered, and the solvents were removed under reduced pressure to give the title compound as a yellow oil. LC-MS-conditions O$_2$: t$_R$=0.98 min; [M+H]$^+$=324.42.

5-Phenyl-oxazole-4-carboxylic acid (2-{2-[1-(tert-butyl-dimethyl-silanyloxy)-ethyl]-oxazol-5-ylmethyl}-2H-[1,2,3]triazol-4-yl)-amide In a flame dried round-bottomed flask equipped with a magnetic stir bar and under inert atmosphere (N$_2$), a solution of 5-phenyl-oxazole-4-carboxylic acid (47 mg, 0.25 mmol) in CH$_2$Cl$_2$ (1.5 mL) was treated at rt with HOBt (40 mg, 0.30 mmol), EDC (119 mg, 0.62 mmol), DMAP (8 mg, 0.06 mmol) and the resulting mixture was stirred at rt for 30 min. 2-{2-[1-(tert-Butyl-dimethyl-silanyloxy)-ethyl]-oxazol-5-ylmethyl}-2H-[1,2,3]triazol-4-ylamine (80 mg, 0.25 mmol) in CH$_2$Cl$_2$ (1.0 mL) was then added and the resulting mixture was stirred at rt for 72 h. CH$_2$Cl$_2$ (20 mL) followed by water (15 mL) were added and the aqueous phase was extracted with CH$_2$Cl$_2$. The combined organic phases were washed with water, brine, dried over MgSO$_4$, filtered, and the solvent removed under reduced pressure to give the title compound as a yellow oil. LC-MS-conditions 02: t$_R$=1.17 min, [M+H]$^+$=495.54.

5-Phenyl-oxazole-4-carboxylic acid {2-[2-(1-hydroxy-ethyl)-oxazol-5-ylmethyl]-2H-[1,2,3]triazol-4-yl}-amide In a flame dried round-bottomed flask equipped with a magnetic stir bar and under inert atmosphere (N$_2$), a solution of 5-phenyl-oxazole-4-carboxylic acid (2-{2-[1-(tert-butyl-dimethyl-silanyloxy)-ethyl]-oxazol-5-ylmethyl}-2H-[1,2,3]triazol-4-yl)-amide (120 mg, 0.24 mmol) in dry THF (2.1 mL) was treated at 0° C. with TBAF (0.48 mL of a 1M solution in THF, 0.48 mmol). The reaction mixture was stirred at 0° C. for 45 min. The mixture was then diluted with EA (10 mL), washed with NaHCO$_3$ (10 mL) followed by brine (3×10 mL), dried over MgSO$_4$, filtered and concentrated under reduced pressure. Purification of the residue by FC (19:1 CH$_2$Cl$_2$-MeOH) gave the title compound as a white foam. TLC:rf (19:1 CH$_2$Cl$_2$-MeOH)=0.19. LC-MS-conditions 02: t$_R$=0.88 min; [M+H]$^+$=381.23.

1-(2-Bromo-thiazol-5-yl)-ethanol

In a flame dried round-bottomed flask equipped with a magnetic stir bar and under inert atmosphere (N$_2$), a solution of commercially available 2-bromo-thiazole-5-carbaldehyde (1.80 g, 9.37 mmol) in CH$_2$Cl$_2$ (70.0 mL) was treated at 0° C. with trimethylaluminum (46.0 mL of a 1M solution in heptane, 46 mmol). The reaction mixture was then stirred at 0° C. for 45 min. CH$_2$Cl$_2$ (100.0 mL) followed by sat. aq. NH$_4$Cl (100 mL) was then added. The mixture was then treated with 1N HCl (50 mL) and the aq. layer was extracted with CH$_2$Cl$_2$ (150 mL). The combined org. extracts were dried over MgSO$_4$, filtered, and the solvents were removed under reduced pressure to give the title compound as a yellow oil. TLC:rf (1:2 hept-EA)=0.40. LC-MS-conditions 02: t$_R$=0.70 min; [M+AcCN+H]$^+$=249.17.

1-(2-Bromo-thiazol-5-yl)-ethanone

In a flame dried round-bottomed flask equipped with a magnetic stir bar and under inert atmosphere (N$_2$), a solution of 1-(2-bromo-thiazol-5-yl)-ethanol (1.95 g, 9.37 mmol) in AcCN (90.0 mL) was treated at rt with MnO$_2$ (4.53 g, 46.86 mmol) and the reaction mixture was stirred for 16 h at rt before being filtered through Celite. The solvent was removed under reduced pressure to give the title compound as a yellow solid. LC-MS-conditions 02: t$_R$=0.80 min.

2-Bromo-5-(2-methyl-[1,3]dioxolan-2-yl)-thiazole

In a flame dried round-bottomed flask equipped with a magnetic stir bar and a condenser under inert atmosphere (N$_2$), a solution of 1-(2-bromo-thiazol-5-yl)-ethanone (2.20 g, 10.68 mmol) in ethylene glycol (11.46 mL, 205.53 mmol) was treated with trimethylorthoformate (2.39 mL, 21.76 mmol) followed by LiBF$_4$ (204 mg, 2.14 mmol). The reaction mixture was heated at 95° C. for 2 days. Sat. aq. NaHCO$_3$ (50 mL) was added and the mixture was extracted with EA (50 mL). The org. extracts were washed with brine (2×50 mL), dried over MgSO$_4$, filtered, and the solvent was removed under reduced pressure. Purification of the residue by FC (20:1 to 3:1 hept-EA) gave the title compound as a yellow oil. TLC:rf (1:1 hept-EA)=0.80. LC-MS-conditions 01: t$_R$=0.84 min; [M+H]$^+$=251.85.

5-(2-Methyl-[1,3]dioxolan-2-yl)-thiazole-2-carbaldehyde

In a flame dried round-bottomed flask equipped with a magnetic stir bar and under inert atmosphere (N$_2$), a solution of 2-bromo-5-(2-methyl-[1,3]dioxolan-2-yl)-thiazole (780 mg, 3.12 mmol) in dry Et$_2$O (10 mL) was added to a n-BuLi (1.25 mL of a 2.5M solution in hexanes, 3.13 mmol) solution in Et$_2$O (10 mL) at −78° C. The reaction mixture was then stirred for 30 min at −78° C. before DMF (0.29 mL, 3.78 mmol) was added dropwise. The reaction mixture was allowed to warm up to −20° C. and stirred at this temperature for 20 min. Sat. aq. NH$_4$Cl (10 mL) was added, the layers separated and the aq. layer extracted with Et$_2$O (3×10 mL). The combined org. extracts were dried over Na$_2$SO$_4$, filtered, and the solvent was removed under reduced pressure. Purification of the residue by FC (10:1 to 3:1 hept-EA) gave the title compound as a yellow oil. TLC:rf (1:1 hept-EA)=0.50. LC-MS-conditions 01: $t_R$=0.78 min; [M+H]$^+$=199.93.

[5-(2-Methyl-[1,3]dioxolan-2-yl)-thiazol-2-yl]-methanol

In a flame dried round-bottomed flask equipped with a magnetic stir bar and under inert atmosphere (N$_2$), 5-(2-methyl-[1,3]dioxolan-2-yl)-thiazole-2-carbaldehyde (555 mg, 2.79 mmol) was dissolved in MeOH (5 mL). NaBH$_4$ (136 mg, 3.46 mmol) was added portionwise at 0° C. and the reaction mixture stirred at rt for 1 h. Water (10 mL) was added and the mixture extracted with EA (3×20 mL). The combined org. extracts were dried over Na$_2$SO$_4$, filtered, and the solvents were removed under reduced pressure to give the title compound as a yellow oil. TLC:rf (1:1 hept-EA)=0.25. LC-MS-conditions 02: $t_R$=0.64 min; [M+H]$^+$=202.48.

Methanesulfonic acid 5-(2-methyl-[1,3]dioxolan-2-yl)-thiazol-2-ylmethyl ester

In a flame dried round-bottomed flask equipped with a magnetic stir bar and under inert atmosphere (N$_2$), a solution of [5-(2-methyl-[1,3]dioxolan-2-yl)-thiazol-2-yl]-methanol (560 mg, 2.78 mmol) in dry CH$_2$Cl$_2$ (5.0 mL) was treated at 0° C. with Et$_3$N (0.50 mL, 3.60 mmol) followed by DMAP (34 mg, 0.28 mmol) and Ms-Cl (0.28 mL, 3.51 mmol). After stirring at 0° C. for 1 h, the reaction mixture was quenched with water (10 mL), extracted with CH$_2$Cl$_2$ (10 mL) and the combined org. extracts were dried over Na$_2$SO$_4$, filtered, and the solvents were removed under reduced pressure. Purification of the residue by FC (5:1 to 2:1 hept-EA) gave the title compound as a brown oil. LC-MS-conditions 01: $t_R$=0.77 min; [M+H]$^+$=279.88.

2-[5-(2-Methyl-[1,3]dioxolan-2-yl)-thiazol-2-ylmethyl]-4-nitro-2H-[1,2,3]triazole In a flame dried round-bottomed flask equipped with a magnetic stir bar and under inert atmosphere (N$_2$), a solution of methanesulfonic acid 5-(2-methyl-[1,3]dioxolan-2-yl)-thiazol-2-ylmethyl ester (445 mg, 1.59 mmol) in DMF (3.0 mL) was added to a solution of 4-nitro-2H-[1,2,3]triazole (180 mg, 1.58 mmol) in DMF (3.0 mL) pre-treated for 30 min with DIPEA (0.54 mL, 3.16 mmol) and the reaction mixture was stirred for 72 h at 50° C. Water (10 mL), followed by EA (10 mL) were added. The aq. layer was extracted with EA (10 mL) and the combined org. extracts were dried over NaSO$_4$, filtered, and the solvents were removed under reduced pressure. Purification of the residue by FC (5:1 to 2:1 hept-EA) gave the title compound as a pale yellow oil: TLC:rf (1:2 hept-EA)=0.39. LC-MS-conditions 01: $t_R$=0.85 min; [M+H]$^+$=297.91.

2-[5-(2-Methyl-[1,3]dioxolan-2-yl)-thiazol-2-ylmethyl]-2H-[1,2,3]triazol-4-ylamine In a flame dried round-bottomed flask equipped with a magnetic stir bar and under inert atmosphere (N$_2$), a mixture of 2-[5-(2-methyl-[1,3]dioxolan-2-yl)-thiazol-2-ylmethyl]-4-nitro-2H-[1,2,3]triazole (220 mg, 0.74 mmol), iron powder (125 mg, 2.22 mmol) and NH$_4$Cl (200 mg, 3.70 mmol) in a mixture of EtOH (3.0 mL) and water (1.5 mL) was stirred at 75° C. for 60 min. The reaction mixture was filtered while hot and concentrated under reduced pressure. CH$_2$Cl$_2$ (10 mL) was added followed by 1N NaOH (10 mL). The aq. layer was extracted with CH$_2$Cl$_2$ (2×10 mL) and the combined org. extracts were dried over Na$_2$SO$_4$, filtered, and the solvents were removed under reduced pressure to give the title compound as a yellow oil: TLC:rf (19:1 CH$_2$Cl$_2$-MeOH)=0.2. LC-MS-conditions 02: $t_R$=0.66 min.

(4-Bromo-thiophen-2-yl)-methanol

In a flame dried round-bottomed flask equipped with a magnetic stir bar and under inert atmosphere (N$_2$), commercially available 4-bromo-thiophene-2-carbaldehyde (3.93 g, 20.57 mmol) was dissolved in THF (60.0 mL). NaBH$_4$ (892 mg, 22.63 mmol) was added portionwise at 0° C. and the reaction mixture stirred at rt for 30 min. Sat. aq. NaHCO$_3$ was added and the mixture extracted with Et$_2$O. The combined org. extracts were dried over Na$_2$SO$_4$, filtered, and the solvents were removed under reduced pressure to give the title compound as a colorless oil. TLC:rf (2:1 hept-EA)=0.38.

(4-Bromo-thiophen-2-ylmethoxy)-tert-butyl-dimethyl-silane

In a flame dried round-bottomed flask equipped with a magnetic stir bar and under inert atmosphere (N$_2$), (4-bromo-thiophen-2-yl)-methanol (3.97 g, 20.57 mmol) was dissolved in dry CH$_2$Cl$_2$ (50 mL). tert-Butyldimethylsilyl chloride (3.59 g, 22.63 mmol) was added at rt followed by imidazole (1.56 g, 22.63 mmol). The reaction mixture was stirred at rt for 1 h. Water was added, the layers were separated and the org. layer was dried over MgSO$_4$, filtered, and the solvent removed under reduced pressure. Purification of the residue by FC (hept) gave the title compound as a colorless oil. TLC:rf (100:1 hept-EA)=0.44. LC-MS-conditions 02: $t_R$=1.21 min.

1-[5-(tert-Butyl-dimethyl-silanyloxymethyl)-thiophen-3-yl]-ethanone

In a flame dried round-bottomed flask equipped with a magnetic stir bar and under inert atmosphere (N$_2$), a solution of (4-bromo-thiophen-2-ylmethoxy)-tert-butyl-dimethyl-silane (3.07 g, 10.00 mmol) in dry Et$_2$O (10 mL) was added to a solution of n-butyllithium (4.10 mL of a 2.5M solution in hexane, 10.25 mmol) in Et$_2$O (40 mL) at −78° C. while keeping the temperature below −70° C. The reaction mixture was then stirred for 30 min at −78° C. N,N-Dimethyl-acetamide (1.20 mL, 12.91 mmol) was added dropwise at −78° C. The reaction mixture was then stirred for 1 h at −78° C. followed by 1 h at rt. Sat. aq. NH$_4$Cl was added, the layers separated and the aq. layer extracted with Et$_2$O (3×50 mL). The combined org. extracts were dried over Na$_2$SO$_4$, filtered, and the solvent was removed under reduced pressure. Purification of the residue by FC (0:100 to 10:90 EA-Hept) gave the title compound as a yellow solid. TLC:rf (1:9 EA-Hept)= 0.30. LC-MS-conditions 02: $t_R$=1.15 min.

tert-Butyl-dimethyl-[4-(2-methyl-[1,3]dioxolan-2-yl)-thiophen-2-ylmethoxy]-silane In a flame dried round-bottomed flask equipped with a magnetic stir bar and a condenser under inert atmosphere ($N_2$), a solution of 1-[5-(tert-butyl-dimethyl-silanyloxymethyl)-thiophen-3-yl]-ethanone (811 mg, 3.00 mmol) in ethylene glycol (3.5 mL, 62.76 mmol) was treated with trimethylorthoformate (0.66 mL, 6.02 mmol) followed by $LiBF_4$ (57 mg, 0.60 mmol). The reaction mixture was heated at 95° C. for 2 h. Sat. aq. $Na_2CO_3$ (50 mL) was added and the mixture was extracted with $Et_2O$ (2×50 mL), dried over $MgSO_4$, filtered, and the solvent was removed under reduced pressure. Purification of the residue by FC (1:20 EA-Hept) gave the title compound as a yellow oil. TLC:rf (1:10 EA-Hept)=0.34. LC-MS-conditions 02: $t_R$=1.17 min; $[M+H]^+$=315.22.

[4-(2-Methyl-[1,3]dioxolan-2-yl)-thiophen-2-yl]-methanol

In a flame dried round-bottomed flask equipped with a magnetic stir bar and under inert atmosphere ($N_2$), a solution of tert-butyl-dimethyl-[4-(2-methyl-[1,3]dioxolan-2-yl)-thiophen-2-ylmethoxy]-silane (545 mg, 1.73 mmol) in dry THF (5.0 mL) was treated at 0° C. with TBAF (2.6 mL of a 1M solution in THF, 2.60 mmol). The reaction mixture was stirred at 0° C. for 2 h. The mixture was then diluted with EA (10 mL), washed with brine (3×20 mL), dried over $MgSO_4$, filtered and concentrated under reduced pressure. Purification of the residue by FC (1:5 EA-Hept) gave the title compound as a colorless oil. TLC:rf (1:1 EA-Hept)=0.36. LC-MS-conditions 02: $t_R$=0.70 min.

2-[4-(2-Methyl-[1,3]dioxolan-2-yl)-thiophen-2-ylmethyl]-4-nitro-2H-[1,2,3]triazole In a flame dried round-bottomed flask equipped with a magnetic stir bar and under inert atmosphere ($N_2$), a solution of [4-(2-methyl-[1,3]dioxolan-2-yl)-thiophen-2-yl]-methanol (256 mg, 1.28 mmol) in dry $CH_2Cl_2$ (5.0 mL) was treated at 0° C. with $Et_3N$ (0.23 mL, 1.64 mmol) followed by DMAP (16 mg, 0.13 mmol) and Ms-Cl (0.12 mL, 1.55 mmol). After stirring at 0° C. for 30 min and at rt for 1 h, the reaction mixture was quenched with water (10 mL), extracted with $CH_2Cl_2$ (10 mL) and the combined org. extracts were dried over $Na_2SO_4$, filtered, and the solvents were removed under reduced pressure to give crude 2-(5-chloromethyl-thiophen-3-yl)-2-methyl-[1,3]dioxolane (TLC:rf (1:1 EA-Hept)= 0.61). A solution of the crude material in DMF (3 mL) was treated at rt with a solution of (4-nitro-2H-[1,2,3]triazole (124 mg, 1.07 mmol) in DMF (2.0 mL) pre-treated for 30 min with DIPEA (0.40 mL, 2.34 mmol). The resulting mixture was stirred for two weeks at rt. Water (10 mL), followed by EA (10 mL) were added. The org. extract was washed with water (10 mL), dried over $Na_2SO_4$, filtered, and the solvents were removed under reduced pressure. Purification of the residue by FC (hept to 1:1 hept-EA) gave the title compound as a yellow oil: TLC:rf (1:1 hept-EA)=0.48.

2-[4-(2-Methyl-[1,3]dioxolan-2-yl)-thiophen-2-ylmethyl]-2H-[1,2,3]triazol-4-ylamine In a flame dried round-bottomed flask equipped with a magnetic stir bar and under inert atmosphere ($N_2$), a mixture of 1-[4-(2-methyl-[1,3]dioxolan-2-yl)-thiophen-2-ylmethyl]-4-nitro-1H-pyrazole (115 mg, 0.39 mmol), iron powder (65 mg, 1.16 mmol) and $NH_4Cl$ (106 mg, 1.97 mmol) in a mixture of EtOH (3.0 mL) and water (1.5 mL) was stirred at 75° C. for 60 min. The reaction mixture was filtered while hot and concentrated under reduced pressure. The filtrated was dried over $Na_2SO_4$, filtered, and the solvents were removed under reduced pressure to give the title compound as a yellow oil: TLC: rf (EA)=0.63. LC-MS-conditions 02: $t_R$=0.76 min; $[M+H]^+$=267.09.

(E)-2-Styryl-oxazole-4-carboxylic acid ethyl ester

In a flame dried round-bottomed flask equipped with a magnetic stir bar and under inert atmosphere ($N_2$), a suspension of 3-phenyl-acrylamide (10.31 g, 67.95 mmol) and $NaHCO_3$ (28.47 g, 339.73 mmol) in THF (260 mL) was treated with 3-bromo-2-oxo-propionic acid ethyl ester (13.04 mL, 88.33 mmol) and the reaction mixture was heated at reflux for 15 h. 3-Bromo-2-oxo-propionic acid ethyl ester (13.04 mL, 88.33 mmol) was added again and the reaction mixture was stirred at reflux for 15 h. The reaction mixture was then filtered over celite and the solvents were evaporated under reduced pressure. The residue was dissolved in THF (30 mL) and treated at 0° C., dropwise, with trifluoroacetic anhydride (30.0 mL, 215.83 mmol). The reaction mixture was then stirred at rt overnight. Sat. aq. $Na_2CO_3$ was added and the mixture was extracted with EA (3×150 mL), dried over $MgSO_4$, filtered, and the solvent was removed under reduced pressure. Purification of the residue by FC (1:9 EA-Hept) gave the title compound as a yellow solid. TLC:rf (1:9 EA-Hept)=0.1. LC-MS-conditions 02: $t_R$=1.01 min; $[M+H]^+$= 244.48.

2-Formyl-oxazole-4-carboxylic acid ethyl ester

In a flame dried round-bottomed flask equipped with a magnetic stir bar and under inert atmosphere ($N_2$), a solution of $NaIO_4$ (3.21 g, 15.00 mmol) in water (26.0) mL was slowly added to a vigorously stirred suspension of silica gel (15.0 g) in acetone (60.0 mL). The mixture was then concentrated under reduced pressure and the lumpy solid slurried in $CH_2Cl_2$ and the solvent was evaporated under reduced pressure. $CH_2Cl_2$ (40.0 mL) was added and the reaction mixture was treated at rt with (E)-2-styryl-oxazole-4-carboxylic acid ethyl ester (1.22 g, 5.00 mmol) and $RuCl_3$ hydrate (82 mg, 0.15 mmol). The reaction mixture was stirred at rt in the dark for 30 min, filtered and concentrated under reduced pressure. Purification of the residue by FC (1:9 to 1:2 EA-Hept) gave the title compound as a yellow solid. TLC:rf (3:2 EA-Hept)=0.21. LC-MS-conditions 02: $t_R$=0.51 min; $[M+H_2O+H]^+$=188.50.

2-Hydroxymethyl-oxazole-4-carboxylic acid ethyl ester

In a flame dried round-bottomed flask equipped with a magnetic stir bar and under inert atmosphere ($N_2$), 2-formyl-oxazole-4-carboxylic acid ethyl ester (272 mg, 1.61 mmol) was dissolved in EtOH (5.0 mL). $NaBH_4$ (112 mg, 2.84 mmol) was added portionwise at 0° C. and the reaction mixture stirred at 0° C. for 1 h. Sat. aq. $NH_4Cl$ was added and the mixture extracted with EA (5×10 mL). The combined org. extracts were dried over $Na_2SO_4$, filtered, and the solvents were removed under reduced pressure to give the title compound as a yellow oil. TLC: rf (EA)=0.50. LC-MS-conditions 02: $t_R$=0.58 min; [M+H]$^+$=172.03.

2-(tert-Butyl-dimethyl-silanyloxymethyl)-oxazole-4-carboxylic acid ethyl ester In a flame dried round-bottomed flask equipped with a magnetic stir bar and under inert atmosphere (N$_2$), 2-hydroxymethyl-oxazole-4-carboxylic acid ethyl ester (275 mg, 1.61 mmol) was dissolved in dry CH$_2$Cl$_2$ (5.0 mL). tert-Butyldimethylsilyl chloride (510 mg, 3.22 mmol) was added at rt followed by imidazole (221 mg, 3.22 mmol). The reaction mixture was stirred at rt for 30 min. Water was added, the layers were separated and the org. layer was dried over Na$_2$SO$_4$, filtered, and the solvent removed under reduced pressure. Purification of the residue by FC (1:20 to 1:9 EA-Hept) gave the title compound as a colorless oil. TLC:rf (9:1 hept-EA)=0.15. LC-MS-conditions 02: $t_R$=1.10 min; [M+H]$^+$=286.38.

2-(tert-Butyl-dimethyl-silanyloxymethyl)-oxazole-4-carbaldehyde

In a flame dried round-bottomed flask equipped with a magnetic stir bar and under inert atmosphere (N$_2$), a solution of 2-(tert-butyl-dimethyl-silanyloxymethyl)-oxazole-4-carboxylic acid ethyl ester (283 mg, 0.99 mmol) in CH$_2$Cl$_2$ (5.0 mL) was treated at −78° C. with DiBAL (1.85 mL of a 1M sol in toluene, 1.85 mmol) and the reaction mixture was stirred for 1 h at −78° C. MeOH (70 μL) and H$_2$O (100 μL) were added and the reaction mixture was allowed to warm to rt. The reaction mixture was filtered, and the solvent removed under reduced pressure to give the title compound as a colorless oil. TLC:rf (1:1 hept-EA)=0.61. LC-MS-conditions 02: $t_R$=1.03 min; [M+H$_2$O+H]$^+$=260.50.

1-[2-(tert-Butyl-dimethyl-silanyloxymethyl)-oxazol-4-yl]-ethanol

In a flame dried round-bottomed flask equipped with a magnetic stir bar and under inert atmosphere (N$_2$), a solution of 2-(tert-butyl-dimethyl-silanyloxymethyl)-oxazole-4-carbaldehyde (223 mg, 0.92 mmol) in CH$_2$Cl$_2$ (8.0 mL) was treated at 0° C. with trimethylaluminum (2.50 mL of a 2M solution in toluene, 5.00 mmol). The reaction mixture was then stirred at 0° C. for 45 min. Sat. aq. NH$_4$Cl was then added and the aq. layer was extracted twice with CH$_2$Cl$_2$ and twice with EA. The combined org. extracts were dried over Na$_2$SO$_4$, filtered, and the solvents were removed under reduced pressure to give the title compound as a colorless oil. TLC:rf (1:1 hept-EA)=0.32. LC-MS-conditions 02: $t_R$=0.97 min, [M+H]$^+$=258.30.

1-[2-(tert-Butyl-dimethyl-silanyloxymethyl)-oxazol-4-yl]-ethanone

In a flame dried round-bottomed flask equipped with a magnetic stir bar and under inert atmosphere (N$_2$), a solution of 1-[2-(tert-butyl-dimethyl-silanyloxymethyl)-oxazol-4-yl]-ethanol (193 mg, 0.75 mmol) in AcCN (5.0 mL) was treated at rt with MnO$_2$ (362 mg, 3.75 mmol). The reaction mixture was stirred for 16 h at rt before being filtered through Celite. The solvent was removed under reduced pressure to give the title compound as a white solid. TLC:rf (1:1 hept-EA)=0.69. LC-MS-conditions 02: $t_R$=1.04 min, [M+H]$^+$=255.84.

1-(2-Hydroxymethyl-oxazol-4-yl)-ethanone

In a flame dried round-bottomed flask equipped with a magnetic stir bar and under inert atmosphere (N$_2$), a solution of 1-[2-(tert-butyl-dimethyl-silanyloxymethyl)-oxazol-4-yl]-ethanone (192 mg, 0.75 mmol) in dry THF (5.0 mL) was treated at rt with TBAF (1.1 mL of a 1M solution in THF, 1.10 mmol). The reaction mixture was stirred at rt for 1.5 h. The mixture was then diluted with EA (10 mL), washed with brine (3×10 mL), dried over Na$_2$SO$_4$, filtered and concentrated under reduced pressure. Purification of the residue by FC (1:1 to 2:1 EA-Hept) gave the title compound as a pale yellow solid. TLC: rf (EA)=0.37. LC-MS-conditions 02: $t_R$=0.34 min, [M+H]$^+$=142.46.

Methanesulfonic acid 4-acetyl-oxazol-2-ylmethyl ester

In a flame dried round-bottomed flask equipped with a magnetic stir bar and under inert atmosphere (N$_2$), a solution of 1-(2-hydroxymethyl-oxazol-4-yl)-ethanone (75 mg, 0.53 mmol) in dry CH$_2$Cl$_2$ (5.0 mL) was treated at 0° C. with Et$_3$N (0.10 mL, 0.71 mmol) followed by DMAP (6 mg, 0.05 mmol) and Ms-Cl (0.05 mL, 0.66 mmol). After stirring at 0° C. for 30 min, the reaction mixture was quenched with water (10 mL), extracted with CH$_2$Cl$_2$ (10 mL) and the combined org. extracts were dried over Na$_2$SO$_4$, filtered, and the solvents were removed under reduced pressure to give the title compound as a yellow oil. TLC: rf (EA)=0.63. LC-MS-conditions 02: $t_R$=0.64 min; [M+H]$^+$=220.22.

1-[2-(4-Nitro-[1,2,3]triazol-2-ylmethyl)-oxazol-4-yl]-ethanone

In a flame dried round-bottomed flask equipped with a magnetic stir bar and under inert atmosphere (N$_2$), a solution of methanesulfonic acid 4-acetyl-oxazol-2-ylmethyl ester (116 mg, 0.53 mmol) in DMF (3.0 mL) was added to a solution of 4-nitro-2H-[1,2,3]triazole (62 mg, 0.53 mmol) in DMF (2.0 mL) pre-treated for 30 min with DIPEA (0.20 mL, 1.17 mmol) and the reaction mixture was stirred for 20 h at 50° C. Water (10 mL), followed by EA (10 mL) were added. The aq. layer was extracted with EA (10 mL) and the combined org. extracts were dried over NaSO$_4$, filtered, and the solvents were removed under reduced pressure. Purification of the residue by FC (3:1 to 1:1 hept-EA) gave the title compound as a yellow solid. TLC:rf (1:2 hept-EA)=0.49. LC-MS-conditions 01: $t_R$=0.76 min.

1-[2-(4-Amino-[1,2,3]triazol-2-ylmethyl)-oxazol-4-yl]-ethanone

In a flame dried round-bottomed flask equipped with a magnetic stir bar and under inert atmosphere (N$_2$), a mixture of 1-[2-(4-nitro-[1,2,3]triazol-2-ylmethyl)-oxazol-4-yl]-ethanone (48 mg, 0.20 mmol), iron powder (34 mg, 0.61 mmol) and NH$_4$Cl (54 mg, 1.01 mmol) in a mixture of EtOH (2.0 mL) and water (1.0 mL) was stirred at 75° C. for 60 min. The reaction mixture was filtered while hot and concentrated under reduced pressure. The filtrated was dried over Na$_2$SO$_4$, filtered, and the solvents were removed under reduced pressure to give the title compound as a brown oil. TLC: rf (EA)=0.40. LC-MS-conditions 02: $t_R$=0.54 min; [M+H]$^+$=208.44.

5-(3-Fluoro-phenyl)-2-methyl-oxazole-4-carboxylic acid (2-{2-[1-(tert-butyl-dimethyl-silanyloxy)-ethyl]-oxazol-5-ylmethyl}-2H-[1,2,3]triazol-4-yl)-amide In a flame dried round-bottomed flask equipped with a magnetic stir bar and under inert atmosphere (N$_2$), a solution of 5-(3-fluoro-phenyl)-2-methyl-oxazole-4-carboxylic acid (34 mg, 0.16 mmol) in CH$_2$Cl$_2$ (1.0 mL) was treated at rt with HOBt (25 mg, 0.19 mmol), EDC (74 mg, 0.38 mmol), DMAP (5 mg, 0.04 mmol) and the resulting mixture was stirred at rt for 30 min. 2-{2-[1-(tert-Butyl-dimethyl-silanyloxy)-ethyl]-oxazol-5-ylmethyl}-2H-[1,2,3]triazol-4-ylamine (50 mg, 0.16 mmol) in CH$_2$Cl$_2$ (0.6 mL) was then added and the resulting mixture was stirred at rt for 16 h. CH$_2$Cl$_2$ (20 mL) followed by water (15 mL) were added and the aqueous phase was extracted with CH$_2$Cl$_2$. The combined organic phases were washed with water, brine, dried over MgSO$_4$, filtered, and the solvent removed under reduced pressure to give the title compound as a brown oil. LC-MS-conditions 02: $t_R$=1.22 min, [M+H]$^+$=527.5.

5-(3-Fluoro-phenyl)-2-methyl-oxazole-4-carboxylic acid {2-[2-(1-hydroxy-ethyl)-oxazol-5-ylmethyl]-2H-[1,2,3]triazol-4-yl}-amide In a flame dried round-bottomed flask equipped with a magnetic stir bar and under inert atmosphere (N$_2$), a solution of 5-(3-fluoro-phenyl)-2-methyl-oxazole-4-carboxylic acid (2-{2-[1-(tert-butyl-dimethyl-silanyloxy)-ethyl]-oxazol-5-ylmethyl}-2H-[1,2,3]triazol-4-yl)-amide (110 mg, 0.21 mmol) in dry THF (2.1 mL) was treated at 0° C. with TBAF (0.42 mL of a 1M solution in THF, 0.42 mmol). The reaction mixture was stirred at 0° C. for 45 min. The mixture was then diluted with EA (10 mL), washed with NaHCO$_3$ (10 mL) followed by brine (3×10 mL), dried over MgSO$_4$, filtered and concentrated under reduced pressure. Purification of the residue by FC (19:1 CH$_2$Cl$_2$-MeOH) gave the title compound as an orange oil. TLC:rf (19:1 CH$_2$Cl$_2$-MeOH)=0.21. LC-MS-conditions 02: $t_R$=0.94 min; [M+H]$^+$=412.86.

2-Methyl-5-m-tolyl-oxazole-4-carboxylic acid (2-{2-[1-(tert-butyl-dimethyl-silanyloxy)-ethyl]-oxazol-5-ylmethyl}-2H-[1,2,3]triazol-4-yl)-amide In a flame dried round-bottomed flask equipped with a magnetic stir bar and under inert atmosphere (N$_2$), a solution of 2-methyl-5-m-tolyl-oxazole-4-carboxylic acid (34 mg, 0.16 mmol) in CH$_2$Cl$_2$ (1.0 mL) was treated at rt with HOBt (25 mg, 0.19 mmol), EDC (74 mg, 0.38 mmol), DMAP (5 mg, 0.04 mmol) and the resulting mixture was stirred at rt for 30 min. 2-{2-[1-(tert-Butyl-dimethyl-silanyloxy)-ethyl]-oxazol-5-ylmethyl}-2H-[1,2,3]triazol-4-ylamine (50 mg, 0.16 mmol) in CH$_2$Cl$_2$ (0.6 mL) was then added and the resulting mixture was stirred at rt for 16 h. CH$_2$Cl$_2$ (20 mL) followed by water (15 mL) were added and the aqueous phase was extracted with CH$_2$Cl$_2$. The combined organic phases were washed with water, brine, dried over MgSO$_4$, filtered, and the solvent removed under reduced pressure to give the title compound as a brown oil. LC-MS-conditions 02: $t_R$=1.23 min, [M+H]$^+$=523.56.

2-Methyl-5-m-tolyl-oxazole-4-carboxylic acid {2-[2-(1-hydroxy-ethyl)-oxazol-5-ylmethyl]-2H-[1,2,3]triazol-4-yl}-amide In a flame dried round-bottomed flask equipped with a magnetic stir bar and under inert atmosphere (N$_2$), a solution of 2-methyl-5-m-tolyl-oxazole-4-carboxylic acid (2-{2-[1-(tert-butyl-dimethyl-silanyloxy)-ethyl]-oxazol-5-ylmethyl}-2H-[1,2,3]triazol-4-yl)-amide (109 mg, 0.21 mmol) in dry THF (2.0 mL) was treated at 0° C. with TBAF (0.41 mL of a 1M solution in THF, 0.41 mmol). The reaction mixture was stirred at 0° C. for 45 min. The mixture was then diluted with EA (10 mL), washed with NaHCO$_3$ (10 mL) followed by brine (3×10 mL), dried over MgSO$_4$, filtered and concentrated under reduced pressure. Purification of the residue by FC (19:1 CH$_2$Cl$_2$-MeOH) gave the title compound as a yellow oil. TLC:rf (19:1 CH$_2$Cl$_2$-MeOH)=0.23. LC-MS-conditions 02: $t_R$=0.95 min; [M+H]$^+$=409.78.

5-(3-Chloro-phenyl)-2-methyl-oxazole-4-carboxylic acid (2-{2-[1-(tert-butyl-dimethyl-silanyloxy)-ethyl]-oxazol-5-ylmethyl}-2H-[1,2,3]triazol-4-yl)-amide In a flame dried round-bottomed flask equipped with a magnetic stir bar and under inert atmosphere (N$_2$), a solution of 5-(3-chloro-phenyl)-2-methyl-oxazole-4-carboxylic acid (37 mg, 0.16 mmol) in CH$_2$Cl$_2$ (1.0 mL) was treated at rt with HOBt (25 mg, 0.19 mmol), EDC (74 mg, 0.38 mmol), DMAP (5 mg, 0.04 mmol) and the resulting mixture was stirred at rt for 30 min. 2-{2-[1-(tert-Butyl-dimethyl-silanyloxy)-ethyl]-oxazol-5-ylmethyl}-2H-[1,2,3]triazol-4-ylamine (50 mg, 0.16 mmol) in CH$_2$Cl$_2$ (0.6 mL) was then added and the resulting mixture was stirred at rt for 16 h. CH$_2$Cl$_2$ (20 mL) followed by water (15 mL) were added and the aqueous phase was extracted with CH$_2$Cl$_2$. The combined organic phases were washed with water, brine, dried over MgSO$_4$, filtered, and the solvent removed under reduced pressure to give the title compound as a brown oil. LC-MS-conditions 02: $t_R$=1.24 min, [M+H]$^+$=542.92.

5-(3-Chloro-phenyl)-2-methyl-oxazole-4-carboxylic acid {2-[2-(1-hydroxy-ethyl)-oxazol-5-ylmethyl]-2H-[1,2,3]triazol-4-yl}-amide In a flame dried round-bottomed flask equipped with a magnetic stir bar and under inert atmosphere (N$_2$), a solution of 5-(3-chloro-phenyl)-2-methyl-oxazole-4-carboxylic acid (2-{2-[1-(tert-butyl-dimethyl-silanyloxy)-ethyl]-oxazol-5-ylmethyl}-2H-[1,2,3]triazol-4-yl)-amide (106 mg, 0.20 mmol) in dry THF (1.9 mL) was treated at 0° C. with TBAF (0.39 mL of a 1M solution in THF, 0.39 mmol). The reaction mixture was stirred at 0° C. for 45 min. The mixture was then diluted with EA (10 mL), washed with NaHCO$_3$ (10 mL) followed by brine (3×10 mL), dried over MgSO$_4$, filtered and concentrated under reduced pressure. Purification of the residue by FC (19:1 CH$_2$Cl$_2$-MeOH) gave the title compound as a white solide. TLC:rf (19:1 CH$_2$Cl$_2$-MeOH)=0.22. LC-MS-conditions 01: $t_R$=0.93 min; [M+H]$^+$=428.97.

5-m-Tolyl-oxazole-4-carboxylic acid (2-{2-[1-(tert-butyl-dimethyl-silanyloxy)-ethyl]-oxazol-5-ylmethyl}-2H-[1,2,3]triazol-4-yl)-amide In a flame dried round-bottomed flask equipped with a magnetic stir bar and under inert atmosphere (N$_2$), a solution of 5-m-tolyl-oxazole-4-carboxylic acid (31 mg, 0.16 mmol) in CH$_2$Cl$_2$ (1.0 mL) was treated at rt with HOBt (25 mg, 0.19 mmol), EDC (74 mg, 0.38 mmol), DMAP (5 mg, 0.04 mmol) and the resulting mixture was stirred at rt for 30 min. 2-{2-[1-(tert-Butyl-dimethyl-silanyloxy)-ethyl]-oxazol-5-ylmethyl}-2H-[1,2,3]triazol-4-ylamine (50 mg, 0.16 mmol) in CH$_2$Cl$_2$ (0.6 mL) was then added and the resulting mixture was stirred at rt for 16 h. CH$_2$Cl$_2$ (20 mL) followed by water (15 mL) were added and the aqueous phase was extracted with CH$_2$Cl$_2$. The combined organic phases were washed with water, brine, dried over MgSO$_4$, filtered, and the solvent removed under reduced pressure to give the title compound as a brown oil. LC-MS-conditions 02: $t_R$=1.20 min, [M+H]$^+$=509.55.

5-m-Tolyl-oxazole-4-carboxylic acid {2-[2-(1-hydroxy-ethyl)-oxazol-5-ylmethyl]-2H-[1,2,3]triazol-4-yl}-amide In a flame dried round-bottomed flask equipped with a magnetic stir bar and under inert atmosphere (N$_2$), a solution of 5-m-tolyl-oxazole-4-carboxylic acid (2-{2-[1-(tent-butyl-dimethyl-silanyloxy)-ethyl]-oxazol-5-ylmethyl}-2H-[1,2,3]triazol-4-yl)-amide (100 mg, 0.20 mmol) in dry THF (1.9 mL) was treated at 0° C. with TBAF (0.39 mL of a 1M solution in THF, 0.39 mmol). The reaction mixture was stirred at 0° C. for 45 min. The mixture was then diluted with EA (10 mL), washed with NaHCO$_3$ (10 mL) followed by brine (3×10 mL), dried over MgSO$_4$, filtered and concentrated under reduced pressure. Purification of the residue by FC (19:1 CH$_2$Cl$_2$-MeOH) gave the title compound as a yellow oil. TLC:rf (19:1 CH$_2$Cl$_2$-MeOH)=0.21. LC-MS-conditions 02: $t_R$=0.92 min; [M+H]$^+$=395.35.

2-Methyl-5-(3-trifluoromethoxy-phenyl)-oxazole-4-carboxylic acid (2-{2-[1-(tert-butyl-dimethyl-silanyloxy)-ethyl]-oxazol-5-ylmethyl}-2H-[1,2,3]triazol-4-yl)-amide In a flame dried round-bottomed flask equipped with a magnetic stir bar and under inert atmosphere (N$_2$), a solution of 2-methyl-5-(3-trifluoromethoxy-phenyl)-oxazole-4-carboxylic acid (44 mg, 0.16 mmol) in CH$_2$Cl$_2$ (1.0 mL) was treated at rt with HOBt (25 mg, 0.19 mmol), EDC (74 mg, 0.38 mmol), DMAP (5 mg, 0.04 mmol) and the resulting mixture was stirred at rt for 30 min. 2-{2-[1-(tert-Butyl-dimethyl-silanyloxy)-ethyl]-oxazol-5-ylmethyl}-2H-[1,2,3]triazol-4-ylamine (50 mg, 0.16 mmol) in CH$_2$Cl$_2$ (0.6 mL) was then added and the resulting mixture was stirred at rt for 16 h. CH$_2$Cl$_2$ (20 mL) followed by water (15 mL) were added and the aqueous phase was extracted with CH$_2$Cl$_2$. The combined organic phases were washed with water, brine, dried over MgSO$_4$, filtered, and the solvent removed under reduced pressure to give the title compound as a brown oil. LC-MS-conditions 02: $t_R$=1.25 min, [M+H]$^+$=593.58.

2-Methyl-5-(3-trifluoromethoxy-phenyl)-oxazole-4-carboxylic acid {2-[2-(1-hydroxy-ethyl)-oxazol-5-ylmethyl]-2H-[1,2,3]triazol-4-yl}-amide In a flame dried round-bottomed flask equipped with a magnetic stir bar and under inert atmosphere (N$_2$), a solution of 2-methyl-5-(3-trifluoromethoxy-phenyl)-oxazole-4-carboxylic acid (2-{2-[1-(tert-butyl-dimethyl-silanyloxy)-ethyl]-oxazol-5-ylmethyl}-2H-[1,2,3]triazol-4-yl)-amide (122 mg, 0.21 mmol) in dry THF (2.0 mL) was treated at 0° C. with TBAF (0.41 mL of a 1M solution in THF, 0.41 mmol). The reaction mixture was stirred at 0° C. for 45 min. The mixture was then diluted with EA (10 mL), washed with NaHCO$_3$ (10 mL) followed by brine (3×10 mL), dried over MgSO$_4$, filtered and concentrated under reduced pressure. Purification of the residue by FC (19:1 CH$_2$Cl$_2$-MeOH) gave the title compound as a white solid. TLC:rf (19:1 CH$_2$Cl$_2$-MeOH)=0.26. LC-MS-conditions 02: $t_R$=1.01 min; [M+H]$^+$=479.03.

[2-(tert-Butyl-dimethyl-silanyloxymethyl)-oxazol-4-yl]-methanol

In a flame dried round-bottomed flask equipped with a magnetic stir bar and under inert atmosphere (N$_2$), a solution of 2-(tert-butyl-dimethyl-silanyloxymethyl)-oxazole-4-carboxylic acid ethyl ester (830 mg, 2.91 mmol) in THF (15.0 mL) was treated at 0° C. with DiBAL (11.6 mL of a 1M sol in toluene, 11.60 mmol) and the reaction mixture was stirred for 45 min at 0° C. The reaction mixture was then diluted with EA (5.0 mL), sat. aq. Rochelle's salt (20.0 mL) was added and the mixture stirred at rt for 2 h. The layers were separated and the aq. layer extracted with EA (3×20 mL). The combined org. extracts were dried over Na$_2$SO$_4$, filtered, and the solvents were removed under reduced pressure to give the title compound as a yellow solid. TLC: rf (EA)=0.59. LC-MS-conditions 02: $t_R$=0.94 min; [M+H]$^+$=244.46.

Methanesulfonic acid 2-(tert-butyl-dimethyl-silanyloxymethyl)-oxazol-4-ylmethyl ester In a flame dried round-bottomed flask equipped with a magnetic stir bar and under inert atmosphere (N$_2$), a solution of [2-(tert-butyl-dimethyl-silanyloxymethyl)-oxazol-4-yl]-methanol (500 mg, 2.05 mmol) in dry CH$_2$Cl$_2$ (10.0 mL) was treated at 0° C. with Et$_3$N (0.37 mL, 2.65 mmol) followed by DMAP (25 mg, 0.20 mmol) and Ms-Cl (0.20 mL, 2.54 mmol). After stirring at 0° C. for 30 min, the reaction mixture was quenched with water (10 mL), extracted with CH$_2$Cl$_2$ (10 mL) and the combined org. extracts were dried over Na$_2$SO$_4$, filtered, and the solvents were removed under reduced pressure to give the title compound as a yellow oil. TLC:rf (1:1 hept-EA)=0.50. LC-MS-conditions 02: $t_R$=1.05 min; [M+H]$^+$=322.25.

2-[2-(tert-Butyl-dimethyl-silanyloxymethyl)-oxazol-4-ylmethyl]-4-nitro-2H-[1,2,3]triazole In a flame dried round-bottomed flask equipped with a magnetic stir bar and under inert atmosphere (N$_2$), a solution of methanesulfonic acid 2-(tert-butyl-dimethyl-silanyloxymethyl)-oxazol-4-ylmethyl ester (651 mg, 2.02 mmol) in DMF (3.0 mL) was added to a solution of 4-nitro-2H-[1,2,3]triazole (210 mg, 1.84 mmol) in DMF (3.0 mL) pre-treated for 30 min with DIPEA (0.63 mL, 3.68 mmol) and the reaction mixture was stirred for 20 h at 50° C. Water (10 mL), followed by EA (10 mL) were added. The aq. layer was extracted with EA (10 mL) and the combined org. extracts were dried over NaSO$_4$, filtered, and the solvents were removed under reduced pressure. Purification of the residue by FC (5:1 to 2:1 hept-EA) gave the title compound as a yellow oil: TLC:rf (1:2 hept-EA)=0.30. LC-MS-conditions 02: $t_R$=1.10 min; [M+H]$^+$=340.47.

2-[2-(tert-Butyl-dimethyl-silanyloxymethyl)-oxazol-4-ylmethyl]-2H-[1,2,3]triazol-4-ylamine In a flame dried round-bottomed flask equipped with a magnetic stir bar and under inert atmosphere (N$_2$), a solution of 2-[2-(tert-butyl-dimethyl-silanyloxymethyl)-oxazol-4-ylmethyl]-4-nitro-2H-[1,2,3]triazole (103 mg, 0.30 mmol), iron powder (51 mg, 0.91 mmol) and NH$_4$Cl (82 mg, 1.52 mmol) in a mixture of EtOH (3.0 mL) and water (1.5 mL) was stirred at 75° C. for 90 min. The reaction mixture was filtered while hot and concentrated under reduced pressure. The residue was redissolved in CH$_2$Cl$_2$ (20 mL), dried over Na$_2$SO$_4$, filtered, and the solvents were removed under reduced pressure to give the title compound as a yellow oil. TLC:rf (19:1 CH$_2$Cl$_2$-MeOH)=0.20. LC-MS-conditions 02: $t_R$=0.96 min; [M+H]$^+$=310.46.

{2-[2-(tert-Butyl-dimethyl-silanyloxymethyl)-oxazol-4-ylmethyl]-2H-[1,2,3]triazol-4-yl}-carbamic acid 2-chloro-benzyl ester In a flame dried round-bottomed flask equipped with a magnetic stir bar and under inert atmosphere (N$_2$), a solution of 2-[2-(tert-butyl-dimethyl-silanyloxymethyl)-oxazol-4-yl-methyl]-2H-[1,2,3]triazol-4-ylamine (93 mg, 0.30 mmol) in CH$_2$Cl$_2$ (5.0 mL) was treated with DIPEA (0.08 mL, 0.48 mmol) followed by 2-chlorobenzylchloroformate (0.06 mL, 0.39 mmol) at 0° C. The reaction mixture was stirred at 0° C. for 1 h and water (5.0 mL) was added. The layers were separated and the aq. layer extracted with CH$_2$Cl$_2$ (2×10 mL). The combined org. extracts were dried over Na$_2$SO$_4$, filtered, and the solvent was removed under reduced pressure. Purification of the residue by FC (9:1 to 1:1 hept-EA) gave the title compound as an orange solid. TLC:rf (1:1 hept-EA)=0.27. LC-MS-conditions 01: $t_R$=1.11 min; [M+H]$^+$=478.01.

[2-(2-Hydroxymethyl-oxazol-4-ylmethyl)-2H-[1,2,3]triazol-4-yl]-carbamic acid 2-chloro-benzyl ester In a flame dried round-bottomed flask equipped with a magnetic stir bar and under inert atmosphere (N$_2$), a solution of {2-[2-(tert-butyl-dimethyl-silanyloxymethyl)-oxazol-4-ylmethyl]-2H-[1,2,3]triazol-4-yl}-carbamic acid 2-chloro-benzyl ester (144 mg, 0.30 mmol) in dry THF (3.0 mL) was treated at 0° C. with TBAF (0.46 mL of a 1M solution in THF, 0.46 mmol). The reaction mixture was stirred at 0° C. for 30 min. Sat. aq. NH$_4$Cl (5 mL) was added, the layers separated and the aq. layer extracted with EA (3×10 mL). The combined organic extracts were dried over Na$_2$SO$_4$, filtered and concentrated under reduced pressure. Purification of the residue by FC (EA) gave the title compound as a yellow oil. TLC: rf (EA)=0.25. LC-MS-conditions 01: $t_R$=0.82 min; [M+H]$^+$=363.90.

[2-(2-Dihydroxymethyl-oxazol-4-ylmethyl)-2H-[1,2,3]triazol-4-yl]-carbamic acid 2-chloro-benzyl ester In a flame dried round-bottomed flask equipped with a magnetic stir bar and under inert atmosphere (N$_2$), a solution of [2-(2-hydroxymethyl-oxazol-4-ylmethyl)-2H-[1,2,3]triazol-4-yl]-carbamic acid 2-chloro-benzyl ester (37 mg, 0.10 mmol) in AcCN (3.0 mL) was treated at rt with MnO$_2$ (49 mg, 0.51 mmol) and the reaction mixture was stirred at rt for 16 h before being filtered through Celite. The solvent was removed under reduced pressure to give the title compound as a brown solid. TLC: rf (EA)=0.48. LC-MS-conditions 02: $t_R$=0.83 min; [M+H]$^+$=380.69.

{2-[2-(1-Hydroxy-ethyl)-oxazol-4-ylmethyl]-2H-[1,2,3]triazol-4-yl}-carbamic acid 2-chloro-benzyl ester In a flame dried round-bottomed flask equipped with a magnetic stir bar and under inert atmosphere (N$_2$), a solution of [2-(2-dihydroxymethyl-oxazol-4-ylmethyl)-2H-[1,2,3]triazol-4-yl]-carbamic acid 2-chloro-benzyl ester (19 mg, 0.05 mmol) in THF (1.0 mL) was treated at −65° C. with methylmagnesium bromide (0.15 mL of a 1M solution in THF, 0.15 mmol). The reaction mixture was then stirred at −65° C. for 1 h. The reaction mixture was then slowly warmed to rt and stirred at this temperature for 45 min. Sat. aq. NH$_4$Cl was then added and the aq. layer was extracted with EA (3×10 mL). The combined org. extracts were dried over Na$_2$SO$_4$, filtered, and the solvents were removed under reduced pressure. The residue was purified by FC (EA) to give the title compound as a yellow oil. TLC: rf (EA)=0.30. LC-MS-conditions 02: $t_R$=0.89 min, [M+H]$^+$=378.30.

5-(3-Methoxy-phenyl)-2-methyl-oxazole-4-carboxylic acid

Prepared starting from 3-(3-methoxy-phenyl)-3-oxo-propionic acid ethyl ester following sequentially general procedure F, G and E. LC-MS-conditions 02: $t_R$=0.82 min; [M+H]$^+$=234.10.

5-(3,5-Dimethyl-phenyl)-2-methyl-oxazole-4-carboxylic acid

Prepared starting from 3-(3,5-dimethyl-phenyl)-3-oxo-propionic acid ethyl ester following sequentially general procedure F, G and E. LC-MS-conditions 02: $t_R$=0.89 min; [M+H]$^+$=232.12

5-(3-Fluoro-phenyl)-2-methyl-oxazole-4-carboxylic acid

Prepared starting from 3-(3-fluoro-phenyl)-3-oxo-propionic acid ethyl ester following sequentially general procedure F, G and E. LC-MS-conditions 02: $t_R$=0.83 min; [M+H]$^+$=222.14.

2-Methyl-5-m-tolyl-oxazole-4-carboxylic acid

Prepared starting from 3-oxo-3-m-tolyl-propionic acid ethyl ester following sequentially general procedure F, G and E. LC-MS-conditions 02: $t_R$=0.85 min; [M+H]$^+$=218.46.

5-(3-Chloro-phenyl)-2-methyl-oxazole-4-carboxylic acid

Prepared starting from 3-chloro-benzoic acid following sequentially general procedure K, F, G and E. LC-MS-conditions 02: $t_R$=0.87 min; [M+H]$^+$=238.06.

2-Methyl-5-phenyl-oxazole-4-carboxylic acid

Prepared starting from 3-oxo-3-phenyl-propionic acid ethyl ester following sequentially general procedure F, G and E. LC-MS-conditions 02: $t_R$=0.76 min; [M+H]$^+$=204.03.

2-Methyl-5-(3-trifluoromethyl-phenyl)-oxazole-4-carboxylic acid

Prepared starting from 3-trifluoromethyl-benzoic acid following sequentially general procedure K, F, G and E. LC-MS-conditions 02: $t_R$=0.91 min; [M+H]$^+$=272.05.

2-Methyl-5-(3-trifluoromethoxy-phenyl)-oxazole-4-carboxylic acid

Prepared starting from 3-trifluoromethoxy-benzoic acid following sequentially general procedure K, F, G and E. LC-MS-conditions 02: $t_R$=0.93 min; [M+H]$^+$=288.06.

2-Methyl-5-o-tolyl-oxazole-4-carboxylic acid

Prepared starting from 3-oxo-3-o-tolyl-propionic acid ethyl ester following sequentially general procedure F, G and E. LC-MS-conditions 02: $t_R$=0.83 min; [M+H]$^+$=218.16.

5-(3-Trifluoromethyl-phenyl)-oxazole-4-carboxylic acid

Prepared starting from 3-trifluoromethyl-benzoic acid following sequentially general procedure K, J, I, H and E. LC-MS-conditions 02: $t_R$=0.89 min; $[M+AcCN+H]^+$=298.92.

5-(4-Chloro-phenyl)-oxazole-4-carboxylic acid

Prepared starting from 4-chloro-benzoic acid following sequentially general procedure K, J, I, H and E. LC-MS-conditions 02: $t_R$=0.85 min; $[M+AcCN+H]^+$=264.87.

5-(3-Trifluoromethoxy-phenyl)-oxazole-4-carboxylic acid

Prepared starting from 3-trifluoromethoxy-benzoic acid following sequentially general procedure K, J, I, H and E. LC-MS-conditions 02: $t_R$=0.91 min; $[M+AcCN+H]^+$=314.98.

5-(3-Methoxy-4-methyl-phenyl)-oxazole-4-carboxylic acid

Prepared starting from 3-methoxy-4-methyl-benzoic acid following sequentially general procedure K, J, I, H and E. LC-MS-conditions 02: $t_R$=0.86 min; $[M+H]^+$=234.11.

5-(4-Fluoro-phenyl)-oxazole-4-carboxylic acid

Prepared starting from 4-fluoro-benzoic acid following sequentially general procedure K, J, I, H and E. LC-MS-conditions 02: $t_R$=0.80 min; $[M+AcCN+H]^+$=249.04.

5-m-Tolyl-oxazole-4-carboxylic acid

Prepared starting from 3-oxo-3-m-tolyl-propionic acid ethyl ester following sequentially general procedure J, I, H and E. LC-MS-conditions 02: $t_R$=0.83 min; $[M+H]^+$=204.17.

5-(3-Methoxy-phenyl)-oxazole-4-carboxylic acid

Prepared starting from 3-(3-methoxy-phenyl)-3-oxo-propionic acid ethyl ester following sequentially general procedure J, I, H and E. LC-MS-conditions 02: $t_R$=0.80 min; $[M+H]^+$=220.13.

2-Ethyl-5-phenyl-oxazole-4-carboxylic acid

Prepared starting from 3-oxo-3-phenyl-propionic acid ethyl ester following sequentially general procedure J, I, H and E. LC-MS-conditions 02: $t_R$=0.85 min; $[M+H]^+$=218.19.

2-Cyclopropyl-5-phenyl-oxazole-4-carboxylic acid

Prepared starting from 3-oxo-3-phenyl-propionic acid ethyl ester following sequentially general procedure J, I, H and E. LC-MS-conditions 02: $t_R$=0.87 min; $[M+H]^+$=230.17.

5-(3-Fluoro-phenyl)-oxazole-4-carboxylic acid

Prepared starting from 3-fluoro-benzoic acid following sequentially general procedure K, J, I, H and E. LC-MS-conditions 02: $t_R$=0.80 min; $[M+AcCN+H]^+$=249.09.

5-(3-Chloro-phenyl)-oxazole-4-carboxylic acid

Prepared starting from 3-chloro-benzoic acid following sequentially general procedure K, J, I, H and E. LC-MS-conditions 02: $t_R$=0.85 min; $[M+AcCN+H]^+$=265.23.

5-(3-Dimethylamino-phenyl)-oxazole-4-carboxylic acid

Prepared starting from 3-dimethylamino-benzoic acid following sequentially general procedure M and E. LC-MS-conditions 02: $t_R$=0.60 min; $[M+H]^+$=233.36.

5-[3-(2-Hydroxy-ethyl)-phenyl]-oxazole-4-carboxylic acid

Prepared starting from 3-(2-hydroxy-ethyl)-benzoic acid following sequentially general procedures M and E. LC-MS-conditions 02: $t_R$=0.71 min; $[M+H]^+$=234.36.

5-[3-(2-Methoxy-ethyl)-phenyl]-oxazole-4-carboxylic acid

Prepared starting from 5-[3-(2-methoxy-ethyl)-phenyl]-oxazole-4-carboxylic acid methyl ester following general procedure E. LC-MS-conditions 02: $t_R$=0.81 min; $[M+H]^+$=248.37.

2-Methyl-5-m-tolyl-thiazole-4-carboxylic acid

Prepared starting from 3-methyl-benzaldehyde following sequentially general procedures R, S and E. LC-MS-conditions 01: $t_R$=0.83 min; $[M+H]^+$=234.01.

5-[3-(2-Isopropoxy-ethyl)-phenyl]-oxazole-4-carboxylic acid

Prepared starting from 5-[3-(2-isopropoxy-ethyl)-phenyl]-oxazole-4-carboxylic acid isopropyl ester following general procedure E. LC-MS-conditions 02: $t_R$=0.89 min; $[M+H]^+$=275.6.

5-(3-Fluoro-phenyl)-thiazole-4-carboxylic acid

Prepared starting from 3-fluoro-benzaldehyde following sequentially general procedures R, T, U, V and E. LC-MS-conditions 01: $t_R$=0.81 min; $[M+H]^+$=224.38.

2-Methoxymethyl-5-phenyl-oxazole-4-carboxylic acid

Prepared starting from DL-3-phenylserine hydrate following sequentially general procedures W, X with methoxyacetic acid, Y and Z. LC-MS-conditions 02: $t_R$=0.81 min; $[M+H]^+$=234.45.

2-(2-Methoxy-ethyl)-5-phenyl-oxazole-4-carboxylic acid

Prepared starting from DL-3-phenylserine hydrate following sequentially general procedures W, X with 3-methoxy-propionic acid, Y and Z. LC-MS-conditions 01: $t_R$=0.77 min; $[M+H]^+$=247.96.

2-Butyl-5-phenyl-oxazole-4-carboxylic acid

Prepared starting from DL-3-phenylserine hydrate following sequentially general procedures W, X with pentanoic acid, Y and Z. LC-MS-conditions 02: $t_R$=0.95 min; $[M+H]^+$=246.45.

2-Isopropyl-5-phenyl-oxazole-4-carboxylic acid

Prepared starting from DL-3-phenylserine hydrate following sequentially general procedures W, X with isobutyric acid, Y and Z. LC-MS-conditions 02: $t_R$=0.90 min; $[M+H]^+$=232.51.

2-Benzyl-5-phenyl-oxazole-4-carboxylic acid

Prepared starting from DL-3-phenylserine hydrate following sequentially general procedures W, X with phenyl-acetic acid, Y and Z. LC-MS-conditions 02: $t_R$=0.95 min; $[M+H]^+$=220.18.

2-(2-tert-Butoxycarbonyl-ethyl)-5-phenyl-oxazole-4-carboxylic acid

Prepared starting from DL-3-phenylserine hydrate following sequentially general procedures W, X with succinic acid mono-tert-butyl ester, Y and Z. LC-MS-conditions 02: $t_R$=0.95 min; $[M+H]^+$=318.32.

5-(6-Trifluoromethyl-pyridin-2-yl)-oxazole-4-carboxylic acid lithium salt

Prepared starting from 6-trifluoromethyl-pyridine-2-carboxylic acid following sequentially general procedures M and E (using LiOH). LC-MS-conditions 02: $t_R$=0.80 min; $[M+H]^+$=259.12.

PREPARATION OF EXAMPLES

Example 1

5-Phenyl-oxazole-4-carboxylic acid [2-(5-acetyl-furan-2-ylmethyl)-2H-[1,2,3]triazol-4-yl]-amide Following general procedure A followed by either B or C, starting from 2-[5-(2-methyl-[1,3]dioxolan-2-yl)-furan-2-ylmethyl]-2H-[1,2,3]triazol-4-ylamine and 5-phenyl-oxazole-4-carboxylic acid.
LC-MS-conditions 02: $t_R$=0.99 min; $[M+H]^+$=377.99.

Example 2

(E)-N-[2-(5-Acetyl-furan-2-ylmethyl)-2H-[1,2,3]triazol-4-yl]-3-(4-trifluoromethyl-phenyl)-acrylamide Following general procedure A followed by either B or C, starting from 2-[5-(2-methyl-[1,3]dioxolan-2-yl)-furan-2-ylmethyl]-2H-[1,2,3]triazol-4-ylamine and (E)-3-(4-trifluoromethyl-phenyl)-acrylic acid.
LC-MS-conditions 02: $t_R$=1.03 min; $[M+H]^+$=404.99.

Example 3

5-(3-Methoxy-phenyl)-2-methyl-oxazole-4-carboxylic acid [2-(5-acetyl-furan-2-ylmethyl)-2H-[1,2,3]triazol-4-yl]-amide Following general procedure A followed by either B or C, starting from 2-[5-(2-methyl-[1,3]dioxolan-2-yl)-furan-2-ylmethyl]-2H-[1,2,3]triazol-4-ylamine and 5-(3-methoxy-phenyl)-2-methyl-oxazole-4-carboxylic acid.
LC-MS-conditions 02: $t_R$=1.03 min; $[M+H]^+$=421.98.

Example 4

[2-(5-Acetyl-furan-2-ylmethyl)-2H-[1,2,3]triazol-4-yl]-carbamic acid 2-chloro-benzyl ester Following general procedure D followed by either B or C, starting from 2-[5-(2-methyl-[1,3]dioxolan-2-yl)-furan-2-ylmethyl]-2H-[1,2,3]triazol-4-ylamine and (2-chloro-phenyl)-methanol.
LC-MS-conditions 02: $t_R$=1.00 min; $[M+H]^+$=374.97.

Example 5

5-Phenyl-oxazole-4-carboxylic acid [2-(5-oxo-hexyl)-2H-[1,2,3]triazol-4-yl]-amide Following general procedure A followed by B, starting from 2-[4-(2-methyl-[1,3]dioxolan-2-yl)-butyl]-2H-[1,2,3]triazol-4-ylamine and 5-phenyl-oxazole-4-carboxylic acid.
LC-MS-conditions 02: $t_R$=0.99 min; $[M+H]^+$=354.36.

Example 6

(E)-N-[2-(5-Acetyl-furan-2-ylmethyl)-2H-[1,2,3]triazol-4-yl]-3-(4-chloro-phenyl)-acrylamide Following general procedure A followed by L, starting from 2-[5-(2-methyl-[1,3]dioxolan-2-yl)-furan-2-ylmethyl]-2H-[1,2,3]triazol-4-ylamine and (E)-3-(4-chloro-phenyl)-acrylic acid.
LC-MS-conditions 05b: $t_R$=0.7 min; $[M+H]^+$=371.11.

Example 7

(E)-N-[2-(5-Acetyl-furan-2-ylmethyl)-2H-[1,2,3]triazol-4-yl]-3-(2-trifluoromethyl-phenyl)-acrylamide Following general procedure A followed by L, starting from 2-[5-(2-methyl-[1,3]dioxolan-2-yl)-furan-2-ylmethyl]-2H-[1,2,3]triazol-4-ylamine and (E)-3-(2-trifluoromethyl-phenyl)-acrylic acid.
LC-MS-conditions 05b: $t_R$=0.71 min; $[M+H]^+$=405.19.

Example 8

(E)-N-[2-(5-Acetyl-furan-2-ylmethyl)-2H-[1,2,3]triazol-4-yl]-3-(3-trifluoromethoxy-phenyl)-acrylamide Following general procedure A followed by L, starting from 2-[5-(2-methyl-[1,3]dioxolan-2-yl)-furan-2-ylmethyl]-2H-[1,2,3]triazol-4-ylamine and (E)-3-(3-trifluoromethoxy-phenyl)-acrylic acid.
LC-MS-conditions 05b: $t_R$=0.74 min; $[M+H]^+$=421.12.

Example 9

(E)-N-[2-(5-Acetyl-furan-2-ylmethyl)-2H-[1,2,3]triazol-4-yl]-3-o-tolyl-acrylamide Following general procedure A followed by L, starting from 2-[5-(2-methyl-[1,3]dioxolan-2-yl)-furan-2-ylmethyl]-2H-[1,2,3]triazol-4-ylamine and (E)-3-o-tolyl-acrylic acid.
LC-MS-conditions 05b: $t_R$=0.67 min; $[M+H]^+$=351.18.

Example 10

(E)-N-[2-(5-Acetyl-furan-2-ylmethyl)-2H-[1,2,3]triazol-4-yl]-3-(2-chloro-4-fluoro-phenyl)-acrylamide Following general procedure A followed by L, starting from 2-[5-(2-methyl-[1,3]dioxolan-2-yl)-furan-2-ylmethyl]-2H-[1,2,3]triazol-4-ylamine and (E)-3-(2-chloro-4-fluoro-phenyl)-acrylic acid.
LC-MS-conditions 05b: $t_R$=0.7 min; [M+H]$^+$=389.14.

Example 11

(E)-N-[2-(5-Acetyl-furan-2-ylmethyl)-2H-[1,2,3]triazol-4-yl]-3-m-tolyl-acrylamide Following general procedure A followed by L, starting from 2-[5-(2-methyl-[1,3]dioxolan-2-yl)-furan-2-ylmethyl]-2H-[1,2,3]triazol-4-ylamine and (E)-3-m-tolyl-acrylic acid.
LC-MS-conditions 05b: $t_R$=0.68 min; [M+H]$^+$=351.22.

Example 12

(E)-N-[2-(5-Acetyl-furan-2-ylmethyl)-2H-[1,2,3]triazol-4-yl]-3-p-tolyl-acrylamide Following general procedure A followed by L, starting from 2-[5-(2-methyl-[1,3]dioxolan-2-yl)-furan-2-ylmethyl]-2H-[1,2,3]triazol-4-ylamine and (E)-3-p-tolyl-acrylic acid.
LC-MS-conditions 05b: $t_R$=0.68 min; [M+H]$^+$=351.22.

Example 13

(E)-N-[2-(5-Acetyl-furan-2-ylmethyl)-2H-[1,2,3]triazol-4-yl]-3-(4-methoxy-phenyl)-acrylamide Following general procedure A followed by L, starting from 2-[5-(2-methyl-[1,3]dioxolan-2-yl)-furan-2-ylmethyl]-2H-[1,2,3]triazol-4-ylamine and (E)-3-(4-methoxy-phenyl)-acrylic acid.
LC-MS-conditions 05b: $t_R$=0.62 min; [M+H]$^+$=367.18.

Example 14

5-(3,5-Dimethyl-phenyl)-2-methyl-oxazole-4-carboxylic acid [2-(5-acetyl-furan-2-ylmethyl)-2H-[1,2,3]triazol-4-yl]-amide Following general procedure A followed by L, starting from 2-[5-(2-methyl-[1,3]dioxolan-2-yl)-furan-2-ylmethyl]-2H-[1,2,3]triazol-4-ylamine and 5-(3,5-dimethyl-phenyl)-2-methyl-oxazole-4-carboxylic acid.
LC-MS-conditions 05b: $t_R$=0.83 min; [M+H]$^+$=420.21.

Example 15

5-(3-Trifluoromethyl-phenyl)-oxazole-4-carboxylic acid [2-(5-acetyl-furan-2-ylmethyl)-2H-[1,2,3]triazol-4-yl]-amide Following general procedure A followed by L, starting from 2-[5-(2-methyl-[1,3]dioxolan-2-yl)-furan-2-ylmethyl]-2H-[1,2,3]triazol-4-ylamine and 5-(3-trifluoromethyl-phenyl)-oxazole-4-carboxylic acid.
LC-MS-conditions 05b: $t_R$=0.77 min; [M+H]$^+$=446.17.

Example 16

5-(3-Fluoro-phenyl)-2-methyl-oxazole-4-carboxylic acid [2-(5-acetyl-furan-2-ylmethyl)-2H-[1,2,3]triazol-4-yl]-amide Following general procedure A followed by L, starting from 2-[5-(2-methyl-[1,3]dioxolan-2-yl)-furan-2-ylmethyl]-2H-[1,2,3]triazol-4-ylamine and 5-(3-fluoro-phenyl)-2-methyl-oxazole-4-carboxylic acid.
LC-MS-conditions 05b: $t_R$=0.75 min; [M+H]$^+$=410.17.

Example 17

5-(4-Chloro-phenyl)-oxazole-4-carboxylic acid [2-(5-acetyl-furan-2-ylmethyl)-2H-[1,2,3]triazol-4-yl]-amide Following general procedure A followed by L, starting from 2-[5-(2-methyl-[1,3]dioxolan-2-yl)-furan-2-ylmethyl]-2H-[1,2,3]triazol-4-ylamine and 5-(4-chloro-phenyl)-oxazole-4-carboxylic acid.
LC-MS-conditions 05b: $t_R$=0.76 min; [M+H]$^+$=412.13.

Example 18

2-Methyl-5-m-tolyl-oxazole-4-carboxylic acid [2-(5-acetyl-furan-2-ylmethyl)-2H-[1,2,3]triazol-4-yl]-amide Following general procedure A followed by L, starting from 2-[5-(2-methyl-[1,3]dioxolan-2-yl)-furan-2-ylmethyl]-2H-[1,2,3]triazol-4-ylamine and 5-(m-tolyl)-2-methyl-oxazole-4-carboxylic acid.
LC-MS-conditions 05b: $t_R$=0.78 min; [M+H]$^+$=406.18.

Example 19

5-(3-Trifluoromethoxy-phenyl)-oxazole-4-carboxylic acid [2-(5-acetyl-furan-2-ylmethyl)-2H-[1,2,3]triazol-4-yl]-amide Following general procedure A followed by L, starting from 2-[5-(2-methyl-[1,3]dioxolan-2-yl)-furan-2-ylmethyl]-2H-[1,2,3]triazol-4-ylamine and 5-(3-trifluoromethoxy-phenyl)-oxazole-4-carboxylic acid.
LC-MS-conditions 05b: $t_R$=0.79 min; [M+H]$^+$=462.1.

Example 20

5-(3-Chloro-phenyl)-2-methyl-oxazole-4-carboxylic acid [2-(5-acetyl-furan-2-ylmethyl)-2H-[1,2,3]triazol-4-yl]-amide Following general procedure A followed by L, starting from 2-[5-(2-methyl-[1,3]dioxolan-2-yl)-furan-2-ylmethyl]-2H-[1,2,3]triazol-4-ylamine and 5-(3-chloro-phenyl)-2-methyl-oxazole-4-carboxylic acid.
LC-MS-conditions 05b: $t_R$=0.80 min; [M+H]$^+$=426.14.

Example 21

5-(3-Methoxy-4-methyl-phenyl)-oxazole-4-carboxylic acid [2-(5-acetyl-furan-2-ylmethyl)-2H-[1,2,3]triazol-4-yl]-amide Following general procedure A followed by L, starting from 2-[5-(2-methyl-[1,3]dioxolan-2-yl)-furan-2-ylmethyl]-

2H-[1,2,3]triazol-4-ylamine and 5-(3-methoxy-4-methyl-phenyl)-oxazole-4-carboxylic acid.

LC-MS-conditions 05b: $t_R$=0.77 min; [M+H]$^+$=422.19.

Example 22

5-(4-Fluoro-phenyl)-oxazole-4-carboxylic acid [2-(5-acetyl-furan-2-ylmethyl)-2H-[1,2,3]triazol-4-yl]-amide Following general procedure A followed by L, starting from 2-[5-(2-methyl-[1,3]dioxolan-2-yl)-furan-2-ylmethyl]-2H-[1,2,3]triazol-4-ylamine and 5-(4-fluoro-phenyl)-oxazole-4-carboxylic acid.

LC-MS-conditions 05b: $t_R$=0.70 min; [M+H]$^+$=396.18.

Example 23

5-m-Tolyl-oxazole-4-carboxylic acid [2-(5-acetyl-furan-2-ylmethyl)-2H-[1,2,3]triazol-4-yl]-amide Following general procedure A followed by L, starting from 2-[5-(2-methyl-[1,3]dioxolan-2-yl)-furan-2-ylmethyl]-2H-[1,2,3]triazol-4-ylamine and 5-(m-tolyl)-oxazole-4-carboxylic acid.

LC-MS-conditions 05b: $t_R$=0.73 min; [M+H]$^+$=392.19.

Example 24

5-(3-Methoxy-phenyl)-oxazole-4-carboxylic acid [2-(5-acetyl-furan-2-ylmethyl)-2H-[1,2,3]triazol-4-yl]-amide Following general procedure A followed by L, starting from 2-[5-(2-methyl-[1,3]dioxolan-2-yl)-furan-2-ylmethyl]-2H-[1,2,3]triazol-4-ylamine and 5-(3-methoxy-phenyl)-oxazole-4-carboxylic acid.

LC-MS-conditions 05b: $t_R$=0.69 min; [M+H]$^+$=408.22.

Example 25

2-Methyl-5-phenyl-oxazole-4-carboxylic acid [2-(5-acetyl-furan-2-ylmethyl)-2H-[1,2,3]triazol-4-yl]-amide Following general procedure A followed by L, starting from 2-[5-(2-methyl-[1,3]dioxolan-2-yl)-furan-2-ylmethyl]-2H-[1,2,3]triazol-4-ylamine and 5-phenyl-2-methyl-oxazole-4-carboxylic acid.

LC-MS-conditions 05b: $t_R$=0.73 min; [M+H]$^+$=392.18.

Example 26

2-Methyl-5-(3-trifluoromethyl-phenyl)-oxazole-4-carboxylic acid [2-(5-acetyl-furan-2-ylmethyl)-2H-[1,2,3]triazol-4-yl]-amide Following general procedure A followed by L, starting from 2-[5-(2-methyl-[1,3]dioxolan-2-yl)-furan-2-ylmethyl]-2H-[1,2,3]triazol-4-ylamine and 5-(3-trifluoromethyl-phenyl)-2-methyl-oxazole-4-carboxylic acid.

LC-MS-conditions 05b: $t_R$=0.81 min; [M+H]$^+$=460.16.

Example 27

2-Methyl-5-(3-trifluoromethoxy-phenyl)-oxazole-4-carboxylic acid [2-(5-acetyl-furan-2-ylmethyl)-2H-[1,2,3]triazol-4-yl]-amide Following general procedure A followed by L, starting from 2-[5-(2-methyl-[1,3]dioxolan-2-yl)-furan-2-ylmethyl]-2H-[1,2,3]triazol-4-ylamine and 5-(3-trifluoromethoxy-phenyl)-2-methyl-oxazole-4-carboxylic acid.

LC-MS-conditions 05b: $t_R$=0.83 min; [M+H]$^+$=476.12.

Example 28

2-Methyl-5-o-tolyl-oxazole-4-carboxylic acid [2-(5-acetyl-furan-2-ylmethyl)-2H-[1,2,3]triazol-4-yl]-amide Following general procedure A followed by L, starting from 2-[5-(2-methyl-[1,3]dioxolan-2-yl)-furan-2-ylmethyl]-2H-[1,2,3]triazol-4-ylamine and 5-(o-tolyl)-2-methyl-oxazole-4-carboxylic acid.

LC-MS-conditions 05b: $t_R$=0.72 min; [M+H]$^+$=406.2.

Example 29

2-Ethyl-5-phenyl-oxazole-4-carboxylic acid [2-(5-acetyl-furan-2-ylmethyl)-2H-[1,2,3]triazol-4-yl]-amide Following general procedure A followed by L, starting from 2-[5-(2-methyl-[1,3]dioxolan-2-yl)-furan-2-ylmethyl]-2H-[1,2,3]triazol-4-ylamine and 2-ethyl-5-phenyl-oxazole-4-carboxylic acid.

LC-MS-conditions 05b: $t_R$=0.80 min; [M+H]$^+$=406.19.

Example 30

2-Cyclopropyl-5-phenyl-oxazole-4-carboxylic acid [2-(5-acetyl-furan-2-ylmethyl)-2H-[1,2,3]triazol-4-yl]-amide Following general procedure A followed by L, starting from 2-[5-(2-methyl-[1,3]dioxolan-2-yl)-furan-2-ylmethyl]-2H-[1,2,3]triazol-4-ylamine and 2-cyclopropyl-5-phenyl-oxazole-4-carboxylic acid.

LC-MS-conditions 05b: $t_R$=0.81 min; [M+H]$^+$=417.69.

Example 31

5-(3-Fluoro-phenyl)-oxazole-4-carboxylic acid [2-(5-acetyl-furan-2-ylmethyl)-2H-[1,2,3]triazol-4-yl]-amide Following general procedure A followed by L, starting from 2-[5-(2-methyl-[1,3]dioxolan-2-yl)-furan-2-ylmethyl]-2H-[1,2,3]triazol-4-ylamine and 5-(3-fluoro-phenyl)-oxazole-4-carboxylic acid.

LC-MS-conditions 05b: $t_R$=0.71 min; [M+H]$^+$=396.19.

Example 32

5-(3-Chloro-phenyl)-oxazole-4-carboxylic acid [2-(5-acetyl-furan-2-ylmethyl)-2H-[1,2,3]triazol-4-yl]-amide Following general procedure A followed by L, starting from 2-[5-(2-methyl-[1,3]dioxolan-2-yl)-furan-2-ylmethyl]-2H-[1,2,3]triazol-4-ylamine and 5-(3-chloro-phenyl)-oxazole-4-carboxylic acid.

LC-MS-conditions O$_2$b: $t_R$=1.04 min; [M+H]$^+$=411.88.

Example 33

5-Phenyl-oxazole-4-carboxylic acid [2-(5-acetyl-thiophen-2-ylmethyl)-2H-[1,2,3]triazol-4-yl]-amide Following general procedure A followed by B, starting from 2-[5-(2-methyl-[1,3]dioxolan-2-yl)-thiophen-2-ylmethyl]-2H-[1,2,3]triazol-4-ylamine and 5-phenyl-oxazole-4-carboxylic acid.
LC-MS-conditions 02: $t_R$=1.03 min; $[M+H]^+$=394.18.

Example 34

5-Phenyl-oxazole-4-carboxylic acid [2-(3-acetyl-benzyl)-2H-[1,2,3]triazol-4-yl]-amide Following general procedure A followed by B, starting from 2-[3-(2-methyl-[1,3]dioxolan-2-yl)-benzyl]-2H-[1,2,3]triazol-4-ylamine and 5-phenyl-oxazole-4-carboxylic acid.
LC-MS-conditions 02: $t_R$=1.04 min; $[M+H]^+$=388.29.

Example 35

[2-(3-Acetyl-benzyl)-2H-[1,2,3]triazol-4-yl]-carbamic acid 2-chloro-benzyl ester Following general procedure D (step 2) followed by B, starting from 2-[3-(2-methyl-[1,3]dioxolan-2-yl)-benzyl]-2H-[1,2,3]triazol-4-ylamine and 2-chlorobenzylchloroformate.
LC-MS-conditions 01: $t_R$=1.00 min; $[M+H]^+$=384.95.

Example 36

5-Phenyl-oxazole-4-carboxylic acid [2-(5,5-difluoro-hexyl)-2H-[1,2,3]triazol-4-yl]-amide Following general procedure A, starting from 2-(5,5-difluoro-hexyl)-2H-[1,2,3]triazol-4-ylamine and 5-phenyl-oxazole-4-carboxylic acid.
LC-MS-conditions 02: $t_R$=1.09 min; $[M+H]^+$=376.26.

Example 37

5-Phenyl-oxazole-4-carboxylic acid [2-(5-methanesulfonyl-furan-2-ylmethyl)-2H-[1,2,3]triazol-4-yl]-amide Following general procedure A, starting from 2-(5-methanesulfonyl-furan-2-ylmethyl)-2H-[1,2,3]triazol-4-ylamine and 5-phenyl-oxazole-4-carboxylic acid.
LC-MS-conditions 02: $t_R$=0.97 min; $[M+H]^+$=413.84.

Example 38

5-(3-Dimethylamino-phenyl)-oxazole-4-carboxylic acid [2-(5-acetyl-furan-2-ylmethyl)-2H-[1,2,3]triazol-4-yl]-amide Following general procedure A followed by B, starting from 2-[5-(2-methyl-[1,3]dioxolan-2-yl)-furan-2-ylmethyl]-2H-[1,2,3]triazol-4-ylamine and 5-(3-dimethylamino-phenyl)-oxazole-4-carboxylic acid.
LC-MS-conditions 02: $t_R$=0.84 min; $[M+H]^+$=421.37.

Example 39

5-Phenyl-oxazole-4-carboxylic acid [2-(4-acetyl-thiazol-2-ylmethyl)-2H-[1,2,3]triazol-4-yl]-amide Following general procedure A followed by B, starting from 2-[4-(2-methyl-[1,3]dioxolan-2-yl)-thiazol-2-ylmethyl]-2H-[1,2,3]triazol-4-ylamine and 5-phenyl-oxazole-4-carboxylic acid.
LC-MS-conditions 02: $t_R$=0.98 min; $[M+H]^+$=395.0.

Example 40

[2-(4-Acetyl-thiazol-2-ylmethyl)-2H-[1,2,3]triazol-4-yl]-carbamic acid 2-chloro-benzyl ester Following general procedure D (step 2) followed by B, starting from 2-[4-(2-methyl-[1,3]dioxolan-2-yl)-thiazol-2-ylmethyl]-2H-[1,2,3]triazol-4-ylamine and 2-chlorobenzylchloroformate.
LC-MS-conditions 02: $t_R$=0.99 min; $[M+H]^+$=391.9.

Example 41

[2-(4-Acetyl-pyridin-2-ylmethyl)-2H-[1,2,3]triazol-4-yl]-carbamic acid 2-chloro-benzyl ester Following general procedure D (step 2) followed by B, starting from 2-[4-(2-methyl-[1,3]dioxolan-2-yl)-pyridin-2-ylmethyl]-2H-[1,2,3]triazol-4-ylamine and 2-chlorobenzylchloroformate.
LC-MS-conditions 02: $t_R$=0.99 min; $[M+H]^+$=386.3.

Example 42

5-[3-(2-Methoxy-ethyl)-phenyl]-oxazole-4-carboxylic acid [2-(5-acetyl-furan-2-ylmethyl)-2H-[1,2,3]triazol-4-yl]-amide Following general procedure A followed by B, starting from 2-[5-(2-methyl-[1,3]dioxolan-2-yl)-furan-2-ylmethyl]-2H-[1,2,3]triazol-4-ylamine and 5-[3-(2-methoxy-ethyl)-phenyl]-oxazole-4-carboxylic acid.
LC-MS-conditions 02: $t_R$=1.00 min; $[M+H_2O+H]^+$=454.30.

Example 43

5-Phenyl-oxazole-4-carboxylic acid [2-(6-acetyl-pyridin-2-ylmethyl)-2H-[1,2,3]triazol-4-yl]-amide Following general procedure A followed by B, starting from 2-[6-(2-methyl-[1,3]dioxolan-2-yl)-pyridin-2-ylmethyl]-2H-[1,2,3]triazol-4-ylamine and 5-phenyl-oxazole-4-carboxylic acid.
LC-MS-conditions 01: $t_R$=0.98 min; $[M+H]^+$=388.95.

Example 44

5-(3-Methoxymethyl-phenyl)-oxazole-4-carboxylic acid [2-(5-acetyl-furan-2-ylmethyl)-2H-[1,2,3]triazol-4-yl]-amide Following general procedure A followed by B, starting from 2-[5-(2-methyl-[1,3]dioxolan-2-yl)-furan-2-ylmethyl]-2H-[1,2,3]triazol-4-ylamine and 5-(3-methoxymethyl-phenyl)-oxazole-4-carboxylic acid.
LC-MS-conditions 01: $t_R$=0.94 min; $[M+H]^+$=421.95.

Example 45

5-Phenyl-oxazole-4-carboxylic acid [2-(2-acetyl-thiazol-4-ylmethyl)-2H-[1,2,3]triazol-4-yl]-amide Following general procedure A followed by B, starting from 2-[2-(2-methyl-[1,3]dioxolan-2-yl)-thiazol-4-ylmethyl]-2H-[1,2,3]triazol-4-ylamine and 5-phenyl-oxazole-4-carboxylic acid.
LC-MS-conditions 02: $t_R$=1.01 min; $[M+H]^+$=394.81.

Example 46

5-Phenyl-oxazole-4-carboxylic acid [2-(4-acetyl-pyridin-2-ylmethyl)-2H-[1,2,3]triazol-4-yl]-amide Following general procedure A followed by N, starting from 2-[4-(2-methyl-[1,3]dioxolan-2-yl)-pyridin-2-ylmethyl]-2H-[1,2,3]triazol-4-ylamine and 5-phenyl-oxazole-4-carboxylic acid.
LC-MS-conditions 01: $t_R$=0.93 min; $[M+H]^+$=388.95.

Example 47

5-Phenyl-oxazole-4-carboxylic acid [2-(2-acetyl-pyridin-4-ylmethyl)-2H-[1,2,3]triazol-4-yl]-amide Following general procedure A followed by B, starting from 2-[2-(2-methyl-[1,3]dioxolan-2-yl)-pyridin-4-ylmethyl]-2H-[1,2,3]triazol-4-ylamine and 5-phenyl-oxazole-4-carboxylic acid.
LC-MS-conditions 02: $t_R$=1.01 min; $[M+H]^+$=389.64.

Example 48

[2-(2-Acetyl-pyridin-4-ylmethyl)-2H-[1,2,3]triazol-4-yl]-carbamic acid 2-chloro-benzyl ester Following general procedure D (step 2) followed by B, starting from 2-[2-(2-methyl-[1,3]dioxolan-2-yl)-pyridin-4-ylmethyl]-2H-[1,2,3]triazol-4-ylamine and 2-chlorobenzylchloroformate.
LC-MS-conditions 01: $t_R$=0.97 min; $[M+H]^+$=385.93.

Example 49

5-Phenyl-oxazole-4-carboxylic acid [2-(5-acetyl-thiophen-3-ylmethyl)-2H-[1,2,3]triazol-4-yl]-amide Following general procedure A followed by B, starting from 2-[5-(2-methyl-[1,3]dioxolan-2-yl)-thiophen-3-ylmethyl]-2H-[1,2,3]triazol-4-ylamine and 5-phenyl-oxazole-4-carboxylic acid.
LC-MS-conditions 02: $t_R$=1.03 min; $[M+H]^+$=394.0.

Example 50

2-Methyl-5-m-tolyl-thiazole-4-carboxylic acid [2-(5-acetyl-furan-2-ylmethyl)-2H-[1,2,3]triazol-4-yl]-amide Following general procedure A followed by B, starting from 2-[5-(2-methyl-[1,3]dioxolan-2-yl)-furan-2-ylmethyl]-2H-[1,2,3]triazol-4-ylamine and 2-methyl-5-m-tolyl-thiazole-4-carboxylic acid.
LC-MS-conditions 02: $t_R$=1.06 min; $[M+H]^+$=422.18.

Example 51

5-Phenyl-oxazole-4-carboxylic acid [2-(3-acetyl-isoxazol-5-ylmethyl)-2H-[1,2,3]triazol-4-yl]-amide Following general procedure A followed by L (with a reaction time of 3 weeks), starting from 2-[3-(2-methyl-[1,3]dioxolan-2-yl)-isoxazol-5-ylmethyl]-2H-[1,2,3]triazol-4-ylamine and 5-phenyl-oxazole-4-carboxylic acid.
LC-MS-conditions 02: $t_R$=1.01 min; $[M+H]^+$=379.2.

Example 52

5-(3-Isopropoxymethyl-phenyl)-oxazole-4-carboxylic acid [2-(5-acetyl-furan-2-ylmethyl)-2H-[1,2,3]triazol-4-yl]-amide Following general procedure A followed by B, starting from 2-[5-(2-methyl-[1,3]dioxolan-2-yl)-furan-2-ylmethyl]-2H-[1,2,3]triazol-4-ylamine and 5-(3-isopropoxymethyl-phenyl)-oxazole-4-carboxylic acid.
LC-MS-conditions 02: $t_R$=1.04 min; $[M+H_2O+H]^+$=467.82.

Example 53

5-[3-(2-Isopropoxy-ethyl)-phenyl]-oxazole-4-carboxylic acid [2-(5-acetyl-furan-2-ylmethyl)-2H-[1,2,3]triazol-4-yl]-amide Following general procedure A followed by B, starting from 2-[5-(2-methyl-[1,3]dioxolan-2-yl)-furan-2-ylmethyl]-2H-[1,2,3]triazol-4-ylamine and 5-[3-(2-isopropoxy-ethyl)-phenyl]-oxazole-4-carboxylic acid.
LC-MS-conditions 02: $t_R$=1.05 min; $[M+H_2O+H]^+$=481.98.

Example 54

2-Methyl-5-m-tolyl-oxazole-4-carboxylic acid [2-(5-acetyl-thiophen-2-ylmethyl)-2H-[1,2,3]triazol-4-yl]-amide Following general procedure A followed by B, starting from 2-[5-(2-methyl-[1,3]dioxolan-2-yl)-thiophen-2-ylmethyl]-2H-[1,2,3]triazol-4-ylamine and 2-methyl-5-m-tolyl-oxazole-4-carboxylic acid.
LC-MS-conditions 05: $t_R$=0.99 min; $[M+H]^+$=422.13.

Example 55

5-(3-Chloro-phenyl)-2-methyl-oxazole-4-carboxylic acid [2-(5-acetyl-thiophen-2-ylmethyl)-2H-[1,2,3]triazol-4-yl]-amide Following general procedure A followed by B, starting from 2-[5-(2-methyl-[1,3]dioxolan-2-yl)-thiophen-2-ylmethyl]-2H-[1,2,3]triazol-4-ylamine and 5-(3-chloro-phenyl)-2-methyl-oxazole-4-carboxylic acid.
LC-MS-conditions 05: $t_R$=1.01 min; $[M+H]^+$=442.03.

Example 56

5-m-Tolyl-oxazole-4-carboxylic acid [2-(5-acetyl-thiophen-2-ylmethyl)-2H-[1,2,3]triazol-4-yl]-amide Following general procedure A followed by B, starting from 2-[5-(2-methyl-[1,3]dioxolan-2-yl)-thiophen-2-ylmethyl]-2H-[1,2,3]triazol-4-ylamine and 5-m-tolyl-oxazole-4-carboxylic acid.
LC-MS-conditions 05: $t_R$=0.94 min; $[M+H]^+$=408.12.

Example 57

2-Methyl-5-phenyl-oxazole-4-carboxylic acid [2-(5-acetyl-thiophen-2-ylmethyl)-2H-[1,2,3]triazol-4-yl]-amide

Following general procedure A followed by B, starting from 2-[5-(2-methyl-[1,3]dioxolan-2-yl)-thiophen-2-ylmethyl]-2H-[1,2,3]triazol-4-ylamine and 2-methyl-5-phenyl-oxazole-4-carboxylic acid.

LC-MS-conditions 05: $t_R$=0.94 min; [M+H]$^+$=408.12.

Example 58

2-Methyl-5-(3-trifluoromethyl-phenyl)-oxazole-4-carboxylic acid [2-(5-acetyl-thiophen-2-ylmethyl)-2H-[1,2,3]triazol-4-yl]-amide

Following general procedure A followed by B, starting from 2-[5-(2-methyl-[1,3]dioxolan-2-yl)-thiophen-2-ylmethyl]-2H-[1,2,3]triazol-4-ylamine and 2-methyl-5-(3-trifluoromethyl-phenyl)-oxazole-4-carboxylic acid.

LC-MS-conditions 05: $t_R$=1.02 min; [M+H]$^+$=476.0.

Example 59

5-(3-Fluoro-phenyl)-oxazole-4-carboxylic acid [2-(5-acetyl-thiophen-2-ylmethyl)-2H-[1,2,3]triazol-4-yl]-amide

Following general procedure A followed by B, starting from 2-[5-(2-methyl-[1,3]dioxolan-2-yl)-thiophen-2-ylmethyl]-2H-[1,2,3]triazol-4-ylamine and 5-(3-fluoro-phenyl)-oxazole-4-carboxylic acid.

LC-MS-conditions 05: $t_R$=0.91 min; [M+H]$^+$=412.05.

Example 60

5-(3-Dimethylamino-phenyl)-oxazole-4-carboxylic acid [2-(5-acetyl-thiophen-2-ylmethyl)-2H-[1,2,3]triazol-4-yl]-amide

Following general procedure A followed by B, starting from 2-[5-(2-methyl-[1,3]dioxolan-2-yl)-thiophen-2-ylmethyl]-2H-[1,2,3]triazol-4-ylamine and 5-(3-dimethylamino-phenyl)-oxazole-4-carboxylic acid.

LC-MS-conditions 05: $t_R$=0.78 min; [M+H]$^+$=436.98.

Example 61

5-(3-Chloro-phenyl)-oxazole-4-carboxylic acid [2-(5-acetyl-thiophen-2-ylmethyl)-2H-[1,2,3]triazol-4-yl]-amide

Following general procedure A followed by B, starting from 2-[5-(2-methyl-[1,3]dioxolan-2-yl)-thiophen-2-ylmethyl]-2H-[1,2,3]triazol-4-ylamine and 5-(3-chloro-phenyl)-oxazole-4-carboxylic acid.

LC-MS-conditions 05: $t_R$=0.96 min; [M+H]$^+$=427.95.

Example 62

2-Methyl-5-(3-trifluoromethoxy-phenyl)-oxazole-4-carboxylic acid [2-(5-acetyl-thiophen-2-ylmethyl)-2H-[1,2,3]triazol-4-yl]-amide

Following general procedure A followed by B, starting from 2-[5-(2-methyl-[1,3]dioxolan-2-yl)-thiophen-2-ylmethyl]-2H-[1,2,3]triazol-4-ylamine and 2-methyl-5-(3-trifluoromethoxy-phenyl)-oxazole-4-carboxylic acid.

LC-MS-conditions 05: $t_R$=1.04 min; [M+H]$^+$=492.01.

Example 63

5-(4-Fluoro-phenyl)-oxazole-4-carboxylic acid [2-(5-acetyl-thiophen-2-ylmethyl)-2H-[1,2,3]triazol-4-yl]-amide

Following general procedure A followed by B, starting from 2-[5-(2-methyl-[1,3]dioxolan-2-yl)-thiophen-2-ylmethyl]-2H-[1,2,3]triazol-4-ylamine and 5-(4-fluoro-phenyl)-oxazole-4-carboxylic acid.

LC-MS-conditions 05: $t_R$=0.91 min; [M+H]$^+$=412.01.

Example 64

5-(3-Trifluoromethoxy-phenyl)-oxazole-4-carboxylic acid [2-(5-acetyl-thiophen-2-ylmethyl)-2H-[1,2,3]triazol-4-yl]-amide

Following general procedure A followed by B, starting from 2-[5-(2-methyl-[1,3]dioxolan-2-yl)-thiophen-2-ylmethyl]-2H-[1,2,3]triazol-4-ylamine and 5-(3-trifluoromethoxy-phenyl)-oxazole-4-carboxylic acid.

LC-MS-conditions 05: $t_R$=0.99 min; [M+H]$^+$=478.0.

Example 65

5-(3-Methoxy-phenyl)-oxazole-4-carboxylic acid [2-(5-acetyl-thiophen-2-ylmethyl)-2H-[1,2,3]triazol-4-yl]-amide

Following general procedure A followed by B, starting from 2-[5-(2-methyl-[1,3]dioxolan-2-yl)-thiophen-2-ylmethyl]-2H-[1,2,3]triazol-4-ylamine and 5-(3-methoxy-phenyl)-oxazole-4-carboxylic acid.

LC-MS-conditions 05: $t_R$=0.9 min; [M+H]$^+$=424.07.

Example 66

5-(3-Fluoro-phenyl)-thiazole-4-carboxylic acid [2-(5-acetyl-furan-2-ylmethyl)-2H-[1,2,3]triazol-4-yl]-amide

Following general procedure A followed by B, starting from 2-[5-(2-methyl-[1,3]dioxolan-2-yl)-furan-2-ylmethyl]-2H-[1,2,3]triazol-4-ylamine and 5-(3-fluoro-phenyl)-thiazole-4-carboxylic acid.

LC-MS-conditions 02: $t_R$=1.00 min; [M+H]$^+$=411.85.

Example 67

5-Phenyl-oxazole-4-carboxylic acid [2-(2-acetyl-thiazol-5-ylmethyl)-2H-[1,2,3]triazol-4-yl]-amide

Following general procedure A followed by B, starting from 2-[2-(2-methyl-[1,3]dioxolan-2-yl)-thiazol-5-ylmethyl]-2H-[1,2,3]triazol-4-ylamine and 5-phenyl-oxazole-4-carboxylic acid.

LC-MS-conditions 01: $t_R$=0.98 min; [M+H]$^+$=394.94.

Example 68

[2-(2-Acetyl-thiazol-5-ylmethyl)-2H-[1,2,3]triazol-4-yl]-carbamic acid 2-chloro-benzyl ester Following general procedure D followed by B, starting from 2-[2-(2-methyl-[1,3]dioxolan-2-yl)-thiazol-5-ylmethyl]-2H-[1,2,3]triazol-4-ylamine and (2-chloro-phenyl)-methanol.
LC-MS-conditions 01: $t_R$=0.98 min; $[M+H]^+$=391.9.

Example 69

(E)-N-[2-(2-Acetyl-thiazol-5-ylmethyl)-2H-[1,2,3]triazol-4-yl]-3-(4-trifluoromethyl-phenyl)-acrylamide Following general procedure A followed by B, starting from 2-[2-(2-methyl-[1,3]dioxolan-2-yl)-thiazol-5-ylmethyl]-2H-[1,2,3]triazol-4-ylamine and (E)-3-(4-trifluoromethyl-phenyl)-acrylic acid.
LC-MS-conditions 01: $t_R$=1.02 min; $[M+H]^+$=421.90.

Example 70

5-Phenyl-oxazole-4-carboxylic acid [2-(2-acetyl-oxazol-5-ylmethyl)-2H-[1,2,3]triazol-4-yl]-amide In a flame dried round-bottomed flask equipped with a magnetic stir bar and under inert atmosphere ($N_2$), a solution of 5-phenyl-oxazole-4-carboxylic acid {2-[2-(1-hydroxy-ethyl)-oxazol-5-ylmethyl]-2H-[1,2,3]triazol-4-yl}-amide (60 mg, 0.16 mmol) in AcCN (1.6 mL) was treated at rt with $MnO_2$ (114 mg, 1.18 mmol) and the reaction mixture was stirred at rt overnight before being filtered through Celite. The solvent was removed under reduced pressure and the residue was dissolved in EA (10 mL), washed with water (10 mL), and brine. The org. layer was dried over $MgSO_4$, filtered, and the solvents were removed under reduced pressure to give the title compound as a white foam. LC-MS-conditions 02: $t_R$=0.97 min; $[M+H]^+$=379.06.

Example 71

[2-(5-Acetyl-thiazol-2-ylmethyl)-2H-[1,2,3]triazol-4-yl]-carbamic acid 2-chloro-benzyl ester Following general procedure D followed by B, starting from 2-[5-(2-methyl-[1,3]dioxolan-2-yl)-thiazol-2-ylmethyl]-2H-[1,2,3]triazol-4-ylamine and (2-chloro-phenyl)-methanol.
LC-MS-conditions 01: $t_R$=0.96 min; $[M+H]^+$=391.92.

Example 72

5-Phenyl-oxazole-4-carboxylic acid [2-(4-acetyl-thiophen-2-ylmethyl)-2H-[1,2,3]triazol-4-yl]-amide Following general procedure A followed by B, starting from 2-[4-(2-methyl-[1,3]dioxolan-2-yl)-thiophen-2-ylmethyl]-2H-[1,2,3]triazol-4-ylamine and 5-phenyl-oxazole-4-carboxylic acid.
LC-MS-conditions 01: $t_R$=0.99 min; $[M+H]^+$=393.92.

Example 73

5-Phenyl-oxazole-4-carboxylic acid [2-(5-acetyl-thiazol-2-ylmethyl)-2H-[1,2,3]triazol-4-yl]-amide Following general procedure A followed by B, starting from 2-[5-(2-methyl-[1,3]dioxolan-2-yl)-thiazol-2-ylmethyl]-2H-[1,2,3]triazol-4-ylamine and 5-phenyl-oxazole-4-carboxylic acid.
LC-MS-conditions 02: $t_R$=0.99 min; $[M+H]^+$=394.94.

Example 74

(E)-N-[2-(5-Acetyl-thiazol-2-ylmethyl)-2H-[1,2,3]triazol-4-yl]-3-(4-trifluoromethyl-phenyl)-acrylamide Following general procedure A followed by B, starting from 2-[5-(2-methyl-[1,3]dioxolan-2-yl)-thiazol-2-ylmethyl]-2H-[1,2,3]triazol-4-ylamine and (E)-3-(4-trifluoromethyl-phenyl)-acrylic acid.
LC-MS-conditions 02: $t_R$=1.03 min; $[M+H]^+$=421.89.

Example 75

2-Methyl-5-m-tolyl-oxazole-4-carboxylic acid [2-(4-acetyl-thiazol-2-ylmethyl)-2H-[1,2,3]triazol-4-yl]-amide Following general procedure A followed by B, starting from 2-[4-(2-methyl-[1,3]dioxolan-2-yl)-thiazol-2-ylmethyl]-2H-[1,2,3]triazol-4-ylamine and 2-methyl-5-m-tolyl-oxazole-4-carboxylic acid.
LC-MS-conditions 05: $t_R$=0.95 min; $[M+H]^+$=423.12.

Example 76

5-(3-Chloro-phenyl)-2-methyl-oxazole-4-carboxylic acid [2-(4-acetyl-thiazol-2-ylmethyl)-2H-[1,2,3]triazol-4-yl]-amide Following general procedure A followed by B, starting from 2-[4-(2-methyl-[1,3]dioxolan-2-yl)-thiazol-2-ylmethyl]-2H-[1,2,3]triazol-4-ylamine and 5-(3-chloro-phenyl)-2-methyl-oxazole-4-carboxylic acid.
LC-MS-conditions 05: $t_R$=0.98 min; $[M+H]^+$=442.98.

Example 77

2-Methyl-5-phenyl-oxazole-4-carboxylic acid [2-(4-acetyl-thiazol-2-ylmethyl)-2H-[1,2,3]triazol-4-yl]-amide Following general procedure A followed by B, starting from 2-[4-(2-methyl-[1,3]dioxolan-2-yl)-thiazol-2-ylmethyl]-2H-[1,2,3]triazol-4-ylamine and 2-methyl-5-phenyl-oxazole-4-carboxylic acid.
LC-MS-conditions 05: $t_R$=0.90 min; $[M+H]^+$=409.04.

Example 78

2-Methyl-5-(3-trifluoromethyl-phenyl)-oxazole-4-carboxylic acid [2-(4-acetyl-thiazol-2-ylmethyl)-2H-[1,2,3]triazol-4-yl]-amide Following general procedure A followed by B, starting from 2-[4-(2-methyl-[1,3]dioxolan-2-yl)-thiazol-2-ylmethyl]-2H-[1,2,3]triazol-4-ylamine and 2-methyl-5-(3-trifluoromethyl-phenyl)-oxazole-4-carboxylic acid.

LC-MS-conditions 05: $t_R$=0.98 min; [M+H]$^+$=477.16.

Example 79

5-(3-Fluoro-phenyl)-oxazole-4-carboxylic acid [2-(4-acetyl-thiazol-2-ylmethyl)-2H-[1,2,3]triazol-4-yl]-amide Following general procedure A followed by B, starting from 2-[4-(2-methyl-[1,3]dioxolan-2-yl)-thiazol-2-ylmethyl]-2H-[1,2,3]triazol-4-ylamine and 5-(3-fluoro-phenyl)-oxazole-4-carboxylic acid.

LC-MS-conditions 05: $t_R$=0.86 min; [M+H]$^+$=413.12.

Example 80

5-(3-Dimethylamino-phenyl)-oxazole-4-carboxylic acid [2-(4-acetyl-thiazol-2-ylmethyl)-2H-[1,2,3]triazol-4-yl]-amide Following general procedure A followed by B, starting from 2-[4-(2-methyl-[1,3]dioxolan-2-yl)-thiazol-2-ylmethyl]-2H-[1,2,3]triazol-4-ylamine and 5-(3-dimethylamino-phenyl)-oxazole-4-carboxylic acid.

LC-MS-conditions 05: $t_R$=0.71 min; [M+H]$^+$=438.13.

Example 81

5-(3-Chloro-phenyl)-oxazole-4-carboxylic acid [2-(4-acetyl-thiazol-2-ylmethyl)-2H-[1,2,3]triazol-4-yl]-amide Following general procedure A followed by B, starting from 2-[4-(2-methyl-[1,3]dioxolan-2-yl)-thiazol-2-ylmethyl]-2H-[1,2,3]triazol-4-ylamine and 5-(3-chloro-phenyl)-oxazole-4-carboxylic acid.

LC-MS-conditions 05: $t_R$=0.92 min; [M+H]$^+$=429.02.

Example 82

2-Methyl-5-(3-trifluoromethoxy-phenyl)-oxazole-4-carboxylic acid [2-(4-acetyl-thiazol-2-ylmethyl)-2H-[1,2,3]triazol-4-yl]-amide Following general procedure A followed by B, starting from 2-[4-(2-methyl-[1,3]dioxolan-2-yl)-thiazol-2-ylmethyl]-2H-[1,2,3]triazol-4-ylamine and 2-methyl-5-(3-trifluoromethoxy-phenyl)-oxazole-4-carboxylic acid.

LC-MS-conditions 05: $t_R$=1.00 min; [M+H]$^+$=492.95.

Example 83

5-(4-Fluoro-phenyl)-oxazole-4-carboxylic acid [2-(4-acetyl-thiazol-2-ylmethyl)-2H-[1,2,3]triazol-4-yl]-amide Following general procedure A followed by B, starting from 2-[4-(2-methyl-[1,3]dioxolan-2-yl)-thiazol-2-ylmethyl]-2H-[1,2,3]triazol-4-ylamine and 5-(4-fluoro-phenyl)-oxazole-4-carboxylic acid.

LC-MS-conditions 05: $t_R$=0.86 min; [M+H]$^+$=413.09.

Example 84

5-(3-Trifluoromethoxy-phenyl)-oxazole-4-carboxylic acid [2-(4-acetyl-thiazol-2-ylmethyl)-2H-[1,2,3]triazol-4-yl]-amide Following general procedure A followed by B, starting from 2-[4-(2-methyl-[1,3]dioxolan-2-yl)-thiazol-2-ylmethyl]-2H-[1,2,3]triazol-4-ylamine and 5-(3-trifluoromethoxy-phenyl)-oxazole-4-carboxylic acid.

LC-MS-conditions 05: $t_R$=0.95 min; [M+H]$^+$=479.04.

Example 85

5-(3-Methoxy-phenyl)-oxazole-4-carboxylic acid [2-(4-acetyl-thiazol-2-ylmethyl)-2H-[1,2,3]triazol-4-yl]-amide Following general procedure A followed by B, starting from 2-[4-(2-methyl-[1,3]dioxolan-2-yl)-thiazol-2-ylmethyl]-2H-[1,2,3]triazol-4-ylamine and 5-(3-methoxy-phenyl)-oxazole-4-carboxylic acid.

LC-MS-conditions 05: $t_R$=0.85 min; [M+H]$^+$=425.02.

Example 86

(E)-N-[2-(4-Acetyl-thiazol-2-ylmethyl)-2H-[1,2,3]triazol-4-yl]-3-(4-trifluoromethyl-phenyl)-acrylamide Following general procedure A followed by B, starting from 2-[4-(2-methyl-[1,3]dioxolan-2-yl)-thiazol-2-ylmethyl]-2H-[1,2,3]triazol-4-ylamine and (E)-3-(4-trifluoromethyl-phenyl)-acrylic acid.

LC-MS-conditions 05: $t_R$=0.88 min; [M+H]$^+$=422.04.

Example 87

(E)-N-[2-(4-Acetyl-thiazol-2-ylmethyl)-2H-[1,2,3]triazol-4-yl]-3-(3-trifluoromethoxy-phenyl)-acrylamide Following general procedure A followed by B, starting from 2-[4-(2-methyl-[1,3]dioxolan-2-yl)-thiazol-2-ylmethyl]-2H-[1,2,3]triazol-4-ylamine and (E)-3-(3-trifluoromethoxy-phenyl)-acrylic acid.

LC-MS-conditions 05: $t_R$=0.90 min; [M+H]$^+$=438.02.

Example 88

5-(3-Methoxy-phenyl)-2-methyl-oxazole-4-carboxylic acid [2-(4-acetyl-thiazol-2-ylmethyl)-2H-[1,2,3]triazol-4-yl]-amide Following general procedure A followed by B, starting from 2-[4-(2-methyl-[1,3]dioxolan-2-yl)-thiazol-2-ylmethyl]-2H-[1,2,3]triazol-4-ylamine and 5-(3-Methoxy-phenyl)-2-methyl-oxazole-4-carboxylic acid.

LC-MS-conditions 05: $t_R$=0.90 min; [M+H]$^+$=439.04.

Example 89

5-(3-Fluoro-phenyl)-2-methyl-oxazole-4-carboxylic acid [2-(4-acetyl-thiazol-2-ylmethyl)-2H-[1,2,3]triazol-4-yl]-amide Following general procedure A followed by B, starting from 2-[4-(2-methyl-[1,3]dioxolan-2-yl)-thiazol-2-ylmethyl]-2H-[1,2,3]triazol-4-ylamine and 5-(3-fluoro-phenyl)-2-methyl-oxazole-4-carboxylic acid.

LC-MS-conditions 05: $t_R$=0.92 min; [M+H]$^+$=427.00.

Example 90

2-Methyl-5-m-tolyl-thiazole-4-carboxylic acid [2-(4-acetyl-thiazol-2-ylmethyl)-2H-[1,2,3]triazol-4-yl]-amide Following general procedure A followed by B, starting from 2-[4-(2-methyl-[1,3]dioxolan-2-yl)-thiazol-2-ylmethyl]-2H-[1,2,3]triazol-4-ylamine and 2-methyl-5-m-tolyl-thiazole-4-carboxylic acid.

LC-MS-conditions 05: $t_R$=0.96 min; [M+H]$^+$=438.97.

Example 91

5-Phenyl-oxazole-4-carboxylic acid [2-(4-acetyl-oxazol-2-ylmethyl)-2H-[1,2,3]triazol-4-yl]-amide Following general procedure A, starting from 1-[2-(4-amino-[1,2,3]triazol-2-ylmethyl)-oxazol-4-yl]-ethanone and 5-phenyl-oxazole-4-carboxylic acid.

LC-MS-conditions 02: $t_R$=0.94 min; [M+H]$^+$=379.22.

Example 92

2-Methoxymethyl-5-phenyl-oxazole-4-carboxylic acid [2-(5-acetyl-furan-2-ylmethyl)-2H-[1,2,3]triazol-4-yl]-amide Following general procedure A followed by B, starting from 2-[5-(2-methyl-[1,3]dioxolan-2-yl)-furan-2-ylmethyl]-2H-[1,2,3]triazol-4-ylamine and 2-methoxymethyl-5-phenyl-oxazole-4-carboxylic acid.

LC-MS-conditions 02: $t_R$=1.00 min; [M+H]$^+$=422.0.

Example 93

2-(2-Methoxy-ethyl)-5-phenyl-oxazole-4-carboxylic acid [2-(5-acetyl-furan-2-ylmethyl)-2H-[1,2,3]triazol-4-yl]-amide Following general procedure A followed by B, starting from 2-[5-(2-methyl-[1,3]dioxolan-2-yl)-furan-2-ylmethyl]-2H-[1,2,3]triazol-4-ylamine and 2-(2-methoxy-ethyl)-5-phenyl-oxazole-4-carboxylic acid.

LC-MS-conditions 02: $t_R$=1.02 min; [M+H]$^+$=436.08.

Example 94

2-Butyl-5-phenyl-oxazole-4-carboxylic acid [2-(5-acetyl-furan-2-ylmethyl)-2H-[1,2,3]triazol-4-yl]-amide Following general procedure A followed by B, starting from 2-[5-(2-methyl-[1,3]dioxolan-2-yl)-furan-2-ylmethyl]-2H-[1,2,3]triazol-4-ylamine and 2-butyl-5-phenyl-oxazole-4-carboxylic acid.

LC-MS-conditions 02: $t_R$=1.13 min; [M+H]$^+$=433.99.

Example 95

2-Isopropyl-5-phenyl-oxazole-4-carboxylic acid [2-(5-acetyl-furan-2-ylmethyl)-2H-[1,2,3]triazol-4-yl]-amide Following general procedure A followed by B, starting from 2-[5-(2-methyl-[1,3]dioxolan-2-yl)-furan-2-ylmethyl]-2H-[1,2,3]triazol-4-ylamine and 2-isopropyl-5-phenyl-oxazole-4-carboxylic acid.

LC-MS-conditions 02: $t_R$=1.10 min; [M+H]$^+$=420.42.

Example 96

(E)-N-[2-(4-Acetyl-thiazol-2-ylmethyl)-2H-[1,2,3]triazol-4-yl]-3-(2-trifluoromethyl-phenyl)-acrylamide Following general procedure A followed by B, starting from 2-[4-(2-methyl-[1,3]dioxolan-2-yl)-thiazol-2-ylmethyl]-2H-[1,2,3]triazol-4-ylamine and (E)-3-(2-trifluoromethyl-phenyl)-acrylic acid.

LC-MS-conditions 05: $t_R$=0.87 min; [M+H]$^+$=422.02.

Example 97

2-Benzyl-5-phenyl-oxazole-4-carboxylic acid [2-(5-acetyl-furan-2-ylmethyl)-2H-[1,2,3]triazol-4-yl]-amide Following general procedure A followed by B, starting from 2-[5-(2-methyl-[1,3]dioxolan-2-yl)-furan-2-ylmethyl]-2H-[1,2,3]triazol-4-ylamine and 2-benzyl-5-phenyl-oxazole-4-carboxylic acid.

LC-MS-conditions 02: $t_R$=1.11 min; [M+H]$^+$=468.06.

Example 98

3-{4-[2-(5-Acetyl-furan-2-ylmethyl)-2H-[1,2,3]triazol-4-ylcarbamoyl]-5-phenyl-oxazol-2-yl}-propionic acid tert-butyl ester Following general procedure A followed by B, starting from 2-[5-(2-methyl-[1,3]dioxolan-2-yl)-furan-2-ylmethyl]-2H-[1,2,3]triazol-4-ylamine and 2-(2-tert-butoxycarbonyl-ethyl)-5-phenyl-oxazole-4-carboxylic acid.

LC-MS-conditions 02: $t_R$=1.12 min; [M+H]$^+$=506.00.

Example 99

5-(3-Fluoro-phenyl)-2-methyl-oxazole-4-carboxylic acid [2-(2-acetyl-oxazol-5-ylmethyl)-2H-[1,2,3]triazol-4-yl]-amide In a flame dried round-bottomed flask equipped with a magnetic stir bar and under inert atmosphere ($N_2$), a solution of 5-(3-fluoro-phenyl)-2-methyl-oxazole-4-carboxylic acid {2-[2-(1-hydroxy-ethyl)-oxazol-5-ylmethyl]-2H-[1,2,3]triazol-4-yl}-amide (49 mg, 0.12 mmol) in AcCN (2.0 mL) was treated at rt with $MnO_2$ (86 mg, 0.89 mmol) and the reaction mixture was stirred at rt overnight before being filtered through Celite. The solvent was removed under reduced pressure and the residue was dissolved in EA (10 mL), washed with water (10 mL), and brine. The org. layer was dried over $MgSO_4$, filtered, and the solvents were removed under reduced pressure to give the title compound as a yellow solid. LC-MS-conditions 02: $t_R$=1.03 min; [M+H]$^+$=410.85.

Example 100

2-Methyl-5-m-tolyl-oxazole-4-carboxylic acid [2-(2-acetyl-oxazol-5-ylmethyl)-2H-[1,2,3]triazol-4-yl]-amide In a flame dried round-bottomed flask equipped with a magnetic stir bar and under inert atmosphere (N$_2$), a solution of 2-methyl-5-m-tolyl-oxazole-4-carboxylic acid {2-[2-(1-hydroxy-ethyl)-oxazol-5-ylmethyl]-2H-[1,2,3]triazol-4-yl}-amide (60 mg, 0.15 mmol) in AcCN (2.0 mL) was treated at rt with MnO$_2$ (107 mg, 1.11 mmol) and the reaction mixture was stirred at rt overnight before being filtered through Celite. The solvent was removed under reduced pressure and the residue was dissolved in EA (10 mL), washed with water (10 mL), and brine. The org. layer was dried over MgSO$_4$, filtered, and the solvents were removed under reduced pressure to give the title compound as a yellow solid. LC-MS-conditions 02: $t_R$=1.04 min; [M+H]$^+$=407.07.

Example 101

5-(3-Chloro-phenyl)-2-methyl-oxazole-4-carboxylic acid [2-(2-acetyl-oxazol-5-ylmethyl)-2H-[1,2,3]triazol-4-yl]-amide In a flame dried round-bottomed flask equipped with a magnetic stir bar and under inert atmosphere (N$_2$), a solution of 5-(3-chloro-phenyl)-2-methyl-oxazole-4-carboxylic acid {2-[2-(1-hydroxy-ethyl)-oxazol-5-ylmethyl]-2H-[1,2,3]triazol-4-yl}-amide (54 mg, 0.13 mmol) in AcCN (1.5 mL) was treated at rt with MnO$_2$ (91 mg, 0.94 mmol) and the reaction mixture was stirred at rt overnight before being filtered through Celite. The solvent was removed under reduced pressure and the residue was dissolved in EA (10 mL), washed with water (10 mL), and brine. The org. layer was dried over MgSO$_4$, filtered, and the solvents were removed under reduced pressure to give the title compound as a white solid. LC-MS-conditions 02: $t_R$=1.06 min; [M+H]$^+$=426.75.

Example 102

5-m-Tolyl-oxazole-4-carboxylic acid [2-(2-acetyl-oxazol-5-ylmethyl)-2H-[1,2,3]triazol-4-yl]-amide In a flame dried round-bottomed flask equipped with a magnetic stir bar and under inert atmosphere (N$_2$), a solution of 5-m-tolyl-oxazole-4-carboxylic acid {2-[2-(1-hydroxy-ethyl)-oxazol-5-ylmethyl]-2H-[1,2,3]triazol-4-yl}-amide (44 mg, 0.11 mmol) in AcCN (1.5 mL) was treated at rt with MnO$_2$ (81 mg, 0.84 mmol) and the reaction mixture was stirred at rt overnight before being filtered through Celite. The solvent was removed under reduced pressure and the residue was dissolved in EA (10 mL), washed with water (10 mL), and brine. The org. layer was dried over MgSO$_4$, filtered, and the solvents were removed under reduced pressure to give the title compound as a white solid. LC-MS-conditions 02: $t_R$=1.01 min; [M+H]$^+$=392.97.

Example 103

2-Methyl-5-(3-trifluoromethoxy-phenyl)-oxazole-4-carboxylic acid [2-(2-acetyl-oxazol-5-ylmethyl)-2H-[1,2,3]triazol-4-yl]-amide In a flame dried round-bottomed flask equipped with a magnetic stir bar and under inert atmosphere (N$_2$), a solution of 2-methyl-5-(3-trifluoromethoxy-phenyl)-oxazole-4-carboxylic acid {2-[2-(1-hydroxy-ethyl)-oxazol-5-ylmethyl]-2H-[1,2,3]triazol-4-yl]-amide (54 mg, 0.11 mmol) in AcCN (1.5 mL) was treated at rt with MnO$_2$ (85 mg, 0.85 mmol) and the reaction mixture was stirred at rt overnight before being filtered through Celite. The solvent was removed under reduced pressure and the residue was dissolved in EA (10 mL), washed with water (10 mL), and brine. The org. layer was dried over MgSO$_4$, filtered, and the solvents were removed under reduced pressure to give the title compound as a white solid. LC-MS-conditions 02: $t_R$=1.09 min; [M+H]$^+$=476.95.

Example 104

[2-(2-Acetyl-oxazol-4-ylmethyl)-2H-[1,2,3]triazol-4-yl]-carbamic acid 2-chloro-benzyl ester In a flame dried round-bottomed flask equipped with a magnetic stir bar and under inert atmosphere (N$_2$), a solution of {2-[2-(1-hydroxy-ethyl)-oxazol-4-ylmethyl]-2H-[1,2,3]triazol-4-yl}-carbamic acid 2-chloro-benzyl ester (10 mg, 0.03 mmol) in AcCN (5.0 mL) was treated at rt with MnO$_2$ (13 mg, 0.13 mmol) and the reaction mixture was stirred at 50° C. for 2 h before being filtered through Celite. TLC: rf (EA)= 0.60. LC-MS-conditions 02: $t_R$=0.97 min; [M+H]$^+$=376.04.

Example 105

5-(6-Trifluoromethyl-pyridin-2-yl)-oxazole-4-carboxylic acid [2-(5-acetyl-furan-2-ylmethyl)-2H-[1,2,3]triazol-4-yl]-amide Following general procedure Z1 followed by B, starting from 2-[5-(2-methyl-[1,3]dioxolan-2-yl)-furan-2-ylmethyl]-2H-[1,2,3]triazol-4-ylamine and 5-(6-trifluoromethyl-pyridin-2-yl)-oxazole-4-carboxylic acid lithium salt.

LC-MS-conditions 01: $t_R$=0.91 min; [M+H]$^+$=446.99.

II. Biological Assays

In Vitro Assay

The ALX receptor agonistic activity of the compounds of formula (I) is determined in accordance with the following experimental method.

Experimental Method:

Intracellular Calcium Measurements:

Cells expressing recombinant human ALX receptor and the G-protein Gα16 (HEK293-hALXR-Gα16) were grown to 80% confluency in Growing Medium (GM). Cells were detached from culture dishes with a cell dissociation buffer (Invitrogen, 13151-014), and collected by centrifugation at 1,000 rpm at RT for 5 min in Assay Buffer (AB) (equal parts of Hank's BSS (Gibco, 14065-049) and DMEM without Phemol Red (Gibco, 11880-028)). After 60 min incubation at 37° C. under 5% CO$_2$ in AB supplemented with 1 μM Fluo-4 (AM) (TEFLABS.COM, 0152), 0.04% (v/v) Pluronic F-127 (Molecular Probes, P6866), and 20 mM HEPES (Gibco, 15630-056), the cells were washed and resuspended in AB. They were then seeded onto 384-well FLIPR assay plates (Greiner, 781091) at 50'000 cells in 70 μl per well and sedimented by centrifugation at 1'000 rpm for 1 min. Stock solutions of test compounds were made up at a concentration of 10 mM in DMSO, and serially diluted in AB to concentrations required for activation dose response curves. WKYMVm (Phoenix Peptides) was used as a reference agonist. A FLIPR$^{384}$ instrument (Molecular Devices) was operated according to the manufacturer's standard instructions, adding 4 µl of test compound dissolved at 10 mM in DMSO and diluted prior to the experiment in assay buffer to obtain the desired final concentration. Changes in fluorescence were monitored before and after the addition of test compounds at lex=488 nm and lem=540 nm. Emission peak values above base level after compounds addition were exported after base line subtraction. Values were normalized to high-level control (WKYMVm compound, 10 nM final concentration) after subtraction of the base line value (AB addition). The program XLlfit 3.0 (IDBS) was used to fit the data to a single site dose response curve of the equation $(A+((B-A)/(1+((C/x)\hat{}D))))$ and to calculate the $EC_{50}$ values.

Agonistic activities ($EC_{50}$ values) of all exemplified compounds are in the range of 0.03-1850 nM with an average of 60 nM with respect to ALX receptor. Agonistic activities of selected compounds are displayed in Table 1.

TABLE 1

| Compound | $EC_{50}$ [nM] |
|---|---|
| Example 1:<br>5-Phenyl-oxazole-4-carboxylic acid [2-(5-acetyl-furan-2-ylmethyl)-2H-[1,2,3]triazol-4-yl]-amide | 1.8 |
| Example 5:<br>5-Phenyl-oxazole-4-carboxylic acid [2-(5-oxo-hexyl)-2H-[1,2,3]triazol-4-yl]-amide | 1.6 |
| Example 8:<br>(E)-N-[2-(5-Acetyl-furan-2-ylmethyl)-2H-[1,2,3]triazol-4-yl]-3-(3-trifluoromethoxy-phenyl)-acrylamide | 1.2 |
| Example 21:<br>5-(3-Methoxy-4-methyl-phenyl)-oxazole-4-carboxylic acid [2-(5-acetyl-furan-2-ylmethyl)-2H-[1,2,3]triazol-4-yl]-amide | 53 |
| Example 26:<br>2-Methyl-5-(3-trifluoromethyl-phenyl)-oxazole-4-carboxylic acid [2-(5-acetyl-furan-2-ylmethyl)-2H-[1,2,3]triazol-4-yl]-amide | 2.0 |
| Example 30:<br>2-Cyclopropyl-5-phenyl-oxazole-4-carboxylic acid [2-(5-acetyl-furan-2-ylmethyl)-2H-[1,2,3]triazol-4-yl]-amide | 0.8 |
| Example 33:<br>5-Phenyl-oxazole-4-carboxylic acid [2-(5-acetyl-thiophen-2-ylmethyl)-2H-[1,2,3]triazol-4-yl]-amide | 2.8 |
| Example 35:<br>[2-(3-Acetyl-benzyl)-2H-[1,2,3]triazol-4-yl]-carbamic acid 2-chloro-benzyl ester | 8.5 |
| Example 36:<br>5-Phenyl-oxazole-4-carboxylic acid [2-(5,5-difluoro-hexyl)-2H-[1,2,3]triazol-4-yl]-amide | 4.9 |
| Example 37:<br>5-Phenyl-oxazole-4-carboxylic acid [2-(5-methanesulfonyl-furan-2-ylmethyl)-2H-[1,2,3]triazol-4-yl]-amide | 24 |
| Example 38:<br>5-(3-Dimethylamino-phenyl)-oxazole-4-carboxylic acid [2-(5-acetyl-furan-2-ylmethyl)-2H-[1,2,3]triazol-4-yl]-amide | 1.9 |
| Example 40:<br>[2-(4-Acetyl-thiazol-2-ylmethyl)-2H-[1,2,3]triazol-4-yl]-carbamic acid 2-chloro-benzyl ester | 1.3 |
| Example 41:<br>[2-(4-Acetyl-pyridin-2-ylmethyl)-2H-[1,2,3]triazol-4-yl]-carbamic acid 2-chloro-benzyl ester | 21 |
| Example 42:<br>5-[3-(2-Methoxy-ethyl)-phenyl]-oxazole-4-carboxylic acid [2-(5-acetyl-furan-2-ylmethyl)-2H-[1,2,3]triazol-4-yl]-amide | 2.1 |
| Example 43:<br>5-Phenyl-oxazole-4-carboxylic acid [2-(6-acetyl-pyridin-2-ylmethyl)-2H-[1,2,3]triazol-4-yl]-amide | 203 |
| Example 49:<br>5-Phenyl-oxazole-4-carboxylic acid [2-(5-acetyl-thiophen-3-ylmethyl)-2H-[1,2,3]triazol-4-yl]-amide | 57 |
| Example 50:<br>2-Methyl-5-m-tolyl-thiazole-4-carboxylic acid [2-(5-acetyl-furan-2-ylmethyl)-2H-[1,2,3]triazol-4-yl]-amide | 98 |
| Example 71:<br>[2-(5-Acetyl-thiazol-2-ylmethyl)-2H-[1,2,3]triazol-4-yl]-carbamic acid 2-chloro-benzyl ester | 23 |
| Example 91:<br>5-Phenyl-oxazole-4-carboxylic acid [2-(4-acetyl-oxazol-2-ylmethyl)-2H-[1,2,3]triazol-4-yl]-amide | 0.7 |
| Example 93:<br>2-(2-Methoxy-ethyl)-5-phenyl-oxazole-4-carboxylic acid [2-(5-acetyl-furan-2-ylmethyl)-2H-[1,2,3]triazol-4-yl]-amide | 5.2 |
| Example 99:<br>5-(3-Fluoro-phenyl)-2-methyl-oxazole-4-carboxylic acid [2-(2-acetyl-oxazol-5-ylmethyl)-2H-[1,2,3]triazol-4-yl]-amide | 8.1 |

TABLE 1-continued

| Compound | EC$_{50}$ [nM] |
|---|---|
| Example 104: [2-(2-Acetyl-oxazol-4-ylmethyl)-2H-[1,2,3]triazol-4-yl]-carbamic acid 2-chloro-benzyl ester | 1.4 |
| Example 105: 5-(6-Trifluoromethyl-pyridin-2-yl)-oxazole-4-carboxylic acid [2-(5-acetyl-furan-2-ylmethyl)-2H-[1,2,3]triazol-4-yl]-amide | 36 |

The invention claimed is:
1. A compound of formula (I),

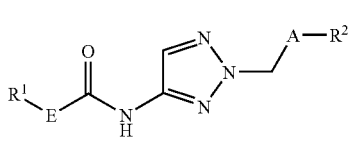

(I)

wherein
A represents a phenyl- or a heterocyclyl-group, wherein the phenyl- or heterocyclyl-group is substituted in a 1,3-arrangement; or A represents propan-1,3-diyl;
E represents *—(C$_1$-C$_4$)alkyl-O—, —CH=CH— or

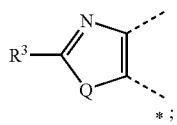

wherein the asterisks indicate the bond which is linked to R$^1$;
Q represents O or S;
R$^3$ represents hydrogen, (C$_1$-C$_4$)alkyl, cyclopropyl, (C$_1$-C$_4$)alkoxy-(C$_1$-C$_2$)alkyl, benzyl or —CH$_2$CH$_2$C(O)OtBu;
R$^1$ represents a pyridyl- or an aryl-group, which group is unsubstituted, mono-, di- or tri-substituted with halogen, (C$_1$-C$_4$)alkyl, (C$_1$-C$_4$)alkoxy, (C$_1$-C$_4$)fluoroalkyl, (C$_1$-C$_4$) fluoroalkoxy, di-[(C$_1$-C$_3$)alkyl]-amino or (C$_1$-C$_4$)alkoxy-(C$_1$-C$_2$)alkyl; and
R$^2$ represents —CO—(C$_1$-C$_3$)alkyl, —CF$_2$—(C$_1$-C$_3$)alkyl, or —SO$_2$—(C$_1$-C$_3$)alkyl;
or a salt thereof.

2. The compound of formula (I) according to claim 1, wherein A represents phenyl-1,3-diyl, furan-2,5-diyl, oxazol-2,4-diyl, oxazol-2,5-diyl, thiophen-2,4-diyl, thiophen-2,5-diyl, thiazol-2,4-diyl, thiazol-2,5-diyl, pyridin-2,4-diyl, pyridin-2,6-diyl or propan-1,3-diyl; or a salt thereof.

3. The compound of formula (I) according to claim 1, wherein A represents furan-2,5-diyl, oxazol-2,4-diyl with R$^2$ being attached in 2-position, oxazol-2,4-diyl with R$^2$ being attached in 4-position, oxazol-2,5-diyl with R$^2$ being attached in 2-position, thiophen-2,5-diyl or thiazol-2,4-diyl with R$^2$ being attached in 4-position; or a salt thereof.

4. The compound of formula (I) according to claim 1, wherein A represents furan-2,5-diyl or thiophen-2,5-diyl; or a salt thereof.

5. The compound of formula (I) according to claim 1, wherein A represents propan-1,3-diyl; or a salt thereof.

6. The compound of formula (I) according to claim 1, wherein E represents *—(C$_1$-C$_4$)alkyl-O— or —CH=CH—; or a salt thereof.

7. The compound of formula (I) according to claim 1, wherein E represents

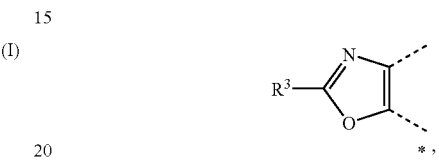

or a salt thereof.

8. The compound of formula (I) according to claim 1, wherein R$^3$ represents hydrogen or methyl;
or a salt thereof.

9. The compound of formula (I) according to claim 1, wherein
R$^1$ represents phenyl, which is unsubstituted, mono- or di-substituted
with halogen, (C$_1$-C$_4$)alkyl, (C$_1$-C$_4$)alkoxy, trifluoromethyl, trifluoromethoxy, or dimethylamino;
or a salt thereof.

10. The compound of formula (I) according to claim 1, wherein R$^2$ represents —CO—(C$_1$-C$_3$)alkyl; or a salt thereof.

11. The compound of formula (I) according to claim 1, wherein the compound is:
5-Phenyl-oxazole-4-carboxylic acid [2-(5-acetyl-furan-2-ylmethyl)-2H-[1,2,3]triazol-4-yl]-amide;
(E)-N-[2-(5-Acetyl-furan-2-ylmethyl)-2H-[1,2,3]triazol-4-yl]-3-(4-trifluoromethyl-phenyl)-acrylamide;
5-(3-Methoxy-phenyl)-2-methyl-oxazolic-4-carboxylic acid [2-(5-acetyl-furan-2-ylmethyl)-2H-[1,2,3]triazol-4-yl]-amide; or
[2-(5-Acetyl-furan-2-ylmethyl)-2H-[1,2,3]triazol-4-yl]-carbamic acid 2-chloro-benzyl ester; or a salt thereof.

12. The compound of formula (I) according to claim 1, wherein the compound is:
5-Phenyl-oxazole-4-carboxylic acid [2-(5-oxo-hexyl)-2H-[1,2,3]triazol-4-yl]-amide;
(E)-N-[2-(5-Acetyl-furan-2-ylmethyl)-2H-[1,2,3]triazol-4-yl]-3-(4-chloro-phenyl)-acrylamide;
(E)-N-[2-(5-Acetyl-furan-2-ylmethyl)-2H-[1,2,3]triazol-4-yl]-3-(4-trifluoromethyl-phenyl)-acrylamide;
(E)-N-[2-(5-Acetyl-furan-2-ylmethyl)-2H-[1,2,3]triazol-4-yl]-3-(3-trifluoromethoxy-phenyl)-acrylamide;
(E)-N-[2-(5-Acetyl-furan-2-ylmethyl)-2H-[1,2,3]triazol-4-yl]-3-o-tolyl-acrylamide;
(E)-N-[2-(5-Acetyl-furan-2-ylmethyl)-2H-[1,2,3]triazol-4-yl]-3-(2-chloro-4-fluoro-phenyl)-acrylamide;
(E)-N-[2-(5-Acetyl-furan-2-ylmethyl)-2H-[1,2,3]triazol-4-yl]-3-m-tolyl-acrylamide;
(E)-N-[2-(5-Acetyl-furan-2-ylmethyl)-2H-[1,2,3]triazol-4-yl]-3-p-tolyl-acrylamide;
(E)-N-[2-(5-Acetyl-furan-2-ylmethyl)-2H-[1,2,3]triazol-4-yl]-3-(4-methoxy-phenyl)-acrylamide;

5-(3,5-Dimethyl-phenyl)-2-methyl-oxazole-4-carboxylic acid [2-(5-acetyl-furan-2-ylmethyl)-2H-[1,2,3]triazol-4-yl]-amide;

5-(3-Trifluoromethyl-phenyl)-oxazole-4-carboxylic acid [2-(5-acetyl-furan-2-ylmethyl) -2H-[1,2,3]triazol-4-yl]-amide;

5-(3-Fluoro-phenyl)-2-methyl-oxazole-4-carboxylic acid [2-(5-acetyl-furan-2-ylmethyl) -2H-[1,2,3]triazol-4-yl]-amide;

5-(4-Chloro-phenyl)-oxazole-4-carboxylic acid [2-(5-acetyl-furan-2-ylmethyl)-2H -[1,2,3]triazol-4-yl]-amide;

2-Methyl-5-m-tolyl-oxazole-4-carboxylic acid [2-(5-acetyl-furan-2-ylmethyl)-2H -[1,2,3]triazol-4yl]-amide;

5-(3-Trifluoromethoxy-phenyl)-oxazole-4-carboxylic acid [2-(5-acetyl-furan-2-ylmethyl)-2H-[1,2,3]triazol-4-yl]-amide;

5-(3-Chloro-phenyl)-2-methyl-oxazole-4-carboxylic acid [2-(5-acetyl-furan-2-ylmethyl) -2H-1,2,3]triazol-4-yl]-amide;

5-(3-Methoxy-4-methyl-phenyl)-oxazole-4-carboxylic acid [2-(5-acetyl-furan-2-ylmethyl)-2H-[1,2,3]triazol-4-yl]-amide;

5-(4-Fluoro-phenyl)-oxazole-4-carboxylic acid [2-(5-acetyl-furan-2-ylmethyl)-2H -[1,2,3]triazol-4-yl]-amide;

5-m-Tolyl-oxazole-4-carboxylic acid [2-(5-acetyl-furan-2-ylmethyl)-2H-1,2,3]triazol-4-yl]-amide;

5-(3-Methoxy-phenyl)-oxazole-4-carboxylic acid [2-(5-acetyl-furan-2-ylmethyl)-2H -[1,2,3]triazol-4-yl]-amide;

2-Methyl-5-phenyl-oxazole-4-carboxylic acid [2-(5-acetyl-furan-2-ylmethyl)-2H -[1,2,3]triazol-4-yl]-amide;

2-Methyl-5-(3-trifluoromethyl-phenyl)-oxazole-4-carboxylic acid [2-(5-acetyl-furan-2-ylmethyl)-2H-[1,2,3]triazol-4-yl]-amide;

2-Methyl-5-(3-trifluoromethoxy-phenyl)-oxazole-4-carboxylic acid [2-(5-acetyl-furan-2-ylmethyl)-2H-[1,2,3]triazol-4-yl]-amide;

2-Methyl-5-o-tolyl-oxazole-4-carboxylic acid [2-(5-acetyl-furan-2-ylmethyl)-2H -[1,2,3]triazol-4-yl]-amide;

2-Ethyl-5-phenyl-oxazole-4-carboxylic acid [2-(5-acetyl-furan-2-ylmethyl)-2H -[1,2,3]triazol-4-yl]-amide;

2-Cyclopropyl-5-phenyl-oxazole-4-carboxylic acid [2-(5-acetyl-furan-2-ylmethyl)-2H -[1,2,3]triazol-4-yl]-amide;

5-(3-Fluoro-phenyl)-oxazole-4-carboxylic acid [2-(5-acetyl-furan-2-ylmethyl)-2H -[1,2,3]triazol-4-yl]-amide;

5-(3-Chloro-phenyl)-oxazole-4-carboxylic acid [2-(5-acetyl-furan-2-ylmethyl)-2H -[1,2,3]triazol-4-yl]-amide;

5-Phenyl-oxazole-4-carboxylic acid [2-(5-acetyl-thiophen-2-ylmethyl)-2H-[1,2,3]triazol -4-yl]-amide;

5-Phenyl-oxazole-4-carboxylic acid [2-(3-acetyl-benzyl)-2H-[1,2,3]triazol-4-yl]-amide;

[2-(3-Acetyl-benzyl)-2H-[1,2,3]triazol-4-yl]-carbamic acid 2-chloro-benzyl ester;

5-Phenyl-oxazole-4-carboxylic acid [2-(5,5-difluoro-hexyl)-2H-[1,2,3]triazol-4-yl]-amide;

5-Phenyl-oxazole-4-carboxylic acid [2-(5-methanesulfonyl-furan-2-ylmethyl)-2H -[1,2,3]triazol-4-yl]-amide;

5-(3-Dimethylamino-phenyl)-oxazole-4-carboxylic acid [2-(5-acetyl-furan-2-ylmethyl) -2H-[1,2,3]triazol-4-yl]-amide;

5-Phenyl-oxazole-4-carboxylic acid [2-(4-acetyl-thiazol-2-ylmethyl)-2H-[1,2,3]triazol-4-yl]-amide;

[2-(4-Acetyl-thiazol-2-ylmethyl)-2H-[1,2,3]triazol-4-yl]-carbamic acid 2-chloro-benzyl ester;

[2-(4-Acetyl-pyridin-2-ylmethyl)-2H-[1,2,3]triazol-4-yl]-carbamic acid 2-chloro-benzyl ester;

5-[3-(2-Methoxy-ethyl)-phenyl]-oxazole-4-carboxylic acid [2-(5-acetyl-furan-2-ylmethyl)-2H-[1,2,3]triazol-4-yl]-amide ;

5-Phenyl-oxazole-4-carboxylic acid [2-(6-acetyl-pyridin-2-ylmethyl)-2H-[1,2,3]triazol-4-yl]-amide;

5-(3-Methoxymethyl-phenyl)-oxazole-4-carboxylic acid [2-(5-acetyl-furan-2-ylmethyl) -2H-[1,2,3]triazol-4-yl]-amide;

5-Phenyl-oxazole-4-carboxylic acid [2-(2-acetyl-thiazol-4-ylmethyl)-2H-[1,2,3]triazol-4-yl]-amide;

5-Phenyl-oxazole-4-carboxylic acid [2-(4-acetyl-pyridin-2-ylmethyl)-2H-[1,2,3]triazol-4-yl]-amide;

5-Phenyl-oxazole-4-carboxylic acid [2-(2-acetyl-pyridin-4-ylmethyl)-2H-[1,2,3]triazol-4-yl]-amide;

[2-(2-Acetyl-pyridin-4-ylmethyl)-2H-[1,2,3]triazol-4-yl]-carbamic acid 2-chloro-benzyl ester;

5-Phenyl-oxazole-4-carboxylic acid [2-(5-acetyl-thiophen-3-ylmethyl)-2H-[1,2,3]triazol-4-yl]-amide; or 2-Methyl-5-m-tolyl-thiazole-4-carboxylic acid [2-(5-acetyl-furan-2-ylmethyl)-2H -[1,2,3]triazol-4-yl]-amide;

or a salt thereof.

13. The compound of formula (I) according to claim 1, wherein the compound is:

5-Phenyl-oxazole-4-carboxylic acid [2-(3-acetyl-isoxazol-5-ylmethyl)-2H-[1,2,3]triazol-4-yl]-amide;

5-(3-Isopropoxymethyl-phenyl)-oxazole-4-carboxylic acid [2-(5-acetyl-furan-2-ylmethyl)-2H-[1,2,3]triazol-4-yl]-amide;

5-[3-(2-Isopropoxy-ethyp-phenyl]-oxazole-4-carboxylic acid [2-(5-acetyl-furan-2-ylmethyl)-2H-[1,2,3]triazol-4-yl]-amide;

2-Methyl-5-m-tolyl-oxazole-4-carboxylic acid [2-(5-acetyl-thiophen-2-ylmethyl)-2H-[1,2,3]triazol-4-yl1-amide;

5-(3-Chloro-phenyl)-2-methyl-oxazole-4-carboxylic acid [2-(5-acetyl-thiophen-2-ylmethyl)-2H-[1,2,3]triazol-4-yl]-amide;

5-m-Tolyl-oxazole-4-carboxylic acid [2-(5-acetyl-thiophen-2-ylmethyl)-2H -[1,2,3]triazol-4-yl]-amide;

2-Methyl-5-phenyl-oxazole-4-carboxylic acid [2-(5-acetyl-thiophen-2-ylmethyl)-2H -[1,2,3]triazol-4-yl]-amide;

2-Methyl-5-(3-trifluoromethyl-phenyl)-oxazole-4-carboxylic acid [2-(5-acetyl-thiophen -2-ylmethyl)-2H1,2,3]triazol-4-yl]-amide ;

5-(3-Fluoro-phenyl)-oxazole-4-carboxylic acid [2-(5-acetyl-thiophen-2-ylmethyl)-2H -[1,2,3]triazol-4-yl]-amide;

5-(3-Dimethylamino-phenyl)-oxazole-4-carboxylic acid [2-(5-acetyl-thiophen-2-ylmethyl)-2H-[1,2,3]triazol-4-yl]-amide;

5-(3-Chloro-phenyl)-oxazole-4-carboxylic acid [2-(5-acetyl-thiophen-2-ylmethyl)-2H -[1,2,3]triazol-4-yl]-amide;

2-Methyl-5-(3-trifluoromethoxy-phenyl)-oxazole-4-carboxylic acid [2-(5-acetyl -thiophen-2-ylmethyl)-2H-[1, 2,3triazol-4-yl]-amide;

5-(4-Fluoro-phenyl)-oxazole-4-carboxylic acid [2-(5-acetyl-thiophen-2-ylmethyl)-2H -[1,2,3]triazol-4-yl]-amide;

5-(3-Trifluoromethoxy-phenyl)-oxazole-4-carboxylic acid [2-(5-acetyl-thiophen-2-ylmethyl)-2H-[1,2,3]triazol-4-yl]-amide;

5-(3-Methoxy-phenyl)-oxazole-4-carboxylic acid [2-(5-acetyl-thiophen-2-ylmethyl)-2H -[1,2,3]triazol-4-yl]-amide;

5-(3-Fluoro-phenyl)-thiazole-4-carboxylic acid [2-(5-acetyl-furan-2-ylmethyl)-2H -[1,2,3]triazol-4-yl]-amide;

5-Phenyl-oxazole-4-carboxylic acid [2-(2-acetyl-thiazol-5-ylmethyl)-2H-[1,2,3]triazol-4-yl]-amide;

[2-(2-Acetyl-thiazol-5-ylmethyl)-2H-[1,2,3]triazol-4-yl]-carbamic acid 2-chloro-benzyl ester;

(E)-N-[2-(2-Acetyl-thiazol-5-ylmethyl)-2H-[1,2,3]triazol-4-yl]-3-(4-trifluoromethyl -phenyl)-acrylamide;

5-Phenyl-oxazole-4-carboxylic acid [2-(2-acetyl-oxazol-5-ylmethyl)-2H-[1,2,3]triazol-4-yl]-amide;

[2-(5-Acetyl-thiazol-2-ylmethyl)-2H-[1,2,3]triazol-4-yl]-carbamic acid 2-chloro-benzyl ester;

5-Phenyl-oxazole-4-carboxylic acid [2-(4-acetyl-thiophen-2-ylmethyl)-2H-[1,2,3]triazol-4-yl]-amide;

5-Phenyl-oxazole-4-carboxylic acid [2-(5-acetyl-thiazol-2-ylmethyl)-2H-[1,2,3]triazol-4-yl]-amide;

(E)-N-[2-(5-Acetyl-thiazol-2-ylmethyl)-2H11,2,3]triazol-4-yl]-3-(4-trifluoromethyl -phenyl)-acrylamide;

2-Methyl-5-m-tolyl-oxazole-4-carboxylic acid [2-(4-acetyl-thiazol-2-ylmethyl)-2H -[1,2,3]triazol-4-yl]-amide;

5-(3-Chloro-phenyl)-2-methyl-oxazole-4-carboxylic acid [2-(4-acetyl-thiazol-2-ylmethyl)-2H-[1,2,3]triazol-4-yl]-amide;

2-Methyl-5-phenyl-oxazole-4-carboxylic acid [2-(4-acetyl-thiazol-2-ylmethyl)-2H -[1,2,3]triazol-4-yl]-amide;

2-Methyl-5-(3-trifluoromethyl-phenyl)-oxazole-4-carboxylic acid [2-(4-acetyl-thiazol-2-ylmethyl)-2H-[1,2,3]triazol-4-yl]-amide;

5-(3-Fluoro-phenyl)-oxazole-4-carboxylic acid [2-(4-acetyl-thiazol-2-ylmethyl)-2H -[1,2,3]triazol-4-yl]-amide;

5-(3-Dimethylamino-phenyl)-oxazole-4-carboxylic acid [2-(4-acetyl-thiazol-2-ylmethyl)-2H-[1,2,3]triazol-4-yl1-amide;

5-(3-Chloro-phenyl)-oxazole-4-carboxylic acid [2-(4-acetyl-thiazol-2-ylmethyl)-2H -[1,2,3]triazol-4-yl]-amide;

2-Methyl-5-(3-trifluoromethoxy-phenyl)-oxazole-4-carboxylic acid [2-(4-acetyl-thiazol-2-ylmethyl)-2H-[1,2,3]triazol-4-yl]-amide;

5-(4-Fluoro-phenyl)-oxazole-4-carboxylic acid [2-(4-acetyl-thiazol-2-ylmethyl)-2H -[1,2,3]triazol-4-yl]-amide;

5-(3-Trifluoromethoxy-phenyl)-oxazole-4-carboxylic acid [2-(4-acetyl-thiazol-2-ylmethyl)-2H-[1,2,3]triazol-4-yl]-amide;

5-(3-Methoxy-phenyl)-oxazole-4-carboxylic acid [2-(4-acetyl-thiazol-2-ylmethyl)-2H -[1,2,3]triazol-4-yl]-amide;

(E)-N42-(4-Acetyl-thiazol-2-ylmethyl)-2H-[1,2,3]triazol-4-yl1-3-(4-trifluoromethyl-phenyl)-acrylamide;

(E)-N-[2-(4-Acetyl-thiazol-2-ylmethyl)-2H-[1,2,3]triazol-4-yl]-3-(3-trifluoromethoxy-phenyl)-acrylamide;

5-(3-Methoxy-phenyl)-2-methyl-oxazole-4-carboxylic acid [2-(4-acetyl-thiazol-2-ylmethyl)-2H-[1,2,3]triazol-4-yl]-amide;

5-(3-Fluoro-phenyl)-2-methyl-oxazole-4-carboxylic acid [2-(4-acetyl-thiazol-2-ylmethyl)-2H-[1,2,3]triazol-4-yl]-amide;

2-Methyl-5-m-tolyl-thiazole-4-carboxylic acid [2-(4-acetyl-thiazol-2-ylmethyl)-2H -[1,2,3]triazol-4-yl]-amide;

5-Phenyl-oxazole-4-carboxylic acid [2-(4-acetyl-oxazol-2-ylmethyl)-2H-[1,2,3triazol-4-yl]-amide;

2-Methoxymethyl-5-phenyl-oxazole-4-carboxylic acid [2-(5-acetyl-furan-2-ylmethyl)-2H-[1,2,3]triazol-4-yl]-amide;

2-(2-Methoxy-ethyl)-5-phenyl-oxazole-4-carboxylic acid [2-(5-acetyl-furan-2-ylmethyl)-2H-[1,2,3]triazol-4-yl]-amide;

2-Butyl-5-phenyl-oxazole-4-carboxylic acid [2-(5-acetyl-furan-2-ylmethyl)-2H -[1,2,3]triazol-4-yll-amide;

2-Isopropyl-5-phenyl-oxazole-4-carboxylic acid [2-(5-acetyl-furan-2-ylmethyl)-2H -[1,2,3]triazol-4-yl]-amide;

(E)-N42-(4-Acetyl-thiazol-2-ylmethyl)-2H-[1,2,3]triazol-4-yl]-3-(2-trifluoromethyl-phenyl)-acrylamide;

2-Benzyl-5-phenyl-oxazole-4-carboxylic acid [2-(5-acetyl-furan-2-ylmethyl)-2H -[1,2,3]triazol-4-yl1-amide;

3- I 4- [2-(5-Acetyl-furan-2-ylmethyl)-2H- [1,2,3]triazol-4-ylcarbamoyl]-5-phenyl-oxazol-2-yl ]-propionic acid tert-butyl ester;

5-(3-Fluoro-phenyl)-2-methyl-oxazole-4-carboxylic acid [2-(2-acetyl-oxazol-5-ylmethyl)-2H-[1,2,3triazol-4-yl]-amide;

2-Methyl-5-m-tolyl-oxazole-4-carboxylic acid [2-(2-acetyl-oxazol-5-ylmethyl)-2H -[1,2,3]triazol-4-ylFamide;

5-(3-Chloro-phenyl)-2-methyl-oxazole-4-carboxylic acid [2-(2-acetyl-oxazol-5-ylmethyl)-2H-[1,2,3]triazol-4-yl]-amide;

5-m-Tolyl-oxazole-4-carboxylic acid [2-(2-acetyl-oxazol-5-ylmethyl)-2H-[1,2,3]triazol-4-yl]-amide;

2-Methyl-5-(3-trifluoromethoxy-phenyl)-oxazole-4-carboxylic acid [2-(2-acetyl-oxazol-5-ylmethyl)-2H-[1,2,3]triazol-4-yl]-amide;

[2-(2-Acetyl-oxazol-4-ylmethyl)-2H-[1,2,3]triazol-4-₃4]-carbamic acid 2-chloro-benzyl ester; or 5-(6-Trifluoromethyl-pyridin-2-yl)-oxazole-4-carboxylic acid [2-(5-acetyl-furan-2-ylmethyl)-2H1,2,3 ] triazol-4-yl]kamide ;

or a salt thereof.

14. A pharmaceutical composition comprising as an active principle the compound of formula (I) according to claim 1 or a pharmaceutically acceptable salt thereof, and at least one therapeutically inert excipient.

15. A method of modulating an immune response comprising the administration of an effective amount of the compound of claim 1 or a pharmaceutically acceptable salt thereof, wherein said effective amount modulates an inflammatory disease or allergic condition and wherein said response is mediated by a lipoxin A4 receptor pathway.

16. A method of modulating an immune response comprising the administration of an effective amount of the composition of claim 14, wherein the effective amount modulates an inflammatory disease or an allergic condition and wherein said response mediated by a lipoxin A4 receptor pathway.

17. A method for the modulation of an immune response comprising the administration of an effective amount of the compound of formula (I) according to claim 1, or a pharmaceutically acceptable salt thereof, wherein said response is mediated by a lipoxin A4 receptor pathway.

18. The compound of formula (I) according to claim 3, wherein E represents

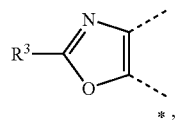

or a salt thereof.

19. The compound of formula (I) according to claim 18, wherein $R^3$ represents hydrogen or methyl;

or a salt thereof.

20. The compound of formula (I) according to claim 19, wherein $R^1$ represents phenyl, which is unsubstituted, mono- or di-substituted
with halogen, $(C_1\text{-}C_4)$alkyl, $(C_1\text{-}C_4)$alkoxy, trifluoromethyl, trifluoromethoxy, or dimethylamino;

or a salt thereof.

21. A method of treating a disease comprising the administration of a therapeutically effective amount of the compound of claim 1 or a pharmaceutically acceptable salt thereof, wherein the disease is Alzheimer's disease.

22. A method of treating a disease comprising the administration of a therapeutically effective amount of the composition of claim 14, wherein the disease is Alzheimer's disease.

* * * * *